(12) United States Patent
Staudinger et al.

(10) Patent No.: US 12,398,212 B2
(45) Date of Patent: Aug. 26, 2025

(54) METHODS FOR TREATING OR PREVENTING ASTHMA BY ADMINISTERING AN IL-4R ANTAGONIST

(71) Applicants: SANOFI BIOTECHNOLOGY, Paris (FR); REGENERON PHARMACEUTICALS, INC., Tarrytown, NY (US)

(72) Inventors: Heribert Staudinger, Bridgewater, NJ (US); Ariel Teper, Bridgewater, NJ (US); Nikhil Amin, Chappaqua, NY (US); Sivan Harel, New York, NY (US); Neil Graham, Croton-on-Hudson, NY (US)

(73) Assignees: SANOFI BIOTECHNOLOGY, Gentilly (FR); REGENERON PHARMACEUTICALS, INC., Tarrytown, NY (US)

(*) Notice: Subject to any disclaimer, the term of this patent is extended or adjusted under 35 U.S.C. 154(b) by 720 days.

(21) Appl. No.: 16/929,624

(22) Filed: Jul. 15, 2020

(65) Prior Publication Data
US 2021/0032354 A1    Feb. 4, 2021

Related U.S. Application Data

(60) Provisional application No. 63/004,084, filed on Apr. 2, 2020, provisional application No. 62/877,031, filed on Jul. 22, 2019, provisional application No. 62/874,747, filed on Jul. 16, 2019.

(30) Foreign Application Priority Data

May 7, 2020 (EP) ..................... 20315237

(51) Int. Cl.
*A61K 39/12* (2006.01)
*A61K 39/00* (2006.01)
*A61P 11/06* (2006.01)
*C07K 16/28* (2006.01)

(52) U.S. Cl.
CPC .......... *C07K 16/2866* (2013.01); *A61K 39/12* (2013.01); *A61P 11/06* (2018.01); *A61K 2039/525* (2013.01); *A61K 2039/545* (2013.01)

(58) Field of Classification Search
CPC .............................. A61K 39/001116
See application file for complete search history.

(56) References Cited

U.S. PATENT DOCUMENTS

| 5,599,905 A | 2/1997 | Mosley et al. |
|---|---|---|
| 5,714,146 A | 2/1998 | Lewis et al. |
| 5,717,072 A | 2/1998 | Mosley et al. |
| 5,856,296 A | 1/1999 | Mosley et al. |
| 5,985,280 A | 11/1999 | Ritter et al. |
| 6,156,877 A | 12/2000 | Ritter et al. |
| 6,391,581 B1 | 5/2002 | Mosley et al. |
| 6,548,655 B1 | 4/2003 | Mosley et al. |
| 6,596,541 B2 | 7/2003 | Murphy et al. |
| 6,716,587 B2 | 4/2004 | Mosley et al. |
| 6,927,044 B2 | 8/2005 | Stahl et al. |
| 7,141,653 B2 | 11/2006 | Greenfeder et al. |
| 7,186,809 B2 | 3/2007 | Pluenneke |
| 7,317,090 B2 | 1/2008 | Mosley et al. |
| 7,422,742 B2 | 9/2008 | Greenfeder et al. |
| 7,465,450 B2 | 12/2008 | Pluenneke |
| 7,531,169 B2 | 5/2009 | Singh et al. |
| 7,582,298 B2 | 9/2009 | Stevens et al. |
| 7,605,237 B2 | 10/2009 | Stevens et al. |
| 7,608,693 B2 | 10/2009 | Martin et al. |
| 7,794,717 B2 | 9/2010 | Stevens et al. |
| 8,030,003 B2 | 10/2011 | Rothenberg |
| 8,075,887 B2 | 12/2011 | Martin et al. |
| 8,075,897 B2 | 12/2011 | Spertini et al. |
| 8,092,802 B2 | 1/2012 | Stevens et al. |
| 8,092,804 B2 | 1/2012 | Eriksson et al. |
| 8,178,098 B2 | 5/2012 | Lahn et al. |
| 8,252,284 B2 | 8/2012 | Singh et al. |
| 8,324,192 B2 | 12/2012 | Dohil et al. |
| 8,337,839 B2 | 12/2012 | Martin et al. |

(Continued)

FOREIGN PATENT DOCUMENTS

| AU | 2009231482 A1 | 10/2009 |
|---|---|---|
| CA | 2737044 A1 | 5/2010 |

(Continued)

OTHER PUBLICATIONS

Corren et al, Annals of Allergy, Asthma and Immunology, (Nov. 2019) vol. 123, No. 5, Supp. Supplement, pp. S15.*
Ramonell et al, J Allergy Clin Immunol Pract. Feb. 2020 ; 8(2): 742-743. doi:10.1016/j.jaip.2019.11.031.*
Semprini R, et al. Thorax, 2019;74:95-98. doi: 10.1136/thoraxjnl-2018-211657.*
Sandeep et al, Lung India • vol 27• Issue 3• Jul.-Sep. 2010.*
Ayars et al. (Mar. 13, 2012) "Pharmacologic Therapies in Pulmonology and Allergy", 2016 Med Clin N Am 100(4): 851-868.

(Continued)

*Primary Examiner* — Prema M Mertz
(74) *Attorney, Agent, or Firm* — LATHROP GPM LLP; James H. Velema, Esq.; Judith L. Stone-Hulslander, Esq.

(57) ABSTRACT

Methods for treating or preventing asthma (e.g., allergic asthma, asthma associated with allergic bronchopulmonary aspergillosis (ABPA), moderate-to-severe asthma, persistent asthma or the like) and associated conditions (e.g., ABPA, ABPA comorbid with asthma, ABPA comorbid with cystic fibrosis (CF), ABPA comorbid with asthma and CF) in a subject are provided. Methods comprising administering to a subject in need thereof a therapeutic composition comprising an interleukin-4 receptor (IL-4R) antagonist, such as an anti-IL-4R antibody or antigen-binding fragment thereof, are provided.

23 Claims, 29 Drawing Sheets
Specification includes a Sequence Listing.

(56) References Cited

U.S. PATENT DOCUMENTS

| | | | |
|---|---|---|---|
| 8,338,135 B2 | 12/2012 | Stevens et al. | |
| 8,497,528 B2 | 7/2013 | Lee et al. | |
| 8,604,171 B2 | 12/2013 | Singh et al. | |
| 8,637,239 B2 | 1/2014 | Furuta et al. | |
| 8,735,095 B2 | 5/2014 | Martin et al. | |
| 8,945,559 B2 | 2/2015 | Dix et al. | |
| 9,238,692 B2 | 1/2016 | Dix et al. | |
| 9,415,015 B2 | 8/2016 | Jacobi et al. | |
| 9,574,004 B2 * | 2/2017 | Ardeleanu | G01N 33/6863 |
| 9,864,091 B2 | 1/2018 | Chen et al. | |
| 10,059,771 B2 | 8/2018 | Mannent et al. | |
| 10,066,017 B2 | 9/2018 | Mannent et al. | |
| 10,137,193 B2 * | 11/2018 | Pirozzi | C07K 16/2866 |
| 10,485,844 B2 | 11/2019 | Radin et al. | |
| 11,034,768 B2 * | 6/2021 | Amin | A61K 31/573 |
| 11,167,004 B2 | 11/2021 | Radin et al. | |
| 11,214,621 B2 | 1/2022 | Mannent et al. | |
| 11,292,847 B2 | 4/2022 | Bansal et al. | |
| 11,771,743 B2 | 10/2023 | Hamilton et al. | |
| 11,845,800 B2 | 12/2023 | Ardeleanu et al. | |
| 11,866,503 B2 | 1/2024 | Orengo et al. | |
| 12,090,201 B2 | 9/2024 | Bansal et al. | |
| 2002/0002132 A1 | 1/2002 | Pluenneke et al. | |
| 2003/0103938 A1 | 6/2003 | Jinquan et al. | |
| 2003/0113387 A1 | 6/2003 | Tsuchida et al. | |
| 2003/0124121 A1 | 7/2003 | Pluenneke | |
| 2005/0031609 A1 | 2/2005 | Hultsch et al. | |
| 2005/0032164 A1 | 2/2005 | Watson et al. | |
| 2005/0074462 A1 | 4/2005 | Holmgren et al. | |
| 2005/0118176 A1 | 6/2005 | Mosley et al. | |
| 2005/0255532 A1 | 11/2005 | Ruben et al. | |
| 2005/0282181 A1 | 12/2005 | Yan et al. | |
| 2006/0013811 A1 | 1/2006 | Dina | |
| 2007/0041976 A1 | 2/2007 | Pluenneke | |
| 2007/0274996 A1 | 11/2007 | Carter et al. | |
| 2008/0054606 A1 | 3/2008 | Mitsuo et al. | |
| 2008/0160035 A1 | 7/2008 | Stevens et al. | |
| 2009/0062168 A1 | 3/2009 | Timar et al. | |
| 2009/0074793 A1 | 3/2009 | Martin et al. | |
| 2009/0098142 A1 | 4/2009 | Kasaian et al. | |
| 2009/0264392 A1 | 10/2009 | Warndahl et al. | |
| 2010/0021476 A1 | 1/2010 | Stevens et al. | |
| 2010/0047254 A1 | 2/2010 | Martin et al. | |
| 2010/0144646 A1 | 6/2010 | Paterson | |
| 2010/0291107 A1 | 11/2010 | Stevens et al. | |
| 2011/0195500 A1 | 8/2011 | Rothenberg | |
| 2012/0004205 A1 | 1/2012 | Rothenberg | |
| 2012/0047954 A1 | 3/2012 | Coppola et al. | |
| 2012/0052072 A1 | 3/2012 | Martin et al. | |
| 2012/0088814 A1 | 4/2012 | Gregory | |
| 2012/0097565 A1 | 4/2012 | Dix et al. | |
| 2012/0135010 A1 | 5/2012 | Stevens et al. | |
| 2012/0164080 A1 | 6/2012 | Hill et al. | |
| 2012/0207815 A1 | 8/2012 | Benhamou et al. | |
| 2012/0240930 A1 | 9/2012 | Kristensson et al. | |
| 2013/0052190 A1 | 2/2013 | Pearce et al. | |
| 2013/0078675 A1 | 3/2013 | Martin et al. | |
| 2013/0324435 A1 | 12/2013 | Rothenberg et al. | |
| 2014/0056920 A1 | 2/2014 | Ardeleanu et al. | |
| 2014/0072583 A1 | 3/2014 | Ardeleanu et al. | |
| 2014/0187523 A1 | 7/2014 | Dohil et al. | |
| 2014/0271658 A1 | 9/2014 | Murphy et al. | |
| 2014/0271681 A1 | 9/2014 | Martin et al. | |
| 2014/0356372 A1 | 12/2014 | Stahl et al. | |
| 2015/0017182 A1 | 1/2015 | Mannent et al. | |
| 2015/0185228 A1 | 7/2015 | Reisacher | |
| 2015/0246119 A1 | 9/2015 | Pirozzi et al. | |
| 2016/0102147 A1 | 4/2016 | Dix et al. | |
| 2016/0152718 A1 | 6/2016 | Kostic et al. | |
| 2016/0185866 A1 | 6/2016 | Mannent et al. | |
| 2018/0016343 A1 | 1/2018 | Ardeleanu et al. | |
| 2018/0155436 A1 | 6/2018 | Orengo et al. | |
| 2019/0040146 A1 | 2/2019 | Mannent et al. | |
| 2019/0040147 A1 | 2/2019 | Mannent et al. | |
| 2019/0078160 A1 | 3/2019 | Dressen et al. | |
| 2019/0125865 A1 | 5/2019 | Pirozzi et al. | |
| 2019/0169299 A1 | 6/2019 | Amin et al. | |
| 2019/0364622 A1 | 11/2019 | Carlsson et al. | |
| 2019/0367622 A1 | 12/2019 | Graham et al. | |
| 2021/0000949 A1 | 1/2021 | Goulaouic et al. | |
| 2021/0087284 A1 | 3/2021 | Xu et al. | |
| 2021/0322546 A1 | 10/2021 | Pirozzi et al. | |
| 2021/0380705 A1 | 12/2021 | Amin et al. | |
| 2022/0169739 A1 | 6/2022 | Xu et al. | |
| 2022/0204631 A1 | 6/2022 | Mannent et al. | |
| 2023/0146317 A1 | 5/2023 | Stjepanovic et al. | |
| 2023/0183362 A1 | 6/2023 | Laws et al. | |
| 2023/0340101 A1 | 10/2023 | Haddad et al. | |
| 2024/0199751 A1 | 6/2024 | Ardeleanu et al. | |
| 2024/0360232 A1 | 10/2024 | Abdulai et al. | |

FOREIGN PATENT DOCUMENTS

| | | |
|---|---|---|
| CN | 101522716 A | 9/2009 |
| CN | 102046658 A | 5/2011 |
| CN | 102197052 A | 9/2011 |
| CN | 105517570 A | 4/2016 |
| CN | 106232140 A | 12/2016 |
| CN | 107206073 A | 9/2017 |
| EP | 0 367 566 A1 | 5/1990 |
| EP | 0 604 693 A1 | 7/1994 |
| EP | 1 229 034 B1 | 4/2005 |
| EP | 1 113 818 B1 | 5/2006 |
| EP | 2 022 507 A1 | 2/2009 |
| EP | 1 527 100 B1 | 7/2009 |
| EP | 1 283 851 B1 | 3/2012 |
| EP | 2 888 281 A1 | 7/2015 |
| EP | 2970460 A2 | 1/2016 |
| EP | 3 010 539 A1 | 4/2016 |
| EP | 3 107 575 A1 | 12/2016 |
| EP | 3 218 412 A1 | 9/2017 |
| EP | 3 470 432 A1 | 4/2019 |
| EP | 3 613 432 A1 | 2/2020 |
| EP | 3962515 A1 | 3/2022 |
| JP | H05-246874 A | 9/1993 |
| JP | 2006-131623 A | 5/2006 |
| JP | 2012-507294 A | 3/2012 |
| JP | 2015-527364 A | 9/2015 |
| JP | 2016-521713 A | 7/2016 |
| JP | 6463351 B2 | 1/2019 |
| RU | 2162711 C2 | 2/2001 |
| RU | 2453303 C1 | 6/2012 |
| RU | 2488595 C2 | 7/2013 |
| RU | 2674680 C2 | 12/2018 |
| TW | 201029664 A | 8/2010 |
| TW | 201221141 A | 6/2012 |
| WO | WO 1992/019259 A1 | 11/1992 |
| WO | WO 1994/014975 A1 | 7/1994 |
| WO | WO 2000/016804 A1 | 3/2000 |
| WO | WO 2001/092340 A2 | 12/2001 |
| WO | WO 2002/007745 A1 | 1/2002 |
| WO | WO 2003/048083 A2 | 6/2003 |
| WO | WO 2003/085089 A2 | 10/2003 |
| WO | WO 2005/047331 A2 | 5/2005 |
| WO | WO 2005/085284 A1 | 9/2005 |
| WO | WO 2006/003407 A2 | 1/2006 |
| WO | WO 2006/072564 A1 | 7/2006 |
| WO | WO 2006/083390 A2 | 8/2006 |
| WO | WO 2007/085815 A2 | 8/2007 |
| WO | WO 2008/054606 A2 | 5/2008 |
| WO | WO 2008/116165 A2 | 9/2008 |
| WO | WO 2009/081201 A2 | 7/2009 |
| WO | WO 2009/124954 A1 | 10/2009 |
| WO | WO 2010/053751 A1 | 5/2010 |
| WO | WO 2010/065557 A2 | 6/2010 |
| WO | WO 2010/120524 A2 | 10/2010 |
| WO | WO 2011/026966 A2 | 3/2011 |
| WO | WO 2011/156000 A2 | 12/2011 |
| WO | WO 2012/047954 A1 | 4/2012 |
| WO | WO 2012/049278 A1 | 4/2012 |
| WO | WO 2012/094643 A2 | 7/2012 |
| WO | WO 2012/177945 A2 | 12/2012 |
| WO | WO 2013/051928 A1 | 4/2013 |
| WO | WO 2013/066780 A2 | 5/2013 |

(56) References Cited

FOREIGN PATENT DOCUMENTS

| | | |
|---|---|---|
| WO | WO 2013/088109 A1 | 6/2013 |
| WO | WO 2013/155010 A1 | 10/2013 |
| WO | WO 2014/031610 A1 | 2/2014 |
| WO | WO 2014/039461 A1 | 3/2014 |
| WO | WO 2014/059178 A1 | 4/2014 |
| WO | WO 2014/031610 A8 | 11/2014 |
| WO | WO 2014/197470 A1 | 12/2014 |
| WO | WO 2014/205365 A1 | 12/2014 |
| WO | WO 2015/006571 A1 | 1/2015 |
| WO | WO 2015/127229 A1 | 8/2015 |
| WO | WO 2016/077675 A1 | 5/2016 |
| WO | WO 2017/143270 A1 | 8/2017 |
| WO | WO 2018/045130 A1 | 3/2018 |
| WO | WO 2018/057776 A1 | 3/2018 |
| WO | WO 2018/102597 A1 | 6/2018 |
| WO | WO 2018/190990 A1 | 10/2018 |
| WO | WO 2019/028367 A1 | 2/2019 |
| WO | WO 2019/089473 A1 | 5/2019 |
| WO | WO 2019/224246 A1 | 11/2019 |
| WO | WO 2020/096381 A1 | 5/2020 |
| WO | WO 2020/135710 A1 | 7/2020 |
| WO | WO 2020/223541 A1 | 11/2020 |
| WO | WO 2021/011614 A1 | 1/2021 |
| WO | WO 2021/119028 A1 | 6/2021 |

OTHER PUBLICATIONS

Blauvelt et al. (Aug. 6, 2018) "Dupilumab does Not Affect Correlates of Vaccine-Induced Immunity: A Randomized, Placebo-Controlled Trial in Adults with Moderate- to-Severe Atopic Dermatitis", Journal of the American Academy of Dermatology, vol. 80, No. 1, p. 158.
Castro et al. (Jun. 28, 2018) "Dupilumab Efficacy and Safety in Moderate-to-Severe Uncontrolled Asthma", New England Journal of Medicine, vol. 378, No. 26, pp. 2486-2496.
Castro et al. (Nov. 1, 2018) "Dupilumab Efficacy and Safety in Uncontrolled, Moderate-to-Severe Allergic Asthma in the Phase 3 Liberty Asthma Quest Study", Annals of Allergy, Asthma and Immunology, p. S8.
Chan et al. (Jun. 2009) "An update on the classifications, diagnosis, and treatment of rhinosinusitis", Current Opinion in Otolaryngology & Head and Neck Surgery, vol. 17, Issue 3, pp. 204-208.
Chin et al., "Nasal polyposis: an inflammatory condition requiring effective anti-inflammatory treatment", Current Opinion in Otolaryngology & Head and Neck Surgery, Feb. 2013, 21(1): 23-30.
Cleveland Clinic (Feb. 2017) "Nasal Polyps", Nasal Polyps: Symptoms, Causes, Prevention and Treatment, pp. 1-6.
Corren (Jun. 6, 2020) "Effects of combined treatment with allergen immunotherapy and dupilumab on nasal allergen challenge and tolerability in immunotherapy", Allergy, p. 78.
Corren et al. (Nov. 1, 2019) "D201 Dupilumab Efficacy in Patients with Uncontrolled, Moderate-to-Severe Asthma and Serologic Evidence of Allergic Bronchopulmonary Aspergillosis", Annals of Allergy, vol. 123, No. 5.
Healthline website (Jan. 25, 2021) "Nasal Polyps", Nasal Polyps: Causes, Symptoms, and Diagnosis, pp. 1-11.
International Nonproprietary Names for Pharmaceutical Substances (INN), WHO Drug Information, 2012, vol. 26, No. 4, obtained from url: https://www.who.int/medicines/publications/druginformation/issues/PL_108.pdf.
International Search Report with Written Opinion corresponding to International Patent Application No. PCT/US2020/042075, mailed Nov. 16, 2020.
Kegg Drug: D10354, Dupilumab, originally retrieved on Aug. 16, 2019, obtained from url: https://www.genome.jp/dbget-bin/www_bget?dr:D10354.
Lange et al., "The Sino-Nasal Outcome Test 22 validated for Danish patients", Dan Med Bull., 2011, 58(2): A4235.

Lommatzsch et al. (Dec. 12, 2014) "Severe Asthma Definiteion, Diagnosis and Treatment", Deutsches Arzteblatt International Feb. 2013, vol. 111, No. 50, pp. 847-855.
Mashovsky (2001) Moscow, 2001 Medicines, 14th edition, v1:8-9 with English Translation.
Mayo Clinic (Jan. 25, 2021) "Nasal Polyps", Nasal Polyps—Symptoms and Causes, pp. 1-4.
Regeneron Pharmaceuticals et al. (Jun. 26, 2019) "Dupilumab as an Adjunct for Subcutaneous Grass Immunotherapy", retrieved from Internet at: https://clinicaltrials.gov/ct2/history/NCT03558997?A=4&B=4&C=merged#StudyPageTop, retrieved on Oct. 20, 2020, 10 pgs.
Regeneron Pharmaceuticals et al. (May 11, 2020) "Dupilumab as an Adjunct for Subcutaneous Grass Immunotherapy", retrieved from Internet at: https://clinicaltrials.gov/ct2/history/NCT03558997?V_5=View#StudyPageTop, retrieved on Oct. 20, 2020, 46 pgs.
Schmidt, (Feb. 2011) "Basophil Sensitivity Decreases During the Updosing on SCIT in Subjects Allergic to Grass Pollen", Journal of Allergy and Clinical Immunology, vol. 127, No. S2, p. AB203.
Sigfried et al., (2019) "Use of Dupilimab in pediatric atopic dermatits: Access, dosing, and implications for managing severe atopic dermatits", Pediatric Dermatology, 36: 172-176.
Sriaroon et al. (Aug. 17, 2014) "Biological Modulators in Eosinophilic Diseases", Clinical Reviews in Allergy and Immunology, vol. 50, No. 2, pp. 252-272.
Tsubouchi et al. (Jan. 1, 2019) "Successful Treatment with Mepolizumab in a Case of Allergic Bronchopulmonary Aspergillosis Complicated with Nontuberculosis Mycobacterial Infection" Respiratory Medicine CME, vol. 28.
YANG (2002) "Anti-IL-4 Receptor mAb Attenuates Allergic Airway Hyperresponsiveness (AHR) and Inflammation in Allergic Mice", J. Allergy Clin. Immunol., Poster 168, Abstracts S69, vol. 109, No. 1, 1 page.
"Clinical Protocol for diagnosing and treating bronchial asthma", Republic of Belarus, Oct. 25, 2006, No. 807, pp. 196-204 [in Russian], obtained from url: https://web.archive.org/web/20170517155846/https://www.bsmu.by/downloads/kafedri/k_p oli_ter/stud/5.pdf.
Bachert et al., "Burden of Disease on Chronic Rhinosinusitis with Nasal Polyps", Journal of Asthma and Allergy, 2021, 14: 127-134.
Besnard et al., "IL-33-activated dendritic cells are critical for allergic airway inflammation", Eur Journal of Immunology, Jun. 2011, 41(6): 1675-1686.
Brahmer, et al., "Safety and Activity of Anti-PD-L1 Antibody In Patients With Advanced Cancer", New England Journal of Medicine, vol. 366, pp. 2455-2465, Jun. 28, 2012.
Donald, et al., Unknown Publication, Current Opinion in Otolaryngology & Head and Neck Surgery, vol. 21 & 23, 2013.
Extended European Search Report for European Patent Application No. 21191120.1, mailed Mar. 2, 2022.
Extended European Search Report for European Patent Application No. 21199451.2, mailed May 9, 2022.
Hambly, et al., "Monoclonal Antibodies for the Treatment of Refractory Asthma", Current Opinion in Pulmonary Medicine, vol. 20, Issue 1, pp. 87-94, Jan. 2014.
International Search Report and Written Opinion for PCT International Patent Application No. PCT/US2020/030824, dated Sep. 1, 2020.
International Search Report and Written Opinion for PCT International Patent Application No. PCT/US2018/058039, mailed Jan. 28, 2019.
International Search Report with Written Opinion corresponding to International Patent Application No. PCT/US2020/066559, mailed May 31, 2021.
Kharkevich, "Pharmacology", 10th Ed., GEOTAR-Media, 2010, 908 pages, p. 42. [Russian w/ English translation].
Kharkevich, "Pharmacology", 9th Ed., Revised, added and corrected, GEOTAR-Media, 2006, pp. 66-67. [Russian language only].
Krylov and Bobyrev, "Pharmacology", Moscow, 1999, "Routes of administration". [Russian language only].
Lee et al., "Blockade of IL-33/ST2 ameliorates airway inflammation in a murine model of allergic asthma", Exp Lung Res., Mar. 2014, 40(2): 66-76.

(56) References Cited

OTHER PUBLICATIONS

Liew et al., "Interleukin-33 in health and disease", Nat Rev immunology, Nov. 2016, 16(11): 676-689.
Liu et al., "Anti-IL-33 antibody treatment inhibits airway inflammation in a murine model of allergic asthma", Biochemical and Biophysical Research Communications, Aug. 14, 2009, 386(1): 181-185.
Maes, et al., "Targeting Interleukin-4 in Asthma: Lost in Translation?", American Journal of Respiratory Cell and Molecular Biology, vol. 47, pp. 261-270, 2012.
Mayo Foundation for Medical Education and Research (MFMER), "Chronic Sinusitis", Aug. 1, 2020.
Mendelsohn, et al., "Revision Rates after Endoscopic Sinus Surgery: A Recurrence Analysis", Annals of Otology, Rhinology & Laryngology, vol. 120, No. 3, pp. 162-166., 2011.
Na et al., "IL-33 enhances Siglec-8 mediated apoptosis of human eosinophils", Cytokine, Oct. 17, 2011, 57(1): 169-174.
Ulashchik, "The targeted transport of the medicinal substances and the therapeutic physical factors", Voprosy kurortologii, fizioterapii, i lechebnoi fizicheskoi kultury 2014, 91(6): 52-61 [in Russian].
US Securities and Exchange Commission Web Site 2019, Form S-1, Dec. 21, 2018, XP055720304, Retrieved from url: <https://www.sec.gov/Archives/edgar/data/1728117/000119312518356444/d626950ds1.htm>.
Zhu et al., "Potential New Targets for Drug Development in Severe Asthma", World Allergy Organization Journal, Oct. 25, 2018, 11(30): 1-9.
Opposition against European Patent No. 3107575 (EP Application No. 15708991.3), filed on May 4, 2022, on behalf of Dr. Hans Ulrich Dörries.
U.S. Appl. No. 61/943,019, filed Feb. 21, 2014, cited in Opposition against European Patent No. 3107575 (EP Application No. 15708991.3), filed on May 4, 2022, on behalf of Dr. Hans Ulrich Dörries.
European Patent Application No. 14306413.7 filed Sep. 15, 2014, cited in Opposition against European Patent No. 3107575 (EP Application No. 15708991.3), filed on May 4, 2022, on behalf of Dr. Hans Ulrich Dörries.
U.S. Appl. No. 62/077,669, filed Nov. 10, 2014, cited in Opposition against European Patent No. 3107575 (EP Application No. 15708991.3), filed on May 4, 2022, on behalf of Dr. Hans Ulrich Dorries.
Barnes, "Scientific rationale for inhaled combination therapy with long-acting β2-agonists and corticosteroids", The European Respiratory Journal, Jan. 2002, 19(1): 182-191.
FDA drug label "Symbicort", revised May 2012, cited in Opposition against European Patent No. 3107575 (EP Application No. 15708991.3), filed on May 4, 2022, on behalf of Dr. Hans Ulrich Dörries.
FDA drug label "Dulera", revised Jun. 2010, cited in Opposition against European Patent No. 3107575 (EP Application No. 15708991.3), filed on May 4, 2022, on behalf of Dr. Hans Ulrich Dörries.
Bice et al., "Biologic targeted therapy in allergic asthma", Annals of Allergy, Asthma & Immunology, 2014, 112(2): 108-115, cited in Opposition against European Patent No. 3107575 (EP Application No. 15708991.3), filed on May 4, 2022, on behalf of Dr. Hans Ulrich Dörries.
Gibaldi, "Biopharmaceutics and Clinical Pharmacokinetics", 4th Edition, 1991, Lea & Febiger, pp. 12-13, cited in Opposition against European Patent No. 3107575 (EP Application No. 15708991.3), filed on May 4, 2022, on behalf of Dr. Hans Ulrich Dörries.
ClinicalTrials.gov, Information about clinical study "NCT01854047", "An Evaluation of Dupilumab in Patients With Moderate to Severe Uncontrolled Asthma", study record version of Feb. 18, 2014, retrieved from the ClinicalTrials.gov archive url: <https://clinicaltrials.ciovict2/show/record/NCT01854047?intr=Dupilumab+OR+REGN-668+OR+REGN668+OR+SAR-231893+OR+SAR231893&phase=1&draw=3&rank=13>, cited in Opposition against European Patent No. 3107575 (EP Application No. 15708991.3), filed on May 4, 2022, on behalf of Dr. Hans Ulrich Dörries.
ClinicalTrials.gov, Information about clinical study "NCT02134028", "Long-Term Safety Evaluation of Dupilumab in Patients With Asthma", study record version of Jan. 8, 2015, retrieved from the ClinicalTrials.gov archive url: <https://clinicaltrials.clovict2/show/record/NCT02134028?term=NCT02134028&draw=2&rank=1>, cited in Opposition against European Patent No. 3107575 (EP Application No. 15708991.3), filed on May 4, 2022, on behalf of Dr. Hans Ulrich Dörries.
Annex to the Notice of Opposition against European Patent No. 3107575 (EP Application No. 15708991.3), Facts and Arguments in accordance with Rule 76(2)(c) EPC, filed on May 25, 2022.
International Nonproprietary Names for Pharmaceutical Substances (INN), pp. 401, 402 and 412 of WHO Drug Information, 2012, 26(4):401-471, cited in Annex to the Notice of Opposition against European Patent No. 3107575 (EP Application No. 15708991.3), Facts and Arguments in accordance with Rule 76(2)(c) EPC, filed on May 25, 2022.
EurekAlert! press release Monoclonal antibody appears effective and safe in asthma Phase lla trial', May 21, 2013, cited in Annex to the Notice of Opposition against European Patent No. 3107575 (EP Application No. 15708991.3), Facts and Arguments in accordance with Rule 76(2)(c) EPC, filed on May 25, 2022.
Chapter 19, "Dosage regimens", of Aulton's Pharmaceutics: The Science of Dosage Form Design, 2nd Edition, 2001, cited in Annex to the Notice of Opposition against European Patent No. 3107575 (EP Application No. 15708991.3), Facts and Arguments in accordance with Rule 76(2)(c) EPC, filed on May 25, 2022.
Ackerman et al., pp. 159 to 162 of Rispens and Vidarsson, Antibody Fc: Linking Adaptive and Innate Immunity, Chapter 9, "Human IgG Subclasses", pp. 159 to 162, 2013; and evidence of its publication date, cited in Annex to the Notice of Opposition against European Patent No. 3107575 (EP Application No. 15708991.3), Facts and Arguments in accordance with Rule 76(2)(c) EPC, filed on May 25, 2022.
Panaccione et al., "Optimal use of biologics in the management of Crohn's disease", Ther. Adv. Gastroenterol., 2010, 3(3):179-189, which is a review article relating to the optimal use of biologics in the inflammatory disorder, Crohn's disease, cited in Annex to the Notice of Opposition against European Patent No. 3107575 (EP Application No. 15708991.3), Facts and Arguments in accordance with Rule 76(2)(c) EPC, filed on May 25, 2022.
ClinicalTrials.gov, NCT01854047 clinical trial protocol version 22 (Feb. 3, 2014), cited in Annex to the Notice of Opposition against European Patent No. 3107575 (EP Application No. 15708991.3), Facts and Arguments in accordance with Rule 76(2)(c) EPC, filed on May 25, 2022.
Global Initiative for Asthma, pp. 29 to 31 and 58 of the Global Strategy for Asthma Management and Prevention, 2009, cited in Annex to the Notice of Opposition against European Patent No. 3107575 (EP Application No. 15708991.3), Facts and Arguments in accordance with Rule 76(2)(c) EPC, filed on May 25, 2022.
Notice of Opposition against European Patent No. 3107575 (EP Application No. 15708991.3) filed on behalf of Regina Neuefeind, dated Jun. 1, 2022.
Applicants' letter dated Sep. 20, 2016, cited in Notice of Opposition against European Patent No. 3107575 (EP Application No. 15708991.3) filed on behalf of Regina Neuefeind, dated Jun. 1, 2022.
Amended claims enclosed with letter dated Sep. 20, 2016, cited in Notice of Opposition against European Patent No. 3107575 (EP Application No. 15708991.3) filed on behalf of Regina Neuefeind, dated Jun. 1, 2022.
Applicants' letter dated Jul. 25, 2019, cited in Notice of Opposition against European Patent No. 3107575 (EP Application No. 15708991.3) filed on behalf of Regina Neuefeind, dated Jun. 1, 2022.
Amended claims enclosed with letter dated Jul. 25, 2019, cited in Notice of Opposition against European Patent No. 3107575 (EP Application No. 15708991.3) filed on behalf of Regina Neuefeind, dated Jun. 1, 2022.
Radin et al., "Abstract 558: First-in-Human Study of REGN668/SAR231893 (IL-4Rα mAb): Safety, Tolerability and Biomarker Results of a Randomized, Double-Blind, Placebo-Controlled, Single Ascending Dose Study in Healthy Volunteers", J Allergy clin Immunol, Feb. 2013, cited in Notice of Opposition against European Patent No. 3107575 (EP Application No. 15708991.3) filed on behalf of Regina Neuefeind, dated Jun. 1, 2022.

(56) References Cited

OTHER PUBLICATIONS

Swanson et al., 2014, "Poster 1023: Dupilumab suppresses Th2 inflammation in adult asthma and atopic dermatitis", World Allergy Organization Journal, Presented on Dec. 13-14, 2013, cited in Notice of Opposition against European Patent No. 3107575 (EP Application No. 15708991.3) filed on behalf of Regina Neuefeind, dated Jun. 1, 2022.

Sanofi and Regeneron Pharmaceuticals Inc., Press Release Nov. 11, 2014, "Dupilumab Demonstrated Improvement in Lung Function, Reductions of Severe Exacerbations", cited in Notice of Opposition against European Patent No. 3107575 (EP Application No. 15708991.3) filed on behalf of Regina Neuefeind, dated Jun. 1, 2022.

Regeneron Pharmaceuticals Inc., Press Release Jul. 9, 2014, at 5:00 PM EDT, "Regeneron and Sanofi Announce Positive Results from Phase 2B Study of Dupilumab in Patients with Moderate-to-Severe Atopic Dermatitis", cited in Notice of Opposition against European Patent No. 3107575 (EP Application No. 15708991.3) filed on behalf of Regina Neuefeind, dated Jun. 1, 2022.

Regeneron Pharmaceuticals Inc., Mar. 2, 2013, at 9:00 AM EST, "Sanofi and Regeneron Report Positive Proof-of-Concept Data for Dupilumab, An IL-4R Alpha Antibody, In Atopic Dermatitis", cited in Notice of Opposition against European Patent No. 3107575 (EP Application No. 15708991.3) filed on behalf of Regina Neuefeind, dated Jun. 1, 2022.

Beck et al., "Dupilumab Treatment in Adults with Moderate-to-Severe Atopic Dermatitis", N Engl J Med, Jul. 10, 2014, 371: 130-139, cited in Notice of Opposition against European Patent No. 3107575 (EP Application No. 15708991.3) filed on behalf of Regina Neuefeind, dated Jun. 1, 2022.

Brusselle et al., "Targeting Immune Pathways for Therapy in Asthma and Chronic Obstructive Pulmonary Disease", Ann Am Thorac Soc, 2014, 11(Suppl. 5): S322-S328, cited in Notice of Opposition against European Patent No. 3107575 (EP Application No. 15708991.3) filed on behalf of Regina Neuefeind, dated Jun. 1, 2022.

Possa et al., "Eosinophilic inflammation in allergic asthma", Frontiers in Pharmacology, 2013, 4(46): 1-9, cited in Notice of Opposition against European Patent No. 3107575 (EP Application No. 15708991.3) filed on behalf of Regina Neuefeind, dated Jun. 1, 2022.

Liang et al., "Moderate Accuracy of Peripheral Eosinophil Count for Predicting Eosinophilic Phenotype in Steroid-Naïve Non-Atopic Adult Asthmatics", Intern Med., 2012, 51: 717-722, cited in Notice of Opposition against European Patent No. 3107575 (EP Application No. 15708991.3) filed on behalf of Regina Neuefeind, dated Jun. 1, 2022.

Katz et al., "Blood Eosinophil Count Is a Useful Biomarker to Identify Patients with Severe Eosinophilic Asthma", Ann Am Thorac Soc., 2014, 11(4): 531-536, cited in Notice of Opposition against European Patent No. 3107575 (EP Application No. 15708991.3) filed on behalf of Regina Neuefeind, dated Jun. 1, 2022.

NHS Health Research Authority, "Dupilumab for adult patients with moderate to severe atopic dermatitis", REC Opinion, May 30, 2014, cited in Notice of Opposition against European Patent No. 3107575 (EP Application No. 15708991.3) filed on behalf of Regina Neuefeind, dated Jun. 1, 2022.

Notice of Opposition against European Patent No. 3470432 (Application No. 18194745.8) filed on Jul. 5, 2022, on behalf of Secerna LLP.

D1—Wenzel, Severe Asthma: from characteristics to phenotypes to endotypes (review), Clinical & Experimental Allergy, Jan. 18, 2012, 42: 650-658, cited in Notice of Opposition against European Patent No. 3470432 (Application No. 18194745.8) filed on Jul. 5, 2022, on behalf of Secerna LLP.

D2—Wenzel, Asthma phenotypes: the evolution from clinical to molecular approaches (review), Nature Medicine, May 4, 2012, 18(5): 716-725, cited in Notice of Opposition against European Patent No. 3470432 (Application No. 18194745.8) filed on Jul. 5, 2022, on behalf of Secerna LLP.

D3—GINA Report Dec. 2011, Global Strategy for Asthma Management and Prevention, GINA © 2011 & Global Initiative for Asthma, reprinted with permission, Available from www.ginasthma.org, cited in Notice of Opposition against European Patent No. 3470432 (Application No. 18194745.8) filed on Jul. 5, 2022, on behalf of Secerna LLP.

D4—GINA Report Dec. 2012, Global Strategy for Asthma Management and Prevention, GINA © 2012 & Global Initiative for Asthma, reprinted with permission, Available from www.ginasthma.org, cited in Notice of Opposition against European Patent No. 3470432 (Application No. 18194745.8) filed on Jul. 5, 2022, on behalf of Secerna LLP.

D5—Wenzel et al., Dupilumab in persistent asthma with elevated eosinophil levels, N Engl J Med., May 21, 2013, 368(26): 2455-2466, cited in Notice of Opposition against European Patent No. 3470432 (Application No. 18194745.8) filed on Jul. 5, 2022, on behalf of Secerna LLP.

D6—Protocol for: Wenzel et al., Dupilumab in persistent asthma with elevated eosinophil levels, N Engl J Med., May 21, 2013, 368(26): 2455-2466, cited in Notice of Opposition against European Patent No. 3470432 (Application No. 18194745.8) filed on Jul. 5, 2022, on behalf of Secerna LLP.

D7—Weschler, Inhibiting interleukin-4 and interleukin-13 in difficult-to-control asthma, N Engl J Med., May 21, 2013, 368: 2511-2513, cited in Notice of Opposition against European Patent No. 3470432 (Application No. 18194745.8) filed on Jul. 5, 2022, on behalf of Secerna LLP.

D8—U.S. Pat. No. 8,075,887 B2, High Affinity Human Antibodies to Human IL-4 Receptor, issued Dec. 13, 2011, cited in Notice of Opposition against European Patent No. 3470432 (Application No. 18194745.8) filed on Jul. 5, 2022, on behalf of Secerna LLP.

D9—PCT International Publication No. WO 2010/053751 A1, High Affinity Human Antibodies to Human IL-4 Receptor, published May 14, 2010, cited in Notice of Opposition against European Patent No. 3470432 (Application No. 18194745.8) filed on Jul. 5, 2022, on behalf of Secerna LLP.

D10—Study NCT01312961 (v31), Efficacy, Safety, and Tolerability of SAR231893 (REGN668) in Patients with Persistent Moderate to Severe Eosinophilic Asthma, Aug. 20, 2012, cited in Notice of Opposition against European Patent No. 3470432 (Application No. 18194745.8) filed on Jul. 5, 2022, on behalf of Secerna LLP.

D11—Press release: Regeneron reports fourth quarter and full year 2011 financial and operating results, Feb. 13, 2012, https://investor.regeneron.com/news-releases/news-release-details/regeneron-reports-fourth-quarter-and-full-year-2011-financial, cited in Notice of Opposition against European Patent No. 3470432 (Application No. 18194745.8) filed on Jul. 5, 2022, on behalf of Secerna LLP.

D12—Otulana et al., A Phase 2b Study of Inhaled Pitrakinra, an IL-4 / IL-13 antagonist, successfully identified responder subpopulations of patients with uncontrolled asthma, American Journal of Respiratory and Critical Care Medicine, May 18, 2011, 183: A6179, cited in Notice of Opposition against European Patent No. 3470432 (Application No. 18194745.8) filed on Jul. 5, 2022, on behalf of Secerna LLP.

D13—Corren et al., A randomized, controlled, Phase 2 study of AMG 317, an IL-4Ra antagonist, in patients with asthma, Am J Respir Crit Care Med., Jan. 7, 2010, 181(8): 788-796, cited in Notice of Opposition against European Patent No. 3470432 (Application No. 18194745.8) filed on Jul. 5, 2022, on behalf of Secerna LLP.

D14—Hashimoto & Bel, Targeting IL-5 in severe asthma: a Dream come true?, The Lancet, Aug. 8, 2012, 380(9842): 626-627, cited in Notice of Opposition against European Patent No. 3470432 (Application No. 18194745.8) filed on Jul. 5, 2022, on behalf of Secerna LLP.

D15—Pavord al., Mepolizumab for severe eosinophilic asthma (Dream): a multicentre, double-blind, placebo-controlled trial, Lancet, Aug. 18, 2012; 380: 651-659, cited in Notice of Opposition against European Patent No. 3470432 (Application No. 18194745.8) filed on Jul. 5, 2022, on behalf of Secerna LLP.

D16—Szefler et al., Asthma Outcomes: Biomarkers, J Allergy Clin Immunol., Mar. 1, 2012, 129: S9-23, cited in Notice of Opposition

(56) References Cited

OTHER PUBLICATIONS against European Patent No. 3470432 (Application No. 18194745.8) filed on Jul. 5, 2022, on behalf of Secerna LLP.
D17—Spector & Tan, Is a single blood eosinophil count a reliable marker for "eosinophilic asthma?", Journal of Asthma, Aug. 20, 2012, 49.8: Early Online: 1-4, cited in Notice of Opposition against European Patent No. 3470432 (Application No. 18194745.8) filed on Jul. 5, 2022, on behalf of Secerna LLP.
D18—WHO Drug Information, vol. 26, No. 4, p. 412, Dec. 9, 2012, cited in Notice of Opposition against European Patent No. 3470432 (Application No. 18194745.8) filed on Jul. 5, 2022, on behalf of Secerna LLP.
D19—Firszt & Kraft, Pharmacotherapy of Severe Asthma, Curr Opin Pharmacol., Jun. 2010, 10(3): 266-271, cited in Notice of Opposition against European Patent No. 3470432 (Application No. 18194745.8) filed on Jul. 5, 2022, on behalf of Secerna LLP.
D20—Darveax & Busse, Biologics in asthma—the next step to personalised treatment, J Allergy Clin Immunol Pract., Mar.-Apr. 2015, 3(2): 152-161, cited in Notice of Opposition against European Patent No. 3470432 (Application No. 18194745.8) filed on Jul. 5, 2022, on behalf of Secerna LLP.
D21—Eisenstein, Something new under the skin, Nature Biotechnology, Feb. 7, 2011, 29(2): 107-109, cited in Notice of Opposition against European Patent No. 3470432 (Application No. 18194745.8) filed on Jul. 5, 2022, on behalf of Secerna LLP.
D22—Chapter 19, "Dosage regimens" of Aulton's Pharmaceutics: The Science of Dosage Form Design, 2nd Edition, 2001, cited in Notice of Opposition against European Patent No. 3470432 (Application No. 18194745.8) filed on Jul. 5, 2022, on behalf of Secerna LLP.
P1—U.S. Appl. No. 61/691,625, filed Aug. 21, 2012, cited in Notice of Opposition against European Patent No. 3470432 (Application No. 18194745.8) filed on Jul. 5, 2022, on behalf of Secerna LLP.
P2—U.S. Appl. No. 61/758,097, filed Jan. 29, 2013, cited in Notice of Opposition against European Patent No. 3470432 (Application No. 18194745.8) filed on Jul. 5, 2022, on behalf of Secerna LLP.
P3—U.S. Appl. No. 61/761,279, filed Feb. 6, 2013, cited in Notice of Opposition against European Patent No. 3470432 (Application No. 18194745.8) filed on Jul. 5, 2022, on behalf of Secerna LLP.
P4—U.S. Appl. No. 61/783,796, filed Mar. 14, 2013, cited in Notice of Opposition against European Patent No. 3470432 (Application No. 18194745.8) filed on Jul. 5, 2022, on behalf of Secerna LLP.
P5—U.S. Appl. No. 61/805,797, filed Mar. 27, 2013, cited in Notice of Opposition against European Patent No. 3470432 (Application No. 18194745.8) filed on Jul. 5, 2022, on behalf of Secerna LLP.
P6—French Patent Application No. 1356994, filed Jul. 16, 2013, cited in Notice of Opposition against European Patent No. 3470432 (Application No. 18194745.8) filed on Jul. 5, 2022, on behalf of Secerna LLP.
A—Divisional Application as filed (EP 18194745.8), dated Sep. 17, 2018, cited in Notice of Opposition against European Patent No. 3470432 (Application No. 18194745.8) filed on Jul. 5, 2022, on behalf of Secerna LLP.
Notice of Opposition against European Patent No. 3470432 (Application No. 18194745.8) filed on Jul. 5, 2022, on behalf of Dr. Hans Ulrich Dorries.
P1—U.S. Appl. No. 61/691,625, filed Aug. 21, 2012, cited in Notice of Opposition against European Patent No. 3470432 (Application No. 18194745.8) filed on Jul. 5, 2022, on behalf of Dr. Hans Ulrich Dorries.
P2—U.S. Appl. No. 61/758,097, filed Jan. 29, 2013, cited in Notice of Opposition against European Patent No. 3470432 (Application No. 18194745.8) filed on Jul. 5, 2022, on behalf of Dr. Hans Ulrich Dorries.
P3—U.S. Appl. No. 61/761,279, filed Feb. 6, 2013, cited in Notice of Opposition against European Patent No. 3470432 (Application No. 18194745.8) filed on Jul. 5, 2022, on behalf of Dr. Hans Ulrich Dorries.
P4—U.S. Appl. No. 61/783,796, filed Mar. 14, 2013, cited in Notice of Opposition against European Patent No. 3470432 (Application No. 18194745.8) filed on Jul. 5, 2022, on behalf of Dr. Hans Ulrich Dorries.
P5—U.S. Appl. No. 61/805,797, filed Mar. 27, 2013, cited in Notice of Opposition against European Patent No. 3470432 (Application No. 18194745.8) filed on Jul. 5, 2022, on behalf of Dr. Hans Ulrich Dorries.
P6—French Patent Application No. 1356994, filed Jul. 16, 2013, cited in Notice of Opposition against European Patent No. 3470432 (Application No. 18194745.8) filed on Jul. 5, 2022, on behalf of Dr. Hans Ulrich Dorries.
PA—PCT International Publication No. 2014/031610 A1 published Feb. 27, 2014, cited in Notice of Opposition against European Patent No. 3470432 (Application No. 18194745.8) filed on Jul. 5, 2022, on behalf of Dr. Hans Ulrich Dorries.
OA—Divisional application as filed resulting in the opposed patent (European Patent Application No. 21199451.2, filed Sep. 28, 2021), cited in Notice of Opposition against European Patent No. 3470432 (Application No. 18194745.8) filed on Jul. 5, 2022, on behalf of Dr. Hans Ulrich Dorries.
D1—Wenzel et al., Dupilumab in persistent asthma with elevated eosinophil levels, N Engl J Med., May 21, 2013, 368(26): 2455-2466, cited in Notice of Opposition against European Patent No. 3470432 (Application No. 18194745.8) filed on Jul. 5, 2022, on behalf of Dr. Hans Ulrich Dorries.
D2—WHO Drug Information, vol. 26, No. 4, pp. 401-471, Proposed INN: List 108, Dec. 9, 2012, cited in Notice of Opposition against European Patent No. 3470432 (Application No. 18194745.8) filed on Jul. 5, 2022, on behalf of Dr. Hans Ulrich Dorries.
D3—O'Byrne et al., Clinical and Experimental Allergy, May 2012, 42(2): 706-711, cited in Notice of Opposition against European Patent No. 3470432 (Application No. 18194745.8) filed on Jul. 5, 2022, on behalf of Dr. Hans Ulrich Dorries.
D4—Corren et al., A randomized, controlled, Phase 2 study of AMG 317, an IL-4Ra antagonist, in patients with asthma, Am J Respir Crit Care Med., Jan. 7, 2010, 181(8): 788-796, cited in Notice of Opposition against European Patent No. 3470432 (Application No. 18194745.8) filed on Jul. 5, 2022, on behalf of Dr. Hans Ulrich Dorries.
D5—PCT International Publication No. WO 2010/053751 A1, High Affinity Human Antibodies to Human IL-4 Receptor, published May 14, 2010, cited in Notice of Opposition against European Patent No. 3470432 (Application No. 18194745.8) filed on Jul. 5, 2022, on behalf of Dr. Hans Ulrich Dorries.
D6—Gibaldi, Biopharmaceutics and Clinical Pharmakokinetics, $4^{th}$ Ed., 1991, Lea & Febiger, pp. 12-13, cited in Notice of Opposition against European Patent No. 3470432 (Application No. 18194745.8) filed on Jul. 5, 2022, on behalf of Dr. Hans Ulrich Dorries.
Notice of Opposition against European Patent No. 3470432 (Application No. 18194745.8) filed on Jul. 6, 2022, on behalf of D. Young & Co.
D1—Corren et al., A randomized, controlled, Phase 2 study of AMG 317, an IL-4Ra antagonist, in patients with asthma, Am J Respir Crit Care Med., Jan. 7, 2010, 181(8): 788-796, cited in Notice of Opposition against European Patent No. 3470432 (Application No. 18194745.8) filed on Jul. 6, 2022, on behalf of D. Young & Co.
D2—pp. 17, 28, 32, 34, 59 and 61 of the Global Initiative for Asthma: Global Strategy for Asthma Management and Prevention, 2009, cited in Notice of Opposition against European Patent No. 3470432 (Application No. 18194745.8) filed on Jul. 6, 2022, on behalf of D. Young & Co.
D3—Borish, Am J Respir Crit Care Med., 2010, 181: 769-772, cited in Notice of Opposition against European Patent No. 3470432 (Application No. 18194745.8) filed on Jul. 6, 2022, on behalf of D. Young & Co.
D4—U.S. Pat. No. 8,075,887 B2, High Affinity Human Antibodies to Human IL-4 Receptor, issued Dec. 13, 2011, cited in Notice of Opposition against European Patent No. 3470432 (Application No. 18194745.8) filed on Jul. 6, 2022, on behalf of D. Young & Co.
D5—Chapter 19, Dosage Regimens, Alton's Pharmaceutics: The Science of Dosage Form Design, $2^{nd}$ Ed., 2001, cited in Notice of

(56) References Cited

OTHER PUBLICATIONS

Opposition against European Patent No. 3470432 (Application No. 18194745.8) filed on Jul. 6, 2022, on behalf of D. Young & Co.
D6—Mould & Sweeney, Current Opinion in Drug Discovery & Development, 2007, 10(1): 84-96, cited in Notice of Opposition against European Patent No. 3470432 (Application No. 18194745.8) filed on Jul. 6, 2022, on behalf of D. Young & Co.
D7—Panaccione and Ghosh, Ther Adv Gastroenterol., 2010, 3(3): 179-189, cited in Notice of Opposition against European Patent No. 3470432 (Application No. 18194745.8) filed on Jul. 6, 2022, on behalf of D. Young & Co.
Notice of Opposition against European Patent No. 3470432 (Application No. 18194745.8) filed on Jul. 6, 2022, on behalf of Ms. Regina Neuefeind.
A—PCT International Publication No. 2014/031610 published Feb. 27, 2014, cited in Notice of Opposition against European Patent No. 3470432 (Application No. 18194745.8) filed on Jul. 6, 2022, on behalf of Ms. Regina Neuefeind.
P1—U.S. Appl. No. 61/691,625, filed Aug. 21, 2012, cited in Notice of Opposition against European Patent No. 3470432 (Application No. 18194745.8) filed on Jul. 6, 2022, on behalf of Ms. Regina Neuefeind.
P2—U.S. Appl. No. 61/758,097, filed Jan. 29, 2013, cited in Notice of Opposition against European Patent No. 3470432 (Application No. 18194745.8) filed on Jul. 6, 2022, on behalf of Ms. Regina Neuefeind.
P3—U.S. Appl. No. 61/761,279, filed Feb. 6, 2013, cited in Notice of Opposition against European Patent No. 3470432 (Application No. 18194745.8) filed on Jul. 6, 2022, on behalf of Ms. Regina Neuefeind.
P4—U.S. Appl. No. 61/783,796, filed Mar. 14, 2013, cited in Notice of Opposition against European Patent No. 3470432 (Application No. 18194745.8) filed on Jul. 6, 2022, on behalf of Ms. Regina Neuefeind.
P5—U.S. Appl. No. 61/805,797, filed Mar. 27, 2013, cited in Notice of Opposition against European Patent No. 3470432 (Application No. 18194745.8) filed on Jul. 6, 2022, on behalf of Ms. Regina Neuefeind.
P6—French Patent Application No. 1356994, filed Jul. 16, 2013, cited in Notice of Opposition against European Patent No. 3470432 (Application No. 18194745.8) filed on Jul. 6, 2022, on behalf of Ms. Regina Neuefeind.
D1—Brusselle and Bracke, Ann Am Thorac Soc., 2014, 11(Suppl. 5): S322-S328, cited in Notice of Opposition against European Patent No. 3470432 (Application No. 18194745.8) filed on Jul. 6, 2022, on behalf of Ms. Regina Neuefeind.
D2—Woodruff et al., Am J Respir Crit Care Med., 2009, 180: 388-395, cited in Notice of Opposition against European Patent No. 3470432 (Application No. 18194745.8) filed on Jul. 6, 2022, on behalf of Ms. Regina Neuefeind.
D3—Liang et al., Intern Med., 2012, 51: 717-722, cited in Notice of Opposition against European Patent No. 3470432 (Application No. 18194745.8) filed on Jul. 6, 2022, on behalf of Ms. Regina Neuefeind.
D4—Gibson, Aust Prescr, 1996, 19: 44-47, cited in Notice of Opposition against European Patent No. 3470432 (Application No. 18194745.8) filed on Jul. 6, 2022, on behalf of Ms. Regina Neuefeind.
D5—WHO Drug Information, vol. 26, No. 4, p. 412, 2012, cited in Notice of Opposition against European Patent No. 3470432 (Application No. 18194745.8) filed on Jul. 6, 2022, on behalf of Ms. Regina Neuefeind.
D6—Pollart et al., American Family Physician, 2009, 79(9): 761-767, cited in Notice of Opposition against European Patent No. 3470432 (Application No. 18194745.8) filed on Jul. 6, 2022, on behalf of Ms. Regina Neuefeind.
D7—Lommatzsch and Virchow, Dtsch Arztebl Int., 2014, 111: 847-855, cited in Notice of Opposition against European Patent No. 3470432 (Application No. 18194745.8) filed on Jul. 6, 2022, on behalf of Ms. Regina Neuefeind.
D8—Applicant's Submission dated Oct. 17, 2019, cited in Notice of Opposition against European Patent No. 3470432 (Application No. 18194745.8) filed on Jul. 6, 2022, on behalf of Ms. Regina Neuefeind.
D9—Wenzel et al., Dupilumab in persistent asthma with elevated eosinophil levels, N Engl J Med., May 21, 2013, 368(26): 2455-2466, cited in Notice of Opposition against European Patent No. 3470432 (Application No. 18194745.8) filed on Jul. 6, 2022, on behalf of Ms. Regina Neuefeind.
D9a—Supplementary Data of D9, cited in Notice of Opposition against European Patent No. 3470432 (Application No. 18194745.8) filed on Jul. 6, 2022, on behalf of Ms. Regina Neuefeind.
D10—Sandeep et al., Lung India, 2010, 27(3), cited in Notice of Opposition against European Patent No. 3470432 (Application No. 18194745.8) filed on Jul. 6, 2022, on behalf of Ms. Regina Neuefeind.
D11—Shannon et al., Chest, 2008, 133: 420-426, cited in Notice of Opposition against European Patent No. 3470432 (Application No. 18194745.8) filed on Jul. 6, 2022, on behalf of Ms. Regina Neuefeind.
D12—De Boever et al., Asthma and Lower Airway Disease, 2014, 133(4): 989-996, cited in Notice of Opposition against European Patent No. 3470432 (Application No. 18194745.8) filed on Jul. 6, 2022, on behalf of Ms. Regina Neuefeind.
D13—Wenzel et al., Severe asthma in adults, Am J Respir Crit Care Med., 172(2): 149-160; cited in Notice of Opposition against European Patent No. 3470432 (Application No. 18194745.8) filed on Jul. 6, 2022, on behalf of Ms. Regina Neuefeind.
D14—Al-Ramli et al., Journal of Asthma, 2008, 45(S1): 41-44, cited in Notice of Opposition against European Patent No. 3470432 (Application No. 18194745.8) filed on Jul. 6, 2022, on behalf of Ms. Regina Neuefeind.
D15—Bossley et al., J Allergy Clin Immunol., 2012, 129(4): 974-982.e13, cited in Notice of Opposition against European Patent No. 3470432 (Application No. 18194745.8) filed on Jul. 6, 2022, on behalf of Ms. Regina Neuefeind.
D16—PCT International Publication No. WO 2010/053751 A1, High Affinity Human Antibodies to Human IL-4 Receptor, published May 14, 2010, cited in Notice of Opposition against European Patent No. 3470432 (Application No. 18194745.8) filed on Jul. 6, 2022, on behalf of Ms. Regina Neuefeind.
D17—Study NCT01312961 (v31), Efficacy, Safety, and Tolerability of SAR231893 (REGN668) in Patients with Persistent Moderate to Severe Eosinophilic Asthma, Aug. 20, 2012, cited in Notice of Opposition against European Patent No. 3470432 (Application No. 18194745.8) filed on Jul. 6, 2022, on behalf of Ms. Regina Neuefeind.
D18—Birkett, 1996, Aust Prescr 1996, 19: 76-78, retrieved from: https://www.nps.org.au/australian-prescriber/articles/pharmacokinetics-made-easy-11-designing-dose-regimens, cited in Notice of Opposition against European Patent No. 3470432 (Application No. 18194745.8) filed on Jul. 6, 2022, on behalf of Ms. Regina Neuefeind.
D19—Applicant's submission dated Dec. 9, 2011, cited in Notice of Opposition against European Patent No. 3470432 (Application No. 18194745.8) filed on Jul. 6, 2022, on behalf of Ms. Regina Neuefeind.
D20—U.S. Pat. No. 8,075,887 B2, High Affinity Human Antibodies to Human IL-4 Receptor, issued Dec. 13, 2011, cited in Notice of Opposition against European Patent No. 3470432 (Application No. 18194745.8) filed on Jul. 6, 2022, on behalf of Ms. Regina D21—Neuefeind.
D21—Regeneron Science to Medicine, J.P. Morgan Healthcare Conference, Jan. 8, 2013, cited in Notice of Opposition against European Patent No. 3470432 (Application No. 18194745.8) filed on Jul. 6, 2022, on behalf of Ms. Regina Neuefeind.
D21a—Proof of publication date of D21, Jan. 8, 2013, cited in Notice of Opposition against European Patent No. 3470432 (Application No. 18194745.8) filed on Jul. 6, 2022, on behalf of Ms. Regina Neuefeind.
(Aug. 28, 2007) "Expert Panel Report 3: Guidelines for the Diagnosis and Management of Asthma", National Heart, Blood and Lung Institute, NIH, 440 Pages.
(Aug. 28, 2007) "Section 3, The Four Components of Asthma Management", Guidelines for the Diagnosis and Management of Asthma, 1 Page.
(Apr. 2011) "Regeneron Annual Report", 12 Pages.
(2012) "WHO Drug Information", vol. 26, No. 4, Proposed INN: List 108, p. 412.

(56) References Cited

OTHER PUBLICATIONS (Apr. 2013) "Annual Report 2013", Receptos Inc., 411 Pages.
(Jan. 1, 2014) "International Nonproprietary Names for Pharmaceutical Substances (INN)", WHO Drug Information records—World Health Organization, pp. 379-422.
(May 7, 2016) "Rhinitis (Hay Fever)", American Academy of Allergy, Asthma & Immunology, 1 Page.
Abonia, et al. (Apr. 2013) "High Prevalence of Eosinophilic Esophagitis in Patients with Inherited Connective Tissue Disorders", Journal of Allergy and Clinical Immunology, vol. 132, No. 2, pp. 378-386.
Aceves, et al. (Feb. 29, 2009) "Relationships Between Eosinophilic Inflammation, Tissue Remodeling and Fibrosis in Eosinophilic Esophagitis", Immunology and Allergy Clinics of North America, vol. 29, No. 1, pp. 197-211.
Akinlade, et al. (Mar. 9, 2019) "Conjunctivitis in Dupilumab Clinical Trials", British Journal of Dermatology, XP55610279, pp. 1-5.
Akiyama, et al. (1997) "A Study on Indoor Allergens Measured in Home Environments of Adult-Asthmatic Patients", Housing Research Foundation, No. 24, 11 Pages.
Al-Lazikani, et al. (Nov. 7, 1997) "Standard Conformations for the Canonical Structures of Immunoglobulins", Journal of Molecular Biology, vol. 273, No. 4, pp. 927-948.
Almagro, et al. (Jan. 1, 2008) "Humanization of Antibodies", Frontiers in Bioscience, vol. 13, pp. 1619-1633.
Alving, et al. (1993) "Increased amount of nitric oxide in exhaled air of asthmatics", European Respiratory Journal, vol. 6, pp. 1368-1370.
Angal, et al. (Jan. 1993) "A Single Amino Acid Substitution Abolishes the Heterogeneity of Chimeric Mouse/Human (IgG4) Antibody", Molecular Immunology, vol. 30, No. 1, pp. 105-108.
Arron, et al. (Feb. 2009) "Peripheral Biomarkers of an IL-13 Induced Bronchial Epithelial Gene Signature in Asthma", Journal of Allergy and Clinical Immunology, vol. 179, No. 2, p. S74.
Assa'Ad, et al. (Aug. 10, 2011) "An Antibody Against IL-5 Reduces Numbers of Esophageal Intraepithelial Eosinophils in Children with Eosinophilic Esophagitis", Gastroenterology, vol. 141, No. 5, pp. 1593-1604.
Assa'Ad, Amal (Feb. 17-19, 2011) "What is New in the Treatment of Eosinophilic Esophagitis", Food Allergy and Anaphylaxis Meeting, Venice, Italy, 1 Page.
Avdeeva, et al. (Apr. 2018) "Precision Medicine in Chronic Rhinosinusitis with Nasal Polyps", Current Allergy and Asthma Reports, vol. 18, No. 4, p. 25.
Bachert, et al. (Sep. 19, 2019) "Efficacy and Safety of Dupilumab in Patients with Severe Chronic Rhinosinusitis with Nasal Polyps (Liberty NP Sinus-24 and Liberty NP Sinus-52): Results from Two Multicentre, Randomised, Double-Blind, Placebo-Controlled, Parallel-Group Phase 3 Trials", The Lancet, vol. 394, pp. 1638-1650.
Bachert, et al. (2005) "Pharmacological Management of Nasal Polyposis", Drugs, vol. 65, No. 11, pp. 1537-1552.
Bagnasco, et al. (Aug. 2016) "A Critical Evaluation of Anti-IL-13 and Anti-IL-4 Strategies in Severe Asthma", International Archives of Allergy and Immunology, vol. 170, No. 2, pp. 122-131.
Balint, et al. (Dec. 27, 1993) "Antibody Engineering by Parsimonious Mutagenesis", Gene, vol. 137, Issue 1, pp. 109-118.
Barnes, et al. (Nov. 3, 2008) "The Cytokine Network in Asthma and Chronic Obstructive Pulmonary Disease", The Journal of Clinical Investigation, vol. 118, No. 11, pp. 3546-3556.
Barranco, et al. (Sep. 1, 2017) "Dupilumab in the Management of Moderate-to-Severe Asthma: The Data So Far", Therapeutics and Clinical Risk Management, vol. 13, pp. 1139-1149.
Barthelemy, "Comprehensive analysis of the factors contributing to the stability and solubility of autonomous human VH domains", Journal of Biological Chemistry, 2008, 283:3639-3654.
Bateman, et al. (Jul. 15, 2004) "Can Guideline-Defined Asthma Control be Achieved? The Gaining Optimal Asthma Control Study", American Journal of Respiratory and Critical Care Medicine, vol. 170, No. 8, pp. 836-844.
Belikov, B.G (1993) "Pharmaceutical Chemistry", Total Pharmaceutical Chemistry, M., Higher School, pp. 43-47.
Beyer, et al. (Apr. 2, 2002) "Human Milk-Specific Mucosal Lymphocytes of the Gastrointestinal Tract Display a Th2 Cytokine Profile", Journal of Allergy and Clinical Immunology, vol. 109, Issue 4, pp. 707-713.
Bhardwaj, et al. (Sep. 2012) "Biomarkers for Eosinophilic Esophagitis: A Review", Annals of Allergy, Asthma & Immunology, vol. 109, Issue 3, pp. 155-159.
Bieber, et al. (2012) "Atopic Dermatitis: A Candidate for Disease-Modifying Strategy", Allergy: vol. 67, pp. 969-975.
Beiboer et al., "Guided selection of a pan carcinoma specific antibody reveals similar binding characteristics yet structural divergence between the original murine antibody and its human equivalent", Journal of Molecular Biology, 2000, 296:833-849.
Blanchard, et al. (Feb. 2009) "Chemotactic Factors Associated with Eosinophilic Gastrointestinal Diseases", Immunology and allergy clinics of North America, vol. 29, No. 1, pp. 141-148.
Blanchard, et al. (Feb. 2005) "Eotaxin-3 and a Uniquely Conserved Gene-Expression Profile in Eosinophilic Esophagitis", The Journal of Clinical Investigation, vol. 116, No. 2, pp. 536-547.
Blanchard, et al. (Sep. 19, 2006) "Eosinophilic Esophagitis: Pathogenesis, Genetics, and Therapy", Journal of Allergy and Clinical Immunology, vol. 118, No. 5, pp. 1054-1049.
Blanchard, et al. (Jan. 1, 2011) "A Striking Local Esophageal Cytokine Expression Profile in Eosinophilic Esophagitis", Journal of Allergy and Clinical Immunology, vol. 127, No. 1, pp. 208-217.
Blanchard, et al. (Apr. 2010) "Coordinate Interaction Between IL-13 and Epithelial Differentiation Cluster Genes in Eosinophilic Esophagitis", The Journal of Immunology, vol. 184, No. 7 (2010), pp. 4033-4041.
Blanchard, et al. (Dec. 2, 2007) "IL-13 Involvement in Eosinophilic Esophagitis: Transcriptome Analysis and Reversibility with Glucocorticoids", Journal of Allergy and Clinical Immunology, vol. 120, No. 6, pp. 1292-1300.
Blanchard, et al. (Aug. 24, 2005) "Inhibition of Human Interleukin-13-Induced Respiratory and Oesophageal Inflammation by Anti-Human-Interleukin-13 Antibody (CAT-354)", Clinical & Experimental Allergy, vol. 35, No. 8, pp. 1096-1103.
Blankestijn et al., "Could Duratumumab be used to treat severe allergy?", Journal of Allergy and Clinical Immunology, vol. 139, No. 5, Jan. 19, 2017, p. 1677-1678.e3.
Blauvelt, et al. (May 4, 2016) "Long-term Management of Moderate-to-Severe Atopic Dermatitis with Dupilumab and 18 Concomitant Topical Corticosteroids {Liberty Ad Chronos): a 1-year, Randomised, Double-Blinded, Placebo-Controlled, Phase 3 Trial", The Lancet, vol. 17, pp. 140-6736.
Borish, et al. (Jun. 1, 2001) "Efficacy of Soluble IL-4 Receptor for the Treatment of Adults with Asthma", The Journal of Allergy and Clinical Immunology, vol. 107, Issue 6, pp. 963-970.
Brorson, et al. (Dec. 15, 1999) "Mutational Analysis of Avidity and Fine Specificity of Anti-Levan Antibodies", The Journal of Immunology, vol. 163, No. 12, pp. 6694-6701.
Brummell, et al. (1993) "Probing the Combining Site of an Anti-Carbohydrate Antibody by Saturation-Mutagenesis: Role of the Heavy-Chain CDR3 Residues", Biochemistry, vol. 32, No. 4, pp. 1180-1187.
Buddenkotte et al., "Pathophysiology and therapy of pruritis in allergic and atopic diseases", Allergy 65 (2010), 805-821.
Burmeister-Getz, et al. (Mar. 7, 2013) "Human pharmacokinetics/pharmacodynamics of an interleukin-4 and interleukin-13 dual antagonist in asthma", The Journal of Clinical Pharmacology, vol. 49, Issue 9, pp. 1025-1036.
Burton, et al. (Nov. 14, 2012) "Direct Effects of IL-4 on Mast Cells Drive Their Intestinal Expansion and Increase Susceptibility to anaphylaxis in a Murine Model of Food Allergy", Mucosal Immunology, vol. 6, No. 4, pp. 740-750.
Carr, Topical Calcineurin Inhibitors for Atopic Dermatitis: Review and Treatment Recommendations, Pediatric Drugs, 2013, vol. 15, pp. 303-310.
Carter, Paul J. (May 2006) "Potent Antibody Therapeutics by Design", Nature Reviews Immunology, vol. 6, No. 5, pp. 343-357.

(56) References Cited

OTHER PUBLICATIONS

Chan, et al. (Oct. 1, 2001) "Expression of Interleukin-4 in the Epidermis of Transgenic Mice Results in a Pruritic Inflammatory Skin Disease: An Experimental Animal Model to Study Atopic Dermatitis", Journal of Investigative Dermatology, vol. 117, No. 4, pp. 977-983.
Chehade, et al. (Feb. 2009) "The Role of Lymphocytes in Eosinophilic Gastrointestinal Disorders", Immunology and Allergy Clinics of North America, vol. 29, Issue 1, pp. 149-158.
Cho, et al. (Apr. 11, 2012) "Spontaneous Eosinophilic Nasal inflammation in a Genetically-Mutant Mouse Comparative Study with an Allergic Inflammation Model", PLoS One, vol. 7, No. 4, pp. 1-8.
Choi et al., "Predicting antibody complementarity determining region structures without classification", Molecular Biosystems, 2011, 7:3327-334.
Clackson, et al. (Aug. 15, 1991) "Making Antibody Fragments Using Phage Display Libraries", Nature, vol. 352, No. 6336, pp. 624-628.
ClinicalTrials.gov Identifier: NTC02407756, Last Update posted Aug. 22, 2016, A Study to Determine the Safety and Tolerability of Dupilumab (REGN668/SAR231893) in Patients Aged >6 to <18 Years With Atopic Dermatitis (Eczema), 11 pages.
Colice, et al. (Aug. 2004) "Categorizing Asthma Severity: An Overview of National Guidelines", Clinical Medicine & Research, vol. 2, No. 3, pp. 155-163.
Collins, et al. "Baseline Characteristics and Correlation Between Dysphagia and Disease Activity in Patients with Eosinophilic Esophagitis in a Randomized, Placebo-Controlled, Phase 2 Dupilumab Trial", Sa115 Abstract, AGA Abstract.
Colman, P M. (Jan. 1994) "Effects of Amino Acid Sequence Changes on Antibody-Antigen Interactions", Research in Immunology, vol. 145, No. 1, pp. 33-36.
Cork, et al. (May 1, 2019) "605 Efficacy and Safety of Dupilumab in Adolescent Patients with Moderate-to-Severe Atopic Dermatitis", XP002793331, 3 Pages.
Cork et al., An open-label phase lla trial assessing the pharmacokinetics, safety and efficacy of dupilumab in a paediatric population with moderate-to-severe atopic dermatitis, P94, British Association of Dermatologists, Jul. 2017, 177 (Suppl. 1), pp. 25-77.
Corren, et al. (Jan. 7, 2010) "A Randomized, Controlled, Phase 2 Study of AMG 317, An IL-4Ra Antagonist, in Patients with Asthma", American Journal of Respiratory and Critical Care Medicine, vol. 181, No. 8, pp. 788-796.
Cortes, et al. (Sep. 13, 2009) "Proton Pump Inhibitors Inhibit IL-4 and IL-13 Signaling STAT6 Activation", Journal of Immunology, vol. 39, p. S204.
Darsow et al., "Pruritus and Atopic Dermatitis", Clinic Rev Allerg Immunol (2011) 41:237-244.
Darveaux, et al. (2015) "Biologics in Asthma—The Next Step Towards Personalized Treatment", Journal of Allergy and Clinical Immunology, vol. 3, No. 2, pp. 152-161.
Davies, et al. (Sep. 1996) "Affinity Improvement of Single Antibody VH Domains: Residues in all Three Hypervariable Regions Affect Antigen Binding", Immunotechnology, vol. 2, Issue 3, pp. 169-179.
Davis, et al. (Aug. 2004) "The Evolutionary and Structural 'Logic' of Antigen Receptor Diversity", Seminars in Immunology, vol. 16, Issue 4, pp. 239-243.
De Genst et al., "Antibody repertoire development in camelids", Developmental and Comparative Immunology, 30 (2006); 187-198.
Dellon, Evan S. (Oct. 14-19, 2016) "19—A Randomized, Double-Blind, Placebo-Controlled Trail of a Novel Recombinant, Humanized, Anti-Interleukin-13 Monoclonal Antibody (RPC4046) in Patients with Active Eosinophilic Esophagitis: Results of the HEROES Study", ACG 2016 Annual Scientific Meeting and PostGraduate Course, The Venetian Las Vegas NV, 3 Pages.
Dellon, Evan S. (Apr. 27, 2013) "The Pathogenesis of Eosinophilic Esophagitis: Beyond the Eosinophil", Digestive Diseases and Sciences, vol. 58, pp. 1445-1448.

Desreumaux, et al. (Mar. 1, 1996) "Interleukin 3, Granulocyte-Macrophage Colony-Stimulating Factor, and Interleukin 5 in Eosinophilic Gastroenteritis", Gastroenterology, vol. 110, No. 3, pp. 768-774.
Djukanovic, et al. (2002) "Standardised Methodology of Sputum Induction and Processing", European Respiratory Journal, pp. 1S-2S.
Dupixent (dupilumab) Injection, for Subcutaneous Use, Patient Information, Issued Mar. 2017, 34 pages.
Durham, et al. (2016) "Targeted Anti-Inflammatory Therapeutics in Asthma and Chronic Obstructive Lung Disease", Transnational Research, vol. 167, No. 1, pp. 192-203.
Extended European Search Report received for European Application No. 19187112.8, mailed on Jan. 23, 2020, 13 Pages.
Extended European Search Report received for European Patent Application No. 18194745.8, mailed on Jan. 16, 2019, 12 Pages.
Figueiredo, et al. (Feb. 2008) "inflammatory Genes in Nasal Polyposis", Current Opinion in Otolaryngology & Head and Neck Surgery, vol. 16, pp. 18-21.
Fillon, et al. (2009) "Epithelial Function in Eosinophilic Gastrointestinal Diseases", Immunology and Allergy Clinics of North America, vol. 29, No. 1, pp. 171-178.
Foroughi, et al. (Sep. 1, 2007) "Anti-IgE Treatment of Eosinophil-Associated Gastrointestinal Disorders", Journal of Allergy and Clinical Immunology, vol. 120, Issue 3, pp. 594-601.
Franciosi, et al. (Feb. 2009) "Eosinophilic Esophagitis", Immunology and Allergy Clinics of North America, vol. 29, Issue 1, pp. 19-27.
Frieri, Marianne (Mar. 28, 2014) "Asthma Linked with Rhinosinusitis: An Extensive Review", Allergy & Rhinology (Providence), vol. 5, No. 1, pp. e41-e49.
Frois, et al. (Dec. 2009) "Inhaled Corticosteroids or Long-Acting Beta-Agonists Alone or in Fixed-dose Combinations in Asthma Treatment: A Systematic Review of Fluticasone/Budesonide and Formoterol/Salmeterol", Clinical Therapeutics, vol. 31, No. 12, pp. 2779-2802.
Gavett, et al. (1997) "Interleukin-4 Receptor Blockade Prevents Airway Responses Induced by Antigen Challenge in Mice", American Journal of Physiology-Lung Cellular and Molecular Physiology, vol. 16, No. 2, pp. 253-261.
Gevaert, et al. (Nov. 2011) "Mepolizumab, A Humanized Anti-IL-5 mAb, as a Treatment Option for Severe Nasal Polyposis", Journal of Allergy and Clinical Immunology, vol. 128, No. 5, pp. 989-995.
Gevaert, et al. (2006) "Nasal IL-5 Levels Determine the Response to Anti-IL-5 Treatment in Patients with Nasal Polyps", Journal of Allergy and Clinical Immunology, vol. 118, No. 5, pp. 1133-1141.
Giembycz, et al. (2008) "A Holy Grail of Asthma Management: Toward Understanding How Long-Acting Beta (2)-24 Adrenoceptor Agonists Enhance the Clinical Efficacy of Inhaled Corticosteroids", British Journal of Pharmacology, vol. 153, pp. 1090-1104.
Glare, et al. (Nov. 1, 1999) "Asthmatic Airway Biopsy Specimens are More Likely to Express the IL-4 Alternative Splice Variant L-452", Journal of Allergy and Clinical Immunology, vol. 104, pp. 978-982.
Goodson, et al. (1984) "Dental Applications", Medical Applications of Controlled Release, vol. 2, pp. 115-138.
Green, et al. (2012) "Molecular Cloning: A Laboratory Manual", Cold Spring Harbor Laboratory Press, Fourth Edition, 34 Pages.
Griffiths et al., "Human anti-self antibodies with high specificity from phage display libraries", The EMBO Journal, 1993, 12:725-734.
Groves, et al. (2007) "Inhibition of IL-4 and IL-13 With An IL-4 Mutein (Aeroderm) Protects Against Flares in Atopic Eczema", Aeroderm in AD. Poster at St. John's Institute of Dermatology, 1 Page.
Grunewald, et al. (1998) "An Antagonistic IL-4 Mutant Prevents Type I Allergy in the Mouse: Inhibition of the IL-4/ IL -13 Receptor System Completely Abrogates Humoral Immune Response to Allergen and Development of Allergic Symptoms in Vivo", The Journal of Immunology, vol. 160, No. 8, pp. 4004-4009.
Gu, et al. (Feb. 2011) "Expression and Role of Acidic Mammalian Chitinase and Eotaxin-3 in Chronic Rhinosinusitis with Nasal Polyps", Journal of Otolaryngology-Head and Neck Surgery, vol. 40, No. 1, pp. 64-69.

(56) References Cited

OTHER PUBLICATIONS

Hamilton, et al. (2015) "Drug Evaluation Review: Dupilumab in Atopic Dermatitis", Immunotherapy, vol. 7, No. 10, 16 Pages.

Healio Gastroenterology, "Novel therapy improved disease features in EoE", Oct. 8, 2019, located online at: https://www.healio.com/news/gastroenterology/20191008/novel-therapy-improves-disease-features-in-eoe, 2 pages.

Hijnen, et al. (Feb. 2004) "Serum Thymus and Activation-Regulated Chemokine (TARC) and Cutaneous T Cell—Attracting Chemokine (CTACK) Levels in Allergic Diseases", Journal of Allergy and Clinical Immunology, vol. 113, No. 2, pp. 334-340.

Hirano, et al. (May 2018) "SA1113—Correlation Between Esophageal Distensibility and Objectivity Measures of Disease in Patients with Active Eosinophilic Esophagitis a Post Hoc Analysis of a Randomized, Placebo-Controlled, Phase 2 Dupilumab Trial", Sa1113 Abstract, AGA Abstract, p. S-244.

Hirano, et al. (Oct. 13-18, 2017) "Dupilumab Efficacy and Safety in Adult Patients with Active Eosinophilic Esophagitis: A Randomized Double-Blind Placebo-Controlled Phase 2 Trial", World Congress of Gastroenterology ACG, Orlando Florida, 20 Pages.

Hirano et al., "Efficacy of Dupilumab in a Phase 2 Randomized Trial of Adults with Active Eosinophilic Esophagitis", Gastroenterology 2020; 158: 111-122.

Holt, et al. (Nov. 2003) "Domain Antibodies: Proteins for therapy", Trends in Biotechnology, vol. 21, Issue 11, pp. 484-490.

Hong, et al. (Jun. 2011) "Management of Itch in Atopic Dermatitis", Seminars in Cutaneous Medicine and Surgery, vol. 30, No. 2, pp. 71-86.

Hopkins, et al. (Oct. 2007) "The Lund-Mackay staging system for chronic rhinosinusitis: How is it used and what does it predict?", Otolaryngology-Head and Neck Surgery, vol. 137, No. 4, pp. 555-561.

Hopkins, et al. (Sep. 24, 2009) "Psychometric Validity of the 22—Item Sinonasal Outcome Test", Clinical Otolaryngology, vol. 34, No. 5, pp. 447-454.

Huang, et al. (May 10, 2018) "Severe Atopic Dermatitis in Children", Current Allergy and Asthma Reports, Current Science, vol. 18, No. 6, XP036511794, pp. 1-8.

International Search Report and Written Opinion received for PCT Patent Application No. PCT/US2018/058039, mailed on Jan. 28, 2019, 11 Pages.

International Search Report and Written Opinion received for PCT Patent Application No. PCT/US2019/031801, mailed on Aug. 20, 2019, 14 Pages.

International Search Report and Written Opinion received for PCT Patent Application No. PCT/US2013/055747, mailed on Feb. 13, 2014, 18 Pages.

International Search Report and Written Opinion received for PCT Patent Application No. PCT/US2015/016852, mailed on May 11, 2015, 9 Pages.

International Search Report and Written Opinion received for PCT Patent Application No. PCT/US2014/043440, mailed on Oct. 6, 2014, 12 Pages.

International Search Report and Written Opinion received for PCT Patent Application No. PCT/US2015/060540, mailed on Feb. 17, 2016, 15 Pages.

Ivashkin, et al. (2012) "Eosinophilic Esophagitis: A Review of the Literature and a Description ofits Own Observation", FUGHC, vol. 22, No. 1, Available at: <<RZHGGK online—www.gastro-j.ru>>, pp. 71-81.

Ivashkin, et al. (2013) "Eosinophilic Esophagitis: A Training Manual for Doctors", Moscow, Russia, pp. 13-21,57-62.

Jahnz-Rozyk, et al. (Apr. 6, 2005) "Serum Thymus and Activation-Regulated Chemokine, Macrophage-Derived Chemokine and Eotaxin as Markers of Severity of Atopic Dermatitis", Allergy, vol. 60, No. 5, pp. 685-688.

Jakubke, et al. (1977) "Amino Acids, Peptides and Proteins: An Introduction", The Macmillan Press Ltd., doi 10.1007/978-1-349-02503, 349 Pages.

Jakubke, et al. (1985) "Amino Acids, Peptides, Proteins", M: Mir, pp. 92-94.

Jia, et al. (Sep. 2012) "Periostin is a Systemic Biomarker of Eosinophilic Airway Inflammationin Asthmatic Patients", The Journal of Allergy and Clinical Immunology, vol. 130, No. 3, pp. 647-654.

Junttila, et al. (2008) "Tuning Sensitivity to IL-4 and IL-13: Differential Expression of IL-4Ra, IL-13Rα1, and Yc Regulates Relative Cytokine Sensitivity", Journal of Experimental Medicine, vol. 205, No. 11, pp. 2595-2608.

Jyonouchi, et al. (2013) "Invariant Natural Killer T cells in children with Eosinophilic Esophagitis", Basic Mechanisms in Allergic Disease, Clinical & Experimental Allergy, vol. 44, No. 1, pp. 58-68.

Kagami, et al. (2003) "Significant Elevation of Serum Levels of Eotaxin-3/CCL26, but not of Eotaxin-2/CCL24, in Patients with Atopic Dermatitis: Serum Eotaxin-3/CCL26 Levels Reflect the Disease Activity of Atopic Dermatitis", Clinical & Experimental Immunology, vol. 134, No. 2, pp. 309-313.

Kakinuma, et al. (2002) "Serum Macrophage-Derived Chemokine (MDC) Levels are Closely Related with the Disease Activity of Atopic Dermatitis", Clinical & Experimental Immunology, vol. 127, No. 2, pp. 270-273.

Kakinuma, et al. (Mar. 1, 2001) "Thymus and Activation-Regulated Chemokine in Atopic Dermatitis: Serum Thymus and Activation-Regulated Chemokine Level is Closely Related with Disease Activity", Journal of Allergy and Clinical Immunology, vol. 107, No. 3, pp. 535-541.

Kakkar, et al. (2011) "Population PK and IgE Pharmacodynamic Analysis of a Fully Human Monoclonal Antibody Against IL4 Receptor", Pharmaceutical Research, vol. 28, No. 10, pp. 2530-2542.

Kanehisa Laboratories (Jan. 12, 2016) "KEGG: Kyoto Encyclopedia of Genes and Genomes", KEGG Drug Entry No. D10354, Retrieved from: <<http://www.genomajp/dbget-bin/www_bget?dr:D10354>>, 2 Pages.

Katial, Rohit (Feb. 2009) "Biomarkers for Nononcologic Gastrointestinal Diseases", Immunology and Allergy Clinics of North America, vol. 29, Issue 1, pp. 119-127.

Kim, et al. (Dec. 1, 2004) "Rebound Eosinophilia after Treatment of Hypereosinophilic Syndrome and Eosinophilic Gastroenteritis with Monoclonal Anti-IL-5 Antibody SCH55700", Journal of Allergy and Clinical Immunology, vol. 114, No. 6, pp. 1449-1455.

Kimura, et al. (Jul. 2011) "Increased Expression and Role of Thymic Stromal lymphopoietin in Nasal Polyposis", Annals of Allergy, Asthma & Immunology, vol. 3, No. 3, pp. 186-193.

Klementina, et al. (Mar. 24, 2018) "Precision Medicine in Chronic Rhinosinusitis with Nasal Polyps", Allergy and Asthma Reports, vol. 18, No. 4, 8 Pages.

Klimka et al., "Human anti-CD30 recombinant antibodies by guided phage antibody selection using cell panning", British Journal of Cancer, 2000, 83:252-260.

Knappik, et al. (2000) "Fully Synthetic Human Combinatorial Antibody Libraries (HuCAL) Based on Modular Consensus Frameworks and CDRs Randomized with Trinucleotides", Journal of Molecular Biology, vol. 296, No. 1, pp. 57-86.

Kobayashi, et al. (Oct. 1999) "Tryptophan H33 Plays an Important Role in Pyrimidine (6-4) Pyrimidone Photoproduct Binding by a High-Affinity Antibody", Protein Engineering, Design and Selection, vol. 12, No. 10, pp. 879-884.

Konikoff, et al. (Nov. 1, 2006) "A Randomized, Double-Blind, Placebo-Controlled Trial of Fluticasone Propionate for Pediatric Eosinophilic Esophagitis", Gastroenterology, vol. 131, No. 5, pp. 1381-1391.

Kopf, et al. (Mar. 18, 1993) "Disruption of the Murine IL-4 Gene Blocks Th2 Cytokine Responses", Nature, vol. 362, No. 6417, pp. 245-248.

Kopp, et al. (Jan. 22, 2009) "Combination of Omalizumab and Specific Immunotherapy Is Superior to Immunotherapy in Patients With Seasonal Allergic Rhinoconjunctivitis and Co-Morbid Seasonal Allergic Asthma", Clinical & Experimental Allergy, vol. 39, Issue 2, pp. 271-279.

(56) References Cited

OTHER PUBLICATIONS

Kostic, et al. (2010) "A Fully Human IL4Rα Antibody for Inhibition of IL-4/IL-13-driven TH2 Responses in Allergic Disease", Clinical Immunology, vol. 135, pp. S105-S106.
Kottyan, et al. (Aug. 2014) "Genome-Wide Association Analysis of Eosinophilic Esophagitis Provides Insight into the Tissue Specificity of this Allergic Disease", Nature Genetics, vol. 46, No. 8, pp. 895-900.
Kroegel, et al. (May 2009) "Global Initiative for Asthma (GINA) guidelines: 15 Years of Application", Expert Review of Clinical Immunology, vol. 5, No. 3, pp. 239-249.
Kulis, et al. (Nov. 19, 2010) "Single-Tree Nut Immunotherapy Attenuates Allergic Reactions in Mice with Hypersensitivity to Multiple Tree Nuts", Journal of Allergy and Clinical Immunology, vol. 127, No. 1, pp. 81-88.
Langer, Robert (Sep. 28, 1990) "New Methods of Drug Delivery", Science, vol. 249, Issue 4976, pp. 1527-1533.
Leung, et al. (Mar. 13, 2003) "Effect of Anti-IgE Therapy in Patients with Peanut Allergy", New England Journal of Medicine, vol. 348, No. 11, pp. 986-993.
Leung, et al. (Apr. 2004) "New Insights into Atopic Dermatitis", The Journal of Clinical Investigation, vol. 113, No. 5, pp. 651-657.
Lezcano-Meza, et al. (Sep. 19, 2003) "Interleukin (IL)-4 and to a Lesser Extent Either IL-13 or Interferon-Gamma Regulate the Reduction of Eotaxin-2/CCL24 in Nasal Polyps", Allergy, vol. 58, No. 10, pp. 1011-1017.
Liacouras, et al. (Apr. 8, 2011) "Eosinophilic Esophagitis: Updated Consensus Recommendations for Children and Adults", Journal of Allergy and Clinical Immunology, vol. 128, No. 1, pp. 3-20.
Lilly, et al. (Oct. 1, 1999) "Elevated Plasma Eotaxin Levels in Patients with Acute Asthma", The Journal of Allergy and Clinical Immunology, vol. 104, No. 4, Point 1, pp. 786-790.
Liu, et al. (Aug. 9, 1999) "Hydrodynamics-Based Transfection in Animals by Systemic Administration of Plasmid DNA", Gene Therapy, vol. 6, No. 7, pp. 1258-1266.
Lucendo, et al. (Nov. 1, 2012) "Adult Versus Pediatric Eosinophilic Esophagitis: Important Differences and Similarities for the Clinician to Understand", Expert Review of Clinical Immunology, vol. 8, No. 8, pp. 733-745.
Ludmila, et al. (Feb. 3, 2014) "Poster 1013: IL-4R Alpha Antibody Inhibits IgE Production and Airway Remodeling in the Mouse Model of House Dust Mite-Induced Eosinophilic Asthma", World Allergy Organization Journal, vol. 7, No. 1, 1 Page.
Lwin, et al. (Apr. 2011) "Eosinophilic Gastritis: Histopathological Characterization and Quantification of the Normal Gastric Eosinophil Content", Modern Pathology, vol. 24, No. 4, pp. 556-563.
Maliszewski, et al. (Jul. 1, 1994) "In Vivo Biological Effects of Recombinant Soluble Interleukin-4 Receptor", Experimental Biology and Medicine, vol. 206, No. 3, pp. 233-237.
Mannon, et al. (2012) "Interleukin 13 and its Role in Gut Defence and Inflammation", Gut, vol. 61, No. 12, pp. 1765-1773.
Marone, et al. (Dec. 6, 2013) "The Intriguing Role of Interleukin 13 in the Pathophysiology of Asthma", Frontiers in Pharmacology, vol. 10, pp. 1-13.
Martel, et al. (Sep. 25, 2017) "Translational Animal Models of Atopic Dermatitis for Preclinical Studies", Yale Journal of Biology and Medicine, vol. 90, 14 Pages.
Martin, et al. (Dec. 1989) "Modeling Antibody Hypervariable Loops: A Combined Algorithm", Proceedings of the National Academy of Sciences, vol. 86, No. 23, pp. 9268-9272.
Masterson, et al. (Oct. 2011) "Update on Clinical and Immunological Features of Eosinophilic Gastrointestinal Diseases", Current Opinion in Gastroenterology, vol. 27, No. 6, pp. 515-522.
Mathias, et al. (Dec. 20, 2010) "IgE-Mediated Systemic Anaphylaxis and Impaired Tolerance to Food Antigens in Mice with Enhanced IL-4 Receptor Signaling", Journal of Allergy and Clinical Immunology, vol. 127, No. 3, pp. 795-805.
Meteran, et al. (Mar. 16, 2017) "Novel Monoclonal Treatments in Severe Asthma", Journal of Asthma, vol. 54, No. 10, pp. 991-1011.
Mishra, et al. (Nov. 1, 2003) "Intratracheal IL-13 Induces Eosinophilic Esophagitis by an IL-5, Eotaxin-1, and STAT6-Dependent Mechanism", Gastroenterology, vol. 125, No. 5, pp. 1419-1427.
Mishra, et al. (Jan. 1, 2001) "An Etiological Role for Aeroallergens and Eosinophils in Experimental Esophagitis", The Journal of Clinical Investigation, vol. 107, No. 1, pp. 83-90.
Mishra, et al. (Mar. 1, 2002) "IL-5 Promotes Eosinophil Trafficking to the Esophagus", The Journal of Immunology, vol. 168, No. 5, pp. 2464-2469.
Molfino, et al. (Sep. 23, 2011) "Molecular and Clinical Rationale for Therapeutic Targeting of Interleukin-5 and its Receptor", Clinical and Experimental Allergy, vol. 42, No. 5, pp. 712-737.
Mordenti, et al. (Nov. 1991) "Interspecies Scaling of Clearance and Volume of Distribution Data for Five Therapeutic Proteins", Pharmaceutical Research, vol. 8, pp. 1351-1359.
Morioka, et al. (Jun. 2009) "IL-4/IL-13 Antagonist DNA Vaccination Successfully Suppresses Th2 Type Chronic Dermatitis", British Journal of Dermatology, vol. 160, No. 6, pp. 1172-1179.
Mueller, et al. (2002) "Structure, Binding, and Antagonists in the IL-4/IL-13 Receptor System", Biochimica et Biophysica Acta, pp. 237-250.
Naclerio, et al. (Feb. 1, 2017) "Dupilumab Improves Sense of Smell and Reduces Anosmia Among Patients with Nasal Polyposis and Chronic Sinusitis: Results from a Phase 2a Trial", Journal of Allergy and Clinical Immunology, vol. 139, No. 2, AB90, 1 Page.
Nadeau, et al. (Jun. 2011) "Rapid Oral Desensitization in Combination with Omalizumab Therapy in Patients with Cow's Milk Allergy", The Journal of Allergy and Clinical Immunology, vol. 127, No. 6, pp. 1622-1624.
Nadeau, et al. (Feb. 1, 2012) "Oral Immunotherapy and Anti-IgE Antibody-Adjunctive Treatment for Food Allergy", Immunology and Allergy Clinics of North America, vol. 32, No. 1, pp. 111-133.
Nagaraju et al., "Bortezomib treatment diminishes hazelnut-induced intestinal anaphylaxis in mice: Immunomodulation", European Journal of Immunology, vol. 46, No. 7, May 11, 2016, pp. 1727-1736.
NCBI (Jan. 12, 2016) "Alignment Heavy Chain Dupilumab with SEQ ID No. 9", Basic Local Alignment Search Tool, XP055240680, 2 Pages.
NCBI (Jan. 12, 2016) "Alignment of Light Chain of Dupilumab With SEQ ID No. 10", XP055240683, 2 Pages.
Newton, et al. (Apr. 2008) "A Review of Nasal Polyposis", Therapeutics and Clinical Risk Management, vol. 4, No. 2, pp. 507-512.
Nguyen, et al. (Jul. 2011) "Immune Modulation for Treatment of Allergic Disease", Immunological Reviews, vol. 242, No. 1, pp. 258-271.
NHLBI (2007) "Quick Reference Charts for the Classification and Step Wise Treatment of Asthma", Adapted from 2007 National Heart, Lung and Blood Institute Guidelines for the Diagnosis and Treatment of Asthma Expert Panel Report 3, 2 Pages.
Nicodeme, et al. (Sep. 2013) "Esophageal Distensibility as a Measure of Disease Severity in Patients with Eosinophilic Esophagitis", Clinical Gastroenterology and Hepatology, vol. 11, No. 9, pp. 1101-1107.
Niederberger, Verena (Feb. 2009) "Allergen Specific Immunotherapy", Immunology Letters, vol. 122, Issue 2, pp. 131-133.
Niranjan, et al. (Jul. 2013) "Pathogenesis of Allergen-Induced Eosinophilic Esophagitis is Independent of Interleukin (IL)-13", Immunology and Cell Biology, vol. 91, No. 6, pp. 408-415.
Noel, et al. (Aug. 24, 2006) "Eosinophilic Esophagitis", The New England Journal of Medicine, vol. 351, pp. 940-941.
Novartis Pharmaceuticals (2013) "A Double Blinded, Randomized, Placebo-Controlled Trial of Intravenous QAX576 in the treatment of Eosinophilic Esophagitis", QAX576.
Oetjen, et al. (Sep. 21, 2017) "Sensory Neurons Co-opt Classical Immune Signaling Pathways to Mediate Chronic Itch", Cell, vol. 171, Issue 1, pp. 217-228.
Oh, et al. (2010) "Investigational Therapeutics Targeting the IL-4/IL-13/STAT-6 Pathway for the Treatment of Asthma", European Respiratory Review, vol. 19, No. 115, pp. 46-54.
Ohno, et al. (May 1, 1985) "Antigen-Binding Specificities of Antibodies are Primarily Determined by Seven Residues of VH", Proceedings of the National Academy of Sciences, vol. 82, No. 9, pp. 2945-2949.

(56) References Cited

OTHER PUBLICATIONS

Ong, Peck Y. (2012) "Editorial Update on Emerging Treatments of Atopic Dermatitis", Expert Opinion on Emerging Drugs, vol. 17, No. 2, pp. 129-133.

Otani, et al. (Apr. 29, 2013) "Anti-IL-5 Therapy Reduces Mast Cell and IL-9 Cell Numbers in Pediatric Patients with Eosinophilic Esophagitis", Journal of Allergy and Clinical Immunology, vol. 131, No. 6, pp. 1576-1582.

Otulana, et al. (2011) "A Phase 2b Study of Inhaled Pitrakinra, An IL-4R/IL-13 Antagonist, Successfully Identified 8 Responder Subpopulations of Patients with Uncontrolled Asthma", Abstract A6179, American Journal of Respiratory and Critical Care Medicine, vol. 183, 1 Page.

Oyoshi, et al. (Jan. 1, 2009) "Cellular and Molecular Mechanisms in Atopic Dermatitis", Advances in Immunology, vol. 102, pp. 135-226.

Paller, et al. (2019) "621 Dupilumab in Adolescents with Moderate-to-Severe Atopic Dermatitis and a History of Inadequate Response, or Intolerance to Cyclosporine: Subgroup Analysis from a Pivotal 16-Week Trial", XP002793332, 2 Pages.

Paller, et al. (Apr. 29, 2019) "Early and Sustained, Clinically Meaningful Responses with Dupilumab Treatment in a Phase 3 Trial in Adolescents with Moderate-to-Severe Atopic Dermatitis", Pediatric Dermatology, vol. 36, Supplement 1, XP55610351, p. S4.

Paton, et al. (Sep. 2017) "Dupilumab: Human Monoclonal Antibody Against IL-4Ralpha for Moderate to Severe Atopic Dermatitis", Drugs Today, vol. 53, No. 9, pp. 477-487.

Pesek, et al. (Jun. 8, 2018) "Emerging Drugs for Eosinophilic Esophagitis", Expert Opinion on Emerging Drugs, vol. 23, No. 2, pp. 173-183.

Peserico, et al. (2008) "Reduction of Relapses of Atopic Dermatitis with Methylprednisolone Aceptonate Cream Twice Weekly in Addition to Maintenance Treatment with Enrollment: A Multicentre, Randomized, Double-Blind, Controlled Study", British Journal of Dermatology, vol. 158, No. 04, pp. 801-807.

Phan, et al. (2012) "Assessment of Pruritus Intensity: Prospective Study on Validity and Reliabilityof the Visual Analogue Scale, Numerical Rating Scale and Verbal Rating Scale in 471 Patients with Chronic Pruritus", Acta Dermato-Venereologica, vol. 92, pp. 449-581.

Portolano, et al. (Feb. 1, 1993) "Lack of Promiscuity in Autoantigen-Specific H and LChain Combinations as Revealed by Human H and L Chain "Roulette"", Journal of Immunology, vol. 150, No. 3, pp. 880-887.

Powell, et al. (Sep.-Oct. 1998) "Compendium of Excipients for Parenteral Formulations", PDA Journal of Pharmaceutical Science and Technology, vol. 52, No. 5, pp. 238-311.

Prieto, et al. (May 24, 2013) "Eosinophilic Esophagitis in Adults: An Update on Medical Management", Current Gastroenterology Reports, vol. 15, No. 6, p. 324.

Prussin, et al. (Dec. 1, 2009) "Eosinophilic Gastrointestinal Disease and Peanut Allergy are Alternatively Associated with IL-51 and IL-5-TH2 Responses", Journal of Allergy and Clinical Immunology, vol. 124, No. 6, pp. 1326-1332.

PubChem (Mar. 14, 2016) "CAS Registry No. 1190264-60-8", PubChem SID No. 172232447. National Center for Biotechnology Information, Retrieved From: <<http://pubchem.ncbi.nlm.nih.gov/substance/172232447#section=Top>>, XP055240678, 5 Pages.

Rafi, et al. (Jan. 1, 2010) "Effects of Omalizumab in Patients with Food Allergy", In Allergy & Asthma Proceedings, vol. 31, No. 1, pp. 76-83.

Rayapudi (Aug. 2010) "Indoor insect Allergens are Potent Inducers of Experimental Eosinophilic Esophagitis in Mice", Journal of Leukocyte Biology, vol. 88, No. 2, pp. 337-346.

Regeneron Phamaceuticals (Apr. 7, 2017) "Highlights of Prescribing Information", XP055534130, Retrieved from URL <<https://www.regeneron.com/sites/defaulllfiles/Dupixent_FPI.pdf>>, 9 Pages.

Regeneron Pharmaceuticals (Mar. 1, 2019) "Dupixent: Highlights of Prescribing Information", XP55610296, Retrieved From URL: <<https://d1egnxy4x1q3f.cloudfront.net/Regeneron/Dupixent_FPI.pdf>>, pp. 1-8.

Regeneron Pharmaceuticals (Sep. 30, 2014) "Regeneron and Sanofi Announce Positive Phase 2 Top-line Dupilumab Results in Patients with Chronic Sinusitis with Nasal Polyps", Acquire Media, XP055240175, 3 Pages.

Regeneron Pharmaceuticals (Oct. 16, 2017) Regeneron and Sanofi Announce Positive Phase 2 Study Results for Dupilumab in Patients Active Moderate'-to-severe Eosinophilic Esophagitis', Acquire Media, 4 Pages.

Regeneron Pharmaceuticals (Mar. 2, 2013) "Sanofi and Regeneron Report Positive Proof-of-Concept Data for Dupilumab, and IL-4R alpha Antibody, in Atopic Dermatitis", Presented at the 71st Annual Meeting of the American Academy of Dermatology.

Regeneron Pharmaceuticals Inc. (Mar. 2017) "Highlights of Prescribing Information (DUPIXENT)", Dupixent Food and Drug Administration Label, 4 Pages.

Regeneron Pharmaceuticals Inc. (May 21, 2013) "Sanofi and Regeneron Announce Publication of Positive 5 Phase 2a Results of Dupilumab in Asthma in the New England Journal of Medicine", Press Release, Acquire Media, 3 Pages.

Regeneron Pharmaceuticals, Inc. (Nov. 22, 2013) "Sanofi and Regeneron report positive results with Sarilumab in first phase 3 rheumatoid arthritis registration trial", Press Release, Acquire Media, 6 pages.

Ring, et al. (2012) "Guidelines for Treatment of Atopic Eczema Part I", Journal of the European Academy of Dermatology and Venereology, vol. 26, pp. 1045-1060.

Rizk, Habib (2011) "Role of Aspirin Desensitization in the Management of Chronic Rhinosinusitis", Current Opinion in Otolaryngology & Head and Neck Surgery, vol. 19, Issue 3, pp. 210-217.

Roitt, et al. (2001) "Immunology—Sixth Edition", Mosby—Harcourt Publishers Limited, pp. 110-111.

Roll, et al. (Jan. 1, 2006) "Safety of Specific Immunotherapy using a Four-Hour Ultra-Rush Induction Scheme in Bee and Wasp Allergy", Journal of Investigational Allergology and Clinical Immunology, vol. 16, No. 2, pp. 79-85.

Romaniuk, L I. (2012) "Allergan-Specific Immunotherapy Mechanisms Methods and Efficacy", Clinical Immunology, Allergology and Infectology, Special Issue, pp. 44-47.

Rothenberg, et al. (Feb. 1, 2015) "Intravenous Anti-IL-13 mAb QAX576 for the Treatment of Eosinophilic Esophagitis", The Journal of Allergy and Clinical Immunology, vol. 135, No. 2, pp. 500-507.

Rothenberg, Marc E. (Oct. 2009) "Eosinophilic Esophagitis: Biology to Therapy", Gastroenterology, vol. 137, No. 4, pp. 1238-1249.

Rothenberg, Marc E. (Jan. 1, 2004) "Eosinophilic Gastrointestinal Disorders (EGID)", Journal of Allergy and Clinical Immunology, vol. 113, No. 1, pp. 11-28.

Saeki, et al. (2009) "Guidelines for Management of Atopic Dermatitis", Advances in Medicine, Special Issue, vol. 228, No. 1, pp. 75-79.

Sampson, et al. (May 2011) "A Phase II, Randomized, Double-Blind, Parallel-Group, Placebo0controlled Oral Food Challenge Trial of Xolair (Omalizumab) in Peanut Allergy", The Journal of Allergy and Clinical Immunology, vol. 127, No. 5, pp. 1309-1310.e1.

Sanofi (Jun. 2014) "An Evaluation of Dupilumab in Patients with Nasal Polyposis and Chronic Symptoms of Sinusitis", Clinical Trials: NCT01920893, 4 Pages.

Sanofi (Nov. 4, 2019) "Efficacy, Safety, and Tolerability of Dupilumab in Patients with Persistent Moderate to Severe Eosinophilic Asthma", Clinical trials, Archive History for NCT01312961, 9 Pages.

Sanofi (Oct. 19, 2018) "Evaluation of Dupilumab in Patients with Severe Steroid Dependent Asthma (Venture)", Archive History for NCT02528214, Retrieved at URL: <<https://clinicaltrials.gov/ct2/history/NCT02528214?V_38=View#StudyPageTop>>, 15 Pages.

Sanofi (Oct. 2, 2012) "Sequential Ascending Dose Study to Assess the Safety and Tolerability of REGN668 (SAR231893) in Patients with Atopic Dermatitis", ClinicalTrials.gov Identifier: NCT01259323, 6 Pages.

(56) References Cited

OTHER PUBLICATIONS

Sanofi (Nov. 13, 2017) "Study of Dupilumab in Adult Patients with Extrinsic Moderate-to-Severe Atopic Dermatitis", ClinicalTrials. gov Identifier: NCT01548404, 7 Pages.
Sanofi (43671) "A Controlled Clinical Study of Dupilumab in Patients with Bilateral Nasal Polyps (Sinus-24)", ClinicalTrials.gov Identifier: NCT02912468, 18 Pages.
Sanofi (Oct. 23, 2019) "Controlled Clinical Study of Dupilumab in Patients with Nasal Polyps (Sinus-52)", ClinicalTrials.gov Identifier: NCT02898454, 18 Pages.
Sanofi (May 18, 2020) "Evaluation of SAR440340 and as Combination Therapy with Dupilumab in Moderate-to-Severe Asthma Participants", Clinical Trials Accession No. NCT03387852, Retrieved from: <<https://clinicaltrials.gov/ct2/show/NCT03387852>>, 10 Pages.
Sato, et al. (Apr. 1, 1993) "Recombinant Soluble Murine IL-4 Receptor can Inhibit or Enhance IgE Responses in Vivo", The Journal of Immunology, vol. 150, No. 7, pp. 2717-2723.
Scavuzzo, et al. (2005) "Inflammatory Mediators and Eosinophilia in Atopic and Non-Atopic Patients with Nasal Polyposis", Biomedicine and Pharmacotherapy, vol. 59, No. 6, pp. 323-329.
Schmidt, J J. (1985) "DNA Cloning: A Practical Approach vols. I and II", Edited by D M Glover, IRL Press Oxford, 1 Page.
Schmidt-Weber, Carsten B. (2012) "Anti-IL-4 as a New Strategy in Allergy", Chemical Immunology and Allergy, vol. 96, pp. 120-125.
Schmitt, et al. (Dec. 1, 2007) "What are the Best Outcome Measurements for Atopic Eczema? A Systematic Review", Journal of Allergy and Clinical Immunology, vol. 120, No. 6, pp. 1389-1398.
Schneider, et al. (Dec. 1, 02) "A Pilot Study of Omalizumab to Facilitate Rapid Oral Desensitization in High-Risk Peanut-Allergic Patients", Journal of Allergy and Clinical Immunology, vol. 132, No. 6, pp. 1368-1374.
Schubert, et al. (Sep. 1, 1998) "Evaluation and Treatment of Allergic Fungal Sinusitis. I. Demographics and Diagnosis", The Journal of Allergy and Clinical Immunology, vol. 102, No. 3, pp. 387-394.
Schubert, et al. (Sep. 1, 1998) "Evaluation and Treatment of Allergic Fungal Sinusitis. II. Treatment and Follow-up", The Journal of Allergy and Clinical Immunology, vol. 102, No. 3, pp. 395-402.
Sefton, MV (Jan. 1, 1987) "Implantable Pumps", Critical Reviews in Biomedical Engineering, vol. 14, No. 3, pp. 201-240.
Sekiya, et al. (Jan. 2002) "Increased Levels of a TH2-type CC Chemokine Thymus and Activation-Regulated Chemokine TARC) in Serum and Induced Sputum of Asthmatics", Allergy, vol. 57, No. 02, pp. 173-177.
Shannon, et al. (Feb. 2008) "Differences in Airway Cytokine Profile in Severe Asthma Compared to Moderate Asthma", Chest, vol. 133, No. 2, pp. 420-426.
Sheahan, et al. (Feb. 2010) "Local IgE Production in Nonatopic Nasal Polyposis", Journal of Otolaryngology—Head and Neck Surgery, vol. 39, No. 1, pp. 45-51.
Silverberg, et al. (Feb. 16-20, 2018) "Dupilumab Treatment Induces Rapid Clinical Improvement of Itch in Patients with Moderate-to-Severe Atopic Dermatitis", 76th American Academy of Dermatology Annual Meeting, San Diego, USA, 1 Page.
Silverberg, et al. (Oct. 26-30, 2017) "Dupilumab Treatment Rapidly Improves Itch in Patients with Moderate to-Severe Atopic Dermatitis", 75th Annual Scientific Meeting of the American College of Asthma, 1 Page.
Simpson, et al. (Jun. 4, 2016) "Dupilumab Therapy Provides Clinically Meaningful Improvement in Patient-Reported 45 Outcomes (PROs): A Phase IIB, Randomized, Placebo-Controlled, Clinical Trial in Adult Patients with Moderate to Severe Topic Dermatitis (AD)", Journal of the American Academy of Dermatology, vol. 75, No. 3, pp. 506-515.
Simpson, et al. (Jan. 14, 2016) "Patient Burden of Moderate to Severe Atopic Dermatitis (AD): Insights from a Phase B Clinical Trial of Dupilumab in Adults", Journal of the American Academy of Dermatology, vol. 74, No. 3, pp. 491-498.
Simpson, et al. (Sep. 30, 2016) "Two Phase 3 Trials of Dupilumab Versus Placebo in Atopic Dermatitis", The New England Journal of Medicine, vol. 375, No. 24, pp. 2335-2348.

Slager, et al. (Apr. 26, 2012) "IL-4 Receptor Polymorphisms Predict Reduction in Asthma Exacerbations During Response to an Anti-IL-4 Receptor Alpha Antagonist", vol. 130, No. 2, pp. 516-522.
Small, et al. (Sep. 27, 2005) "Efficacy and Safety of Mometasone Furoate Nasal Spray in Nasal Polyposis", The Journal of Allergy and Clinical Immunology, vol. 116, Issue 6, pp. 1275-1281.
Stein, et al. (Dec. 1, 2006) "Anti-IL-5 (Mepolizumab) Therapy for Eosinophilic Esophagitis", Journal of Allergy and Clinical Immunology, vol. 118, No. 6, pp. 1312-1319.
Stone, et al. (Dec. 2008) "Immunomodulatory Therapy of Eosinophil-Associated Gastrointestinal Diseases", Clinical & Experimental Allergy, vol. 38, No. 12, pp. 1858-1865.
Straumann, et al. (Jan. 1, 2010) "Anti-Interleukin-5 Antibody Treatment (Mepolizumab) in Active Eosinophilic Oesophagitis: A Randomised, Placebo-Controlled, Double-Blind Trial", Gut, vol. 59, No. 1, pp. 21-30.
Straumann, et al. (Feb. 1, 2009) "Clinical Evaluation of the Adult who has Eosinophilic Esophagitis", Immunology and Allergy Clinics of North America, vol. 29, No. 1, pp. 11-18.
Straumann, et al. (Feb. 1, 2005) "Eosinophilic Esophagitis: Escalating Epidemiology?", Journal of Allergy and Clinical Immunology, vol. 115, 2, pp. 418-419.
Straumann, et al. (Dec. 1, 2001) "Idiopathic Eosinophilic Esophagitis is Associated with a TH2-Type Allergic Inflammatory Response", Journal of Allergy and Clinical Immunology, vol. 108, No. 6, pp. 954-961.
Straumman, et al. (Aug. 2008) "Anti-TNF-[Alpha](Infliximab) Therapy for Severe Adult Eosinophilic Esophagitis", Journal of Allergy and Clinical Immunology, vol. 122, No. 2, pp. 425-427.
Tang, et al. (2010) "YKL-40 in Asthmatic Patients, and its Correlations with Exacerbation, Eosinophils and Immunoglobulin E", European Respiratory Society, vol. 35, pp. 757-760.
Taylor, et al. (Dec. 11, 1992) "A Transgenic Mouse That Expresses a Diversity of Human Sequence Heavy and Light Chain Immunoglobulins", Nucleic Acids Research, vol. 20, No. 23, pp. 6287-6295.
Tazawa, et al. (Mar. 10, 2004) "Relative Importance of IL-4 and IL-13 in Lesional Skin of Atopic Dermatitis", Archives of Dermatological Research Springer, vol. 295, pp. 459-464.
Terui, et al. (2000) "Learning from Fungus Allergy in Atopic Dermatitis Patients", Japanese Journal of Medical Mycology, vol. 41, No. 3, pp. 157-160.
Thaci, et al. (Oct. 8, 2015) "Efficacy and Safety of Dupilumab in Adults with Moderate-to-Severe Atopic Dermatitis 47 Inadequately Controlled by Topical Treatments: A Randomised, Placebo-Controlled, Dose-Ranging Phase 2b Trial", Lancet, vol. 387, No. 10013, pp. 40-52.
Tomkinson, et al. (2001) "A Murine IL-4 Receptor Antagonist that Inhibits IL-4-and IL-13-Induced Responses Prevents Antigen-Induced Airway Eosinophilia and Airway Hyperresponsiveness", The Journal of Immunology, vol. 166, No. 9, pp. 5792-5800.
Trangsrud, et al. (Jan. 12, 2002) "Intranasal Corticosteroids for Allergic Rhinitis", Pharmacotherapy, vol. 22, No. 11, pp. 1458-1467.
Tsianakas, et al. (Oct. 8, 2015) "Dupilumab: A Milestone in the Treatment of Atopic Dermatitis", Lancet, vol. 387, No. 10013, pp. 4-5.
Ul-Haq, et al. (2016) "Interleukin-4 Receptor Signaling and its Binding Mechanism: A therapeutic insight from Inhibitors Tool Box", Cytokine and Growth Factor Reviews, vol. 32, pp. 3-15.
Vakharia, et al. (Oct. 2017) "Monoclonal Antibodies for Atopic Dermatitis: Progress and Potential", BioDrugs, vol. 31, No. 5, pp. 409-422.
Van Zele, et al. (2006) "Differentiation of Chronic Sinus Diseases by Measurement of Inflammatory Mediators", Allergy, vol. 61, No. 11, pp. 1280-1289.
Van Zele, et al. (2010) "Oral Steroids and Doxycycline: Two Different Approaches to Treat Nasal Polyps", Journal of Allergy and Clinical Immunology, vol. 125, No. 5, pp. 1069-1076.
Veerappan, et al. (Apr. 1, 2009) "Prevalence of Eosinophilic Esophagitis in an Adult Population Undergoing Upper Endoscopy: A Prospective Study", Clinical Gastroenterology and Hepatology, vol. 7, No. 4, pp. 420-426.

(56) References Cited

OTHER PUBLICATIONS

Vestergaard, et al. (Oct. 1, 2000) "A Th2 Chemokine, TARC, Produced by Keratinocytes May Recruit CLA+CCR4+ Lymphocytes into Lesional Atopic Dermatitis Skin", Journal of Investigative Dermatology, vol. 115, No. 4, pp. 640-646.

Virchow, et al. (1994) "Cellular and Immunological Markers of Allergic and Intrinsic Bronchial Asthma", Lung, vol. 172, No. 6, pp. 313-334.

Vlaminck, et al. (May-Jun. 2014) "The Importance of Local Eosinophilia in the Surgical Outcome of Chronic Rhinosinusitis: A 3-Year Prospective Observational Study", American Journal of Rhinology & Allergy, vol. 28, No. 3, pp. 260-264.

Walker, et al. (1993) "Atopic Dermatitis: Correlation of Peripheral Blood T Cell Activation, Eosinophilia and Serum Actors with Clinical Severity", Clinical and Experimental Allergy, vol. 23, pp. 143-153.

Walker, et al. (2008) "Use of Biologics as Immunotherapy in Asthma and Related Diseases", Expert Review of Clinical Immunology, vol. 4, No. 6, pp. 743-756.

Wang, et al. (Jul. 12, 2010) "Peanut-Induced Intestinal Allergy is Mediated Through a Mast Cell-IgE-FcepsilonRI-IL-13 Pathway", Journal of Allergy and Clinical Immunology, vol. 126, No. 2, pp. 306-316.

Wang, et al. (Dec. 1, 2008) "The IIL-17 Cytokine Family and their Role in Allergic Inflammation", Current Opinion in Immunology, vol. 20 Number, pp. 697-702.

Ward et al., Binding activities of a repertoire of single immunoglobin variable domains secreted from *Escherichia coli*, Nature, 1989, 341:544-546.

Wark, et al. (Aug. 7, 2006) "Latest Technologies for the Enhancement of Antibody Affinity", Advanced Drug Delivery Reviews, vol. 58, No. 5-6, pp. 657-670.

Weber, et al. (Mar. 13, 2012) "Anti-IL-4 as a New Strategy in Allergy", Chemical immunology and Allergy, vol. 96, pp. 120-125.

Wegmann, et al. (2017) "Targeting Cytokines in Asthma Therapy: Could IL-37 be a Solution?", Expert Review of Respiratory Medicine, vol. 11, No. 9, pp. 675-677.

Weihrauch, et al. (Jul. 1, 2005) "Elevated Serum Levels of CC Thymus and Activation-Related Chemokine (Tarc) in Primary Hodgkin's Disease: Potential for a Prognostic Factor", Cancer Research, vol. 65, No. 13, pp. 5516-5519.

Weinbrand-Goichberg, et al. (Jul. 1, 2013) "Eosinophilic Esophagitis: An Immune-Mediated Esophageal Disease", Immunologic Research, vol. 56, No. 2-3, pp. 249-260.

Wenzel, et al. (Jul. 2, 2016) "Dupilumab Efficacy and Safety in Adults with Uncontrolled Persistent Asthma Despite use of Medium-To-High-Dose Inhaled Corticosteroids Plus a Long-Acting B2 Agonist: A Randomised Double-Blind Placebo-Controlled Pivotal Phase 2b Dose-Ranging Trial", Lancet, vol. 388, No. 10039, pp. 31-44.

Wenzel, et al. (May 21, 2013) "Dupilumab in Persistent Asthma with Elevated Eosinophil Levels", The New England, Journal of Medicine, vol. 368, No. 26, pp. 2455-2466.

Wenzel, et al. (2007) "Effect of An Interleukin-4 Variant on Late Phase Asthmatic Response to Allergen Challenge in Asthmatic Patients: Results of Two Phase 2A Studies", The Lancet, vol. 370, No. 9596, pp. 1422-1431.

Wenzel, et al. (Sep. 21, 2010) "Late Breaking Abstract: Inhaled Pitrakinra, an IL-4/IL-13 Antagonist, Reduced Exacerbations in Patients with Eosinophilic Asthma", ERS-Programme, European Respiratory Society, Annual Congress, p. 3980.

Wershil, Barry K. (Feb. 1, 2009) "Exploring the Role of Mast Cells in Eosinophilic Esophagitis", Immunology and Allergy Clinics of North America, vol. 29, No. 1, pp. 189-195.

Whalley, et al. (Feb. 2004) "A New Instrument for Assessing Quality of Life in Atopic Dermatitis: International Development of the Quality of Life Index for Atopic Dermatitis (Qoliad)", British Journal of Dermatology, vol. 150, pp. 274-283.

WHO (Jan. 1, 2012) "International Nonproprietary Names for Pharmaceutical Substances (INN)", World Health Organization, Drug Information, vol. 26, No. 4, XP055084074, pp. 401-471.

Wilhelm, et al. (Nov. 28, 2011) "Innate Lymphoid Cells and Type 2 ($T_H2$) Mediated Immune Responses—Pathogenic or Beneficial?", Frontiers in Immunology, vol. 2, Article 68, pp. 1-4.

Wills-Karp, et al. (Dec. 23, 2008) "Untangling the Complex Web of IL-4 and IL-13 Mediated Signaling Pathways", Science Signaling, vol. 1, No. 51, pp. 1-5.

Winter et al., "Pathogenic Long-Lived Plasma Cells and Their Survival Niches in Autoimmunity, Malignancy, and Allergy", The Journal of Immunology, vol. 189, No. 11, Nov. 19, 2012, pp. 5105-5111.

Wong, et al. (Sep. 2017) "Guidelines for the Management of Atopic Dermatitis (eczema) for Pharmacists", Canadian Pharmacists Journal, vol. 150, No. 5, pp. 285-297.

Woodruff, et al. (May 29, 2009) "T-Helper Type 2-Driven Inflammation Defines Major Subphenotypes of Asthma", American Journal of Respiratory and Critical Care Medicine, vol. 180, No. 5, pp. 388-395.

Wu, et al. (Apr. 5, 1987) "Receptor-Mediated In Vitro Gene Transformation by a Soluble DNA Carrier System", Journal of Biological Chemistry, vol. 262, No. 10, pp. 4429-4432.

Yamanaka, et al. (2011) "The Role of Cytokines/Chemokines in the Pathogenesis of Atopic Dermatitis", Current Problems in Dermatology, vol. 41, pp. 80-92.

Yasuhara, et al. (Jul. 2010) "Fundamentals of Clinical Pharmacokinetics", Clinical Pharmacology, vol. 41, Issue 4, pp. 155-158.

Zuo, et al. (2010) "IL-13 Induces Esophageal Remodeling and Gene Expression by an Eosinophil-Independent, L-13R {alpha} 2-Inhibited Pathway", Journal of Immunology, vol. 185, pp. 660-669.

Zurawski, et al. (1995) "The Primary Binding Subunit of the Human Interleukin-4 Receptor is Also a Component of the Interleukin-13 Receptor", Journal of Biological Chemistry, vol. 270, No. 23, pp. 13869-13878.

Degirmenci et al., Analysis of the Association of Chronic Spontaneous Urticaria With Interlekin-4, -10, Transforming Growth Factor-β1, Interferon-γ, Interleukin-17a and -23 by Autologous Serum Skin Test, Advances in Dermatology and Allergology/Postpy Dermatologii i Alergologii, vol. 34, No. 1, pp. 70-76, 2017.

FDA (Mar. 1, 2019) "Highlights of Prescribing Information", Sep. 29, 2022, Retrieved from url: https://www.accessdata.fda.gov/drugsatfda_docs/label/2022/761055s044lbl.pdf.

Maurer, et al., Unmet Clinical Needs in Chronic Spontaneous Urticaria. A GA2LEN Task Force Reportt, Allergy, vol. 66, No. 3, pp. 317-330, 2011.

Abe, Yasuhiko, et al., "Advances in the Diagnosis and Treatment of Eosinophilic Esophagitis", (English abstract), Gastroenterological Endoscopy, 2014, vol. 56, Issue 9, pp. 3378-3393.

Alobid et al., "Role of Medical Therapy on the Management of Nasal Polyps", Curr Allergy Asthma Rep., 2012, 12: 144-153.

Bacharier et al., "Dupilumab in Children with Uncontrolled Moderate-to-Severe Asthma", NEJM, Dec. 9, 2021, vol. 385, No. 24, pp. 2230-2240, Retrieved from url: https://www.nejm.org/doi/pdf/10.1056/NEJMoa2106567?articleTools=true.

Bachert et al., "ICON: Chronic Rhinosinusitis", World Allergy Organization, 2014, 7(25): 1-28.

Baiardini, et al., A New Tool to Evaluate the Impact of Chronic Urticaria on Quality of Life: Chronic Urticaria Quality of Life Questionnaire (CU-Q2oL), European Academy of Allergy and Clinical Immunology, vol. 60, No. 8, pp. 1073-1078, 2005.

Bergmann, M.M. et al., "Evaluation of Food Allergy in Patients with Atopic Dermatitis", J Allergy Clin Immunol, 1, pp. 22-28, Jan. 1, 2013.

Blakely, Kim et al., "Dupilumab, a monoclonal antibody for atopic dermatitis: a review of current literature", Skin Therapy Letter, Mar.-Apr. 2016, vol. 21, No. 2, Dupilumab Clinical Trials in AD, 13 pages.

Bloomstein et al., "Simultaneous treatment of Samter triad and prurigo nodularis with dupilumab", JAAD Case Reports, Dec. 1, 2021, vol. 18, p. 20-22, Retrieved from the Internet: url: https://www.jaadcasereports.org/article/S2352-5126(21)00725-6/pdf.

Boguniewicz, Mark et al., "Recent insights into atopic dermatitis and implications for management of infectious complications", Journal of Allergy and Clinical Immunology, Jan. 2010, 125(1):4-13.

(56) References Cited

OTHER PUBLICATIONS

Brandt et al., "Th2 Cytokines and Atopic Dermatitis", J Clin Cell Immunol., Aug. 10, 2011, 2(3): 110.
Bruton, Kelly et al., "Interrupting reactivation of immunologic memory diverts the allergic response and prevents anaphylaxis", Journal of Allergy and Clinical Immunology, vol. 147, No. 4, Dec. 15, 2020, pp. 1381-1392.
Canonica, et al., The EAACI/GA2LEN/EDF/WAO Guideline for the Definition, Classification, Diagnosis, and Management of Urticaria: The 2013 Revision and Update, European Academy of Allergy and Clinical Immunology, vol. 69, No. 7, pp. 868-887, 2014.
Casale, et al., Similar Efficacy with Omalizumab in Chronic Idiopathic/Spontaneous Urticaria Despite Different Background Therapy, The Journal of Allergy and Clinical Immunology: In Practice, vol. 3, No. 5, pp. 743-750.e1, 2015.
Celakovska, J. et al., "Sensitization to aeroallergens in atopic dermatitis patients: association with concomitant allergic diseases", JEADV 2015; 29, 1500-1505.
Chaker, Adam et al., "Short-term subcutaneous grass pollen immunotherapy under the umbrella of anti-IL-4: A randomized controlled trial", Journal of Allergy and Clinical Immunology, vol. 137, No. 2, Oct. 31, 2015, 19 pages.
Chen, Ching, et al., "Enhancement and destruction of antibody function by somatic mutation: unequal occurrence is controlled by V gene combinatorial associations", The EMBO Journal vol. 15, No. 12, pp. 2784-2794, 1995.
Chen, et al., Different Expression Patterns of Plasma Th1-, Th2-, Th17- and Th22-related Cytokines Correlate With Serum Autoreactivity and Allergen Sensitivity in Chronic Spontaneous Urticaria, Journal of the European Academy of Dermatology & Venereology, vol. 32, No. 3, pp. 441-448, Mar. 2018.
Clinical Trials, Study NCT00436670, "Phase II Study to Evaluate the Efficacy of AMG 317", first posted Feb. 19, 2007, Amgen actual study completion date—Feb. 2009, 7 pages.
Clinical Trials, Study NCT01859988, phase 2b, "Study of Dupilumab Administered to Adult Patients With Moderate-to-Severe Atopic Dermatitis", study completion date—Sep. 2014, 10 pages.
ClinicalTrials.gov Identifier: NCT02948959, Oct. 27, 2016, Evaluation of Dupilumab in Children with Uncontrolled Asthma (Voyage).
Clinical Trials, Study NCT03682770—"Study in Pediatric Subjects With Peanut Allergy to Evaluate Efficacy and Safety of Dupilumab as Adjunct to AR10 Immunotherapy" Aug. 20, 2020, located at: URL:https://clinicaltrials.gov/ct2/history/NCT03682770?V_8=View#StudyPageTop, (retrieved on Mar. 10, 2022), 7 pages.
Confino-Cohen et al., Low Stimulated Il-4 Secretion in Pbmc From Patients With Chronic Idiopathic Urticaria, Cytokine, vol. 27, No. 2-3, pp. 74-80, 2004.
Corren, Jonathan et al., "Short-term subcutaneous allergy immunotherapy and dupilumab are well-tolerated in allergic rhinitis: A randomized trial", Journal of Asthma and Allergy, vol. 14, Aug. 16, 2021, pp. 1045-1063.
D'Erme, Angelo et al., "Spotlight on dupilumab in the treatment of atopic dermatitis: design, development, and potential place in therapy", Drug Des Devel Ther, 2017, vol. 11, p. 1473-1480, DOI:10.2147/DDDT.S113192, Abstract, c. 1475-1478, 8 pages.
Degirmenci et al., Analysis of the Association of Chronic Spontaneous Urticaria With Interlekin-4, -10, Transforming Growth Factor-β1, Interferon-γ, Interleukin-17a and -23 by Autologous Serum Skin Test, Advances in Dermatology and Allergology/Postępy Dermatologii i Alergologii, vol. 34, No. 1, pp. 70-76, 2017.
drugs.com, "Asthma Medications", 2014, obtained from url: <http://web.archive.org/web/20140131041952/http://www.drugs.com/asthma.html>.
Errichetti et al., "Recalcitrant chronic urticaria treated with dupilumab: Report of two instances refractory to H1-antihistamines, omalizumab and cyclosporine and brief literature review", Dermatologic Therapy, Mar./Apr. 2021, 34(2): e14821.

Extended European Search Report for European Application No. 23202532.0, mailed on Mar. 27, 2024.
FDA "Highlights of Prescribing Information", Sep. 29, 2022, Retrieved from url: https://www.accessdata.fda.gov/drugsatfda_docs/label/2022/761055s044lbl.pdf.
Finkelman, Fred, et al., "Regulation of murine in vivo IgG and IgE responses by a monoclonal anti-IL-4 receptor antibody", Jun. 1991;3(6); 599-607.
Garraud, Olivier, et al., "Regulation of immunoglobulin production in hyper-IgE (Job's) syndrome", J. Allergy Clin. Immunol., Feb. 1999. (2 Pt. 1): 333-340.
Giménez-Arnau, et al., The Pathogenesis of Chronic Spontaneous Urticaria: The Role of Infiltrating Cells, The Journal of Allergy and Clinical Immunology: In Practice, vol. 9, No. 6, pp. 2195-2208, Jun. 2021.
Gong, J.Q. et al., "Skin Colonization by *Staphylococcus aureus* in patients with eczema and atopic dermatitis and relevant combined topical therapy: a double-blind multicentre randomized controlled trial", British Journal of Dermatology, No. 155, pp. 680-687 (2006), Mar. 28, 2006.
Gonnet, et al., Exhaustive Matching of the Entire Protein Sequence Database, Science, vol. 256, No. 5062, pp. 1443-1445, Jun. 5, 1992.
Grob, et al., Comparative Study of the Impact of Chronic Urticaria, Psoriasis and Atopic Dermatitis on the Quality of Life, British Journal of Dermatology, vol. 152, No. 2, pp. 289-295, 2005.
Harris, Jeffrey et al., "A randomized trial of the efficacy and safety of quilizumab in adults with inadequately controlled allergic asthma", Respiratory Research (2016) 17:29, 11 pages.
Hawro, et al., The Urticaria Activity Score—Validity, Reliability, and Responsiveness, The Journal of Allergy and Clinical Immunology: In Practice, vol. 6, No. 4, pp. 1185-1190.e1, 2018.
Hendricks et al., "Dupilumab use in dermatologic conditions beyond atopic dermatitis—a systematic review", Journal of Dermatological Treatment, 2023, 23(1): 19-28.
Herdman, et al., Development and Preliminary Testing of the New Five-level Version of EQ-5D (EQ-5D-5L), Quality of Life Research, vol. 20, No. 10, pp. 1727-1736, Apr. 9, 2011.
Hollis, et al., Comparison of Urticaria Activity Score Over 7 Days (UAS7) Values Obtained from Once-Daily and Twice-Daily Versions: Results from the Assure-CSU Study, American Journal of Clinical Dermatology, vol. 19, No. 2, pp. 267-274, Jan. 24, 2018.
Igelman, Sean et al., "Off-label use of dupilumab for pediatric patients with atopic dermatitis: A multicenter retrospective review", Journal of the American Academy of Dermatology, Mosby, Inc., US, vol. 82, No. 2, Oct. 10, 2019, pp. 407-411.
International Search Report with Written Opinion for PCT International Patent Application No. PCT/US2021/053328, mailed Feb. 23, 2022.
International Search Report with Written Opinion for PCT International Patent Application No. PCT/US2022/038185, mailed Jan. 10, 2023.
International Search Report with Written Opinion for PCT International Patent Application No. PCT/US2022/078341 mailed Mar. 7, 2023.
Kim et al., "Engineering of anti-human interleukin-4 receptor alpha antibodies with potent antagonistic activity", Scientific Reports, 2019, vol. 9, Article No. 7772, pp. 1-12.
Kussie, Paul, et al., "A Single Engineered Amino Acid Substitution Changes Antibody Fine Specificity", Journal of Immunology:152, pp. 146-152, 1994.
Kwiatek, Monika et al., "Mechanical properties of the esophagus in eosinophilic esophagitis" Gastroenterology, 2011, vol. 140, No. 1, pp. 82-90.
Langley, R.G., et al., "Secukinumab in plaque psoriasis—results of two phase 3 trials", New England Journal of Medicine, Jul. 24, 2014, 371:4, pp. 326-338.
Lee et al., "Dupilumab as a novel therapy for difficult to treat chronic spontaneous urticaria", Clinical Communicatinos, May 2019, 7(5): p. 1659-1661.E1.
Linden, Carey et al., "Analysis of allergen specific IgE cut points to cat and dog in the Childhood Allergy Study", Annals of Allergy, Asthma & Immunology, 2011, 106.2: 153-158. e2.

(56) References Cited

OTHER PUBLICATIONS

Lucae, S. et al., "IgE responses to exogenous and endogenous allergens in atopic dermatitis patients under long-term systemic cyclosporine A treatment", Allergy 71 (2016); 115-118.
Mathias, et al., Evaluating the Minimally Important Difference of the Urticaria Activity Score and Other Measures of Disease Activity in Patients With Chronic Idiopathic Urticaria, Annals of Allergy, Asthma & Immunology, vol. 108, No. 1, pp. 20-24, Jan. 2012.
Maurer, et al., Omalizumab for the Treatment of Chronic Idiopathic or Spontaneous Urticaria, The New England Journal of Medicine, vol. 368, No. 10, pp. 924-935, Feb. 24, 2013.
Maurer, et al., Unmet Clinical Needs in Chronic Spontaneous Urticaria. A GA2LEN Task Force Report†, Allergy, vol. 66, No. 3, pp. 317-330, 2011.
McGregor et al., "Role of Biologics in Asthma", Am J Respir Crit Care Med., Feb. 15, 2019, 1999(4): 433-445.
Mlynek, et al., How to Assess Disease Activity in Patients With Chronic Urticaria?, European Academy of Allergy and Clinical Immunology, vol. 63, No. 6, pp. 777-780, 2008.
Moestrup et al., "Patient-reported outcomes (PROs) in chronic urticaria", Int'l Journal opf Dermatology, Dec. 2017, 56(12): 1342-1348.
Mulder, DJ et al., "Understanding eosinophilic esophagitis: the cellular and molecular mechanisms of an emerging disease", Mucosal Immunology, Mar. 2011, vol. 4, No. 2, pp. 139-147.
Navarini, A., et al., "Interrupting IL-6-receptor signaling improves atopic dermatitis but associates with bacterial superinfection", Nov. 2011 J Allergy Clin Immunol, Letters to the Editor, pp. 1128-1130.
Paller et al., "Efficacy and safety of dupilumab with concomitant topical corticosteroids in children 6 to 11 years old with severe atopic dermatitis: A randomized, double-blinded, placebo-controlled phase 3 trial", J Am Acad Dermatol., Nov. 2020, vol. 83, No. 5, pp. 1282-1293, Epub Jun. 20, 2020.
Peters et al., "Uncontrolled asthma: a review of the prevalence, disease burden and options for treatment", Respir Med., Jul. 2006, 100(7): 1139-1151.
Radin et al., "First-in-Human Study of REGN668/SAR231893 (IL-4Rα mAb): Safety, Tolerability and Biomarker Results of a Randomized, Double-Blind, Placebo-Controlled, Single Ascending Dose Study in Healthy Volunteers", J. Allergy Clin. Immunol., 2013, vol. 131(2), Suppl., p. AB158, (made available on Jan. 26, 2013), 2 pgs.
Ramonell et al., Dupilumab treatment for allergic bronchopulmonary aspergillosis: A case series, J Clin Innunol Pract., Feb. 2020, 8(2): 742-743.
Reed, Craig, et al., "Patient-reported outcomes in esophageal diseases", Clinical Gastroenterology and Hepatology, Elsevier, Amsterdam, NL, vol. 16. No. 3, pp. 305-310.
Sandeep et al., Evaluation of serum immunoglobulin E levels in bronchial asthma, Lung India, Jul.-Sep. 2010, 27(3).
Sanofi (Dec. 22, 2017) "Evaluation of SAR440340 and as Combination Therapy with Dupilumab in Moderate-to-Severe Asthma Participants", Clinical Trials Accession No. A327NCT03387852, Retrieved from: <<https://clinicaltrials.gov/ct2/show/NCT03387852>>.
Sanofi, "Dupixent (dupilumab) significantly reduced severe asthma attacks in children and is the only biologic to demonstrate improvement in children's lung function in a randomized Phase 3 trial", Oct. 13, 2020, pp. 1-6, retireved from url: https://ml-eu.globenewswire.com/Resource/Download/326080b9-593f-4d56-8035-48827a7b5bf4.
Sanofi, clinicaltrials.gov (Aug. 20, 2012) "Efficacy, Safety, and Tolerability of Dupilumab in Patients With Persisten Moderate to Severe Eosinophilic Asthma," [accessible on the internet at: https://clinicaltrials.gov/ct2/show/NCT01312961].
Semprini et al., Change in biomarkers of type-2 inflammation following severe exacerbations of asthma, Thorax, 2019, 74: 95-98.
Shikiar, et al., Minimal Important Difference (MID) of the Dermatology Life Quality Index (DLQI): Results From Patients With Chronic Idiopathic Urticaria, Health and Quality of Life Outcomes, vol. 3, No. 36, pp. 1-5, May 20, 2005.
Staubach et al., "Severe chronic spontaneous urticaria in children—treatment options according to the guidelines and beyond—a 10 years review", Journal of Dermatological Treatment, 2022, 33(2): 1119-1122.
Stull et al., "Analysis of disease activity categories in chronic spontaneous/idiopathic urticaria", British Journal of Dermatology, Oct. 1, 2017, 177(4): 1093-1101.
Tanis et al., "Dupilumab treatment for prurigo nodularis", J Drugs Dermatol., Sep. 1, 2019, 18(9): 940-942, Retrieved from url: https://pubmed.ncbi.nlm.nih.gov/31524352/.
Vincent, M. et al., "Single-Dose, First-in-Human Study of AMG 317: Pharmacokinetics and Safety in Healthy and Asthmatic Adults", the Journal of Allergy and Clinical Immunology, vol. 121, Issue 2, Supplement 1, S10, Abstract, Feb. 1, 2008, 1 page.
Waccholz et al., "Detection of Allergen-Specific IgE Antibody Responses", 2005, Journal of Immunotoxicology, 1:3-4, 189-199.
Wambre, ER, "Baseline characteristics of peanut-allergic individuals during the dupilumab as adjunct to AR101 clinical trial", Abstract, retrieved at: https://onlinelibrary.wiley.com/doi/10.1111/all.14506, Sep. 7, 2020, 1 page.
Weller, Development and Validation of the Urticaria Control Test: a Patient-reported Outcome Instrument for Assessing Urticaria Control, Journal of Allergy and Clinical Immunology, vol. 133, No. 5, pp. 1365-1372.e6, 2014.
Weller, et al., Development, Validation, and Initial Results of the Angioedema Activity Score, European Academy of Allergy and Clinical Immunology, vol. 68, No. 9, pp. 1185-1192, 2013.
Wille, et al., Development of the EQ-5D-Y: a Child-friendly Version of the EQ-5D, Quality of Life Research, vol. 19, No. 6, pp. 875-886, Apr. 20, 2010.
Yamashita, Shuya et al., "Flavones suppress type I IL-4 receptor signaling by down-regulating the expression of common gamma chain", FEBS Letters, 2010, vol. 584, issue 4, p. 775-779, Abstract, Introduction, located at: https://febs.onlinelibrary.wiley.com/doi/full/10.1016/j.febslet.2009.12.044, 13 pages.
Zuberbier, et al., Epidemiology of Urticaria: a Representative Cross-sectional Population Survey, Clinical and Experimental Dermatology, vol. 35, No. 8, pp. 869-873, 2010.
Zuberbier, et al., The EAACI/GA²LEN/EDF/WAO Guideline for the Definition, Classification, Diagnosis and Management of Urticaria, European Academy of Allergy and Clinical Immunology, vol. 73, No. 7, pp. 1393-1414, 2018.
Third Party Observation dated Aug. 1, 2023 for European Publication No. 4011915 (Application No. 21199451.2).
D1—GINA Report Dec. 2011, Global Strategy for Asthma Management and Prevention, GINA © 2011 & Global Initiative for Asthma, reprinted with permission, Available from www.ginasthma org, cited in Third Party Observation dated Aug. 1, 2023, for European Publication No. 4011915 (Application No. 21199451.2).
D2—Wenzel, Severe Asthma: from characteristics to phenotypes to endotypes (review), Clinical & Experimental Allergy, Jan. 18, 2012, 42: 650-658, cited in Third Party Observation dated Aug. 1, 2023, for European Publication No. 4011915 (Application No. 21199451.2).
D3—Wenzel, Asthma phenotypes: the evolution from clinical to molecular approaches (review), Nature Medicine, May 4, 2012, 18(5): 716-725, cited in Third Party Observation dated Aug. 1, 2023, for European Publication No. 4011915 (Application No. 21199451.2).
D4—U.S. Pat. No. 8,075,887 B2, High Affinity Human Antibodies to Human IL-4 Receptor, issued Dec. 13, 2011, cited in Third Party Observation dated Aug. 1, 2023, for European Publication No. 4011915 (Application No. 21199451.2).
U.S. Appl. No. 13/971,334 2014/0056920 U.S. Pat. No. 9,574,004, filed Aug. 20, 2013 Feb. 27, 2014 Feb. 21, 2017, Marius Ardeleanu, Methods for Treating or Preventing Asthma by Administering an IL-4R Antagonist.
U.S. Appl. No. 15/400,076, filed Jan. 6, 2017, Marius Ardeleanu, Methods for Treating or Preventing Asthma by Administering an IL-4R Antagonist.

(56) References Cited

OTHER PUBLICATIONS

U.S. Appl. No. 15/627,669 2018/0016343 U.S. Pat. No. 11,845,800, filed Jun. 20, 2017 Jan. 18, 2018 Dec. 19, 2023, Marius Ardeleanu, Methods for Treating or Preventing Asthma by Administering an IL-4R Antagonist.
U.S. Appl. No. 18/495,182 2024/0199751, filed Oct. 26, 2023 Jun. 20, 2024, Marius Ardeleanu, Methods for Treating or Preventing Asthma by Administering an IL-4R Antagonist.
U.S. Appl. No. 14/627,728 2015/0246119 U.S. Pat. No. 10,137,193, filed Feb. 20, 2015 Sep. 3, 2015 Nov. 27, 2018, Gianluca Pirozzi, Methods for Treating or Preventing Asthma by Administering an IL-4R Antagonist.
U.S. Appl. No. 16/157,708 2019/0125865, filed Oct. 11, 2018 May 2, 2019, Gianluca Pirozzi, Methods for Treating or Preventing Asthma by Administering an IL-4R Antagonist.
U.S. Appl. No. 17/215,604 2021/0322546, filed Mar. 29, 2021 Oct. 21, 2021, Gianluca Pirozzi, Methods for Treating or Preventing Asthma by Administering an IL-4R Antagonist.
U.S. Appl. No. 14/310,419 2015/0017182 U.S. Pat. No. 10,059,771, filed Jun. 20, 2014 Jan. 15, 2015 Aug. 28, 2018, Leda Mannent, Methods for Treating Nasal Polyposis by Administering an IL-4R Antagonist.
U.S. Appl. No. 16/038,816 2019/0040146, filed Jul. 18, 2018 Feb. 7, 2019, Leda Mannent, Methods for Treating Nasal Polyposis by Administering an IL-4R Antagonist.
U.S. Appl. No. 14/940,431 2016/0185866 U.S. Pat. No. 10,066,017, filed Nov. 13, 2015 Jun. 30, 2016 Sep. 4, 2018, Leda Mannent, Methods for Treating Nasal Polyposis by Administering an IL-4R Antagonist.
U.S. Appl. No. 16/038,925 2019/0040147 U.S. Pat. No. 11,214,621, filed Jul. 18, 2018 Feb. 7, 2019 Jan. 4, 2022, Leda Mannent, Methods for Treating Nasal Polyposis by Administering an IL-4R Antagonist.
U.S. Appl. No. 17/534,106 2022/0204631, filed Nov. 23, 2021 Jun. 30, 2022, Leda Mannent, Methods for Treating Nasal Polyposis by Administering an IL-4R Antagonist.
U.S. Appl. No. 16/173,848 2019/0169299 U.S. Pat. No. 11,034,768, filed Oct. 29, 2018 Jun. 6, 2019 Jun. 15, 2021, Nikhil Amin, Methods for Treating Nasal Polyposis by Administering an IL-4R Antagonist.
U.S. Appl. No. 17/314,251 2021/0380705, filed May 7, 2021 Dec. 9, 2021, Nikhil Amin, Methods for Treating Nasal Polyposis by Administering an IL-4R Antagonist.
U.S. Appl. No. 16/863,800 2021/0000949, filed Apr. 30, 2020 Jan. 7, 2021, Helene Goulaouic, Methods for Treating Nasal Polyposis by Administering an IL-4R Antagonist.
*U.S. Appl. No. 16/929,624 2021/0032354, filed Jul. 15, 2020 Feb. 4, 2021, Heribert Staudinger, Methods for Treating Nasal Polyposis by Administering an IL-4R Antagonist.
U.S. Appl. No. 17/872,225 2023/0146317, filed Jul. 25, 2022 May 11, 2023, Aleksandra Stjepanovic, Methods for Treating Chronic Spontaneous Urticaria by Administering an IL-4R Antagonist.
U.S. Appl. No. 17/786,226 2023/0340101, filed Jun. 16, 2022 Oct. 26, 2023, El-Bdaoui Haddad, Methods for Treating or Preventing Allergic Asthma by Administring an IL-33 Antagonist and/or ab IL-4R Antagonist.
U.S. Appl. No. 17/493,101 2022/0169739, filed Oct. 4, 2021 Jun. 2, 2022 Christine Xu, Methods for Treating Asthma in Pediatric Subjects by Administering an IL-4R Antagonist.
U.S. Appl. No. 17/969,033 2023/0183362, filed Oct. 19, 2022 Jun. 15, 2023, Ashish Bansal, Methods for Treating Prurigo Nodularis by Administering an IL-4R Antagonist.
U.S. Appl. No. 18/612,039 2024/0360232, filed Mar. 21, 2024 Oct. 31, 2024, Raolat Abdulai, Methods for Treating Chronic Obstructive Pulmonary Disease (COPD) by Administering an IL-4R Antagonist.
Baturin V.A., et al., Micogenic sensibilization in pateints having a controlled bronchial asthma, Scientific notes of Orel State University, No. 6, (56), pp. 187-191, 2013.
ClinicalTrials.gov Identifier NCT02528214, Oct. 24, 2017, Evaluation of Dupilumab in Patients with Severe Steroid Dependent Asthma (Venture).
Extended European Search Report for European Application No. 23206862.7, dated Apr. 24, 2024.
Extended European Search Report for European Application No. 24150594.0, dated Jul. 5, 2024.
Goryachkina L.A., et al., Allergic bronchopulmonary aspergillosis, Allergiology, n.2, 2008, pp. 11-14.
Inoue et al., "Periostin as a biomarker for the diagnosis of pediatric asthma", Pediatr Allergy Asthma, Aug. 2016, 27(5): 521-526, Epublished Apr. 7, 2016.
Macharadze D., Modern Clinical Aspects of total and Specific IGE evaluation, Pediatrics, 2017, vol. 96, No. 2, pp. 121-127.
Aldington, S. et al., "Asthma exacerbations .5: Assessment and management of severe asthma in adults in hospital", Thorax May 1, 2007, 62(5): 447-458.
Alotaibi et al. , "Dupilumab as a treatment for allergic fungal rhinosinusitis: a case series", Rhinology Online, Aug. 11, 2023, 6(18): 18-24.
Beck et al., "Dupilumab Treatment for Generalized Prurigo Nodularis", JAMA Dermatol., Jan. 2019, 155(1): 118-120.
Bhatt et al., "Dupilumab for COPD with Type 2 Inflammation Indicated by Eosinophil Counts", NEJM, May 21, 2023, 389(3): 205-214.
Calugareanu et al., "Dramatic improvement of generalized prurigo nodularis with dupilumab", J Eur Acad Dermatol Venereol, Aug. 2019, 33(8): e303-e304.
Caswell-Smith et al., "Day-time variation of serum periostin in asthmatic adults treated with ICS/LABA and adults without asthma", Allergy Asthma Clin Immunol., 2017, 13: 8, Epublished Feb. 8, 2007.
Center for Drug Evaluation and Research, (Jun. 26, 2019) "Approval Package for Dupixent Solution for Injection", Application No. 761055Orig1s014, Generic Name: dupilumab, Sponsored by Regeneron Pharmaceuticals, Inc.
ClinicalTrials.gov, "An Evaluation of Dupilumab in Patients With Moderate to Severe Uncontrolled Asthma", Clinical Trial Protocol Version 22, Feb. 3, 2014, ClinicalTrials.gov ID: NCT01854047.
Endo et al., "The Interleukin-33-p38 Kinase Axis Confers Memory T Helper 2 Cell Pathogenicity in the Airway", Immunity, Feb. 17, 2015, 42(2): 294-308.
International Search Report with Written Opinion for PCT International Patent Application No. PCT/US2024/020860 mailed Aug. 26, 2024, 2023.
Lee et al., "Inhibition of Murine Allergic Response by Monoclonal Interleukin-4 Receptor Antibody", J Rhinol., 2000, 7(2): 149-153.
Lee et al., "Targeting eosinophils in respiratory diseases: Biological axis, emerging therapeutics and treatment modalities", Life Sciences, 2018, 267: 118973.
Mollanazar et al., "Reduced Itch Associated with Dupilumab Treatment in 4 Patients with Prurigo Nodularis", JAMA Dermatology, Jan. 2019, 155(1): 121-122.
Notice of Opposition against European Patent No. 3973987 (Application No. 21191120.1) filed on Oct. 1, 2024, on behalf of Dr. H. Ulrich Dörries.
P1—U.S. Appl. No. 61/943,019 (Feb. 21, 2014), cited in Notice of Opposition against European Patent No. 3973987 (Application No. 21191120.1) filed on Oct. 1, 2024, on behalf of Dr. H. Ulrich Dörries.
P2—EP 14306413.7 (Sep. 15, 2014), cited in Notice of Opposition against European Patent No. 3973987 (Application No. 21191120.1) filed on Oct. 1, 2024, on behalf of Dr. H. Ulrich Dörries.
P3—U.S. Appl. No. 62/077,669 (Nov. 10, 2014), cited in Notice of Opposition against European Patent No. 3973987 (Application No. 21191120.1) filed on Oct. 1, 2024, on behalf of Dr. H. Ulrich Dörries.
WO—WO 2015/127229, parent application as filed, cited in Notice of Opposition against European Patent No. 3973987 (Application No. 21191120.1) filed on Oct. 1, 2024, on behalf of Dr. H. Ulrich Dörries.
D1—Wenzel et al., The New England Journal of Medicine, 368(26):2455-66, published online on May 21, 2013, cited in Notice

(56) References Cited

OTHER PUBLICATIONS of Opposition against European Patent No. 3973987 (Application No. 21191120.1) filed on Oct. 1, 2024, on behalf of Dr. H. Ulrich Dörries.
D1a—Supplementary Appendix to D1, published together with D1, cited in Notice of Opposition against European Patent No. 3973987 (Application No. 21191120.1) filed on Oct. 1, 2024, on behalf of Dr. H. Ulrich Dörries.
D2—Gibaldi M., "Biopharmaceutics and Clinical Pharmacokinetics", 4th Edition, 1991, Lea & Febiger, pp. 12-13, cited in Notice of Opposition against European Patent No. 3973987 (Application No. 21191120.1) filed on Oct. 1, 2024, on behalf of Dr. H. Ulrich Dörries.
D3—NCT01312961 clinical trial protocol, version 36, Jan. 13, 2014, cited in Notice of Opposition against European Patent No. 3973987 (Application No. 21191120.1) filed on Oct. 1, 2024, on behalf of Dr. H. Ulrich Dörries.
D4—NCT01854047 clinical trial protocol, version 23, Feb. 18, 2014, cited in Notice of Opposition against European Patent No. 3973987 (Application No. 21191120.1) filed on Oct. 1, 2024, on behalf of Dr. H. Ulrich Dörries.
D5—WO 2014/031610 A1, published on Feb. 27, 2014, cited in Notice of Opposition against European Patent No. 3973987 (Application No. 21191120.1) filed on Oct. 1, 2024, on behalf of Dr. H. Ulrich Dörries.
D6—Wenzel S. et al., Lancet, 388:31-44, published online on Apr. 26, 2016, cited in Notice of Opposition against European Patent No. 3973987 (Application No. 21191120.1) filed on Oct. 1, 2024, on behalf of Dr. H. Ulrich Dörries.
D7—pp. 401, 402 and 412 of WHO Drug Information, vol. 26, No. 4, 2012, cited in Notice of Opposition against European Patent No. 3973987 (Application No. 21191120.1) filed on Oct. 1, 2024, on behalf of Dr. H. Ulrich Dörries.
D8—EurekAlert!, press release; "Monoclonal antibody appears effective and safe in, cited in Notice of Opposition against European Patent No. 3973987 (Application No. 21191120.1) filed on Oct. 1, 2024, on behalf of Dr. H. Ulrich Dörries. asthma Phase IIa trial", May 21, 2013.
D9—Chapter 19, "Dosage regimens", of Aulton's Pharmaceutics: The Science of Dosage Form Design, 2nd Edition, 2001, cited in Notice of Opposition against European Patent No. 3973987 (Application No. 21191120.1) filed on Oct. 1, 2024, on behalf of Dr. H. Ulrich Dörries.
D10—Panaccione R. and Ghosh S., Therapeutic Advances in Gastroenterology, 3(3):179-189, published on May 2010, cited in Notice of Opposition against European Patent No. 3973987 (Application No. 21191120.1) filed on Oct. 1, 2024, on behalf of Dr. H. Ulrich Dörries.
D11—Press release from Regeneron Pharmaceuticals Inc., Mar. 2, 2013, cited in Notice of Opposition against European Patent No. 3973987 (Application No. 21191120.1) filed on Oct. 1, 2024, on behalf of Dr. H. Ulrich Dörries.
D12—Global Initiative for Asthma (GINA) Guidelines 2012, updated in 2012, cited in Notice of Opposition against European Patent No. 3973987 (Application No. 21191120.1) filed on Oct. 1, 2024, on behalf of Dr. H. Ulrich Dörries.
D13—Jin et al., Therapeutics and Clinical Risk Management, 4(1): 269-286, 2008, cited in Notice of Opposition against European Patent No. 3973987 (Application No. 21191120.1) filed on Oct. 1, 2024, on behalf of Dr. H. Ulrich Dörries.
D14—NCT01015027 clinical trial protocol, version 7, Jun. 13, 2013, cited in Notice of Opposition against European Patent No. 3973987 (Application No. 21191120.1) filed on Oct. 1, 2024, on behalf of Dr. H. Ulrich Dörries.
D15—NCT01484600 clinical trial protocol, version 2, Mar. 12, 2012, cited in Notice of Opposition against European Patent No. 3973987 (Application No. 21191120.1) filed on Oct. 1, 2024, on behalf of Dr. H. Ulrich Dörries.
D16—NCT01537653 clinical trial protocol, version 7, Dec. 5, 2013, cited in Notice of Opposition against European Patent No. 3973987 (Application No. 21191120.1) filed on Oct. 1, 2024, on behalf of Dr. H. Ulrich Dörries.
D17—NCT01537640 clinical trial protocol, version 6, Dec. 5, 2013, cited in Notice of Opposition against European Patent No. 3973987 (Application No. 21191120.1) filed on Oct. 1, 2024, on behalf of Dr. H. Ulrich Dörries.
D18—NCT01259323 clinical trial protocol, version 6, Oct. 2, 2012, cited in Notice of Opposition against European Patent No. 3973987 (Application No. 21191120.1) filed on Oct. 1, 2024, on behalf of Dr. H. Ulrich Dörries.
D19—NCT01385657 clinical trial protocol, version 4, Sep. 27, 2013, cited in Notice of Opposition against European Patent No. 3973987 (Application No. 21191120.1) filed on Oct. 1, 2024, on behalf of Dr. H. Ulrich Dörries.
Notice of Opposition against European Patent No. 3973987 (Application No. 21191120.1) filed on Oct. 9, 2024, on behalf of Secerna LLP.
D1—WHO Drug Information, vol. 26, No. 4, p. 412, Dec. 9, 2012, cited in Notice of Opposition against European Patent No. 3973987 (Application No. 21191120.1) filed on Oct. 9, 2024, on behalf of Secerna LLP.
D2—Wenzel et al., Dupilumab in persistent asthma with elevated eosinophil levels. N Engl J Med. 2013; 368(26):2455-66, May 21, 2013, cited in Notice of Opposition against European Patent No. 3973987 (Application No. 21191120.1) filed on Oct. 9, 2024, on behalf of Secerna LLP.
D3—Protocol for: Wenzel et al. Dupilumab in persistent asthma with elevated eosinophil levels. N Engl J Med 2013; 368:2455-66, May 21, 2013, cited in Notice of Opposition against European Patent No. 3973987 (Application No. 21191120.1) filed on Oct. 9, 2024, on behalf of Secerna LLP.
D4—Study NCT01854047, An Evaluation of Dupilumab in Patients with Moderate to Severe Uncontrolled Asthma, Feb. 18, 2014, cited in Notice of Opposition against European Patent No. 3973987 (Application No. 21191120.1) filed on Oct. 9, 2024, on behalf of Secerna LLP.
D5—Press release: Sanofi and Regeneron Announce Positive Results from Phase 2b Study of Dupilumab in Patients with Moderate-to-Severe Asthma, https://investor.regeneron.com/news-releases/news-release-details/regeneron-and-sanofi-announce-positive-results-phase-2b-study-0, Nov. 11, 2014, cited in Notice of Opposition against European Patent No. 3973987 (Application No. 21191120.1) filed on Oct. 9, 2024, on behalf of Secerna LLP.
D6—WO 2014/031610 A1 published Feb. 27, 2014, cited in Notice of Opposition against European Patent No. 3973987 (Application No. 21191120.1) filed on Oct. 9, 2024, on behalf of Secerna LLP.
D7—Aulton. Pharmaceutics The Science of Dosage Form Design 2nd Edition. Chapter 19, 275-288, Oct. 2001, cited in Notice of Opposition against European Patent No. 3973987 (Application No. 21191120.1) filed on Oct. 9, 2024, on behalf of Secerna LLP.
D8—Panaccione & Ghosh. Optimal use of biologics in the management of Crohn's disease. Therapeutic Advances in Gastroenterology 2010, 3(3), 179-189, May 2010, cited in Notice of Opposition against European Patent No. 3973987 (Application No. 21191120.1) filed on Oct. 9, 2024, on behalf of Secerna LLP.
D9—Mould & Green, Pharmacokinetics and Pharmacodynamics of Monoclonal Antibodies. Concepts and Lessons for Drug Development, 2010, 24(1), 23-39, Feb. 1, 2010, cited in Notice of Opposition against European Patent No. 3973987 (Application No. 21191120.1) filed on Oct. 9, 2024, on behalf of Secerna LLP.
D10—Eisenstein. Something new under the skin. Nature Biotechnology 2011 29(2), 107-109, Feb. 7, 2011, cited in Notice of Opposition against European Patent No. 3973987 (Application No. 21191120.1) filed on Oct. 9, 2024, on behalf of Secerna LLP.
D11—Costantino et al., Intranasal delivery: Physicochemical and therapeutic, aspects, International Journal of Pharmaceutics, 2007, 337(1-2), Abstract, cited in Notice of Opposition against European Patent No. 3973987 (Application No. 21191120.1) filed on Oct. 9, 2024, on behalf of Secerna LLP.
D12—Gibaldi. Biopharmaceutics and clinical pharmacokinetics. Fourth Edition 1991. 12-13, cited in Notice of Opposition against

(56) References Cited

OTHER PUBLICATIONS

European Patent No. 3973987 (Application No. 21191120.1) filed on Oct. 9, 2024, on behalf of Secerna LLP.
D13—Press Release: Sanofi and Regeneron Report Positive Proof-of-Concept Data for Dupilumab, an IL-4R alpha Antibody, in Atopic Dermatitis. https://investor.regeneron.com/news-releases/news-release-details/sanofi-and-regeneron-report-positive-proof-concept-data, Mar. 2, 2013, cited in Notice of Opposition against European Patent No. 3973987 (Application No. 21191120.1) filed on Oct. 9, 2024, on behalf of Secerna LLP.
D14—WO 2022/076289 A1 (pp. 1 to 4), published Apr. 14, 2022, cited in Notice of Opposition against European Patent No. 3973987 (Application No. 21191120.1) filed on Oct. 9, 2024, on behalf of Secerna LLP.
D15—Shannon et al. Differences in Airway Cytokine Profile in Severe Asthma Compared to Moderate Asthma, Chest 2007, 133(2), 420-6, Dec. 10, 2007., cited in Notice of Opposition against European Patent No. 3973987 (Application No. 21191120.1) filed on Oct. 9, 2024, on behalf of Secerna LLP.
D16—Bossley et al. Paediatric severe asthma is characterized by eosinophilia and remodelling without TH2 cytokines. J Allergy Clin Immunol. 2012, 129(4), 974-982, Apr. 2012, cited in Notice of Opposition against European Patent No. 3973987 (Application No. 21191120.1) filed on Oct. 9, 2024, on behalf of Secerna LLP.
D17—EMEA. Annex I Summary of product characteristics for dupilumab, Sep. 2, 2022, cited in Notice of Opposition against European Patent No. 3973987 (Application No. 21191120.1) filed on Oct. 9, 2024, on behalf of Secerna LLP.
D18—Wenzel. Severe Asthma: from characteristics to phenotypes to endotypes. Clinical & Experimental Allergy 2012, 42, 650-658, Jan. 18, 2012, cited in Notice of Opposition against European Patent No. 3973987 (Application No. 21191120.1) filed on Oct. 9, 2024, on behalf of Secerna LLP.
D19—Wenzel. Severe Asthma in Adults. Am J Respir Crit Care Med. 2005 172(2) 149-160, cited in Notice of Opposition against European Patent No. 3973987 (Application No. 21191120.1) filed on Oct. 9, 2024, on behalf of Secerna LLP.
D20—Nakawah et al. Asthma, Chronic Obstructive Pulmonary Disease (COPD), and the Overlap Syndrome. 2013 J Am Board Fam Med 2013 26:4 470-477, Jul. 2013, cited in Notice of Opposition against European Patent No. 3973987 (Application No. 21191120.1) filed on Oct. 9, 2024, on behalf of Secerna LLP.
D21—Firszt & Kraft, Pharmacotherapy of severe asthma. Curr Opin Pharmacol. 2010. 10(3), 266-271, Jun. 2010, cited in Notice of Opposition against European Patent No. 3973987 (Application No. 21191120.1) filed on Oct. 9, 2024, on behalf of Secerna LLP.
D22—Al-Ramli et al. Th-17 cell-related cytokines' potential role in the pathogenesis of severe asthma. J Asthma. 2008 45, Suppl 1: 41-44, Jul. 2, 2009, cited in Notice of Opposition against European Patent No. 3973987 (Application No. 21191120.1) filed on Oct. 9, 2024, on behalf of Secerna LLP.
D23—Jennifer D Hamilton et al. Biomarkers elevated in atopic dermatitis (AD) are reduced by therapeutic blockade of IL-4 receptor alpha signalling with patients with moderate-to-severe AD. Abstract 1042, International Investigative Dermatology, XP055566280,, cited in Notice of Opposition against European Patent No. 3973987 (Application No. 21191120.1) filed on Oct. 9, 2024, on behalf of Secerna LLP. Edinburgh, May 8, 2013.
D24—EMEA Guideline for Industry—dose-response information to support drug registration ICH-E4, Nov. 1994, cited in Notice of Opposition against European Patent No. 3973987 (Application No. 21191120.1) filed on Oct. 9, 2024, on behalf of Secerna LLP.
D25—Dirks & Meibohm. Population Pharmacokinetics of Therapeutic Monoclonal Antibodies. Clin. Pharmacokinet. 2010; 49 (10) 633-659, cited in Notice of Opposition against European Patent No. 3973987 (Application No. 21191120.1) filed on Oct. 9, 2024, on behalf of Secerna LLP.
D26—Bai et al. A guide to rational dosing of monoclonal antibodies. Clin. Pharmacokinet. 2012, 52(2)119-135, cited in Notice of Opposition against European Patent No. 3973987 (Application No. 21191120.1) filed on Oct. 9, 2024, on behalf of Secerna LLP.
P1—U.S. Appl. No. 61/943,019 (Provisional), filed Feb. 21, 2014, cited in Notice of Opposition against European Patent No. 3973987 (Application No. 21191120.1) filed on Oct. 9, 2024, on behalf of Secerna LLP.
P2—EP 14306413.7, filed on Sep. 15, 2014, cited in Notice of Opposition against European Patent No. 3973987 (Application No. 21191120.1) filed on Oct. 9, 2024, on behalf of Secerna LLP.
P3—U.S. Appl. No. 62/077,669 (Provisional), filed Nov. 10, 2014, cited in Notice of Opposition against European Patent No. 3973987 (Application No. 21191120.1) filed on Oct. 9, 2024, on behalf of Secerna LLP.
A—Divisional application as filed, Apr. 30, 2022, cited in Notice of Opposition against European Patent No. 3973987 (Application No. 21191120.1) filed on Oct. 9, 2024, on behalf of Secerna LLP.
Notice of Opposition against European Patent No. 3973987 (Application No. 21191120.1) filed on Oct. 10, 2024, on behalf of Dr. Luigi Rumi.
TM1—WO 2015/127229 A1, published Aug. 27, 2015, cited in Notice of Opposition against European Patent No. 3973987 (Application No. 21191120.1) filed on Oct. 10, 2024, on behalf of Dr. Luigi Rumi.
TM2—U.S. Appl. No. 61/943,019 (Provisional), filed Feb. 21, 2014, cited in Notice of Opposition against European Patent No. 3973987 (Application No. 21191120.1) filed on Oct. 10, 2024, on behalf of Dr. Luigi Rumi.
TM3—EP 14306413, filed on Sep. 15, 2014, cited in Notice of Opposition against European Patent No. 3973987 (Application No. 21191120.1) filed on Oct. 10, 2024, on behalf of Dr. Luigi Rumi.
TM4—U.S. Appl. No. 62/077,669 (Provisional), filed Nov. 10, 2014, cited in Notice of Opposition against European Patent No. 3973987 (Application No. 21191120.1) filed on Oct. 10, 2024, on behalf of Dr. Luigi Rumi.
TM5—EP 3973987 A1, published Mar. 30, 2022 (divisional application as filed resulting in the opposed patent), cited in Notice of Opposition against European Patent No. 3973987 (Application No. 21191120.1) filed on Oct. 10, 2024, on behalf of Dr. Luigi Rumi.
TM6—WHO Drug Information vol. 26(4), 412, Dec. 9, 2012, cited in Notice of Opposition against European Patent No. 3973987 (Application No. 21191120.1) filed on Oct. 10, 2024, on behalf of Dr. Luigi Rumi.
TM7—Regeneron press release, "Sanofi and Regeneron report positive proof-of-concept data for dupilumab, an IL-4R alpha antibody in atopic dermatitis", Mar. 2, 2013, cited in Notice of Opposition against European Patent No. 3973987 (Application No. 21191120.1) filed on Oct. 10, 2024, on behalf of Dr. Luigi Rumi.
TM8—Pollart S.M. and Elward K.S. Overview of changes to asthma guidelines: diagnosis and screening. Am Fam Physician. May 1, 2009;79(9):761-7, cited in Notice of Opposition against European Patent No. 3973987 (Application No. 21191120.1) filed on Oct. 10, 2024, on behalf of Dr. Luigi Rumi.
TM9—"Global Strategy for Asthma Management and Prevention", Global Initiative for Asthma (GINA), 2011, cited in Notice of Opposition against European Patent No. 3973987 (Application No. 21191120.1) filed on Oct. 10, 2024, on behalf of Dr. Luigi Rumi.
TM10—Wenzel S. et al. Dupilumab in persistent asthma with elevated eosinophil levels. N Engl J Med. Jun. 27, 2013;368(26):2455-66. doi: 10.1056/NEJMoa1304048. Epub May 21, 2013, cited in Notice of Opposition against European Patent No. 3973987 (Application No. 21191120.1) filed on Oct. 10, 2024, on behalf of Dr. Luigi Rumi.
TM11—Mutschler Arzneimittelwirkungen—Lehrbuch der Pharmakologie and Toxikologie, p. 83, 3.3.1 Dosierung, "Initialdosis, Erhaltungsdosis", cited in Notice of Opposition against European Patent No. 3973987 (Application No. 21191120.1) filed on Oct. 10, 2024, on behalf of Dr. Luigi Rumi.
TM12—NCT01854047, Feb. 18, 2014 (v23), cited in Notice of Opposition against European Patent No. 3973987 (Application No. 21191120.1) filed on Oct. 10, 2024, on behalf of Dr. Luigi Rumi.

(56) References Cited

OTHER PUBLICATIONS

TM13—WO 2014/031610 A1, published Feb. 27, 2014, cited in Notice of Opposition against European Patent No. 3973987 (Application No. 21191120.1) filed on Oct. 10, 2024, on behalf of Dr. Luigi Rumi.
Notice of Opposition against European Patent No. 3973987 (Application No. 21191120.1) filed on Oct. 10, 2024, on behalf of Boult Wade Tennant LLP.
PA—Text of EP 21191120.1—divisional application as originally filed, cited in Notice of Opposition against European Patent No. 3973987 (Application No. 21191120.1) filed on Oct. 10, 2024, on behalf of Boult Wade Tennant LLP.
WO229—WO 2015/127229, published Aug. 27, 2015—PCT publication of the parent application, cited in Notice of Opposition against European Patent No. 3973987 (Application No. 21191120.1) filed on Oct. 10, 2024, on behalf of Boult Wade Tennant LLP.
D1—Wenzel et al., "Dupilumab in Persistent Asthma with Elevated Eosinophil Levels" New England Journal of Medicine, vol. 368 No. 26: 2455-2466, Jun. 27, 2013, cited in Notice of Opposition against European Patent No. 3973987 (Application No. 21191120.1) filed on Oct. 10, 2024, on behalf of Boult Wade Tennant LLP.
D2—Supplementary Appendix of Wenzel, 2013 (D1), cited in Notice of Opposition against European Patent No. 3973987 (Application No. 21191120.1) filed on Oct. 10, 2024, on behalf of Boult Wade Tennant LLP.
D3—NCT01854047 "An evaluation of dupilumab in subjects with moderate to severe uncontrolled asthma", Clinical trial study record, Version 23, Feb. 18, 2014, cited in Notice of Opposition against European Patent No. 3973987 (Application No. 21191120.1) filed on Oct. 10, 2024, on behalf of Boult Wade Tennant LLP.
D4—U.S. Pat. No. 8,075,887 B2, issued Dec. 13, 2011, cited in Notice of Opposition against European Patent No. 3973987 (Application No. 21191120.1) filed on Oct. 10, 2024, on behalf of Boult Wade Tennant LLP.
D5—GINA Guidelines, 2009, cited in Notice of Opposition against European Patent No. 3973987 (Application No. 21191120.1) filed on Oct. 10, 2024, on behalf of Boult Wade Tennant LLP.
D6—WHO Drug Information, vol. 26, No. 4, pp. 401-402 and 412, extract from "Proposed INN: List 108", published on Dec. 9, 2012, cited in Notice of Opposition against European Patent No. 3973987 (Application No. 21191120.1) filed on Oct. 10, 2024, on behalf of Boult Wade Tennant LLP.
D7—Radin, et al., Abstract 558, J Clin Immunol., Feb. 2013, cited in Notice of Opposition against European Patent No. 3973987 (Application No. 21191120.1) filed on Oct. 10, 2024, on behalf of Boult Wade Tennant LLP.
D8—Hashimoto and Bel, "Current treatment of severe asthma", Clinical & Experimental Allergy, vol. 42, pp. 693-705, 2012, cited in Notice of Opposition against European Patent No. 3973987 (Application No. 21191120.1) filed on Oct. 10, 2024, on behalf of Boult Wade Tennant LLP.
D9—Regeneron Press Release, May 21, 2013, cited in Notice of Opposition against European Patent No. 3973987 (Application No. 21191120.1) filed on Oct. 10, 2024, on behalf of Boult Wade Tennant LLP.
D10—Eurekalert! Press Release, "Monoclonal antibody appears effective and safe in asthma Phase IIa trial", May 21, 2013, cited in Notice of Opposition against European Patent No. 3973987 (Application No. 21191120.1) filed on Oct. 10, 2024, on behalf of Boult Wade Tennant LLP.
D11—Mould and Green, "Pharmacokinetics and Pharmacodynamics of Monoclonal Antibodies", Biodrugs, vol. 24(1), pp. 23-39, 2010, cited in Notice of Opposition against European Patent No. 3973987 (Application No. 21191120.1) filed on Oct. 10, 2024, on behalf of Boult Wade Tennant LLP.
D12—Galli et al., "Atopic Dermatitis and Asthma", Allergy Asthma Proc., vol. 28, pp. 540-543, 2007, cited in Notice of Opposition against European Patent No. 3973987 (Application No. 21191120.1) filed on Oct. 10, 2024, on behalf of Boult Wade Tennant LLP.
D13—NCT01312961 clinical trial study record, Version 36, Jan. 13, 2014, cited in Notice of Opposition against European Patent No. 3973987 (Application No. 21191120.1) filed on Oct. 10, 2024, on behalf of Boult Wade Tennant LLP.
D14—NCT01015027 clinical trial study record, Version 7, Jun. 13, 2013, cited in Notice of Opposition against European Patent No. 3973987 (Application No. 21191120.1) filed on Oct. 10, 2024, on behalf of Boult Wade Tennant LLP.
D15—NCT01484600 clinical trial study record, Version 2, Mar. 12, 2012, cited in Notice of Opposition against European Patent No. 3973987 (Application No. 21191120.1) filed on Oct. 10, 2024, on behalf of Boult Wade Tennant LLP.
D16—NCT01537653 clinical trial study record, Version 7, Dec. 5, 2013, cited in Notice of Opposition against European Patent No. 3973987 (Application No. 21191120.1) filed on Oct. 10, 2024, on behalf of Boult Wade Tennant LLP.
D17—NCT01537640 clinical trial study record, Version 6, Dec. 5, 2013, cited in Notice of Opposition against European Patent No. 3973987 (Application No. 21191120.1) filed on Oct. 10, 2024, on behalf of Boult Wade Tennant LLP.
D18—NCT01259323 clinical trial study record, Version 6, Oct. 2, 2012, cited in Notice of Opposition against European Patent No. 3973987 (Application No. 21191120.1) filed on Oct. 10, 2024, on behalf of Boult Wade Tennant LLP.
D19—NCT01385657 clinical trial study record, Version 4, Sep. 27, 2013, cited in Notice of Opposition against European Patent No. 3973987 (Application No. 21191120.1) filed on Oct. 10, 2024, on behalf of Boult Wade Tennant LLP.
P1—U.S. Appl. No. 61/943,019 (Provisional), filed Feb. 21, 2014, cited in Notice of Opposition against European Patent No. 3973987 (Application No. 21191120.1) filed on Oct. 10, 2024, on behalf of Boult Wade Tennant LLP.
P2—EP 14306413.7, filed on Sep. 15, 2014, cited in Notice of Opposition against European Patent No. 3973987 (Application No. 21191120.1) filed on Oct. 10, 2024, on behalf of Boult Wade Tennant LLP.
P3—U.S. Appl. No. 62/077,669 (Provisional), filed Nov. 10, 2014, cited in Notice of Opposition against European Patent No. 3973987 (Application No. 21191120.1) filed on Oct. 10, 2024, on behalf of Boult Wade Tennant LLP.
Notice of Opposition against European Patent No. 3973987 (Application No. 21191120.1) filed on Oct. 10, 2024, on behalf of Michaelski Hüttermann & Partner Patentanwalte mbD.
D1—Wenzel et al., 2013, cited in Notice of Opposition against European Patent No. 3973987 (Application No. 21191120.1) filed on Oct. 10, 2024, on behalf of Michaelski Hüttermann & Partner Patentanwalte mbD.
D2—Steinke et Borish, 2002, cited in Notice of Opposition against European Patent No. 3973987 (Application No. 21191120.1) filed on Oct. 10, 2024, on behalf of Michaelski Hüttermann & Partner Patentanwalte mbD.
D3—Wenzel et al., 2007, cited in Notice of Opposition against European Patent No. 3973987 (Application No. 21191120.1) filed on Oct. 10, 2024, on behalf of Michaelski Hüttermann & Partner Patentanwalte mbD.
D4—Corren et al., 2010, cited in Notice of Opposition against European Patent No. 3973987 (Application No. 21191120.1) filed on Oct. 10, 2024, on behalf of Michaelski Hüttermann & Partner Patentanwalte mbD.
D5—US 2003185821, cited in Notice of Opposition against European Patent No. 3973987 (Application No. 21191120.1) filed on Oct. 10, 2024, on behalf of Michaelski Hüttermann & Partner Patentanwalte mbD.
D6—Pollart et al., 2009, cited in Notice of Opposition against European Patent No. 3973987 (Application No. 21191120.1) filed on Oct. 10, 2024, on behalf of Michaelski Hüttermann & Partner Patentanwalte mbD.
D7—Wenzel et al., 2005, cited in Notice of Opposition against European Patent No. 3973987 (Application No. 21191120.1) filed on Oct. 10, 2024, on behalf of Michaelski Hüttermann & Partner Patentanwalte mbD.
D8—Study Record Version 22 of clinical trial NCT01854047, Feb. 3, 2014, cited in Notice of Opposition against European Patent No.

(56) References Cited

OTHER PUBLICATIONS 3973987 (Application No. 21191120.1) filed on Oct. 10, 2024, on behalf of Michaelski Hüttermann & Partner Patentanwalte mbD.
D9—Ramli et al., 2008, cited in Notice of Opposition against European Patent No. 3973987 (Application No. 21191120.1) filed on Oct. 10, 2024, on behalf of Michaelski Hüttermann & Partner Patentanwalte mbD.
D10—EP 3470432 A1, published Mar. 30, 2022, cited in Notice of Opposition against European Patent No. 3973987 (Application No. 21191120.1) filed on Oct. 10, 2024, on behalf of Michaelski Hüttermann & Partner Patentanwalte mbD.
D11—Chames et al. 2009, cited in Notice of Opposition against European Patent No. 3973987 (Application No. 21191120.1) filed on Oct. 10, 2024, on behalf of Michaelski Hüttermann & Partner Patentanwalte mbD.
D12—Bumbacea et al., 2004, cited in Notice of Opposition against European Patent No. 3973987 (Application No. 21191120.1) filed on Oct. 10, 2024, on behalf of Michaelski Hüttermann & Partner Patentanwalte mbD.
D13—Jenkins et al., 2003, cited in Notice of Opposition against European Patent No. 3973987 (Application No. 21191120.1) filed on Oct. 10, 2024, on behalf of Michaelski Hüttermann & Partner Patentanwalte mbD.
D14—Reasons for the decision in the parent patent (EP 15708991.3); dated Mar. 7, 2024, cited in Notice of Opposition against European Patent No. 3973987 (Application No. 21191120.1) filed on Oct. 10, 2024, on behalf of Michaelski Hüttermann & Partner Patentanwalte mbD.
D15—Greulich et al., 2010, cited in Notice of Opposition against European Patent No. 3973987 (Application No. 21191120.1) filed on Oct. 10, 2024, on behalf of Michaelski Hüttermann & Partner Patentanwalte mbD.
D16—Birkett et al., 1996, cited in Notice of Opposition against European Patent No. 3973987 (Application No. 21191120.1) filed on Oct. 10, 2024, on behalf of Michaelski Hüttermann & Partner Patentanwalte mbD.
D17—Pavord et al., 2012, cited in Notice of Opposition against European Patent No. 3973987 (Application No. 21191120.1) filed on Oct. 10, 2024, on behalf of Michaelski Hüttermann & Partner Patentanwalte mbD.
D18—Bousquet et al., 1990, cited in Notice of Opposition against European Patent No. 3973987 (Application No. 21191120.1) filed on Oct. 10, 2024, on behalf of Michaelski Hüttermann & Partner Patentanwalte mbD.
D19—Haldar et al., 2009, cited in Notice of Opposition against European Patent No. 3973987 (Application No. 21191120.1) filed on Oct. 10, 2024, on behalf of Michaelski Hüttermann & Partner Patentanwalte mbD.
D20—List of approved antibodies until 2014, cited in Notice of Opposition against European Patent No. 3973987 (Application No. 21191120.1) filed on Oct. 10, 2024, on behalf of Michaelski Hüttermann & Partner Patentanwalte mbD.
D21—Convolutum of clinical trial protolcols completed before the priority date, cited in Notice of Opposition against European Patent No. 3973987 (Application No. 21191120.1) filed on Oct. 10, 2024, on behalf of Michaelski Hüttermann & Partner Patentanwalte mbD.
D22—Tan et al., 2006, cited in Notice of Opposition against European Patent No. 3973987 (Application No. 21191120.1) filed on Oct. 10, 2024, on behalf of Michaelski Hüttermann & Partner Patentanwalte mbD.
D23—Onrust et al., 1999, cited in Notice of Opposition against European Patent No. 3973987 (Application No. 21191120.1) filed on Oct. 10, 2024, on behalf of Michaelski Hüttermann & Partner Patentanwalte mbD.
D24—Spratlin et al., 2010, cited in Notice of Opposition against European Patent No. 3973987 (Application No. 21191120.1) filed on Oct. 10, 2024, on behalf of Michaelski Hüttermann & Partner Patentanwalte mbD.
D25—Chmielowski, 2013, cited in Notice of Opposition against European Patent No. 3973987 (Application No. 21191120.1) filed on Oct. 10, 2024, on behalf of Michaelski Hüttermann & Partner Patentanwalte mbD.
D26—Cohenuram and Saif, 2007, cited in Notice of Opposition against European Patent No. 3973987 (Application No. 21191120.1) filed on Oct. 10, 2024, on behalf of Michaelski Hüttermann & Partner Patentanwalte mbD.
D27—Rau, 2002, cited in Notice of Opposition against European Patent No. 3973987 (Application No. 21191120.1) filed on Oct. 10, 2024, on behalf of Michaelski Hüttermann & Partner Patentanwalte mbD.
D28—Metzger-Filho, 2013, cited in Notice of Opposition against European Patent No. 3973987 (Application No. 21191120.1) filed on Oct. 10, 2024, on behalf of Michaelski Hüttermann & Partner Patentanwalte mbD.
D29—Frampton, 2013, cited in Notice of Opposition against European Patent No. 3973987 (Application No. 21191120.1) filed on Oct. 10, 2024, on behalf of Michaelski Hüttermann & Partner Patentanwalte mbD.
D30—Leyland-Jones, 2003, cited in Notice of Opposition against European Patent No. 3973987 (Application No. 21191120.1) filed on Oct. 10, 2024, on behalf of Michaelski Hüttermann & Partner Patentanwalte mbD.
D31—Washburn et al., 2006, cited in Notice of Opposition against European Patent No. 3973987 (Application No. 21191120.1) filed on Oct. 10, 2024, on behalf of Michaelski Hüttermann & Partner Patentanwalte mbD.
D32—WO 2014/031610 A1, published on Feb. 27, 2014, cited in Notice of Opposition against European Patent No. 3973987 (Application No. 21191120.1) filed on Oct. 10, 2024, on behalf of Michaelski Hüttermann & Partner Patentanwalte mbD.
D33—Wang et al., 2008, cited in Notice of Opposition against European Patent No. 3973987 (Application No. 21191120.1) filed on Oct. 10, 2024, on behalf of Michaelski Hüttermann & Partner Patentanwalte mbD.
D34—Mould and Sweeney 2007, cited in Notice of Opposition against European Patent No. 3973987 (Application No. 21191120.1) filed on Oct. 10, 2024, on behalf of Michaelski Hüttermann & Partner Patentanwalte mbD.
Notice of Opposition against European Patent No. 3973987 (Application No. 21191120.1) filed on Oct. 10, 2024, on behalf of Hampton Knowles Limited.
D1—Wenzel et al., N. Engl. J. Med., 2013, 368(26):2455-2466, cited in Notice of Opposition against European Patent No. 3973987 (Application No. 21191120.1) filed on Oct. 10, 2024, on behalf of Hampton Knowles Limited.
D5—WO 2014/031610 A1, published Feb. 27, 2014, cited in Notice of Opposition against European Patent No. 3973987 (Application No. 21191120.1) filed on Oct. 10, 2024, on behalf of Hampton Knowles Limited.
D7—pp. 401, 402 and 412 of WHO Drug Information, 2012, 26(4):401-471, cited in Notice of Opposition against European Patent No. 3973987 (Application No. 21191120.1) filed on Oct. 10, 2024, on behalf of Hampton Knowles Limited.
D8—EurekAlert! press release "Monoclonal antibody appears effective and safe in asthma Phase IIa trial", May 21, 2013, cited in Notice of Opposition against European Patent No. 3973987 (Application No. 21191120.1) filed on Oct. 10, 2024, on behalf of Hampton Knowles Limited.
D9—Chapter 19, "Dosage regimens", of Aulton's Pharmaceutics: The Science of Dosage Form Design, 2nd Edition, 2001, cited in Notice of Opposition against European Patent No. 3973987 (Application No. 21191120.1) filed on Oct. 10, 2024, on behalf of Hampton Knowles Limited.
D10—Panaccione and Ghosh, Ther. Adv. Gastroenterol., 2010, 3(3):179-189, which is a review article relating to the optimal use of biologics in the inflammatory disorder, Crohn's disease, cited in Notice of Opposition against European Patent No. 3973987 (Application No. 21191120.1) filed on Oct. 10, 2024, on behalf of Hampton Knowles Limited.
D11—Regeneron press release "Sanofi and Regeneron report positive proof-of-concept data for dupilumab, an IL-4R alpha antibody,

(56) References Cited

OTHER PUBLICATIONS in atopic dermatitis", dated Mar. 2, 2013, cited in Notice of Opposition against European Patent No. 3973987 (Application No. 21191120.1) filed on Oct. 10, 2024, on behalf of Hampton Knowles Limited.
DYC01—pp. 159 to 162 of Rispens and Vidarsson, Antibody Fc: Linking Adaptive and Innate Immunity, Chapter 9, "Human IgG Subclasses", pp. 159 to 162, 2013; and evidence of its publication date, cited in Notice of Opposition against European Patent No. 3973987 (Application No. 21191120.1) filed on Oct. 10, 2024, on behalf of Hampton Knowles Limited.
DYC02—Interlocutory decision in Opposition proceedings for EP3107575B, dated Mar. 7, 2024, cited in Notice of Opposition against European Patent No. 3973987 (Application No. 21191120.1) filed on Oct. 10, 2024, on behalf of Hampton Knowles Limited.
DYC03—NCT01854047 clinical trial protocol version 22 (Feb. 3, 2014), cited in Notice of Opposition against European Patent No. 3973987 (Application No. 21191120.1) filed on Oct. 10, 2024, on behalf of Hampton Knowles Limited.
DYC04—Regeneron press release "Sanofi and Regeneron announce publication of positive Phase 2A results of dupilumab in asthma in the New England Journal of Medicine", May 21, 2013, cited in Notice of Opposition against European Patent No. 3973987 (Application No. 21191120.1) filed on Oct. 10, 2024, on behalf of Hampton Knowles Limited.
DYC05—Swanson et al., World Allergy Organization Journal, 2014, 7(Suppl 1):P13, poster abstract 1023, cited in Notice of Opposition against European Patent No. 3973987 (Application No. 21191120.1) filed on Oct. 10, 2024, on behalf of Hampton Knowles Limited.
DYC06—Radin et al., J Allergy Clin Immunol, 2013, 131(2_Suppl):AB158, abstract 558, cited in Notice of Opposition against European Patent No. 3973987 (Application No. 21191120.1) filed on Oct. 10, 2024, on behalf of Hampton Knowles Limited.
DYC07—Mould and Sweeney, Current Opinion in Drug Discovery & Development, 2007, 10(1):84-96, cited in Notice of Opposition against European Patent No. 3973987 (Application No. 21191120.1) filed on Oct. 10, 2024, on behalf of Hampton Knowles Limited.
DYC08—Wang et al., Clinical Pharmacology & Therapeutics, 2008, 84(5):548-558, cited in Notice of Opposition against European Patent No. 3973987 (Application No. 21191120.1) filed on Oct. 10, 2024, on behalf of Hampton Knowles Limited.
DYC09—Fracasso et al., Clin Cancer Res, 2007, 13(3):986-993, cited in Notice of Opposition against European Patent No. 3973987 (Application No. 21191120.1) filed on Oct. 10, 2024, on behalf of Hampton Knowles Limited.
DYC10—Mould et al., Br J Clin Pharmacol, 2007, 64(3):278-291, cited in Notice of Opposition against European Patent No. 3973987 (Application No. 21191120.1) filed on Oct. 10, 2024, on behalf of Hampton Knowles Limited.
DYC11—Sohn et al., Br J Clin Pharmacol, 2014, 78(3):477-487, cited in Notice of Opposition against European Patent No. 3973987 (Application No. 21191120.1) filed on Oct. 10, 2024, on behalf of Hampton Knowles Limited.
DYC12—Dostalek et al., Clin Pharmacokinet, 2013, 52:83-124, cited in Notice of Opposition against European Patent No. 3973987 (Application No. 21191120.1) filed on Oct. 10, 2024, on behalf of Hampton Knowles Limited.
DYC13—Corren et al., Am. J. Respir. Crit. Care Med., 2010, 181:788-796, cited in Notice of Opposition against European Patent No. 3973987 (Application No. 21191120.1) filed on Oct. 10, 2024, on behalf of Hampton Knowles Limited.
DYC14—Borish, Am. J. Respir. Crit. Care Med., 2010, 181:769-772, cited in Notice of Opposition against European Patent No. 3973987 (Application No. 21191120.1) filed on Oct. 10, 2024, on behalf of Hampton Knowles Limited.
DYC15—Wenzel, Clinical & Experimental Allergy, 2012, 42:650-658, cited in Notice of Opposition against European Patent No. 3973987 (Application No. 21191120.1) filed on Oct. 10, 2024, on behalf of Hampton Knowles Limited.
DYC16—Hashimoto, The Lancet, 2012, 380:626-627, cited in Notice of Opposition against European Patent No. 3973987 (Application No. 21191120.1) filed on Oct. 10, 2024, on behalf of Hampton Knowles Limited.
DYC17—Szefler et al., J Allergy Clin Immunol, 2012, 129:S9-23, cited in Notice of Opposition against European Patent No. 3973987 (Application No. 21191120.1) filed on Oct. 10, 2024, on behalf of Hampton Knowles Limited.
Matsumoto, "Serum periostin: a novel biomarker for asthma management", Allergol Int., Jun. 2014, 63(2): 153-160, Epub Apr. 25, 2014. doi: 10.2332/allergolint. 13-RAI-0678.

* cited by examiner

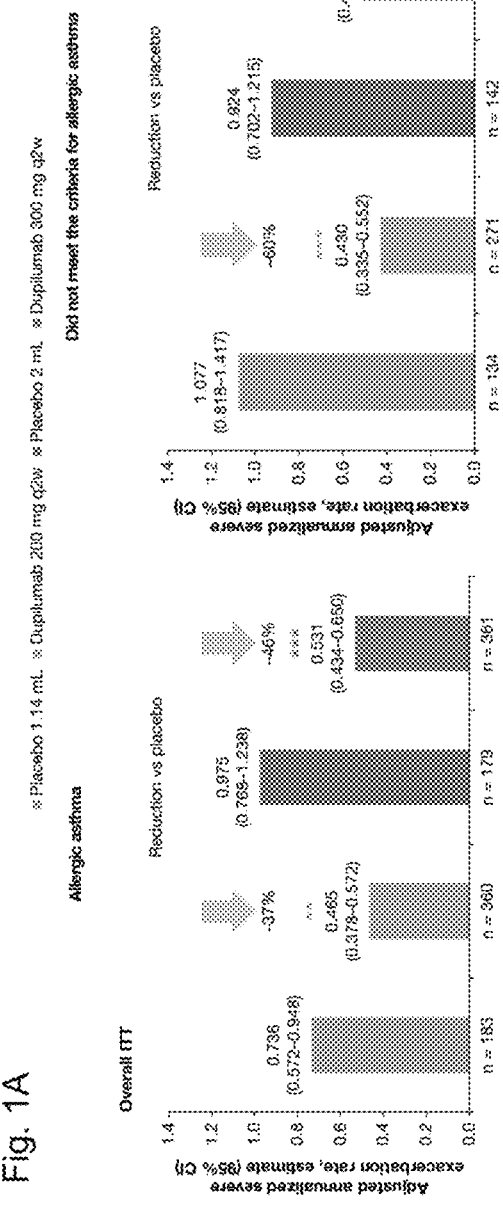
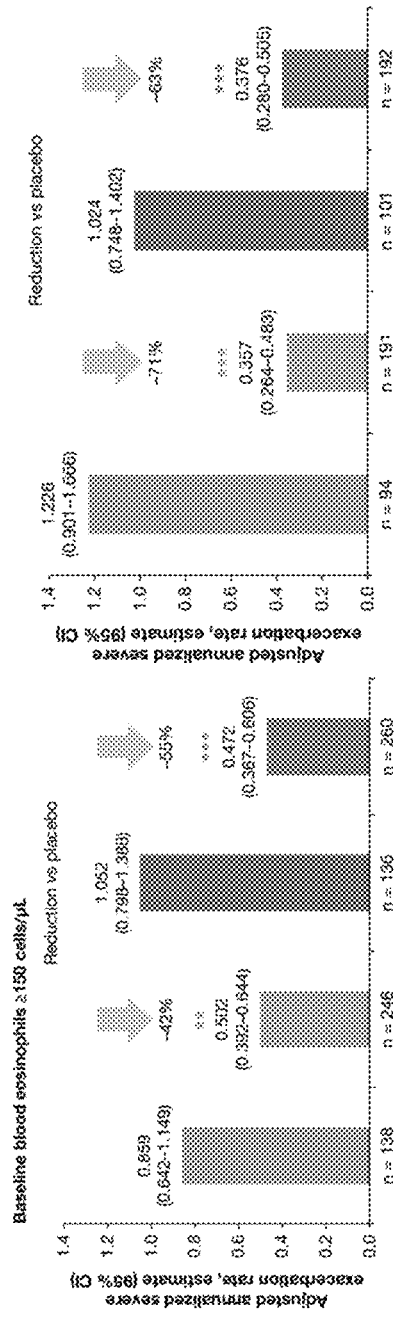
Fig. 1A
Fig. 1B

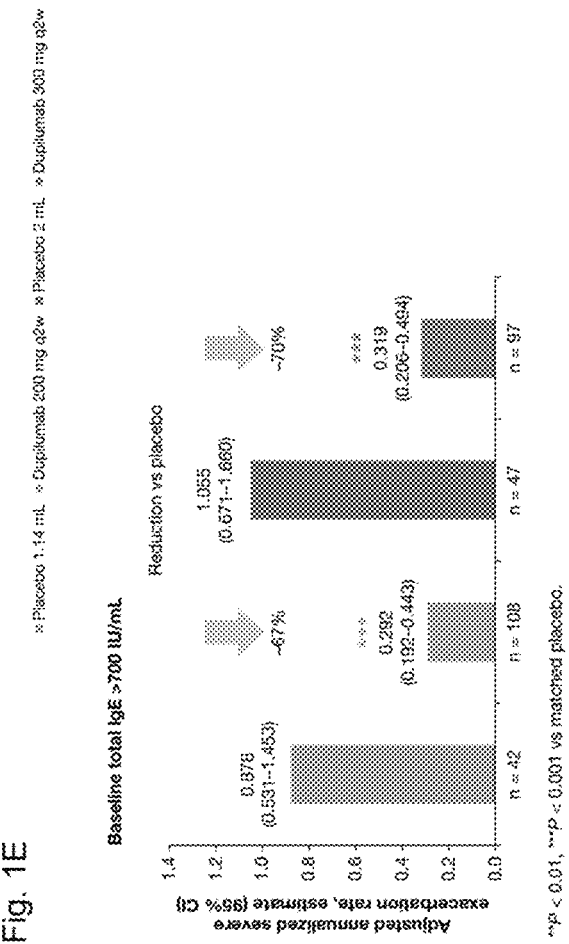

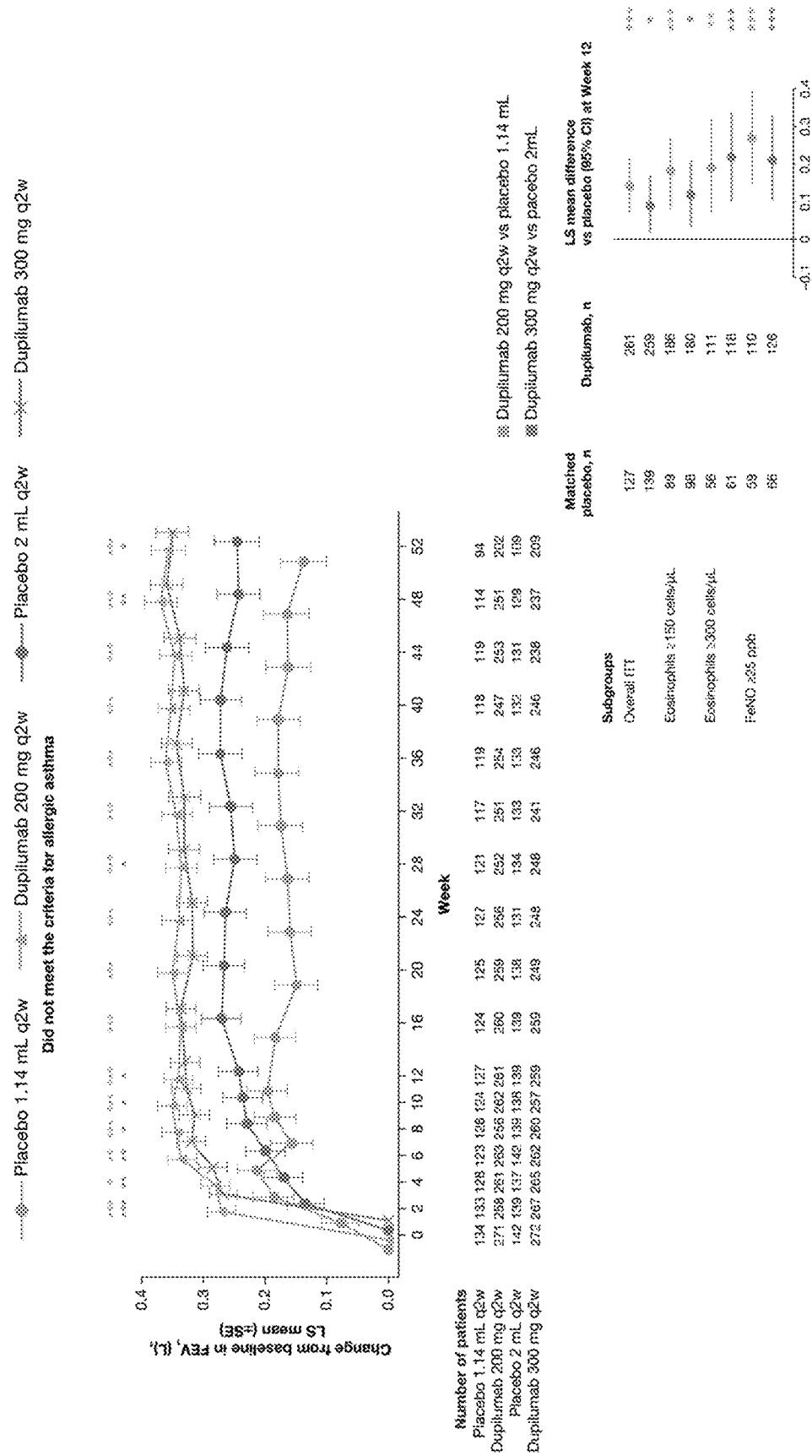

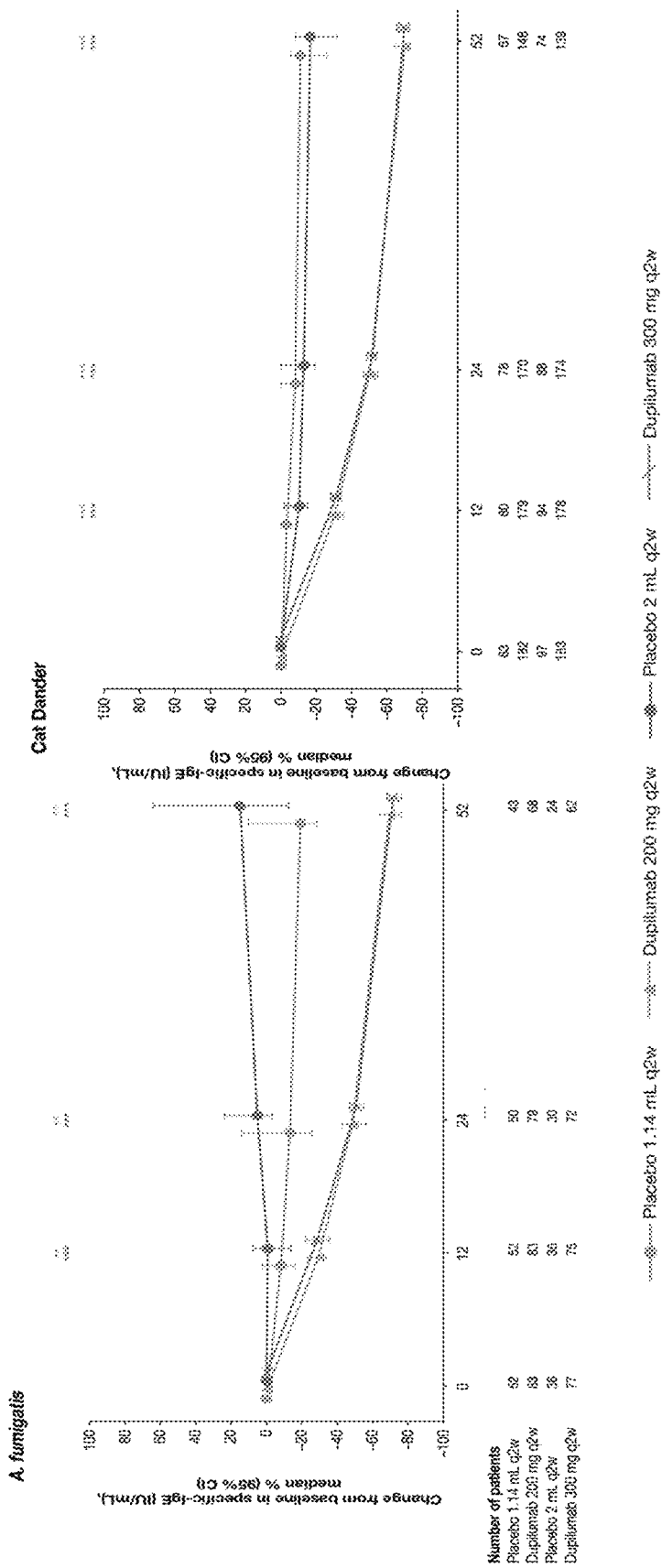

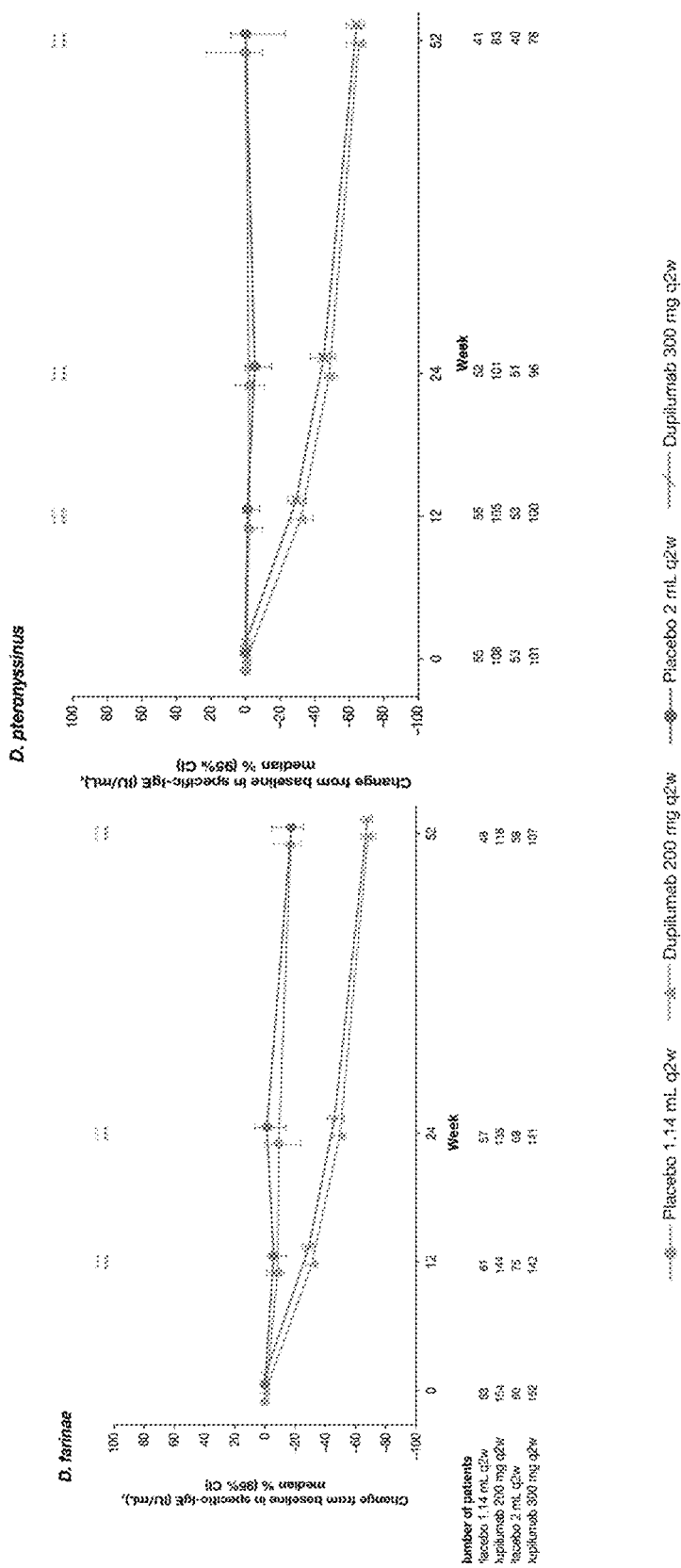

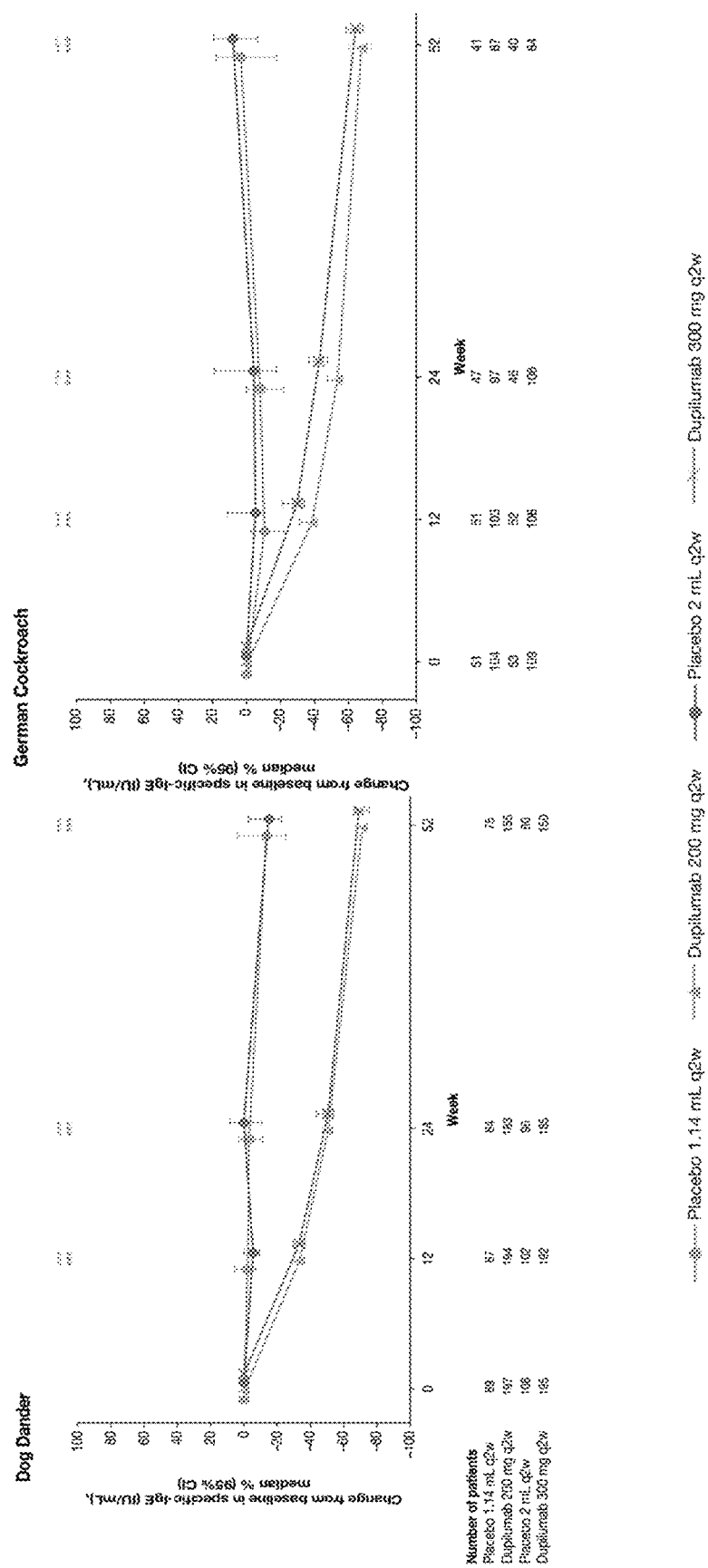

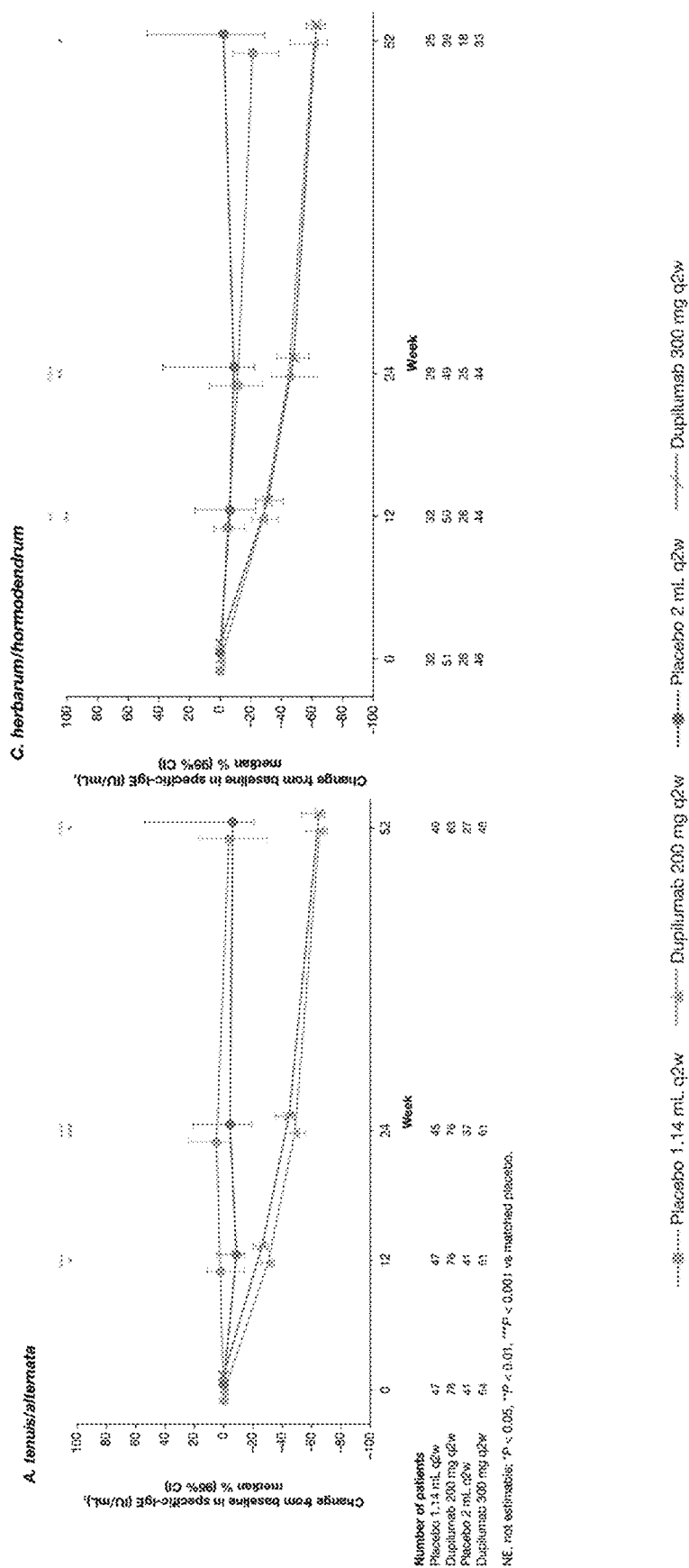

Fig. 7

Annualized event rate of severe exacerbation during 52-week treatment period for patients with allergic bronchopulmonary aspergillosis (ABPA) - ITT population

| | Combined | |
|---|---|---|
| | Placebo (N=12) | Dupilumab (N=18) |
| Patients with ≥1 severe exacerbation events [n(%)] | | |
| Number | 12 | 18 |
| No | 4 (33.3%) | 15 (83.3%) |
| Yes | 8 (66.7%) | 3 (16.7%) |
| Number of severe exacerbation events | | |
| 0 | 4 (33.3%) | 15 (83.3%) |
| 1 | 3 (25.0%) | 2 (11.1%) |
| 2 | 2 (16.7%) | 1 (5.6%) |
| 3 | 2 (16.7%) | 0 |
| ≥4 | 1 (8.3%) | 0 |
| Total number of severe exacerbation events | 17 | 4 |
| Total patient-years followed | 12.0 | 17.8 |
| Unadjusted annualized rate of severe exacerbation events [a] | | |
| Estimate [b] (95% CI) | 1.421 | 0.225 |
| Relative risk [b] vs. matching placebo (95% CI) | 1.419 (0.783, 2.574) | 0.225 (0.078, 0.649) |
| P-value [b] vs. matching placebo | | 0.159 (0.047, 0.534) |
| Risk difference [d] vs. matching placebo (95% CI) | | 0.0043 |
| | | -1.194 (-2.072, -0.317) |
| Adjusted annualized rate of severe exacerbation events | | |
| Estimate [c] (95% CI) | 1.180 (0.507, 2.657) | 0.220 (0.075, 0.647) |
| Relative risk [c] vs. matching placebo (95% CI) | | 0.189 (0.052, 0.693) |
| P-value [c] vs. matching placebo | | 0.0140 |
| Risk difference [d] vs. matching placebo (95% CI) | | -0.940 (-1.908, 0.027) |

Fig. 8

| Pre-bronchodilator FEV1 (L) | Placebo (N=12) | Dupilumab (N=18) |
|---|---|---|
| Baseline | | |
| Value | | |
| Number | 12 | 18 |
| Mean (SD) | 1.59 (0.49) | 2.00 (0.68) |
| Median | 1.51 | 1.84 |
| Q1 : Q3 | 1.23 : 1.80 | 1.44 : 2.33 |
| Min : Max | 1.0 : 2.5 | 1.1 : 3.4 |
| Week 24 | | |
| Change from baseline | | |
| Number | 11 | 18 |
| Mean (SD) | 0.07 (0.30) | 0.40 (0.41) |
| LS Mean (SE) [a] | 0.07 (0.10) | 0.40 (0.08) |
| LS Mean Diff vs. matching placebo (95% CI) [a] | | 0.33 (0.05, 0.60) |
| P-value vs. matching placebo [a] | | 0.0202 |
| LS Mean (SE) [b] | 0.11 (0.11) | 0.37 (0.08) |
| LS Mean Diff vs. matching placebo (95% CI) [b] | | 0.26 (-0.04, 0.56) |
| P-value vs. matching placebo [b] | | 0.0867 |
| Week 52 | | |
| Change from baseline | | |
| Number | 11 | 15 |
| Mean (SD) | 0.08 (0.24) | 0.51 (0.59) |
| LS Mean (SE) [a] | 0.14 (0.13) | 0.55 (0.11) |
| LS Mean Diff vs. matching placebo (95% CI) [a] | | 0.41 (0.08, 0.75) |
| P-value vs. matching placebo [a] | | 0.0181 |
| LS Mean (SE) [b] | 0.18 (0.13) | 0.51 (0.10) |
| LS Mean Diff vs. matching placebo (95% CI) [b] | | 0.33 (-0.02, 0.68) |
| P-value vs. matching placebo [b] | | 0.0654 |

Combined

Fig. 9

|  | Combined | |
|---|---|---|
|  | Placebo (N=12) | Dupilumab (N=18) |
| Total IgE | | |
| Baseline | | |
| Value | | |
| Number | 12 | 18 |
| Mean (SD) | 2128.6 (676.2) | 3335.7 (1697.7) |
| Median | 2148.0 | 3383.0 |
| 95% CI of median | 1441.0 , 2778.0 | 1480.0 , 5000.0 |
| Q1 : Q3 | 1445.5 : 2734.0 | 1480.0 : 5000.0 |
| Min : Max | 1014 : 3749 | 1008 : 5000 |
| Total IgE | Placebo (N=12) | Dupilumab (N=18) |
| Week 52 | | |
| Value | | |
| Number | 11 | 14 |
| Mean (SD) | 1719.3 (925.6) | 1461.5 (1485.1) |
| Median | 1714.0 | 691.5 |
| 95% CI of median | 727.0 , 3046.0 | 323.0 , 2617.0 |
| Q1 : Q3 | 727.0 : 2402.0 | 323.0 : 2440.0 |
| Min : Max | 630 : 3084 | 126 : 4524 |
| Change from baseline | | |
| Number | 11 | 14 |
| Mean (SD) | -350.3 (860.1) | -1903.1 (1209.2) |
| Median | -701.0 | -1633.5 |
| 95% CI of median | -976.0 , 1274.0 | -2560.0 , -868.0 |
| Q1 : Q3 | -976.0 : -36.0 | -2560.0 : -882.0 |
| Min : Max | -1704 : 1562 | -4637 : -476 |
| P-value a | | 0.0047 |

Fig. 10

| | Combined | |
|---|---|---|
| | Placebo (N=12) | Dupilumab (N=18) |
| Aspergillus fumigatus IgE | | |
| Baseline | | |
| Value | | |
| Number | 12 | 18 |
| Mean (SD) | 11,978 (17,026) | 7,271 (10,336) |
| Median | 2,955 | 2,435 |
| 95% CI of median | 0.520, 28.860 | 0.640, 11.280 |
| Q1 : Q3 | 0.810 : 18.905 | 0.640 : 11.280 |
| Min : Max | 0.43 : 50.40 | 0.42 : 35.10 |

| | Placebo (N=12) | Dupilumab (N=18) |
|---|---|---|
| Aspergillus fumigatus IgE | | |
| Week 52 | | |
| Value | | |
| Number | 11 | 14 |
| Mean (SD) | 13,493 (28,292) | 1,606 (2,489) |
| Median | 4.610 | 0.825 |
| 95% CI of median | 0.630, 21.500 | 0.120, 2.570 |
| Q1 : Q3 | 0.630 : 10.600 | 0.120 : 1.450 |
| Min : Max | 0.15 : 96.70 | 0.05 : 9.40 |
| Change from baseline | | |
| Number | 11 | 14 |
| Mean (SD) | 0.901 (25.371) | -4.527 (6.120) |
| Median | -0.590 | -1.610 |
| 95% CI of median | -4.480, 3.510 | -3.390, -0.360 |
| Q1 : Q3 | -4.480 : 1.110 | -3.390 : -0.550 |
| Min : Max | -39.60 : 67.90 | -19.50 : -0.07 |
| P-value$^a$ | | 0.2728 |

Fig. 11

| | Combined | |
|---|---|---|
| | Placebo (N=12) | Dupilumab (N=18) |
| FeNO | | |
| Baseline | | |
| Value | | |
| Number | 12 | 18 |
| Mean (SD) | 39.1 (27.2) | 50.3 (30.1) |
| Median | 31.0 | 49.0 |
| 95% CI of median | 19.0, 53.0 | 24.0, 68.0 |
| Q1 : Q3 | 19.5 : 53.0 | 24.0 : 68.0 |
| Min : Max | 10 : 104 | 9 : 129 |
| FeNO | Placebo (N=12) | Dupilumab (N=18) |
| Week 52 | | |
| Value | | |
| Number | 8 | 13 |
| Mean (SD) | 27.5 (16.4) | 18.8 (8.1) |
| Median | 25.0 | 18.0 |
| 95% CI of median | 10.0, 56.0 | 12.0, 26.0 |
| Q1 : Q3 | 15.0 : 38.0 | 13.0 : 29.0 |
| Min : Max | 8 : 56 | 6 : 33 |
| Change from baseline | | |
| Number | 8 | 13 |
| Mean (SD) | -7.0 (19.6) | -32.3 (31.2) |
| Median | -3.0 | -19.0 |
| 95% CI of median | -34.0, 16.0 | -51.0, -10.0 |
| Q1 : Q3 | -29.5 : 8.0 | -48.0 : -11.0 |
| Min : Max | -35 : 16 | -111 : 4 |
| P-value a | | 0.0485 |

*P < 0.05 vs placebo.
ABPA, allergic bronchopulmonary aspergillosis; CI, confidence interval; ITT, intention-to-treat; q2w, every 2 weeks.

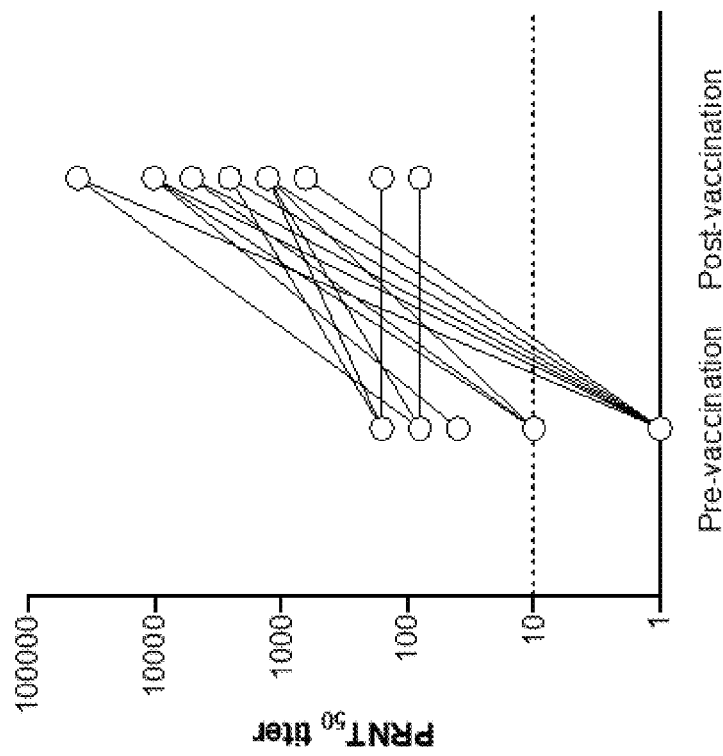

METHODS FOR TREATING OR PREVENTING ASTHMA BY ADMINISTERING AN IL-4R ANTAGONIST

RELATED APPLICATIONS

This application claims the benefit of priority of U.S. Provisional Application No. 63/004,084, filed Apr. 2, 2020, U.S. Provisional Application No. 62/877,031, filed Jul. 22, 2019, U.S. Provisional Application No. 62/874,747, filed Jul. 16, 2019, and European Application No. 20315237.6, filed May 7, 2020, the contents of which are incorporated by reference in their entireties for all purposes.

FIELD OF THE INVENTION

The invention relates to the treatment and/or prevention of asthma, e.g., allergic asthma, and related conditions, e.g., allergic bronchopulmonary aspergillosis (ABPA). The invention relates to the administration of an interleukin-4 receptor (IL-4R) antagonist to treat or prevent asthma, e.g., allergic asthma, asthma associated with ABPA, or the like, in a patient in need thereof. The invention also relates to the administration of an interleukin-4 receptor (IL-4R) antagonist to treat or prevent ABPA in a patient in need thereof, e.g., ABPA comorbid with asthma, ABPA comorbid with cystic fibrosis and/or ABPA comorbid with both asthma and cystic fibrosis.

BACKGROUND

Asthma is a chronic inflammatory disease of the airways characterized by airway hyper responsiveness, acute and chronic bronchoconstriction, airway edema and mucus plugging. The inflammation component of asthma is thought to involve many cell types, including mast cells, eosinophils, T lymphocytes, neutrophils, epithelial cells, and their biological products. Patients with asthma most often present with symptoms of wheezing, shortness of breath, cough, and chest tightness. For most asthma patients, a regimen of controller therapy and bronchodilator therapy provides adequate long-term control. Inhaled corticosteroids (ICS) are considered the "gold standard" in controlling asthma symptoms, and inhaled beta2-agonists are the most effective bronchodilators currently available. Studies have shown that combination therapy of an ICS with an inhaled long-acting beta2-agonist (LABA) provides better asthma control than high doses of ICS alone. Consequently, combination therapy has been the recommended treatment for subjects who are not controlled on low doses of ICS alone.

Nonetheless, it is estimated that 5% to 10% of the population with asthma has symptomatic disease despite maximum recommended treatment with combinations of anti-inflammatory and bronchodilator drugs. Furthermore, this severe asthma population accounts for up to 50% of the total health cost through hospital admissions, use of emergency services, and unscheduled physician visits. There is an unmet need for a new therapy in this severe asthma population as many of these patients are poorly responsive to ICS due to a number of cellular and molecular mechanisms. In addition, the long term adverse effects of systemic and inhaled corticosteroids on bone metabolism, adrenal function, and growth in children lead to attempts to minimize the amount of corticosteroid usage. Although a large portion of asthma patients are managed reasonably well with current treatments, patients with severe uncontrolled asthma (e.g., severe corticosteroid-refractory asthma or steroid-intolerant asthma) have few therapeutic treatment options that can adequately control the disease. The consequence of unresponsiveness to therapy or lack of compliance with therapy is loss of asthma control and ultimately asthma exacerbation.

An estimated 45% of patients with severe asthma require systemic glucocorticoids to control their disease, and to prevent life-threatening exacerbations associated with increased risk of permanent damage to lung tissue, progressive fixed airway obstruction, and accelerated decline in lung function. However, systemic glucocorticoids act non-selectively and are associated with significant multi-organ toxicities and broad immunosuppression. There is a need for safer and more effective targeted therapies that prevent exacerbations and lung function impairment, improve asthma symptoms and control, and reduce or obviate the need for oral glucocorticoids.

Approximately 20% of patients with asthma have uncontrolled, moderate-to-severe disease with recurrent exacerbations and persistent symptoms despite maximized standard-of-care controller therapy. This population is at an increased risk of morbidity (especially exacerbations) and accounts for significant healthcare resources. These patients have substantially reduced lung function, despite maximum treatment, and are destined to inexorably further lose lung function. No currently approved treatments have been shown to slow this inexorable decline in these patients, or to consistently and meaningfully increase lung function.

Type 2-high asthma is the most prevalent type of persistent, uncontrolled asthma (Fahy (2015) Nat. Rev. Immunol. 15:57-65). It includes the overlapping phenotypes allergic asthma (characterized by increased expression of specific immunoglobulin E (IgE) to aeroallergens) and eosinophilic asthma (characterized by blood and/or airway/tissue eosinophilia) (Fahy, Supra; Campo et al. (2013) J. Investig. Allergol. Clin. Immunol. 23:76-88; Wenzel (2012) Clin Exp Allergy 42:650-8).

Allergic sensitization is a strong risk factor for asthma inception and severity in children and in adults (Gough et al. (2015) Pediatr. Allergy Immunol. 26:431-437). Current allergic asthma therapies that address symptoms and the ongoing inflammatory process of the disease do not affect the underlying, dysregulated immune response and, therefore, are very limited in controlling allergic asthma progression (Dhami et al. (2017) Eur. J. Allergy Clin. Immunol. 72(12):1825-1848)).

ABPA is an allergic pulmonary disorder caused by hypersensitivity to *Aspergillus* species (e.g., *A. fumigatus*) colonized in airways. ABPA most often occurs in subjects having asthma or cystic fibrosis.

ABPA is clinically characterized by wheezing, dyspnea, respiratory exacerbations, bronchial hyperreactivity, hemoptysis or productive cough (expectoration of brownish black mucus plugs in 31 to 69% of patients), central bronchiectasis with mucus plugging, and markedly elevated IgE and blood and tissue eosinophilia.

There are currently no approved drugs specific for ABPA. The current mainstay of treatment is systemic corticosteroids, and antifungals are used as an adjuvant therapy. However, greater than 50% of ABPA patients are under-treated or not treated effectively either due to limitations in treatment efficacy or the considerable side effects of corticosteroids. Accordingly, patients with ABPA have a high unmet medical need.

Cystic fibrosis (CF), also known as mucoviscidosis, is a genetic disorder that affects mostly the lungs, but also the pancreas, liver, kidneys, and intestine. Long-term issues include difficulty breathing and coughing up mucus as a result of frequent lung infections. Other signs and symptoms include sinus infections, poor growth, fatty stool, clubbing of the fingers and toes, and infertility in males among others. Subjects may have varying degrees of symptoms.

CF is inherited in an autosomal recessive manner. It is caused by the presence of mutations in both copies of the gene for the cystic fibrosis transmembrane conductance regulator (CFTR) protein. Those with a single working copy are carriers and otherwise mostly normal. CFTR is involved in production of sweat, digestive fluids, and mucus. When CFTR is not functional, secretions, which are usually thin, instead become thick. The condition is diagnosed by a sweat test and genetic testing. Screening of infants at birth takes place in some areas of the world.

There is no cure for cystic fibrosis. Lung infections are treated with antibiotics which may be given intravenously, inhaled, or by mouth. Sometimes the antibiotic azithromycin is used long term. Inhaled hypertonic saline and salbutamol may also be useful. Lung transplantation may be an option if lung function continues to worsen. Pancreatic enzyme replacement and fat-soluble vitamin supplementation are important, especially in the young. The average life expectancy is between 42 and 50 years in the developed world. While CF is a multi-organ disease, lung problems are the dominant cause of morbidity and mortality. Other CF symptoms include pancreatic insufficiency, intestinal obstruction, elevated electrolyte levels in sweat (the basis of the most common diagnostic test), and male infertility. CF is most common among people of Northern European ancestry and affects about one out of every 2,500 to 4,000 newborns. About one in 25 people are carriers. While treatments for CF are available, more effective therapies are needed.

A need exists for novel targeted therapies for the treatment and/or prevention of asthma, e.g., allergic asthma, asthma associated with ABPA, and the like, as well as disorders such as ABPA, including ABPA that is comorbid with CF, ABPA that is comorbid with asthma, and ABPA that is comorbid with both asthma and CF.

BRIEF SUMMARY OF THE INVENTION

According to one aspect, a method for treating a subject having allergic asthma is provided. The method includes administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a total serum IgE level of at least about 700 IU/mL.

In certain exemplary embodiments, the subject has a baseline blood eosinophil count of at least about 150 cells/µl or at least about 300 cells/µl.

In certain exemplary embodiments, the subject has a baseline fractional exhaled nitric oxide (FeNO) level of at least about 25 ppb, or at least about 20 ppb.

In certain exemplary embodiments, the subject has an allergen-specific IgE level of at least about 0.35 kU/L.

In certain exemplary embodiments, the allergen is selected from the group consisting of animal (e.g., dust mite (e.g., *Dermatophagoides farinae* or *Dermatophagoides pteronyssinus*), cockroach, cat or dog), fungus (e.g., *Alternaria alternata*, *Cladosporium herbarum* or *Aspergillus fumigatus*) and plant.

In certain exemplary embodiments, the allergen is selected from the group consisting of cat dander, dog dander, German cockroach and Oriental cockroach.

In certain exemplary embodiments, the antibody or antigen-binding fragment thereof is administered to the subject as a loading dose followed by a plurality maintenance doses.

In certain exemplary embodiments, the antibody or antigen-binding fragment thereof is administered using an auto-injector, a needle and syringe, or a pen.

In certain exemplary embodiments, a maintenance dose of antibody or antigen-binding fragment thereof is administered once every other week (q2w).

In certain exemplary embodiments, the loading dose is about 600 mg of the antibody or the antigen-binding fragment thereof. In certain exemplary embodiments, the loading dose is about 400 mg of the antibody or the antigen-binding fragment thereof.

In certain exemplary embodiments, each maintenance dose of antibody or antigen-binding fragment thereof is about 300 mg of the antibody or the antigen-binding fragment thereof.

In certain exemplary embodiments, each maintenance dose of the antibody or antigen-binding fragment thereof is about 200 mg of the antibody or the antigen-binding fragment thereof.

In certain exemplary embodiments, the maintenance doses of the antibody or antigen-binding fragment thereof are administered for at least 24 weeks.

In certain exemplary embodiments, a first maintenance dose of antibody or antigen-binding fragment thereof is administered two weeks after the loading dose of antibody or antigen-binding fragment thereof.

In certain exemplary embodiments, treatment results in a reduction in annualized severe asthma exacerbations.

In certain exemplary embodiments, treatment results in an improvement in lung function as measured by forced expiratory volume ($FEV_1$) or by forced expiratory flow at 25-75% of the pulmonary volume (FEF25-75%).

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has moderate-to-severe uncontrolled allergic asthma.

In certain exemplary embodiments, the subject exhibits comorbid cystic fibrosis. In certain exemplary embodiments, the subject exhibits comorbid allergic asthma and comorbid cystic fibrosis.

In certain exemplary embodiments, the subject is an adult. In certain exemplary embodiments, the subject is an adolescent. In certain exemplary embodiments, the subject is a child.

According to another aspect, a method for treating a subject having allergic asthma is provided, comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a baseline blood eosinophil level of at least about 300 cells/µl.

In certain exemplary embodiments, the subject has a baseline fractional exhaled nitric oxide (FeNO) level of at least about 25 ppb, or at least about 20 ppb.

In certain exemplary embodiments, the subject has a total serum IgE level of at least about 700 IU/mL.

In certain exemplary embodiments, the subject has an allergen-specific IgE level of at least about 0.35 kU/L.

In certain exemplary embodiments, the allergen is selected from the group consisting of dust mite, cockroach, cat dander, dog dander, *Dermatophagoides farinae, Dermatophagoides pteronyssinus, Alternaria alternata, Cladosporium herbarum, Aspergillus fumigatus*, German cockroach and Oriental cockroach.

In certain exemplary embodiments, the antibody or antigen-binding fragment thereof is administered to the subject as a loading dose followed by a plurality maintenance doses.

In certain exemplary embodiments, the antibody or antigen-binding fragment thereof is administered using an auto-injector, a needle and syringe, or a pen.

In certain exemplary embodiments, a maintenance dose of antibody or antigen-binding fragment thereof is administered once every other week (q2w)

In certain exemplary embodiments, the loading dose is about 600 mg of the antibody or the antigen-binding fragment thereof. In certain exemplary embodiments, the loading dose is about 400 mg of the antibody or the antigen-binding fragment thereof.

In certain exemplary embodiments, each maintenance dose of antibody or antigen-binding fragment thereof is about 300 mg of the antibody or the antigen-binding fragment thereof. In certain exemplary embodiments, each maintenance dose of the antibody or antigen-binding fragment thereof is about 200 mg of the antibody or the antigen-binding fragment thereof.

In certain exemplary embodiments, the maintenance doses of the antibody or antigen-binding fragment thereof are administered for at least 24 weeks.

In certain exemplary embodiments, a first maintenance dose of antibody or antigen-binding fragment thereof is administered two weeks after the loading dose of antibody or antigen-binding fragment thereof.

In certain exemplary embodiments, treatment results in a reduction in annualized severe asthma exacerbations.

In certain exemplary embodiments, treatment results in an improvement in lung function as measured by forced expiratory volume ($FEV_1$) or by forced expiratory flow at 25-75% of the pulmonary volume (FEF25-75%).

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has moderate-to-severe uncontrolled allergic asthma.

In certain exemplary embodiments, the subject exhibits comorbid cystic fibrosis. In certain exemplary embodiments, the subject exhibits comorbid allergic asthma and comorbid cystic fibrosis.

In certain exemplary embodiments, the subject is an adult. In certain exemplary embodiments, the subject is an adolescent. In certain exemplary embodiments, the subject is a child.

According to another aspect, a method for treating a subject having allergic asthma is provided, comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a baseline fractional exhaled nitric oxide (FeNO) level of at least about 20 ppb.

In certain exemplary embodiments, the subject has a baseline FeNO level of at least 25 ppb.

In certain exemplary embodiments, the subject has a baseline blood eosinophil count of at least about 150 cells/µl. In certain exemplary embodiments, the subject has a baseline blood eosinophil count of at least about 300 cells/µl.

In certain exemplary embodiments, the subject has a total serum IgE level of at least about 700 IU/mL.

In certain exemplary embodiments, the subject has an allergen-specific IgE level of at least about 0.35 kU/L.

In certain exemplary embodiments, the allergen is selected from the group consisting of dust mite, cockroach, cat dander, dog dander, *Dermatophagoides farinae, Dermatophagoides pteronyssinus, Alternaria alternata, Cladosporium herbarum, Aspergillus fumigatus*, German cockroach and Oriental cockroach.

In certain exemplary embodiments, the antibody or antigen-binding fragment thereof is administered to the subject as a loading dose followed by a plurality maintenance doses.

In certain exemplary embodiments, the antibody or antigen-binding fragment thereof is administered using an auto-injector, a needle and syringe, or a pen.

In certain exemplary embodiments, a maintenance dose of antibody or antigen-binding fragment thereof is administered once every other week (q2w).

In certain exemplary embodiments, the loading dose is about 600 mg of the antibody or the antigen-binding fragment thereof. In certain exemplary embodiments, the loading dose is about 400 mg of the antibody or the antigen-binding fragment thereof.

In certain exemplary embodiments, each maintenance dose of antibody or antigen-binding fragment thereof is about 300 mg of the antibody or the antigen-binding fragment thereof. In certain exemplary embodiments, each maintenance dose of antibody or antigen-binding fragment thereof is about 200 mg of the antibody or the antigen-binding fragment thereof.

In certain exemplary embodiments, the maintenance doses of the antibody or antigen-binding fragment thereof are administered for at least 24 weeks.

In certain exemplary embodiments, a first maintenance dose of antibody or antigen-binding fragment thereof is administered two weeks after the loading dose of antibody or antigen-binding fragment thereof.

In certain exemplary embodiments, treatment results in a reduction in annualized severe asthma exacerbations.

In certain exemplary embodiments, treatment results in an improvement in lung function as measured by forced expiratory volume ($FEV_1$) or by forced expiratory flow at 25-75% of the pulmonary volume (FEF25-75%).

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject exhibits comorbid cystic fibrosis. In certain exemplary embodiments, the subject exhibits comorbid allergic asthma and comorbid cystic fibrosis.

In certain exemplary embodiments, the subject is an adult. In certain exemplary embodiments, the subject is an adolescent. In certain exemplary embodiments, the subject is a child.

In another aspect, a method of improving lung function as measured by forced expiratory volume ($FEV_1$) or by forced expiratory flow at 25-75% of the pulmonary volume (FEF25-75%) in a subject having allergic asthma is provided, comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a total serum IgE level of at least about 700 IU/mL.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has moderate-to-severe uncontrolled allergic asthma.

In certain exemplary embodiments, the subject exhibits comorbid cystic fibrosis. In certain exemplary embodiments, the subject exhibits comorbid allergic asthma and comorbid cystic fibrosis.

In certain exemplary embodiments, the subject is an adult. In certain exemplary embodiments, the subject is an adolescent. In certain exemplary embodiments, the subject is a child.

In another aspect, a method of reducing annualized severe asthma exacerbations in a subject having allergic asthma is provided, comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a total serum IgE level of at least about 700 IU/mL.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has moderate-to-severe uncontrolled allergic asthma.

In certain exemplary embodiments, the subject exhibits comorbid cystic fibrosis. In certain exemplary embodiments, the subject exhibits comorbid allergic asthma and comorbid cystic fibrosis.

In certain exemplary embodiments, the subject is an adult. In certain exemplary embodiments, the subject is an adolescent. In certain exemplary embodiments, the subject is a child.

In another aspect, a method of improving Asthma Control Questionnaire (ACQ-5) score in a subject having allergic asthma is provided, comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a total serum IgE level of at least about 700 IU/mL.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has moderate-to-severe uncontrolled allergic asthma.

In certain exemplary embodiments, the subject exhibits comorbid cystic fibrosis. In certain exemplary embodiments, the subject exhibits comorbid allergic asthma and comorbid cystic fibrosis.

In certain exemplary embodiments, the subject is an adult. In certain exemplary embodiments, the subject is an adolescent. In certain exemplary embodiments, the subject is a child.

In another aspect, a method for treating a subject having allergic bronchopulmonary aspergillosis (ABPA) is provided, comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, wherein the subject has a total serum IgE level of at least about 1000 IU/mL.

In certain exemplary embodiments, the subject has a baseline blood eosinophil count of at least about 500 cells/µl.

In certain exemplary embodiments, the subject has an allergen-specific serum IgE level of at least about 0.35 kU/L. In certain exemplary embodiments, the allergen is *Aspergillus fumigatus*.

In certain exemplary embodiments, the antibody or antigen-binding fragment thereof is administered to the subject as a loading dose followed by a plurality maintenance doses.

In certain exemplary embodiments, the antibody or antigen-binding fragment thereof is administered using an autoinjector, a needle and syringe, or a pen.

In certain exemplary embodiments, a maintenance dose of antibody or antigen-binding fragment thereof is administered once every other week (q2w).

In certain exemplary embodiments, the loading dose is about 600 mg of the antibody or the antigen-binding fragment thereof. In certain exemplary embodiments, the loading dose is about 400 mg of the antibody or the antigen-binding fragment thereof.

In certain exemplary embodiments, each maintenance dose of antibody or antigen-binding fragment thereof is about 300 mg of the antibody or the antigen-binding fragment thereof. In certain exemplary embodiments, each maintenance dose of the antibody or antigen-binding fragment thereof is about 200 mg of the antibody or the antigen-binding fragment thereof.

In certain exemplary embodiments, the maintenance doses of the antibody or antigen-binding fragment thereof are administered for at least 24 weeks.

In certain exemplary embodiments, a first maintenance dose of antibody or antigen-binding fragment thereof is administered two weeks after the loading dose of antibody or antigen-binding fragment thereof.

In certain exemplary embodiments, treatment results in a reduction in annualized severe asthma exacerbations. In certain exemplary embodiments, treatment results in an improvement in lung function as measured by forced expiratory volume ($FEV_1$) or by forced expiratory flow at 25-75% of the pulmonary volume (FEF25-75%). In certain exemplary embodiments, treatment results in a decrease in the total serum IgE level. In certain exemplary embodiments, treatment results in a decrease in serum *Aspergillus fumigatus*-specific IgE. In certain exemplary embodiments, treatment results in a decrease in one or more of TARC levels, eotaxin-3 levels and peripheral blood eosinophil levels. In certain exemplary embodiments, FeNO (ppb) is reduced.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has moderate-to-severe uncontrolled asthma. In certain exemplary embodiments, the subject exhibits comorbid cystic fibrosis. In certain exemplary embodiments, the subject exhibits comorbid asthma and comorbid cystic fibrosis.

In certain exemplary embodiments, the subject is an adult. In certain exemplary embodiments, the subject is an adolescent. In certain exemplary embodiments, the subject is a child.

In another aspect, a method for treating a subject having allergic bronchopulmonary aspergillosis (ABPA) is provided, comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has an *Aspergillus fumigatus*-specific IgE level of greater than 0.35 kU/L.

In certain exemplary embodiments, the subject has a baseline blood eosinophil count of at least about 300 cells/µL.

In certain exemplary embodiments, the subject has a total serum IgE level of at least about 1000 IU/mL.

In certain exemplary embodiments, the subject has a baseline blood eosinophil count of at least about 500 cells/µL.

In certain exemplary embodiments, the antibody or antigen-binding fragment thereof is administered to the subject as a loading dose followed by a plurality maintenance doses.

In certain exemplary embodiments, the antibody or antigen-binding fragment thereof is administered using an autoinjector, a needle and syringe, or a pen.

In certain exemplary embodiments, a maintenance dose of antibody or antigen-binding fragment thereof is administered once every other week (q2w).

In certain exemplary embodiments, the loading dose is about 600 mg of the antibody or the antigen-binding fragment thereof. In certain exemplary embodiments, the loading dose is about 400 mg of the antibody or the antigen-binding fragment thereof.

In certain exemplary embodiments, each maintenance dose of antibody or antigen-binding fragment thereof is about 300 mg of the antibody or the antigen-binding fragment thereof.

In certain exemplary embodiments, each maintenance dose of the antibody or antigen-binding fragment thereof is about 200 mg of the antibody or the antigen-binding fragment thereof.

In certain exemplary embodiments, the maintenance doses of the antibody or antigen-binding fragment thereof are administered for at least 24 weeks.

In certain exemplary embodiments, a first maintenance dose of antibody or antigen-binding fragment thereof is administered two weeks after the loading dose of antibody or antigen-binding fragment thereof.

In certain exemplary embodiments, treatment results in a reduction in annualized severe asthma exacerbations. In certain exemplary embodiments, treatment results in an improvement in lung function as measured by forced expiratory volume ($FEV_1$) or by forced expiratory flow at 25-75% of the pulmonary volume (FEF25-75%). In certain exemplary embodiments, treatment results in a decrease in the total serum IgE level. In certain exemplary embodiments, treatment results in a decrease in serum *Aspergillus fumigatus*-specific IgE. In certain exemplary embodiments, treatment results in a decrease in one or more of TARC levels, eotaxin-3 levels and peripheral blood eosinophil levels. In certain exemplary embodiments, FeNO (ppb) is reduced.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has moderate-to-severe uncontrolled asthma. In certain exemplary embodiments, the subject exhibits comorbid cystic fibrosis. In certain exemplary embodiments, the subject exhibits comorbid asthma and comorbid cystic fibrosis.

In certain exemplary embodiments, the subject is an adult. In certain exemplary embodiments, the subject is an adolescent. In certain exemplary embodiments, the subject is a child.

In another aspect, a method for treating a subject having allergic bronchopulmonary aspergillosis (ABPA) is provided, comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a baseline blood eosinophil count of at least about 500 cells/µl.

In certain exemplary embodiments, the subject has an allergen-specific serum IgE level of at least about 0.35 kU/L.

In certain exemplary embodiments, the allergen is *Aspergillus fumigatus*.

In certain exemplary embodiments, the subject has a total serum IgE level of at least about 1000 IU/mL.

In certain exemplary embodiments, the antibody or antigen-binding fragment thereof is administered to the subject as a loading dose followed by a plurality maintenance doses.

In certain exemplary embodiments, the antibody or antigen-binding fragment thereof is administered using an autoinjector, a needle and syringe, or a pen.

In certain exemplary embodiments, a maintenance dose of antibody or antigen-binding fragment thereof is administered once every other week (q2w).

In certain exemplary embodiments, the loading dose is about 600 mg of the antibody or the antigen-binding fragment thereof. In certain exemplary embodiments, the loading dose is about 400 mg of the antibody or the antigen-binding fragment thereof.

In certain exemplary embodiments, each maintenance dose of antibody or antigen-binding fragment thereof is about 300 mg of the antibody or the antigen-binding fragment thereof. In certain exemplary embodiments, each maintenance dose of the antibody or antigen-binding fragment thereof is about 200 mg of the antibody or the antigen-binding fragment thereof.

In certain exemplary embodiments, the maintenance doses of the antibody or antigen-binding fragment thereof are administered for at least 24 weeks.

In certain exemplary embodiments, a first maintenance dose of antibody or antigen-binding fragment thereof is administered two weeks after the loading dose of antibody or antigen-binding fragment thereof.

In certain exemplary embodiments, treatment results in a reduction in annualized severe asthma exacerbations. In certain exemplary embodiments, treatment results in an improvement in lung function as measured by forced expiratory volume ($FEV_1$) or by forced expiratory flow at 25-75% of the pulmonary volume (FEF25-75%). In certain exemplary embodiments, treatment results in a decrease in the total serum IgE level. In certain exemplary embodiments, treatment results in a decrease in serum *Aspergillus fumigatus*-specific IgE. In certain exemplary embodiments, treatment results in a decrease in one or more of TARC levels, eotaxin-3 levels and peripheral blood eosinophil levels. In certain exemplary embodiments, FeNO (ppb) is reduced.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has moderate-to-severe uncontrolled asthma. In certain exemplary embodiments, the subject exhibits comorbid cystic fibrosis. In certain exemplary embodiments, the subject exhibits comorbid asthma and comorbid cystic fibrosis.

In certain exemplary embodiments, the subject is an adult. In certain exemplary embodiments, the subject is an adolescent. In certain exemplary embodiments, the subject is a child.

In another aspect, a method of improving lung function as measured by forced expiratory volume ($FEV_1$) or by forced expiratory flow at 25-75% of the pulmonary volume (FEF25-75%) in a subject having asthma associated with allergic bronchopulmonary aspergillosis (ABPA) is provided, comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a total serum IgE level of at least about 1000 IU/mL.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the subject has moderate-to-severe uncontrolled allergic asthma. In certain exemplary embodiments, the subject exhibits comorbid cystic fibrosis. In certain exemplary embodiments, the subject exhibits comorbid asthma and comorbid cystic fibrosis.

In certain exemplary embodiments, the antibody is dupilumab.

In certain exemplary embodiments, the subject is an adult. In certain exemplary embodiments, the subject is an adolescent. In certain exemplary embodiments, the subject is a child.

In another aspect, a method of reducing annualized severe asthma exacerbations in a subject having asthma associated with allergic bronchopulmonary aspergillosis (ABPA) is provided, comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a total serum IgE level of at least about 1000 IU/mL.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has moderate-to-severe uncontrolled allergic asthma. In certain exemplary embodiments, the subject exhibits comorbid cystic fibrosis. In certain exemplary embodiments, the subject exhibits comorbid asthma and comorbid cystic fibrosis.

In certain exemplary embodiments, the subject is an adult. In certain exemplary embodiments, the subject is an adolescent. In certain exemplary embodiments, the subject is a child.

In another aspect, a method of improving Asthma Control Questionnaire (ACQ-5) score in a subject having asthma associated with allergic bronchopulmonary aspergillosis (ABPA) is provided, comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a total serum IgE level of at least about 1000 IU/mL.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has moderate-to-severe uncontrolled allergic asthma. In certain exemplary embodiments, the subject exhibits comorbid cystic fibrosis. In certain exemplary embodiments, the subject exhibits comorbid asthma and comorbid cystic fibrosis.

In certain exemplary embodiments, the subject is an adult. In certain exemplary embodiments, the subject is an adolescent. In certain exemplary embodiments, the subject is a child.

In another aspect, a method for treating a subject having comorbid allergic bronchopulmonary aspergillosis (ABPA) and cystic fibrosis (CF) comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, is provided. In some embodiments, the subject has a total serum IgE level of at least about 1000 IU/mL.

In certain exemplary embodiments, the subject has a baseline blood eosinophil count of at least about 500 cells/µl.

In certain exemplary embodiments, the subject has an allergen-specific serum IgE level of at least about 0.35 kU/L. In certain exemplary embodiments, the allergen is *Aspergillus fumigatus*.

In certain exemplary embodiments, the antibody or antigen-binding fragment thereof is administered to the subject as a loading dose followed by a plurality maintenance doses.

In certain exemplary embodiments, the antibody or antigen-binding fragment thereof is administered using an autoinjector, a needle and syringe, or a pen.

In certain exemplary embodiments, a maintenance dose of antibody or antigen-binding fragment thereof is administered once every other week (q2w).

In certain exemplary embodiments, the loading dose is about 600 mg of the antibody or the antigen-binding fragment thereof. In certain exemplary embodiments, each maintenance dose of antibody or antigen-binding fragment thereof is about 300 mg of the antibody or the antigen-binding fragment thereof.

In certain exemplary embodiments, the loading dose is about 400 mg of the antibody or the antigen-binding fragment thereof. In certain exemplary embodiments, each maintenance dose of the antibody or antigen-binding fragment thereof is about 200 mg of the antibody or the antigen-binding fragment thereof.

In certain exemplary embodiments, the maintenance doses of the antibody or antigen-binding fragment thereof are administered for at least 24 weeks.

In certain exemplary embodiments, a first maintenance dose of antibody or antigen-binding fragment thereof is administered two weeks after the loading dose of antibody or antigen-binding fragment thereof.

In certain exemplary embodiments, treatment results in an improvement in lung function as measured by forced expiratory volume ($FEV_1$) or by forced expiratory flow at 25-75% of the pulmonary volume (FEF25-75%).

In certain exemplary embodiments, treatment results in a decrease in one or both of total serum IgE levels and serum *Aspergillus fumigatus*-specific IgE levels. In certain exemplary embodiments, treatment results in a decrease in one or more of TARC levels, eotaxin-3 levels and peripheral blood eosinophil levels. In certain exemplary embodiments, FeNO (ppb) is reduced.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has asthma. In certain exemplary embodiments, treatment results in a reduction in annualized asthma exacerbations.

In certain exemplary embodiments, the subject is an adult. In certain exemplary embodiments, the subject is an adolescent. In certain exemplary embodiments, the subject is a child.

In another aspect, a method for treating a subject having comorbid allergic bronchopulmonary aspergillosis (ABPA) and cystic fibrosis (CF) comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has an *Aspergillus fumigatus*-specific IgE level of greater than 0.35 kU/L, is provided.

In certain exemplary embodiments, the subject has a baseline blood eosinophil count of at least about 300 cells/µl.

In certain exemplary embodiments, the subject has a total serum IgE level of at least about 1000 IU/mL. In certain exemplary embodiments, the subject has a baseline blood eosinophil count of at least about 500 cells/μl.

In certain exemplary embodiments, the antibody or antigen-binding fragment thereof is administered to the subject as a loading dose followed by a plurality maintenance doses.

In certain exemplary embodiments, the antibody or antigen-binding fragment thereof is administered using an autoinjector, a needle and syringe, or a pen.

In certain exemplary embodiments, a maintenance dose of antibody or antigen-binding fragment thereof is administered once every other week (q2w).

In certain exemplary embodiments, the loading dose is about 600 mg of the antibody or the antigen-binding fragment thereof. In certain exemplary embodiments, each maintenance dose of antibody or antigen-binding fragment thereof is about 300 mg of the antibody or the antigen-binding fragment thereof.

In certain exemplary embodiments, the loading dose is about 400 mg of the antibody or the antigen-binding fragment thereof. In certain exemplary embodiments, each maintenance dose of the antibody or antigen-binding fragment thereof is about 200 mg of the antibody or the antigen-binding fragment thereof.

In certain exemplary embodiments, the maintenance doses of the antibody or antigen-binding fragment thereof are administered for at least 24 weeks.

In certain exemplary embodiments, a first maintenance dose of antibody or antigen-binding fragment thereof is administered two weeks after the loading dose of antibody or antigen-binding fragment thereof.

In certain exemplary embodiments, treatment results in an improvement in lung function as measured by forced expiratory volume ($FEV_1$) or by forced expiratory flow at 25-75% of the pulmonary volume (FEF25-75%).

In certain exemplary embodiments, treatment results in a decrease in one or both of total serum IgE levels and serum *Aspergillus fumigatus*-specific IgE levels. In certain exemplary embodiments, treatment results in a decrease in one or more of TARC levels, eotaxin-3 levels and peripheral blood eosinophil levels. In certain exemplary embodiments, FeNO (ppb) is reduced.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has asthma. In certain exemplary embodiments, treatment results in a reduction in annualized asthma exacerbations.

In certain exemplary embodiments, the subject is an adult. In certain exemplary embodiments, the subject is an adolescent. In certain exemplary embodiments, the subject is a child.

In another aspect, a method for treating a subject having comorbid allergic bronchopulmonary aspergillosis (ABPA) and cystic fibrosis (CF) comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a baseline blood eosinophil count of at least about 500 cells/μl, is provided.

In certain exemplary embodiments, the subject has an allergen-specific serum IgE level of at least about 0.35 kU/L. In certain exemplary embodiments, the allergen is *Aspergillus fumigatus*.

In certain exemplary embodiments, the subject has a total serum IgE level of at least about 1000 IU/mL.

In certain exemplary embodiments, the antibody or antigen-binding fragment thereof is administered to the subject as a loading dose followed by a plurality maintenance doses.

In certain exemplary embodiments, the antibody or antigen-binding fragment thereof is administered using an autoinjector, a needle and syringe, or a pen.

In certain exemplary embodiments, a maintenance dose of antibody or antigen-binding fragment thereof is administered once every other week (q2w).

In certain exemplary embodiments, the loading dose is about 600 mg of the antibody or the antigen-binding fragment thereof. In certain exemplary embodiments, each maintenance dose of antibody or antigen-binding fragment thereof is about 300 mg of the antibody or the antigen-binding fragment thereof.

In certain exemplary embodiments, the loading dose is about 400 mg of the antibody or the antigen-binding fragment thereof. In certain exemplary embodiments, each maintenance dose of the antibody or antigen-binding fragment thereof is about 200 mg of the antibody or the antigen-binding fragment thereof.

In certain exemplary embodiments, the maintenance doses of the antibody or antigen-binding fragment thereof are administered for at least 24 weeks.

In certain exemplary embodiments, a first maintenance dose of antibody or antigen-binding fragment thereof is administered two weeks after the loading dose of antibody or antigen-binding fragment thereof.

In certain exemplary embodiments, treatment results in an improvement in lung function as measured by forced expiratory volume ($FEV_1$) or by forced expiratory flow at 25-75% of the pulmonary volume (FEF25-75%).

In certain exemplary embodiments, treatment results in a decrease in one or both of total serum IgE levels and serum *Aspergillus fumigatus*-specific IgE levels. In certain exemplary embodiments, treatment results in a decrease in one or more of TARC levels, eotaxin-3 levels and peripheral blood eosinophil levels. In certain exemplary embodiments, FeNO (ppb) is reduced.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has asthma. In certain exemplary embodiments, treatment results in a reduction in annualized asthma exacerbations.

In certain exemplary embodiments, the subject is an adult. In certain exemplary embodiments, the subject is an adolescent. In certain exemplary embodiments, the subject is a child.

In another aspect, a method for treating a subject having allergic bronchopulmonary aspergillosis (ABPA) comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, wherein the subject has a total serum IgE level of at least about 1000 IU/mL, an *Aspergillus fumigatus*-specific IgE level of greater than 0.35 kU/L, or a baseline blood eosinophil count of at least about 500 cells/µl, is provided.

In certain exemplary embodiments, the subject has at least two of a total serum IgE level of at least about 1000 IU/mL, an *Aspergillus fumigatus*-specific IgE level of greater than 0.35 kU/L, and a baseline blood eosinophil count of at least about 500 cells/µl. In certain exemplary embodiments, the subject has a total serum IgE level of at least about 1000 IU/mL, an *Aspergillus fumigatus*-specific IgE level of greater than 0.35 kU/L, and a baseline blood eosinophil count of at least about 500 cells/µl.

In certain exemplary embodiments, the antibody or antigen-binding fragment thereof is administered to the subject as a loading dose followed by a plurality maintenance doses. In certain exemplary embodiments, the antibody or antigen-binding fragment thereof is administered using an autoinjector, a needle and syringe, or a pen. In certain exemplary embodiments, a maintenance dose of antibody or antigen-binding fragment thereof is administered once every other week (q2w).

In certain exemplary embodiments, the loading dose is about 600 mg of the antibody or the antigen-binding fragment thereof. In certain exemplary embodiments, each maintenance dose of antibody or antigen-binding fragment thereof is about 300 mg of the antibody or the antigen-binding fragment thereof.

In certain exemplary embodiments, the loading dose is about 400 mg of the antibody or the antigen-binding fragment thereof. In certain exemplary embodiments, each maintenance dose of the antibody or antigen-binding fragment thereof is about 200 mg of the antibody or the antigen-binding fragment thereof.

In certain exemplary embodiments, the maintenance doses of the antibody or antigen-binding fragment thereof are administered for at least 24 weeks.

In certain exemplary embodiments, a first maintenance dose of antibody or antigen-binding fragment thereof is administered two weeks after the loading dose of antibody or antigen-binding fragment thereof.

In certain exemplary embodiments, treatment results in an improvement in lung function as measured by forced expiratory volume ($FEV_1$) or by forced expiratory flow at 25-75% of the pulmonary volume (FEF25-75%).

In certain exemplary embodiments, treatment results in a decrease in one or both of total serum IgE levels and serum *Aspergillus fumigatus*-specific IgE levels. In certain exemplary embodiments, treatment results in a decrease in one or more of TARC levels, eotaxin-3 levels and peripheral blood eosinophil levels. In certain exemplary embodiments, FeNO (ppb) is reduced.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject has moderate-to-severe uncontrolled asthma. In certain exemplary embodiments, treatment results in a reduction in annualized severe asthma exacerbations.

In certain exemplary embodiments, the subject exhibits comorbid asthma. In certain exemplary embodiments, the subject exhibits comorbid cystic fibrosis. In certain exemplary embodiments, the subject exhibits comorbid asthma and comorbid cystic fibrosis.

In certain exemplary embodiments, the subject is an adult. In certain exemplary embodiments, the subject is an adolescent. In certain exemplary embodiments, the subject is a child.

In another aspect, a method for treating a subject having asthma comprising administering to the subject two or more doses of an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject is further administered a vaccine, is provided.

In certain exemplary embodiments, administration of the antibody or antigen-binding fragment thereof is temporarily suspended prior to administering the vaccine.

In certain exemplary embodiments, the vaccine is administered at least 7 days after the antibody or antigen-binding fragment thereof was last administered to the subject. In certain exemplary embodiments, the vaccine is administered between about 7 days and about 60 days after the antibody or antigen-binding fragment thereof was last administered to the subject.

In certain exemplary embodiments, administration of the antibody or antigen-binding fragment thereof is resumed following administration of the vaccine.

In certain exemplary embodiments, the antibody or antigen-binding fragment thereof is administered between about 1 day and about 90 days after administration of the vaccine. In certain exemplary embodiments, the antibody or antigen-binding fragment thereof is administered about 7 days after administration of the vaccine. In certain exemplary embodiments, the antibody or antigen-binding fragment thereof is administered about 14 days after administration of the vaccine.

In certain exemplary embodiments, the antibody or an antigen-binding fragment thereof is administered about 21 days after administration of the vaccine.

In certain exemplary embodiments, efficacy of the antibody or antigen-binding fragment thereof is not decreased by administration of the vaccine.

In certain exemplary embodiments, forced expiratory volume ($FEV_1$) of the subject is approximately the same before and after administration of the vaccine.

In certain exemplary embodiments, vaccine efficacy in the subject is not decreased by administration of the antibody or antigen-binding fragment thereof.

In certain exemplary embodiments, the subject develops a seroprotective neutralization titer after administration of the vaccine.

In certain exemplary embodiments, the vaccine is a live vaccine. In certain exemplary embodiments, the vaccine comprises a live-attenuated yellow fever virus. In certain exemplary embodiments, the vaccine is specific against yellow fever virus.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject exhibits comorbid cystic fibrosis. In certain exemplary embodiments, the subject exhibits comorbid asthma and comorbid cystic fibrosis.

In certain exemplary embodiments, the subject is an adult. In certain exemplary embodiments, the subject is an adolescent. In certain exemplary embodiments, the subject is a child.

In another aspect, a method for administrating a vaccine to a subject, wherein before, during, or after administration of the vaccine, the subject is administered at least one dose of an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, is provided.

In certain exemplary embodiments, the subject has a type 2 inflammatory disease. In certain exemplary embodiments, the type 2 inflammatory disease is selected from the group consisting of one or any combination of asthma, allergic rhinitis, chronic rhinosinusitis with nasal polyps (CRSsNP), eosinophilic esophagitis (EoE), atopic dermatitis (AD), food and environmental allergies, aspirin exacerbated respiratory disease (AERD), and respiratory disease exacerbated by other non-steroidal anti-inflammatory drugs (NSAID).

In certain exemplary embodiments, the vaccine is administered to the subject about 1 day to about 90 days after the last dose of the antibody or an antigen-binding fragment thereof.

In certain exemplary embodiments, the antibody or antigen-binding fragment thereof comprises a heavy chain variable region (HCVR) sequence of SEQ ID NO: 1 and a light chain variable region (LCVR) sequence of SEQ ID NO: 2.

In certain exemplary embodiments, the antibody or antigen-binding fragment thereof comprises a heavy chain sequence of SEQ ID NO: 9 and a light chain sequence of SEQ ID NO: 10.

In certain exemplary embodiments, the antibody is dupilumab.

In certain exemplary embodiments, the subject exhibits asthma. In certain exemplary embodiments, the subject exhibits cystic fibrosis. In certain exemplary embodiments, the subject exhibits comorbid asthma and comorbid cystic fibrosis.

In certain exemplary embodiments, the subject is an adult. In certain exemplary embodiments, the subject is an adolescent. In certain exemplary embodiments, the subject is a child.

Other embodiments will become apparent from a review of the ensuing detailed description, drawings, tables and accompanying claims.

BRIEF DESCRIPTION OF THE FIGURES

The foregoing and other features and advantages of the present invention will be more fully understood from the following detailed description of illustrative embodiments taken in conjunction with the accompanying drawings.

FIG. 1A-FIG. 1E depict the effect of dupilumab on annualized severe exacerbation rates. FIG. 1A shows that dupilumab reduced the overall annualized severe exacerbation rates in the overall allergic asthma subgroup as well as in the overall asthma subgroup that did not meet the criteria for allergic asthma. FIG. 1B depicts the effect of dupilumab in an allergic asthma subgroup as well as in an asthma subgroup that did not meet the criteria for allergic asthma, wherein the subjects had blood eosinophil levels of ≥150 cells/µL. FIG. 1C depicts the effect of dupilumab in an allergic asthma subgroup as well as an asthma subgroup that did not meet the criteria for allergic asthma, wherein the subjects had blood eosinophil levels of ≥300 cells/µL. FIG. 1D depicts the effect of dupilumab in an allergic asthma subgroup as well as in an asthma subgroup that did not meet the criteria for allergic asthma, wherein the subjects had a baseline blood FeNO of ≥25 ppb. FIG. 1E depicts the effect of dupilumab in an allergic asthma subgroup as well as in an asthma subgroup that did not meet the criteria for allergic asthma, wherein the subjects had serum total IgE>700 IU/mL. CI, confidence interval; FeNO, fractional exhaled nitric oxide; ITT, intention-to-treat; q2w, every 2 weeks.

FIG. 2A-FIG. 2B depict the effect of dupilumab on $FEV_1$ (L) in the overall allergic asthma subgroup and in the overall asthma subgroup that did not meet the criteria for allergic asthma. FIG. 2A depicts the change in baseline $FEV_1$ during a 52-week treatment period in the overall allergic asthma subgroup, and depicts the magnitude of effects in subgroups that were further defined by baseline blood eosinophil levels, FeNO levels, or baseline serum total IgE levels at week 12. FIG. 2B depicts the change in the baseline $FEV_1$ during a 52-week treatment period in the overall asthma subgroup that did not meet the criteria for allergic asthma, and depicts the magnitude of effects in subgroups that were further defined by baseline blood eosinophil levels, FeNO levels, or baseline serum total IgE levels at week 12.

FIG. 4A depicts the effect of dupilumab on serum total IgE levels. FIG. 4B depicts the effect of dupilumab on FeNO levels. FIG. 4C depicts the effect of dupilumab on serum TARC levels during the 52-week treatment period in the overall allergic asthma subgroup and the overall asthma subgroup that did not meet the criteria for allergic asthma (exposed population). CI, confidence interval; FeNO, fractional exhaled nitric oxide; q2w, every 2 weeks; TARC, thymus and activation-regulated chemokine.

FIG. 5A-FIG. 5H depict the effect of dupilumab on antigen-specific serum IgE levels during the 52-week treatment period in the allergic asthma subgroup. FIG. 5A depicts the effect of dupilumab on antigen-specific serum IgE levels ≥0.35 kU/mL (exposed population) in an allergic asthma subgroup exposed to *A. fumigatus*. FIG. 5B depicts the effect of dupilumab on antigen-specific serum IgE levels in an allergic asthma subgroup exposed to cat dander. FIG. 5C depicts the effect of dupilumab on antigen-specific serum IgE levels in an allergic asthma subgroup exposed to *D. farinae*. FIG. 5D depicts the effect of dupilumab on antigen-specific serum IgE levels in an allergic asthma subgroup exposed to *D. pteronyssinus*. FIG. 5E depicts the effect of dupilumab on antigen-specific serum IgE levels in an allergic asthma subgroup exposed to dog dander. FIG. 5F depicts the effect of dupilumab on antigen-specific serum IgE levels in an allergic asthma subgroup exposed to German cockroach. FIG. 5G depicts the effect of dupilumab on antigen-specific serum IgE levels in an allergic asthma subgroup exposed to *A. tenuis/alternata*. FIG. 5H depicts the effect of dupilumab on antigen-specific serum IgE levels in an allergic asthma subgroup exposed to and *C. herbarum/hormodendrum*. CI, confidence interval; q2w, every 2 weeks.

FIG. 6A depicts a histogram of the residuals to ensure normal distribution. FIG. 6B depicts a q-q plot showing a normal distribution.

FIG. 7 depicts the annualized rate of severe exacerbations during a 52-week treatment period for patients with allergic bronchopulmonary aspergillosis (ABPA) in an intention to treat (ITT) population.

FIG. 8 depicts least squares (LS) mean change from baseline in pre-bronchodilator forced expiratory volume in one second ($FEV_1$) at weeks 24 and 52 in an ITT population.

FIG. 9 depicts total serum IgE levels at week 52 in a patient population that was exposed to *Aspergillus fumigatus* (Af).

FIG. 10 depicts total serum Af-specific IgE levels at week 52 in a patient population that was exposed to Af.

FIG. 11 graphically depicts absolute FeNO (ppb) levels at week 52 in a patient population that was exposed to Af.

FIG. 17A-FIG. 17B graphically depict plaque reduction neutralization titers ($PRNT_{50}$) of neutralizing YFV-17D antibody pre- and post-vaccination. FIG. 17A depicts matched neutralization titers for 23 patients where pre-vaccination titers were obtained. FIG. 17B depicts pre- and post-vaccination data for all patients. In FIG. 17B, patients with dupilumab concentrations lower than the mean $C_{trough}$ concentration of 37.4 mg/L are indicated in black circles, whereas those patients with serum concentrations greater than 37.4 mg/L are indicated in open circles. A titer <1:10 is defined as seronegative and those values were designated '1'. FIG. 17A-FIG. 17B shows that all 37 vaccinated patients had seroprotective yellow fever neutralization titers post-vaccination.

FIG. 19 shows that the $FEV_1$ was stable between the visit before the YFV was administered and at the first visit after YFV was administered. BL: baseline of the parent study; Pre-YF: the last visit before yellow fever vaccination; Post-YF: the first visit after yellow fever vaccination; FU: follow-up visit.

FIG. 20 shows that the $FEV_1$ was stable between the visit before the YFV was administered and at the first visit after YFV was administered. BL: baseline of the parent study; Pre-YF: the last visit before yellow fever vaccination; Post-YF: the first visit after yellow fever vaccination; FU: follow-up visit.

DETAILED DESCRIPTION

Figure 1C:
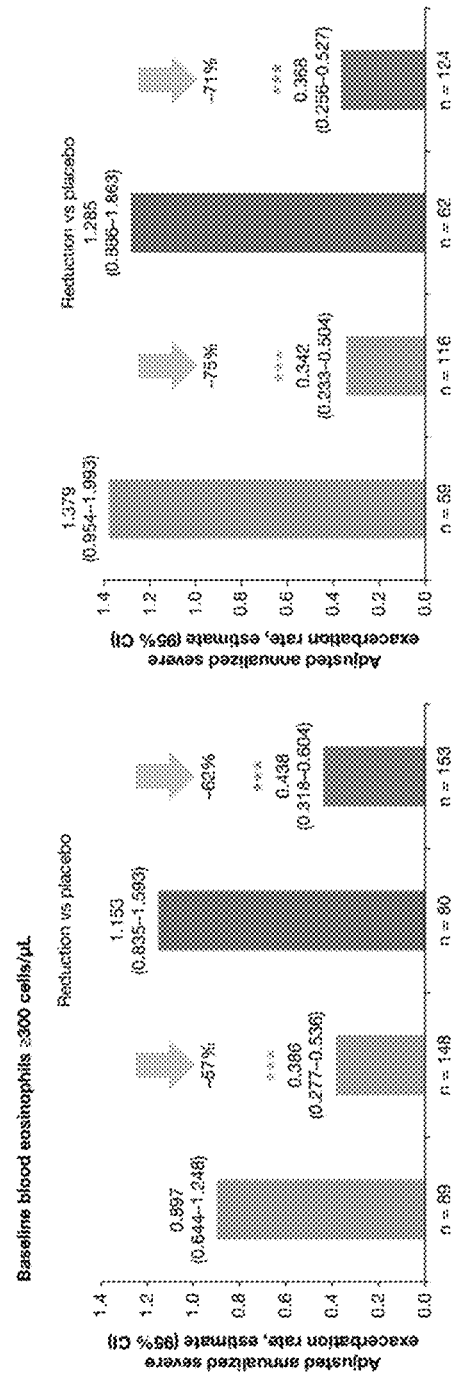

Before the invention is described, it is to be understood that this invention is not limited to particular methods and experimental conditions described, as such methods and conditions may vary. It is also to be understood that the terminology used herein is for the purpose of describing particular embodiments only, and is not intended to be limiting, because the scope of the invention will be limited only by the appended claims.

Unless defined otherwise, all technical and scientific terms used herein have the same meaning as commonly understood by one of ordinary skill in the art to which this invention belongs.

As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

As used herein, the terms "treat," "treating," or the like, mean to alleviate symptoms, eliminate the causation of symptoms either on a temporary or permanent basis, or to prevent or slow the appearance of symptoms of the named disorder or condition.

Although any methods and materials similar or equivalent to those described herein can be used in the practice of the invention, the typical methods and materials are now described. All publications mentioned herein are incorporated herein by reference in their entirety.

Methods for Reducing the Incidence of Asthma and/or ABPA Exacerbations

Methods for reducing the incidence of asthma (e.g., allergic asthma, asthma associated with ABPA, moderate-to-severe asthma, persistent asthma or the like) and/or ABPA (ABPA, ABPA associated with asthma, ABPA associated with CF, ABPA associated with asthma and CF, or the like) exacerbations in a subject in need thereof comprising administering a pharmaceutical composition comprising an IL-4R antagonist to the subject are provided. According to certain embodiments, the IL-4R antagonist is an antibody or antigen-binding fragment thereof that specifically binds IL-4R. Exemplary anti-IL-4R antibodies that can be used in the context of the methods featured here are described elsewhere herein.

As used herein, the expression "asthma exacerbation" means an increase in the severity and/or frequency and/or duration of one or more symptoms or indicia of asthma (e.g., allergic asthma, asthma associated with ABPA, moderate-to-severe asthma, persistent asthma or the like). An "asthma exacerbation" also includes any deterioration in the respiratory health of a subject that requires and or is treatable by a therapeutic intervention for asthma (such as, e.g., steroid treatment, inhaled corticosteroid treatment, hospitalization, etc.). There are two types of asthma exacerbation events: a loss of asthma control (LOAC) event and a severe exacerbation event.

As used herein, the expression "allergic bronchopulmonary aspergillosis exacerbation" or "ABPA exacerbation" means an increase in the severity and/or frequency and/or duration of one or more symptoms or indicia of ABPA including, but not limited to, wheezing, dyspnea, respiratory exacerbations, bronchial hyperreactivity, hemoptysis, productive cough (expectoration of brownish-black mucus plugs), central bronchiectasis with mucus plugging, markedly elevated total IgE, markedly elevated Af-specific IgE, and tissue eosinophilia.

According to certain embodiments, an ABPA exacerbation occurs in a subject having an HLA-DR2 serotype (e.g., subtype HLA-DRB1*1501, subtype *HLA-DRB1*1503, or subtype *HLA-DRB1*1601) or an HLA-DR5 serotype (e.g., subtype HLA-DRB1*1101, subtype HLA-DRB1*1104, or subtype HLA-DRB1*1202), optionally wherein the subject and has an increased susceptibility of developing ABPA when exposed to Af antigen relative to a subject that does not have one of these serotypes and/or subtypes.

According to certain embodiments, a loss of asthma control (LOAC) event is defined as one or more of the following: (a) greater than or equal to 6 additional reliever puffs of salbutamol/albuterol or levosalbutamol/levalbuterol in a 24 hour period (compared to baseline) on 2 consecutive days; (b) an increase in ICS greater than or equal to 4 times the dose at visit 2; and (c) use of systemic corticosteroids for greater than or equal to 3 days; or (d) hospitalization or emergency room visit because of asthma, requiring systemic corticosteroids.

In certain instances, an asthma (e.g., allergic asthma, asthma associated with ABPA, moderate-to-severe asthma, persistent asthma or the like) exacerbation may be categorized as a "severe asthma exacerbation event." A severe asthma (e.g., severe allergic asthma) exacerbation event means an incident requiring immediate intervention in the form of treatment with either systemic corticosteroids or with inhaled corticosteroids at four or more times the dose taken prior to the incident. According to certain embodiments, a severe asthma (e.g., severe allergic asthma) exacerbation event is defined as a deterioration of asthma (e.g., allergic asthma, asthma associated with ABPA, moderate-to-severe asthma, persistent asthma or the like) requiring: use of systemic corticosteroids for greater than or equal to 3 days; or hospitalization or emergency room visit because of asthma, requiring systemic corticosteroids. The general expression "asthma exacerbation" therefore includes and encompasses the more specific subcategory of "severe asthma exacerbations." Accordingly, methods for reducing the incidence of severe asthma exacerbations in a patient in need thereof are included.

A "reduction in the incidence" of an asthma (e.g., allergic asthma, asthma associated with ABPA, moderate-to-severe asthma, persistent asthma or the like) and/or an ABPA exacerbation means that a subject who has received a pharmaceutical composition comprising an IL-4R antagonist experiences fewer asthma or ABPA exacerbations (i.e., at least one fewer exacerbation) after treatment than before treatment, or experiences no asthma exacerbations for at least 4 weeks (e.g., 4, 6, 8, 12, 14, or more weeks) following initiation of treatment with the pharmaceutical composition. A "reduction in the incidence" of an asthma and/or an ABPA exacerbation alternatively means that, following administration of the pharmaceutical composition, the likelihood that a subject experiences an asthma exacerbation is decreased by at least 10% (e.g., 10%, 15%, 20%, 25%, 30%, 35%, 40%, 45%, 50%, or more) as compared to a subject who has not received the pharmaceutical composition.

Methods for reducing the incidence of asthma (e.g., allergic asthma, asthma associated with ABPA, moderate-to-severe asthma, persistent asthma or the like) and/or ABPA exacerbations in a subject in need thereof comprising administering a pharmaceutical composition comprising an IL-4R antagonist to the subject as well as administering to the subject one or more maintenance doses of an inhaled corticosteroid (ICS) and/or one or more maintenance doses of a second controller, e.g., a long-acting beta-agonist (LABA) or a leukotriene receptor antagonist (LTA), are provided. Suitable ICSs include, but are not limited to, fluticasone (e.g., fluticasone propionate, e.g., Flovent™), budesonide, mometasone (e.g., mometasone furoate, e.g., Asmanex™), flunisolide (e.g., Aerobid™), dexamethasone acetate/phenobarbital/theophylline (e.g., Azmacort™), beclomethasone dipropionate HFA (Qvar™), and the like. Suitable LABAs include, but are not limited to, salmeterol (e.g., Serevent™), formoterol (e.g., Foradil™), and the like. Suitable LTAs include, but are not limited to, montelukast (e.g., Singulaire™), zafirlukast (e.g., Accolate™), and the like.

Methods for reducing the incidence of asthma (e.g., allergic asthma, asthma associated with ABPA, moderate-to-severe asthma, persistent asthma or the like) and/or ABPA exacerbations in a subject in need thereof comprising administering a pharmaceutical composition comprising an IL-4R antagonist to the subject as well as administering to the subject one or more reliever medications to eliminate or reduce one or more asthma-associated symptoms, are provided. Suitable reliever medications include, but are not limited to, quick-acting beta2-adrenergic receptor agonists such as, e.g., albuterol (i.e., salbutamol, e.g., Proventil™, Ventolin™, Xopenex™ and the like), pirbuterol (e.g., Maxair™), metaproterenol (e.g., Alupent™) and the like.

Methods for Improving Asthma-Associated and/or ABPA-Associated Parameters

Methods for improving one or more asthma-associated and/or ABPA-associated parameters in a subject in need thereof, wherein the methods comprise administering a pharmaceutical composition comprising an IL-4R antagonist to the subject, are also provided. A reduction in the incidence of an asthma exacerbation and/or an ABPA exacerbation (as described above) may correlate with an improvement in one or more asthma-associated parameters and/or ABPA-associated parameters; however, such a correlation is not necessarily observed in all cases.

Examples of "asthma-associated parameters," "asthma-associated with ABPA parameters" and "allergic asthma-associated parameters" include: (1) relative percent change from baseline (e.g., at week 12) in forced expiratory volume in 1 second ($FEV_1$); (2) a relative percent change from baseline (e.g., at week 12) as measured by forced expiratory flow at 25-75% of the pulmonary volume (FEF25-75%); (3) annualized rate of loss of asthma control events during the treatment period; (4) annualized rate of severe exacerbation events during the treatment period; (5) time to loss of asthma control events during the treatment period; (6) time to severe exacerbation events during the treatment period; (7) time to loss of asthma control events during overall study period; (8) time to severe exacerbation events during overall study period; (9) health care resource utilization; (10) change from baseline (e.g., at week 12) in: i) morning and evening asthma symptom scores, ii) ACQ-5 score, iii) AQLQ score, iv) morning and evening PEF, v) number of inhalations/day of salbutamol/albuterol or levosalbutamol/levalbuterol for symptom relief, vi) nocturnal awakenings; or (11) change from baseline (e.g., at week 12 or week 24) in: i) 22-item Sino Nasal Outcome Test (SNOT-22), ii) Hospital Anxiety and Depression Score (HADS), iii) EuroQual questionnaire (EQ-5D-3L or EQ-5D-5L). An "improvement in an asthma-associated parameter" means an increase from baseline of one or more of $FEV_1$, AM PEF or PM PEF, and/or a decrease from baseline of one or more of daily albuterol/levalbuterol use, ACQ5 score, average nighttime awakenings or SNOT-22 score. As used herein, the term "baseline," with regard to an asthma-associated parameter, means the numerical value of the asthma-associated parameter for a patient prior to or at the time of administration of a pharmaceutical composition comprising an IL-4R antagonist.

To determine whether an asthma-associated (e.g., an allergic asthma-associated) parameter or an asthma associated with ABPA parameter has "improved," the parameter is quantified at baseline and at a time point after administration of the pharmaceutical composition described herein. For example, an asthma-associated parameter may be measured at day 1, day 2, day 3, day 4, day 5, day 6, day 7, day 8, day 9, day 10, day 11, day 12, day 14, or at week 3, week 4, week 5, week 6, week 7, week 8, week 9, week 10, week 11, week 12, week 13, week 14, week 15, week 16, week 17, week 18, week 19, week 20, week 21, week 22, week 23, week 24, or longer, after the initial treatment with the pharmaceutical: composition. The difference between the value of the parameter at a particular time point following initiation of treatment and the value of the parameter at baseline is used to establish whether there has been an "improvement" in the asthma associated parameter (e.g., an increase or decrease, as the case may be, depending on the specific parameter being measured).

The terms "acquire" or "acquiring" as used herein, refer to obtaining possession of a physical entity, or a value, e.g., a numerical value, by "directly acquiring" or "indirectly acquiring" the physical entity or value, such as an asthma-associated parameter. "Directly acquiring" means performing a process (e.g., performing a synthetic or analytical method) to obtain the physical entity or value. "Indirectly acquiring" refers to receiving the physical entity or value from another party or source (e.g., a third-party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis").

Information that is acquired indirectly can be provided in the form of a report, e.g., supplied in paper or electronic form, such as from an online database or application (an "App"). The report or information can be provided by, for example, a healthcare institution, such as a hospital or clinic; or a healthcare provider, such as a doctor or nurse.

Forced Expiratory Volume in 1 Second ($FEV_1$). According to certain embodiments, administration of an IL-4R antagonist to a patient results in an increase from baseline of forced expiratory volume in 1 second ($FEV_1$). Methods for measuring $FEV_1$ are known in the art. For example, a spirometer that meets the 2005 American Thoracic Society (ATS)/European Respiratory Society (ERS) recommendations can be used to measure $FEV_1$ in a patient. The ATS/ERS Standardization of Spirometry may be used as a guideline. Spirometry is generally performed between 6 and 10 AM after an albuterol withhold of at least 6 hours. Pulmonary function tests are generally measured in the sitting position, and the highest measure is recorded for $FEV_1$ (in liters).

Therapeutic methods that result in an increase of $FEV_1$ from baseline of at least 0.05 L at week 12 following initiation of treatment with a pharmaceutical composition comprising an anti-IL-4R antagonist are provided. For example, administration of an IL-4R antagonist to a subject in need thereof causes an increase of $FEV_1$ from baseline of about 0.05 L, 0.10 L, 0.12 L, 0.14 L, 0.16 L, 0.18 L, 0.20 L, 0.22 L, 0.24 L, 0.26 L, 0.28 L, 0.30 L, 0.32 L, 0.34 L, 0.36 L, 0.38 L, 0.40 L, 0.42 L, 0.44 L, 0.46 L, 0.48 L, 0.50 L, or more at week 12.

FEF25-75%. According to certain embodiments, administration of an IL-4R antagonist to a patient results in an increase from baseline of FEF25-75%. Methods for measuring FEF are known in the art. For example, a spirometer that meets the 2005 American Thoracic Society (ATS)/European Respiratory Society (ERS) recommendations can be used to measure $FEV_1$ in a patient. The FEF25-75% (forced expiratory flow between 25% and 75%) is the speed (in liters per second) at which a person can empty the middle half of his or her air during a maximum expiration (i.e., Forced Vital Capacity or FVC). The parameter relates to the average flow from the point at which 25 percent of the FVC has been exhaled to the point at which 75 percent of the FVC has been exhaled. The FEF25-75% of a subject provides information regarding small airway function, such as the extent of small airway disease and/or inflammation. A change in FEF25-75% is an early indicator of obstructive lung disease. In certain embodiments, an improvement and/or increase in the FEF25-75% parameter is an improvement of at least 10%, 25%, 50% or more as compared to baseline. In certain embodiments, the methods described herein result in normal FEF25-75% values in a subject (e.g., values ranging from 50-60% and up to 130% of the average).

Morning and Evening Peak Expiratory Flow (AM PEF and PM PEF). According to certain embodiments, administration of an IL-4R antagonist to a patient results in an increase from baseline of morning (AM) and/or evening (PM) peak expiratory flow (AM PEF and/or PM PEF). Methods for measuring PEF are known in the art. For example, according to one method for measuring PEF, patients are issued an electronic PEF meter for recording morning (AM) and evening (PM) PEF (as well as daily albuterol use, morning and evening asthma symptom scores, and number of nighttime awakenings due to asthma symptoms that require rescue medications). Patients are instructed on the use of the device, and written instructions on the use of the electronic PEF meter are provided to the patients. In addition, a medical professional may instruct the patients on how to record pertinent variables in the electronic PEF meter. AM PEF is generally performed within 15 minutes after arising (between 6 am and 10 am) prior to taking any albuterol. PM PEF is generally performed in the evening (between 6 μm and 10 pm) prior to taking any albuterol. Subjects should try to withhold albuterol for at least 6 hours prior to measuring their PEF. Three PEF efforts are performed by the patient and all 3 values are recorded by the electronic PEF meter. Usually the highest value is used for evaluation. Baseline AM PEF may be calculated as the mean AM measurement recorded for the 7 days prior to administration of the first dose of pharmaceutical composition comprising the IL-4R antagonist, and baseline PM PEF may be calculated as the mean PM measurement recorded for the 7 days prior to administration of the first dose of pharmaceutical composition comprising the IL-4R antagonist.

Therapeutic methods that result in an increase in AM PEF and/or PM PEF from baseline of at least 1.0 L/min at week 12 following initiation of treatment with a pharmaceutical composition comprising an anti-IL-4R antagonist are provided. For example, according to exemplary embodiments, administration of an IL-4R antagonist to a subject in need thereof causes an increase in PEF from baseline of about 0.5 L/min, 1.0 L/min, 1.5 L/min, 2.0 L/min, 2.5 L/min, 3.0 L/min, 3.5 L/min, 4.0 L/min, 4.5 L/min, 5.0 L/min, 5.5 L/min, 6.0 L/min, 6.5 L/min, 7.0 L/min, 7.5 L/min, 8.0 L/min, 8.5 L/min, 9.0 L/min, 9.5 L/min, 10.0 L/min, 10.5 L/min, 11.0 L/min, 12.0 L/min, 15 L/min, 20 L/min, or more at week 12.

Albuterol/Levalbuterol Use. According to certain embodiments, administration of an IL-4R antagonist to a patient results in a decrease from baseline of daily albuterol or levalbuterol use. The number of albuterol/levalbuterol inhalations can be recorded daily by the patients in a diary, PEF meter, or other recording device. During treatment with the pharmaceutical composition described herein, use of albuterol/levalbuterol typically may be on an as-needed basis for symptoms, not on a regular basis or prophylactically. The baseline-number of albuterol/levalbuterol inhalations/day may be calculated based on the mean for the 7 days prior to administration of the first dose of pharmaceutical composition comprising the IL-4R antagonist.

Therapeutic methods are provided that result in a decrease in albuterol/levalbuterol use from baseline of at least 0.25 puffs per day at week 12 following initiation of treatment with a pharmaceutical composition comprising an anti-IL-4R antagonist. For example, administration of an IL-4R antagonist to a subject in need thereof causes a decrease in albuterol/levalbuterol use from baseline of about 0.25 puffs per day, 0.50 puffs per day, 0.75 puffs per day, 1.00 puff per day, 1.25 puffs per day, 1.5 puffs per day, 1.75 puffs per day, 2.00 puffs per day, 2.25 puffs per day, 2.5 puffs per day, 2.75 puffs per day, 3.00 puffs per day, or more at week 12.

OCS Use. According to certain embodiments, administration of an IL-4R antagonist to a patient can be used in conjunction with an OCS such as oral prednisone. The number of OCS administrations can be recorded daily by the patients in a diary, PEF meter, or other recording device. During treatment with the pharmaceutical composition described herein, occasional short-term use of prednisone typically can be used to control acute asthmatic episodes, e.g., episodes in which bronchodilators and other anti-inflammatory agents fail to control symptoms. In other aspects, prednisone is used concurrent with or as a substitution for ICS. Oral prednisone may be administered in dosages of about 5 mg, 10 mg, 15 mg, 20 mg, 25 mg, 30 mg, 35 mg or 40 mg. OCS can optionally be administered once a day or multiple times a day (e.g., twice a day, three times a day, four times a day, etc.)

In certain exemplary embodiments, methods for reducing or eliminating the dependency of the subject on OCS use are provided. The reduction or elimination of steroid dependency is highly advantageous and desirable. In certain embodiments, a reduction of 50% or greater (e.g., 50%, 60%, 70%, 80%, 90% or more) in the OCS dose is achieved after administration of IL-4R antibody therapy at a period of time (e.g., at week 24 In certain embodiments, the OCS is substantially eliminated after 40 weeks, 45 weeks, 50 weeks, 52 weeks, or greater after first dose following administration of the loading dose. In other embodiments, the level of OCS use is reduced to less than 5 mg per day (e.g., less than 5 mg, 4 mg, 3 mg, 2 mg or less per day). In other embodiments, the dependency on OCS use is substantially eliminated after 3 months, 6 months, 9 months or 1 year following treatment with IL4R antibody or fragment thereof.

5-Item Asthma Control Questionnaire (ACQ) Score. According to certain embodiments, administration of an IL-4R antagonist to a patient results in a decrease from baseline of five-item Asthma Control Questionnaire (ACQ5) score. The ACQ5 is a validated questionnaire to evaluate asthma control.

Therapeutic methods are provided that result in a decrease in ACQ5 score from baseline of at least 0.10 points at week 12 following initiation of treatment with a pharmaceutical composition comprising an anti-IL-4R antagonist. For example, administration of an IL-4R antagonist to a subject in need thereof causes a decrease in ACQ score from baseline of about 0.10 points, 0.15 points, 0.20 points, 0.25 points, 0.30 points, 0.35 points, 0.40 points, 0.45 points, 0.50 points, 0.55 points, 0.60 points, 0.65 points, 0.70 points, 0.75 points, 0.80 points, 0.85 points, or more at week 12.

Night-Time Awakenings. According to certain embodiments, administration of an IL-4R antagonist to a patient results in a decrease from baseline of average number of nighttime awakenings.

In certain embodiments, the methods decrease the average number of nighttime awakenings from baseline by at least about 0.10 times per night at week 12 following initiation of treatment. For example, administration of an IL-4R antagonist to a subject in need thereof can cause a decrease in average number of nighttime awakenings from baseline of about 0.10 times per night, 0.15 times per night, 0.20 times per night, 0.25 times per night, 0.30 times per night, 0.35 times per night, 0.40 times per night, 0.45 times per night, 0.50 times per night, 0.55 times per night, 0.60 times per night, 0.65 times per night, 0.70 times per night, 0.75 times per night, 0.80 times per night, 0.85 times per night, 0.90 times per night, 0.95 times per night, 1.0 times per night, 2.0 times per night, or more at week 12.

22-Item Sinonasal Outcome Test (SNOT-22) Score. According to certain embodiments, administration of an IL-4R antagonist to a patient results in a decrease from baseline of 22-item Sinonasal Outcome Test (SNOT-22). The SNOT-22 is a validated questionnaire to assess the impact of chronic rhinosinusitis on quality of life (Hopkins et al 2009, Clin. Otolaryngol. 34:447-454).

Therapeutic methods are provided that result in a decrease in SNOT-22 score from baseline of at least 1 point at week 12 following initiation of treatment with a pharmaceutical composition comprising an anti-IL-4R antagonist. For example, administration of an IL-4R antagonist to a subject in need thereof can cause a decrease in SNOT-22 score from baseline of about 1, 2, 3, 4, 5, 6, 7, 8, 9, 10, 11, 12, 13 points, or more at week 12.

Biomarkers. In certain embodiments, the subject experiences an improvement in lung function as measured by a biomarker, e.g., a biomarker associated with allergic asthma (e.g., severe uncontrolled allergic asthma) and/or a biomarker associated with ABPA. For example, the biomarker may be fractional exhaled nitric oxide (FeNO), eotaxin-3, total IgE, allergen-specific IgE (e.g., Af-associated IgE), periostin, eosinophil (Eos) level, or thymus and activation-regulated chemokine (TARC). In certain embodiments, an improvement in lung function is indicated by a reduction or an increase (as appropriate) at week 4, week 12 or week 24 following treatment.

Methods for Treating Asthma and/or ABPA

In some embodiments, methods are provided for treating asthma, including, e.g., allergic asthma, asthma associated with ABPA, moderate-to-severe uncontrolled asthma or inadequately controlled asthma, as well as allergic forms of any of these, in a subject in need thereof, wherein the methods comprise administering a pharmaceutical composition comprising an IL-4R antagonist to the subject. In particular embodiments, the methods are useful for treating allergic asthma, e.g., moderate-to-severe uncontrolled allergic asthma, in a subject. In other particular embodiments, the methods are useful for treating asthma associated with ABPA in a subject.

In some embodiments, methods are provided for treating ABPA in a subject in need thereof, wherein the methods comprise administering a pharmaceutical composition comprising an IL-4R antagonist to the subject. In particular embodiments, the methods are useful for treating ABPA in a subject having comorbid asthma, e.g., moderate-to-severe uncontrolled asthma.

As used herein, the term "asthma" can be used interchangeably with "intermittent asthma," or "bronchial asthma." "Asthma," "bronchial asthma" and "intermittent asthma," and allergic forms of each of these, refer to asthma in which one or any combination of the following are true: symptoms occur 2 or fewer days per week; symptoms do not interfere with normal activities; nighttime symptoms occur fewer than 2 days per month; or one or more lung function tests (e.g., forced expiratory volume in one second ($FEV_1$) and/or peak expiratory flow (PEF) of greater than 80%) are normal when the subject is not suffering from an asthma attack.

As used herein, the term "allergic bronchopulmonary aspergillosis" or "ABPA" refers to a hypersensitive reaction to an *Aspergillus* antigen, typically, *Aspergillus fumigatus* in the lungs of a subject which may damage the airways and result in permanent lung damage. ABPA can be diagnosed by any combination of patient health history (including the presence of asthma and/or cystic fibrosis), X-ray and/or CT scans, allergy skin testing, and blood IgE levels (e.g., total IgE and/or *Aspergillus*-specific IgE, e.g., Af-specific IgE). In certain embodiments, ABPA is diagnosed by a combination of one or more of: (1) total serum IgE levels; (2) eosinophilia; (3) *Aspergillus*-specific IgE, e.g., Af-specific serum IgE; and (4) *Aspergillus*-specific IgE, e.g., Af-specific serum IgG. In particularly exemplary embodiments, a subject is diagnosed with ABPA is the subject exhibits one or more (e.g., one, two, or all three) of the following biomarkers: (1) a baseline serum IgE level of greater than 1000 IU/mL; (2) an Af-specific baseline serum IgE level of greater than 0.35 kU/L; and (3) a baseline blood eosinophil level of greater than 500 cells/µL.

In certain embodiments, ABPA is diagnosed in a subject having an HLA-DR2 serotype (e.g., subtype HLA-DRB1*1501, subtype *HLA-DRB1*1503, or subtype *HLA-DRB1*1601) or an HLA-DR5 serotype (e.g., subtype HLA-DRB1*1101, subtype HLA-DRB1*1104, or subtype HLA-DRB1*1202).

As used herein, the term "asthma associated with ABPA" refers to a subject that has comorbid asthma and ABPA.

"IgE" refers to an antibody isotype that contains the ε heavy chain, and is a monomer having five domains in the immunoglobulin structure. IgE is typically present in plasma at a concentration of less than 1 µg/mL, and has a half-life of about 2 days in serum (Abbas and Lichtman (2004) Basic Immunology functions and disorders of the immune system. 2nd ed. Philadelphia: Saunders). The units kU/L or IU/mL (which units can be used interchangeably) are often used to express the level of IgE in peripheral blood, with one kU/L is equal to 2.4 ng/ml (Seagroatt and Anderson (1981) E. J. Biol Stand. 9:431).

IgE (e.g., total serum IgE and/or allergen specific IgE) can be determined using a variety of methods known in the art. For example, PRIST (paper radioimmunosorbent test) can be used, in which serum samples react with IgE that has been tagged with radioactive iodine. Bound radioactive iodine is detected, and is proportional to the amount of total IgE in the serum sample. In clinical immunology, levels of individual classes of immunoglobulins can be measured by nephelometry (or turbidimetry) to characterize the antibody profile of a subject. Other methods of measuring IgE levels include, but are not limited to, ELISA, immunofluorescence, Western blot, immunodiffusion, immunoelectrophoresis and the like. Measurement of a serum IgE concentration can be performed using a UniCAP 250® system (Pharmacia, Uppsala, Sweden) (See G. J. Gleich, A. K. Averbach and N. A. Swedlund, Measurement of IgE in normal and allergic serum by radioimmunoassay. *J. Lab. Clin. Med.* 77 (1971), p. 690.)

Allergic asthma refers to asthma that is triggered by allergens, e.g., inhaled allergens, such as dust mites, pet dander, pollen, fungi and the like. As used herein, the term "allergic asthma" refers to asthma in combination with one or more allergic markers, e.g., total serum IgE (e.g., a total serum IgE of ≥30 IU/mL, a total serum IgE of ≥700 IU/mL, or total serum IgE of ≥1000 IU/mL), and/or at least one positive allergen-specific IgE value (e.g., an allergen-specific IgE value of ≥0.35 kU/L). In certain embodiments, the allergen is an airborne aeroallergen (e.g., an annual aeroallergen or a perennial aeroallergen).

In certain exemplary embodiments, a subject having allergic asthma has a total serum IgE level of about ≥5 IU/mL, about ≥10 IU/mL, about ≥20 IU/mL, about ≥30 IU/mL, about ≥40 IU/mL, about ≥50 IU/mL, about ≥60 IU/mL, about ≥70 IU/mL, about ≥80 IU/mL, about ≥90 IU/mL, about ≥100 IU/mL, about ≥110 IU/mL, about ≥120 IU/mL, about ≥130 IU/mL, about ≥140 IU/mL, about ≥150 IU/mL, about ≥160 IU/mL, about ≥170 IU/mL, about ≥180 IU/mL, about ≥190 IU/mL, about ≥200 IU/mL, about ≥250 IU/mL, about ≥300 IU/mL, about ≥350 IU/mL, about ≥400 IU/mL, about ≥450 IU/mL, about ≥500 IU/mL, about ≥550 IU/mL, about ≥600 IU/mL, about ≥650 IU/mL, about ≥700 IU/mL, about ≥750 IU/mL, about ≥800 IU/mL, about ≥850 IU/mL, about ≥900 IU/mL, about ≥950 IU/mL, about ≥1000 IU/mL or greater. In particularly exemplary embodiments, a subject having allergic asthma has a total serum IgE of greater than about 700 IU/mL (e.g., high total serum IgE). In other particularly exemplary embodiments, a subject having allergic asthma has a total serum IgE of greater than about 1000 IU/mL (e.g., very high total serum IgE). In certain exemplary embodiments, a subject has a total serum IgE level of at least 700 IU/mL as measured using an ImmunoCAP assay. In certain exemplary embodiments, a subject has a total serum IgE level of at least 1000 IU/mL as measured using an ImmunoCAP assay.

In certain exemplary embodiments, a subject having allergic asthma has at least one positive allergen-specific IgE value present in an amount of about ≥0.05 kU/L, about ≥0.10 kU/L, about ≥0.15 kU/L, about ≥0.20 kU/L, about ≥0.21 kU/L, about ≥0.22 kU/L, about ≥0.23 kU/L, about ≥0.24 kU/L, about ≥0.25 kU/L, about ≥0.26 kU/L, about ≥0.27 kU/L, about ≥0.28 kU/L, about ≥0.29 kU/L, about ≥0.30 kU/L, about ≥0.31 kU/L, about ≥0.32 kU/L, about ≥0.33 kU/L, about ≥0.34 kU/L, about ≥0.35 kU/L, about ≥0.36 kU/L, about ≥0.37 kU/L, about ≥0.38 kU/L, about ≥0.39 kU/L, about ≥0.40 kU/L, about ≥0.45 kU/L, about ≥0.50 kU/L, about ≥0.55 kU/L, about ≥0.60 kU/L, about ≥0.65 kU/L, about ≥0.70 kU/L or greater.

As used herein, a "perennial aeroallergen" refers to airborne allergens that can be present in the environment year-round, such as dust mites, fungi, dander and the like. Perennial aeroallergens include, but are not limited to, *Alternaria alternata, Aspergillus fumigatus, Aureobasidium pullulans, Candida albicans, Cladosporium herbarum, Dermatofagoides farinae, Dermatofagoides pteronyssinus, Mucor racemosus, Penicillium chrysogenum, Phoma betae, Setomelanomma rostrata, Stemphylium herbarum*, cat dander, dog dander, cow dander, chicken feathers, goose feathers, duck feathers, cockroach (e.g., German cockroach, Oriental cockroach), mouse urine, peanut dust, tree nut dust, and the like.

As used herein, a "seasonal aeroallergen" refers to airborne allergens that are present in the environment seasonally, such as pollens and spores. Seasonal aeroallergens include, but are not limited to, tree pollen (e.g., birch, alder, cedar, hazel, hornbeam, horse chestnut, willow, poplar, linden, pine, maple, oak, olive and the like), grass pollen (e.g., ryegrass, cat's tail and the like), weed pollen (e.g., ragweed, plantain, nettles, mugwort, fat hen, sorrel and the like), fungal spores that increase during particular seasons, temperatures, etc. (e.g., molds), and the like.

As used herein, the term "persistent asthma" or "persistent bronchial asthma" refers to asthma that is more severe than (bronchial) asthma/intermittent (bronchial) asthma. A subject suffering from persistent asthma or persistent bronchial asthma experiences one or more of the following: symptoms more than 2 days per week; symptoms that interfere with normal activities; nighttime symptoms that occur more than 2 days per month; or one or more lung function tests (e.g., forced expiratory volume in one second ($FEV_1$) and/or peak expiratory flow (PEF) of less than 80%) that are not normal when the subject is not suffering from an asthma attack; the subject relies on daily asthma control medication; the subject has taken a systemic steroid more than once in the last year after a severe asthma flare-up; or use of a short-acting beta-2 agonist more than two days per week for relief of asthma symptoms.

Asthma/intermittent asthma, bronchial asthma/intermittent bronchial asthma, and persistent asthma/persistent bronchial asthma, and allergic forms of each of these, can be categorized as "mild," "moderate," "severe" or "moderate-to-severe." "Mild intermittent asthma" or "mild intermittent bronchial asthma" is defined as having symptoms less than once a week, and having forced expiratory volume in one second ($FEV_1$) or peak expiratory flow (PEF) ≥80%. "Mild persistent asthma" or "mild persistent bronchial asthma" differs in that symptoms frequency is greater than once per week but less than once per day, and variability in $FEV_1$ or PEF is <20%-30%. "Moderate intermittent asthma" or "moderate intermittent bronchial asthma" is defined as having symptoms less than once a week, and having forced expiratory volume in one second ($FEV_1$) or peak expiratory flow (PEF) of 60-80%. "Moderate persistent asthma" or "moderate persistent bronchial asthma," or an allergic form thereof, is defined as having daily symptoms, exacerbations that may affect activity and/or sleep, nocturnal symptoms more than once a week, daily use of inhaled short-acting beta-2 agonist and having forced expiratory volume in one second ($FEV_1$) or peak expiratory flow (PEF) of 60-80%. "Severe intermittent asthma" or "severe intermittent bronchial asthma," or an allergic form thereof, is defined as having symptoms less than once a week, and having forced expiratory volume in one second ($FEV_1$) or peak expiratory flow (PEF) of 60%. "Severe persistent asthma" or "severe persistent bronchial asthma" is defined as having daily symptoms, frequent exacerbations that may affect activity and/or sleep, frequent nocturnal symptoms, limitation of physical activities, daily use of inhaled short-acting beta-2 agonist, and having forced expiratory volume in one second ($FEV_1$) or peak expiratory flow (PEF) of 60%. "Moderate-to-severe intermittent asthma" or "moderate-to-severe intermittent bronchial asthma," or an allergic form thereof, is defined as having symptoms between those of moderate intermittent asthma/moderate intermittent bronchial asthma and severe intermittent asthma/severe intermittent bronchial asthma. "Moderate-to-severe persistent asthma" or "moderate-to-severe persistent bronchial asthma," or an allergic form thereof, is defined as having symptoms between those of moderate persistent asthma/moderate persistent bronchial asthma and severe persistent asthma/severe persistent bronchial asthma.

As used herein, the term "inadequately controlled asthma," or an allergic form thereof, refers to patients whose asthma is either "not well controlled" or "very poorly controlled" as defined by the "Expert Panel Report 3: Guidelines for the Diagnosis and Management of Asthma," National Heart, Blood and Lung Institute, NIH, Aug. 28, 2007. "Not well controlled asthma," or an allergic form thereof, is defined as having symptoms greater than two days per week, nighttime awakenings one to three times per week, some limitations on normal activity, short-acting beta2-agonist use for symptom control greater than two days per week, FEV: of 60-80% of predicted and/or personal best, an ATAQ score of 1-2, an ACQ score of 1.5 or greater, and an ACT score of 16-19. "Very poorly controlled asthma," or an allergic form thereof, is defined as having symptoms throughout the day, nighttime awakenings four times or more per week, extreme limitations on normal activity, short-acting beta2-agonist use for symptom control several times per day, $FEV_1$ of less than 60% of predicted and/or personal best, an ATAQ score of 3-4, an ACQ score of N/A, and an ACT score of less than or equal to 15.

In some embodiments, a subject is identified as having "moderate-to-severe uncontrolled" asthma (e.g., allergic asthma, asthma associated with ABPA, moderate-to-severe asthma, persistent asthma or the like) if the subject receives such a diagnosis from a physician, based on the Global Initiative for Asthma (GINA) 2009 Guidelines, and one or more of the following criteria: i) Existing treatment with moderate- or high-dose ICS/LABA (2 fluticasone propionate 250 µg twice daily or equipotent ICS daily dosage) with a stable dose of ICS/LABA for greater than or equal to 1 month prior to administration of the loading dose of IL-4R antagonist; ii) $FEV_1$ 40 to 80% predicted normal prior to administration of the loading dose of IL-4R antagonist; iii) ACQ-5 score greater than or equal to 1.5 prior to administration of the loading dose of IL-4R antagonist; iv) reversibility of at least 12% and 200 mL in $FEV_1$ after 200 µg to 400 µg (2 to 4 inhalations) of salbutamol/albuterol prior to administration of the loading dose of IL-4R antagonist; or v) has experienced, within 1 year prior to administration of the loading dose of IL-4R antagonist, any of the following events: (a) treatment with greater than or equal to 1 systemic (oral or parenteral) steroid burst for worsening asthma, (b) hospitalization or an emergency/urgent medical care visit for worsening asthma.

"Severe asthma" or "severe allergic asthma" refers to asthma in which adequate control cannot be achieved by high-dose treatment with inhaled corticosteroids and additional controllers (e.g., long-acting inhaled beta 2 agonists, montelukast, and/or theophylline) or by oral corticosteroid treatment (e.g., for at least six months per year), or is lost when the treatment is reduced. In certain embodiments, severe asthma includes asthma that is treated with high-dose ICS and at least one additional controller (e.g., LABA, montelukast, or theophylline) or oral corticosteroids >6 months/year, wherein at least one of the following occurs or would occur if treatment is reduced: ACT<20 or ACQ>1.5; at least 2 exacerbations in the last 12 months; at least 1 exacerbation treated in hospital or requiring mechanical ventilation in the last 12 months; or $FEV_{1<80}$% (if $FEV_1$/FVC below the lower limit of normal).

"Steroid-dependent asthma" or "steroid-dependent allergic asthma" refers to asthma which requires one or more of the following treatments: frequent, short term oral corticosteroid treatment bursts in the past 12 months; regular use of high dose inhaled corticosteroids in the past 12 months; regular use of injected long acting corticosteroids; daily use of oral corticosteroids; alternate-day oral corticosteroids; or prolonged use of oral corticosteroids in the past year.

"Oral corticosteroid-dependent asthma" of "oral corticosteroid-dependent allergic asthma" refers to a subject having ≥3 30-day oral corticosteroid (OCS) fills over a 12-month period and a primary asthma diagnosis within 12 months of the first OCS fill. Subjects with OCS-dependent asthma may also experience one or any combination of the following: have received physician prescribed LABA and high dose ICS (total daily dose >500 µg fluticasone propionate dry powder formulation equivalent) for at least 3 months (the ICS and LABA can be parts of a combination product, or given by separate inhalers); have received additional maintenance asthma controller medications according to standard practice of care e.g., leukotriene receptor antagonists (LTRAs), theophylline, long-acting muscarinic antagonists (LAMAs), secondary ICS and cromones; received OCS for the treatment of asthma at a dose of between ≥7.5 to ≤30 mg (prednisone or prednisolone equivalent); have received an OCS dose administered every other day (or different doses every other day); morning pre-bronchodilator (BD) $FEV_1$ of <80% predicted normal; have evidence of asthma as documented by post-BD (albuterol/salbutatomol) reversibility of $FEV_1$≥12% and ≥200 mL (15-30 min after administration of 4 puffs of albuterol/salbutamol); or have a history of at least one asthma exacerbation event within 12 months.

In one aspect, methods for treating asthma are provided comprising: (a) selecting a patient that exhibits a blood eosinophil level of at least 300 cells per microliter; and (b) administering to the patient a pharmaceutical composition comprising an IL-4R antagonist.

In another aspect, methods for treating asthma are provided comprising: (a) selecting a patient that exhibits a blood eosinophil level of 200-299 cells per microliter; and (b) administering to the patient a pharmaceutical composition comprising an IL-4R antagonist.

In another aspect, methods for treating asthma are provided comprising: (a) selecting a patient that exhibits a blood eosinophil level of less than 200 cells per microliter; and (b) administering to the patient a pharmaceutical composition comprising an IL-4R antagonist.

In one aspect, methods for treating asthma are provided comprising: (a) selecting a patient that exhibits a blood eosinophil level of at least 150 cells per microliter; and (b) administering to the patient a pharmaceutical composition comprising an IL-4R antagonist.

In one aspect, methods for treating asthma are provided comprising: (a) selecting a patient that exhibits a blood eosinophil level of at least 300 cells per microliter; and (b) administering to the patient a pharmaceutical composition comprising an IL-4R antagonist.

In one aspect, methods for treating asthma are provided comprising: (a) selecting a patient that exhibits a baseline FeNO level of ≥20 ppb; and (b) administering to the patient a pharmaceutical composition comprising an IL-4R antagonist.

In one aspect, methods for treating asthma are provided comprising: (a) selecting a patient that exhibits a baseline FeNO level of ≥25 ppb; and (b) administering to the patient a pharmaceutical composition comprising an IL-4R antagonist.

In one aspect, methods for treating asthma are provided comprising: (a) selecting a patient that exhibits a baseline FeNO level of ≥50 ppb; and (b) administering to the patient a pharmaceutical composition comprising an IL-4R antagonist.

In one aspect, methods for treating asthma are provided comprising: (a) selecting a patient that exhibits a baseline total IgE level of ≥30 IU/mL; and (b) administering to the patient a pharmaceutical composition comprising an IL-4R antagonist.

In one aspect, methods for treating asthma are provided comprising: (a) selecting a patient that exhibits a baseline total IgE level of ≥700 IU/mL; and (b) administering to the patient a pharmaceutical composition comprising an IL-4R antagonist.

In one aspect, methods for treating asthma are provided comprising: (a) selecting a patient that exhibits a baseline total IgE level of ≥1000 IU/mL; and (b) administering to the patient a pharmaceutical composition comprising an IL-4R antagonist.

In one aspect, methods for treating asthma are provided comprising: (a) selecting a patient that exhibits a baseline allergen-specific IgE of ≥0.15 kU/L; and (b) administering to the patient a pharmaceutical composition comprising an IL-4R antagonist.

In one aspect, methods for treating asthma are provided comprising: (a) selecting a patient that exhibits a baseline allergen-specific IgE of ≥0.35 kU/L; and (b) administering to the patient a pharmaceutical composition comprising an IL-4R antagonist.

In a related aspect, methods for treating asthma comprising an add-on therapy to background therapy are provided. In certain embodiments, an IL-4R antagonist is administered as an add-on therapy to an asthma patient who is on background therapy for a certain period of time (e.g., 1 week, 2 weeks, 3 weeks, 1 month, 2 months, 5 months, 12 months, 18 months, 24 months, or longer) (also called the "stable phase"). In some embodiments, the background therapy comprises a ICS and/or a LABA.

In some embodiments, a method for reducing an asthma patient's dependence on ICS and/or LABA for the treatment of one or more asthma exacerbations comprising: (a) selecting a patient who has moderate-to-severe asthma that is uncontrolled with a background asthma therapy comprising an ICS, a LABA, or a combination thereof; and administering to the patient a pharmaceutical composition comprising an IL-4R antagonist, is provided.

In some embodiments methods to treat or alleviate conditions or complications associated with asthma or comorbid with asthma, such as chronic rhinosinusitis, allergic rhinitis, allergic fungal rhinosinusitis, chronic sinusitis, allergic bronchopulmonary aspergillosis (ABPA), unified airway disease, eosinophilic granulomatosis with polyangiitis (EGPA, formerly known as Churg-Strauss syndrome), gastroesophageal reflux disease (GERD), atopic conjunctivitis, atopic dermatitis, vasculitis, cystic fibrosis (CF), chronic obstructive pulmonary disease (COPD), chronic eosinophilic pneumonia (CEP) and exercise induced bronchospasm, are provided.

Methods for treating persistent asthma (e.g., persistent allergic asthma) are also provided. As used herein, the term "persistent asthma" means that the subject has symptoms at least once a week at day and/or at night, with the symptoms lasting a few hours to a few days. In certain alternative embodiments, the persistent asthma is "mildly persistent" (e.g., more than twice a week but less than daily with symptoms severe enough to interfere with daily activities or sleep and/or where pulmonary function is normal or reversible with inhalation of a bronchodilator), "moderately persistent" (e.g., symptoms occurring daily with sleep interrupted at least weekly and/or with pulmonary function moderately abnormal), or "severely persistent" (e.g., continuous symptoms despite the correct use of approved medications and/or where pulmonary function is severely affected).

Interleukin-4 Receptor Antagonists

The methods featured herein comprise administering to a subject in need thereof a therapeutic composition comprising an IL-4R antagonist. As used herein, an "IL-4R antagonist" is any agent that binds to or interacts with IL-4R and inhibits the normal biological signaling function of IL-4R when IL-4R is expressed on a cell in vitro or in vivo. Non-limiting examples of categories of IL-4R antagonists include small molecule IL-4R antagonists, anti-IL-4R aptamers, peptide-based IL-4R antagonists (e.g., "peptibody" molecules), and antibodies or antigen-binding fragments of antibodies that specifically bind human IL-4R. According to certain embodiments, the IL-4R antagonist comprises an anti-IL-4R antibody that can be used in the context of the methods described elsewhere herein. For example, in one embodiment, the IL-4R antagonist is an antibody or antigen-binding fragment thereof that specifically binds to an IL-4R, and comprises the heavy chain and light chain (Complementarity Determining Region) CDR sequences from the Heavy Chain Variable Region (HCVR) and Light Chain Variable Region (LCVR) of SEQ ID NOs: 1 and 2, respectively.

The term "human IL4R" (hIL-4R) refers to a human cytokine receptor that specifically binds to interleukin-4 (IL-4), such as IL-4Rα.

The term "antibody" refers to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$, and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the anti-IL-4R antibody (or antigen-binding portion thereof) may be identical to the human germline sequences, or may be naturally or artificially modified. An amino acid consensus sequence may be defined based on a side-by-side analysis of two or more CDRs.

The term "antibody" also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds to an antigen to form a complex. Antigen-binding fragments of an antibody may be derived, e.g., from full antibody molecules using any suitable standard techniques, such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment."

An antigen-binding fragment of an antibody will typically comprise at least one variable domain. The variable domain may be of any size or amino acid composition and will generally comprise at least one CDR that is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody described herein include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids that result in a flexible or semi-flexible linkage between adjacent variable and/or constant domains in a single polypeptide molecule, typically the hinge region may consist of between 2 to 60 amino acids, typically between 5 to 50, or typically between 10 to 40 amino acids. Moreover, an antigen-binding fragment of an antibody described herein may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, may be adapted for use in the context of an antigen-binding fragment of an antibody described herein using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody" includes antibodies having variable and constant regions derived from human germline immunoglobulin sequences. The human antibodies described herein may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody" does not include antibodies in which CDR sequences derived from the germline of another mammalian species, such as a mouse, have been grafted onto human framework sequences.

The term "recombinant human antibody" includes all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. Antibodies having one or more mutations in the hinge, $C_H2$, or $C_H3$ region, which may be desirable, for example, in production, to improve the yield of the desired antibody form, are provided.

An "isolated antibody" means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody". An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IL-4R includes antibodies that bind IL-4R or portion thereof with a $K_D$ of less than about 1000 nM, less than: about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM, or less than about 0.5 nM, as measured in a surface plasmon resonance assay. An isolated antibody that specifically binds human IL-4R may, however, have cross-reactivity to other antigens, such as IL-4R molecules from other (non-human) species.

The anti-IL-4R antibodies useful for the methods may comprise one or more amino acid substitutions, insertions, and/or deletions (e.g. 1, 2, 3, 4, 5, 6, 7, 8, 9, or 10 substitutions and/or 1, 2, 3, 4, 5, 6, 7, 8, 9, or 10 insertions and/or 1, 2, 3, 4, 5, 6, 7, 8, 9, or 10 deletions) in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. Methods involving the use of antibodies, and antigen-binding fragments thereof, that are derived from any of the amino acid sequences disclosed herein, wherein one or more amino acids (e.g. 1, 2, 3, 4, 5, 6, 7, 8, 9, or 10 amino acids) within one or more framework and/or one or more (e.g. 1, 2, 3, 4, 5, 6, 7, 8, 9, 10, 11 or 12 with respect to the tetrameric antibody or 1, 2, 3, 4, 5 or 6 with respect to the HCVR and LCVR of an antibody) CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"), are provided. A person of ordinary skill in the art, starting with the heavy and light chain variable region sequences disclosed herein, can easily produce numerous antibodies and antigen-binding fragments that comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the invention.

Methods involving the use of anti-IL-4R antibodies comprising variants of any of the HCVR, LCVR, and/or CDR amino acid sequences disclosed herein having one or more conservative substitutions. For example, the use of anti-IL-4R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein, are provided.

The term "surface plasmon resonance" refers to an optical phenomenon that allows for the analysis of real-time interactions by detection of alterations in protein concentrations within a biosensor matrix, for example using the BIAcore™ system (Biacore Life Sciences division of GE Healthcare, Piscataway, NJ).

The term "$K_D$" refers to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Preparation of Human Antibodies

Methods for generating human antibodies in transgenic mice are known in the art. Any such known methods can be used to make human antibodies that specifically bind to human IL-4R.

Using VELOCIMMUNE® technology (see, for example, U.S. Pat. No. 6,596,541, Regeneron Pharmaceuticals) or any other known method for generating monoclonal antibodies, high affinity chimeric antibodies to IL-4R are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc., using standard procedures known to those skilled in the art. The mouse constant regions are replaced with a desired human constant region to generate a fully human antibody described herein, for example wild-type or modified IgG1 or IgG4. While the constant region selected may vary according to specific use, high affinity antigen-binding and target specificity characteristics reside in the variable region.

In general, the antibodies that can be used in the methods possess high affinities, as described above, when measured by binding to antigen either immobilized on solid phase or in solution phase. The mouse constant regions are replaced with desired human constant regions to generate the fully-human antibodies described herein. While the constant region selected may vary according to specific use, high affinity antigen-binding and target specificity characteristics reside in the variable region.

In one embodiment, human antibody or antigen-binding fragment thereof that specifically binds IL-4R that can be used in the context of the methods described herein comprises the three heavy chain CDRs (HCDR1, HCDR2 and HCDR3) contained within a heavy chain variable region (HCVR) having an amino acid sequence of SEQ ID NO: 1. The antibody or antigen-binding fragment may comprise the three light chain CDRs (LCVR1, LCVR2, LCVR3) contained within a light chain variable region (LCVR) having an amino acid sequence of SEQ ID NO: 2. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

In certain embodiments, the antibody or antigen-binding fragment thereof comprises the six CDRs (HCDR1, HCDR2, HCDR3, LCDR1, LCDR2 and LCDR3) from the heavy and light chain variable region amino acid sequence pairs (HCVR/LCVR) of SEQ ID NOs: 1 and 2.

In certain embodiments, the antibody or antigen-binding fragment thereof comprises six CDRs (HCDR1/HCDR2/HCDR3/LCDR1/LCDR2/LCDR3) having the amino acid sequences of SEQ ID NOs: 3/4/5/6/7/8.

In certain embodiments, the antibody or antigen-binding fragment thereof comprises HCVR/LCVR amino acid sequence pair of SEQ ID NOs: 1 and 2.

In certain embodiments, the antibody is dupilumab, which comprises the HCVR/LCVR amino acid sequence pair of SEQ ID NOs: 1 and 2.

In certain embodiments, the antibody sequence is dupilumab, which comprises the heavy chain/light chain amino acid sequence pair of SEQ ID NOs: 9 and 10.

```
Dupilumab HCVR amino acid sequence:
                                            (SEQ ID NO: 1)
EVQLVESGGGLEQPGGSLRLSCAGSGFTFRDYAMTWVRQAPGKGLEWVSS

ISGSGGNTYYADSVKGRFTISRDNSKNTLYLQMNSLRAEDTAVYYCAKDR

LSITIRPRYYGLDVWGQGTTVTVS.

Dupilumab LCVR amino acid sequence:
                                            (SEQ ID NO: 2)
DIVMTQSPLSLPVTPGEPASISCRSSQSLLYSIGYNYLDWYLQKSGQSPQ

LLIYLGSNRASGVPDRFSGSGSGTDFTLKISRVEAEDVGFYYCMQALQTP

YTFGQGTKLEIK.

Dupilumab HCDR1 amino acid sequence:
                                            (SEQ ID NO: 3)
GFTFRDYA.

Dupilumab HCDR2 amino acid sequence:
                                            (SEQ ID NO: 4)
ISGSGGNT.

Dupilumab HCDR3 amino acid sequence:
                                            (SEQ ID NO: 5)
AKDRLSITIRPRYYGL.

Dupilumab LCDR1 amino acid sequence:
                                            (SEQ ID NO: 6)
QSLLYSIGYNY.

Dupilumab LCDR2 amino acid sequence:
                                            (SEQ ID NO: 7)
LGS.

Dupilumab LCDR3 amino acid sequence:
                                            (SEQ ID NO: 8)
MQALQTPYT.

Dupilumab HC amino acid sequence:
                                            (SEQ ID NO: 9)
EVQLVESGGGLEQPGGSLRLSCAGSGFTFRDYAMTWVRQAPGKGLEWVSS

ISGSGGNTYYADSVKGRFTISRDNSKNTLYLQMNSLRAEDTAVYYCAKDR

LSITIRPRYYGLDVWGQGTTVTVSSASTKGPSVFPLAPCSRSTSESTAAL

GCLVKDYFPEPVTVSWNSGALTSGVHTFPAVLQSSGLYSLSSVVTVPSSS

LGTKTYTCNVDHKPSNTKVDKRVESKYGPPCPPCPAPEFLGGPSVFLFPP

KPKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPRE

PQVYTLPPSQEEMTKNQVSLTCLVKGFYPSDIAVEWESNGQPENNYKTTP

PVLDSDGSFFLYSRLTVDKSRWQEGNVFSCSVMHEALHNHYTQKSLSLSL

G
(amino acids 1-124 = HCVR; amino acids 125-451 =
HC constant).

Dupilumab LC amino acid sequence:
                                            (SEQ ID NO: 10)
DIVMTQSPLSLPVTPGEPASISCRSSQSLLYSIGYNYLDWYLQKSGQSPQ

LLIYLGSNRASGVPDRFSGSGSGTDFTLKISRVEAEDVGFYYCMQALQTP
```

-continued

```
YTFGQGTKLEIKRTVAAPSVFIFPPSDEQLKSGTASVVCLLNNFYPREAK

VQWKVDNALQSGNSQESVTEQDSKDSTYSLSSTLTLSKADYEKHKVYACE

VTHQGLSSPVTKSFNRGEC
(amino acids 1-112 = LCVR; amino acids 112-219 =
LC constant).
```

Pharmaceutical Compositions:

Methods that comprise administering an IL-4R antagonist to a patient, wherein the IL-4R antagonist is contained within a pharmaceutical composition are provided. The pharmaceutical compositions described herein are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, PA. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol. 52:238-311.

The dose of antibody administered to a patient may vary depending upon the age and the size of the patient, symptoms, conditions, route of administration, and the like. The dose is typically calculated according to body weight or body surface area. Depending on the severity of the condition, the frequency and the duration of the treatment can be adjusted. Effective dosages and schedules for administering pharmaceutical compositions comprising anti-IL-4R antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, Pharmaceut. Res. 8:1351).

Various delivery systems are known and can be used to administer the pharmaceutical compositions described herein, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, intra-tracheal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition described herein can be delivered subcutaneously or intravenously with a standard needle and syringe. In addition, with respect to subcutaneous delivery, a pen delivery device (e.g., an autoinjector pen) readily has applications in delivering a pharmaceutical composition described herein. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen delivery devices having applications in subcutaneous delivery of a pharmaceutical composition described herein include, but are not limited to the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park Ill.), to name only a few. Examples of large-volume delivery devices (e.g., large-volume injectors) include, but are not limited to, bolus injectors such as, e.g., BD Libertas West SmartDose, Enable Injections, Steady-Med PatchPump, Sensile SenseTrial, YPsomed YpsoDose, Bespak Lapas, and the like.

For direct administration to the sinuses, the pharmaceutical compositions described herein may be administered using, e.g., a microcatheter (e.g., an endoscope and microcatheter), an aerosolizer, a powder dispenser, a nebulizer or an inhaler. The methods include administration of an IL-4R antagonist to a subject in need thereof, in an aerosolized formulation. For example, aerosolized antibodies to IL-4R may be administered to treat asthma (e.g., allergic asthma, asthma associated with ABPA, moderate-to-severe asthma, persistent asthma or the like) and/or ABPA in a patient. Aerosolized antibodies can be prepared as described in, for example, U.S. Pat. No. 8,178,098, incorporated herein by reference in its entirety.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Florida. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant (e.g., polysorbate 80, HCO-50 (polyoxyethylene (50 mol) adduct of hydrogenated castor oil)), etc. As the oily medium, there are employed, e.g., sesame oil, soybean oil, etc., which may be used in combination with a solubilizing agent such as benzyl benzoate, benzyl alcohol, etc. The injection thus prepared is typically filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-4R antibody that can be used as described herein are disclosed, e.g., in U.S. Patent Application Publication No. 2012/0097565.

Dosage

The amount of IL-4R antagonist (e.g., anti-IL-4R antibody) administered to a subject according to the methods described herein is, generally, a therapeutically effective amount. As used herein, the phrase "therapeutically effective amount" means an amount of IL-4R antagonist that results in one or more of: (a) a reduction in the incidence of asthma exacerbations; (b) an improvement in one or more asthma-associated parameters (as defined elsewhere herein); and/or (c) a detectable improvement in one or more symptoms or indicia of an upper airway inflammatory condition. A "therapeutically effective amount" also includes an amount of IL-4R antagonist that inhibits, prevents, lessens, or delays the progression of asthma in a subject.

In the case of an anti-IL-4R antibody, a therapeutically effective amount can be from about 0.05 mg to about 700 mg, e.g., about 0.05 mg, about 0.1 mg, about 1.0 mg, about 1.5 mg, about 2.0 mg, about 3.0 mg, about 5.0 mg, about 7.0 mg, about 10 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, about 600 mg, about 610 mg, about 620 mg, about 630 mg, about 640 mg, about 650 mg, about 660 mg, about 670 mg, about 680 mg, about 690 mg, or about 700 mg of the anti-IL-4R antibody. In certain embodiments, 300 mg of an anti-IL-4R antibody is administered.

The amount of IL-4R antagonist contained within the individual doses may be expressed in terms of milligrams of antibody per kilogram of patient body weight (i.e., mg/kg). For example, the IL-4R antagonist may be administered to a patient at a dose of about 0.0001 to about 10 mg/kg of patient body weight. For example, the IL-4R antagonist can be administered at a dose of 1 mg/kg, 2 mg/kg, 3 mg/kg, 4 mg/kg, 5 mg/kg or 6 mg/kg.

In some embodiments, the dose of IL-4R antagonist may vary according to eosinophil count. For example, the subject may have a blood eosinophil count (i.e., a high blood eosinophil count) ≥300 cells/µL, or 300-499 cells/µL or ≥500 cells/µL (HEos); a blood eosinophil count of 200 to 299 cells/µL (moderate blood eosinophils); or a blood eosinophil count <200 cells/µL (low blood eosinophils).

In some embodiments, the dose of IL-4R antagonist may vary according to FeNO value. For example, the subject may have an FeNO value of ≥50 ppb (e.g., high FeNO); an FeNO value of ≥25 ppb; an FeNO value of between about 25 ppb and about 50 ppb; an FeNO value of <50 ppb; an FeNO value of <25 ppb (e.g., low FeNO); or an FeNO value of <20 ppb (e.g., low FeNO).

In some embodiments, the dose of IL-4R antagonist may vary according to total serum IgE value. For example, the subject may have a total serum IgE value of ≥30 IU/mL; a total serum IgE value of ≥700 IU/mL (e.g., high serum IgE); or a total serum IgE value of ≥1000 IU/mL (e.g., very high serum IgE).

In some embodiments, the dose of IL-4R antagonist may vary according to allergen-specific IgE value. In some embodiments, the dose of IL-4R antagonist may vary according to Af-specific IgE value. For example, the subject may have an allergen-specific IgE value of ≥0.15 kU/L; or an allergen-specific IgE value of ≥0.35 kU/L.

In certain embodiments, the methods comprise a loading dose of about 400 to about 600 mg of an IL-4R antagonist.

In certain embodiments, the methods comprise one or more maintenance doses of about 200 to about 300 mg of the IL-4R antagonist.

In certain embodiments, the ICS and LABA are administered for the duration of administration of the IL-4R antagonist.

In certain embodiments, the loading dose comprises 600 mg of an anti-IL-4R antibody or antigen-binding fragment thereof, and the one or more maintenance doses comprises 300 mg of the antibody or antigen-binding fragment thereof administered every other week.

In certain embodiments, the loading dose comprises 400 mg of an anti-IL-4R antibody or antigen-binding fragment thereof, and the one or more maintenance dose comprises 200 mg of the antibody or antigen-binding fragment thereof administered every other week.

In certain embodiments, the loading dose comprises 400 mg of an anti-IL-4R antibody or antigen-binding fragment thereof, and the one or more maintenance dose comprises 200 mg of the antibody or antigen-binding fragment thereof administered every other week, which may be increased to 300 mg of the antibody or antigen-binding fragment thereof administered every other week.

In other embodiments, the loading dose comprises 600 mg of an anti-IL-4R antibody or antigen-binding fragment thereof, and the one or more maintenance doses comprises 300 mg of the antibody or antigen-binding fragment thereof administered every fourth week.

In other embodiments, the loading dose comprises 400 mg of an anti-IL-4R antibody or antigen-binding fragment thereof, and the one or more maintenance doses comprises 200 mg of the antibody or antigen-binding fragment thereof administered every fourth week.

In other embodiments, the loading dose comprises 600 mg of an anti-IL-4R antibody or antigen-binding fragment thereof, and the one or more maintenance doses comprises 300 mg of the antibody or antigen-binding fragment thereof administered once a week.

In other embodiments, the loading dose comprises 400 mg of an anti-IL-4R antibody or antigen-binding fragment thereof, and the one or more maintenance doses comprises 200 mg of the antibody or antigen-binding fragment thereof administered once a week.

In other embodiments, the loading dose comprises 600 mg of an anti-IL-4R antibody or antigen-binding fragment thereof, and the one or more maintenance doses comprises 300 mg of the antibody or antigen-binding fragment thereof administered every third week.

In other embodiments, the loading dose comprises 400 mg of an anti-IL-4R antibody or antigen-binding fragment thereof, and the one or more maintenance doses comprises 200 mg of the antibody or antigen-binding fragment thereof administered every third week.

In one embodiment, the subject is 6 to <18 years old and the IL-4R antibody or antigen binding fragment thereof is administered at 2 mg/kg or 4 mg/kg.

In another embodiment, the subject is 12 to <18 years old and the IL-4R antibody or antigen binding fragment thereof is administered at 2 mg/kg or 4 mg/kg.

In another embodiment, the subject is 6 to <12 years old and the IL-4R antibody or antigen binding fragment thereof is administered at 2 mg/kg or 4 mg/kg.

In another embodiment, the subject is 2 to <6 years old and the IL-4R antibody or antigen binding fragment thereof is administered at 2 mg/kg or 4 mg/kg.

In yet another embodiment, the subject is <2 years old and the IL-4R antibody or antigen binding fragment thereof is administered at 2 mg/kg or 4 mg/kg.

Combination Therapies

Certain embodiments of the methods described herein comprise administering to the subject one or more additional therapeutic agents in combination with the IL-4R antagonist. As used herein, the expression "in combination with" means that the additional therapeutic agents are administered before, after, or concurrent with the pharmaceutical composition comprising the IL-4R antagonist. In some embodiments, the term "in combination with" includes sequential or concomitant administration of an IL-4R antagonist and a second therapeutic agent. Methods to treat asthma (e.g., allergic asthma, asthma associated with ABPA, moderate-to-severe asthma, persistent asthma or the like) or an associated condition or complication or to reduce at least one exacerbation, comprising administration of an IL-4R antagonist in combination with a second therapeutic agent for additive or synergistic activity, are provided.

For example, when administered "before" the pharmaceutical composition comprising the IL-4R antagonist, the additional therapeutic agent may be administered about 72 hours, about 60 hours, about 48 hours, about 36 hours, about 24 hours, about 12 hours, about 10 hours, about 8 hours, about 6 hours, about 4 hours, about 2 hours, about 1 hour, about 30 minutes, about 15 minutes, or about 10 minutes prior to the administration of the pharmaceutical composition comprising the IL-4R antagonist. When administered "after" the pharmaceutical composition comprising the IL-4R antagonist, the additional therapeutic agent may be administered about 10 minutes, about 15 minutes, about 30 minutes, about 1 hour, about 2 hours, about 4 hours, about 6 hours, about 8 hours, about 10 hours, about 12 hours, about 24 hours, about 36 hours, about 48 hours, about 60 hours, or about 72 hours after the administration of the pharmaceutical composition comprising the IL-4R antagonist. Administration "concurrent" with the pharmaceutical composition comprising the IL-4R antagonist means that the additional therapeutic agent is administered to the subject in a separate dosage form within less than 5 minutes (before, after, or at the same time) of administration of the pharmaceutical composition comprising the IL-4R antagonist, or administered to the subject as a single combined dosage formulation comprising both the additional therapeutic agent and the IL-4R antagonist.

The additional therapeutic agent may be, e.g., another IL-4R antagonist, an IL-1 antagonist (including, e.g., an IL-1 antagonist as set forth in U.S. Pat. No. 6,927,044), an IL-6 antagonist, an IL-6R antagonist (including, e.g., an anti-IL-6R antibody as set forth in U.S. Pat. No. 7,582,298), a TNF antagonist, an IL-8 antagonist, an IL-9 antagonist, an IL-17 antagonist, an IL-5 antagonist, an IgE antagonist, a CD48 antagonist, a leukotriene inhibitor, an anti-fungal agent, an NSAID, a long-acting beta2 agonist (e.g., salmeterol or formoterol), an inhaled corticosteroid (e.g., fluticasone or budesonide), a systemic corticosteroid (e.g., oral or intravenous), methylxanthine, nedocromil sodium, cromolyn sodium, or combinations thereof. For example, in certain embodiments, the pharmaceutical composition comprising an IL-4R antagonist is administered in combination with a combination comprising a long-acting beta2 agonist and an inhaled corticosteroid (e.g., fluticasone+salmeterol (e.g., Advair® (GlaxoSmithKline)); or budesonide+formoterol (e.g., SYMBICORT® (Astra Zeneca))).

In some embodiments, an additional therapeutic agent administered in combination with the IL-4R antagonist is a vaccine. In certain exemplary embodiments, the vaccine is a viral vaccine or a bacterial vaccine. In certain exemplary embodiments, the vaccine is a live (e.g., live-attenuated) viral vaccine or a live (e.g., live-attenuated) bacterial vaccine.

Suitable vaccines include, but are not limited to adenovirus, anthrax (e.g., AVA vaccine (BioThrax)), cholera (e.g., Vaxchora), diphtheria (e.g., DTaP (Daptacel, Infanrix), Td (Tenivac, generic), DT (generic), Tdap (Adacel, Boostrix), DTaP-IPV (Kinrix, Quadracel), DTaP-HepB-IPV (Pediarix), DTaP-IPV/Hib (Pentacel)), hepatitis A (e.g., HepA (Havrix, Vaqta), HepA-HepB (Twinrix)), hepatitis B (e.g., HepB (Engerix-B, Recombivax HB, Heplisav-B), DTaP-HepB-IPV (Pediarix), HepA-HepB (Twinrix)), *Haemophilus influenzae* type b (Hib) (e.g., Hib (ActHIB, PedvaxHIB, Hiberix), DTaP-IPV/Hib (Pentacel)), human papillomavirus (HPV) (e.g., HPV9 (Gardasil 9)), influenza (flu) (e.g., IIV (also called IIV3, IIV4, RIV3, RIV4 and ccIIV4) (Afluria, Fluad, Flublok, Flucelvax, FluLaval, Fluarix, Fluvirin, Fluzone, Fluzone High-Dose, Fluzone Intradermal), LAIV (FluMist)), Japanese encephalitis (e.g., JE (Ixiaro)), measles (e.g., MMR (M-M-R II), MMRV (ProQuad)), meningococcus (e.g., MenACWY (Menactra, Menveo), MenB (Bexsero, Trumenba)), mumps (e.g., MMR (M-M-R II), MMRV (ProQuad)), pertussis (e.g., DTaP (Daptacel, Infanrix), Tdap (Adacel, Boostrix), DTaP-IPV (Kinrix, Quadracel), DTaP-HepB-IPV (Pediarix), DTaP-IPV/Hib (Pentacel)), pneumococcus (e.g., PCV13 (Prevnar13), PPSV23 (Pneumovax 23)), polio (e.g., Polio (Ipol), DTaP-IPV (Kinrix, Quadracel), DTaP-HepB-IPV (Pediarix), DTaP-IPV/Hib (Pentacel)), rabies (e.g., Rabies (Imovax Rabies, RabAvert)), rotavirus (e.g., RV1 (Rotarix), RV5 (RotaTeq)), rubella (e.g., MMR (M-M-R II), MMRV (ProQuad)), shingles (e.g., ZVL (Zostavax), RZV (Shingrix)), smallpox (e.g., Vaccinia (ACAM2000)), tetanus (e.g., DTaP (Daptacel, Infanrix), Td (Tenivac, generic), DT (generic), Tdap (Adacel, Boostrix), DTaP-IPV (Kinrix, Quadracel), DTaP-HepB-IPV (Pediarix), DTaP-IPV/Hib (Pentacel)), tuberculosis, typhoid fever (e.g., Typhoid Oral (Vivotif), Typhoid Polysaccharide (Typhim Vi)), varicella (e.g., VAR (Varivax), MMRV (ProQuad)), yellow fever (e.g., YF (YF-Vax)) and the like. Suitable vaccines are also listed at the US Centers for Disease Control vaccine list, incorporated herein in its entirety for all purposes (cdc.gov/vaccines/vpd/vaccines-list.html).

In some embodiments, the vaccine is an inactivated vaccine, a recombinant vaccine, a conjugate vaccine, a subunit vaccine, a polysaccharide vaccine, or a toxoid vaccine. In some embodiments, the vaccine is a yellow fever vaccine. In some embodiments, the subject treated with the vaccine is concurrently treated for a type 2 inflammatory disease with an IL-4R antagonist. In some embodiments, the subject treated with the vaccine is concurrently treated for asthma with an IL-4R antagonist.

In certain embodiments, treatment with an IL-4R antagonist is suspended or terminated prior to treatment with the vaccine. In certain embodiments, treatment with the IL-4R antagonist is suspended about 1 to about 9 (e.g., about 1, about 1½, about 2, about 2½, about 3, about 3½, about 4, about 4½, about 5, about 5½, about 6, about 6½, about 7, about 7½, about 8, about 8½, about 9, or more) weeks prior to administration of the vaccine. In some embodiments, treatment with the IL-4R antagonist is suspended about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60 days prior to administration of the vaccine.

In certain embodiments, treatment with the IL-4R antagonist is resumed subsequent to treatment with the vaccine. In certain embodiments, treatment with the IL-4R antagonist is resumed about 1 to about 14 (e.g., about 1, about 1½, about 2, about 2½, about 3, about 3½, about 4, about 4½, about 5, about 5½, about 6, about 6½, about 7, about 7½, about 8, about 8½, about 9, about 9½, about 10, about 10½, about 11, about 11½, about 12, about 12½, about 13, about 13½, about 14, about 14½, or more) weeks subsequent to administration of the vaccine. In some embodiments, treatment with the IL-4R antagonist is resumed about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, or about 90 days subsequent to administration of the vaccine.

In certain embodiments, the effectiveness of the IL-4R antagonist is not decreased by administration in combination with the vaccine, or by subsequent administration of the vaccine. In some embodiments, the subject's forced expiratory volume ($FEV_1$) is stable before and after administration of the vaccine.

In some embodiments, the effectiveness of the vaccine is not decreased by administration in combination with the IL-4R antagonist, or by previous and/or subsequent administration of the IL-4R antagonist. In some embodiments, the subject develops seroprotective neutralization titers to the vaccine when the vaccine is co-administered with the IL-4R antagonist.

In certain exemplary embodiments, a subject is administered a vaccine described herein, wherein before, during, or after administration of the vaccine, the subject is administered at least one dose of IL-4R antagonist.

In some embodiments, the subject administered the vaccine has a type 2 inflammatory disease. In certain exemplary embodiments, the type 2 inflammatory disease is one or any combination of asthma, allergic rhinitis, chronic rhinosinusitis, chronic rhinosinusitis with nasal polyps (CRSsNP), eosinophilic esophagitis (EoE), atopic dermatitis (AD), food and environmental allergies, aspirin exacerbated respiratory disease (AERD), or a respiratory disease exacerbated by non-steroidal anti-inflammatory drugs (NSAIDs).

Administration Regimens

According to certain embodiments, multiple doses of an IL-4R antagonist may be administered to a subject over a defined time course. Such methods comprise sequentially administering to a subject multiple doses of an IL-4R antagonist. As used herein, "sequentially administering" means that each dose of IL-4R antagonist is administered to the subject at a different point in time, e.g., on different days separated by a predetermined interval (e.g., hours, days, weeks, or months). Methods that comprise sequentially administering to the patient a single initial dose of an IL-4R antagonist, followed by one or more secondary doses of the IL-4R antagonist, and optionally followed by one or more tertiary doses of the IL-4R antagonist, are provided.

Methods comprising administering to a subject a pharmaceutical composition comprising an IL-4R antagonist at a dosing frequency of about four times a week, twice a week, once a week (q1w), once every two weeks (every two weeks is used interchangeably with every other week, bi-weekly or q2w), once every three weeks (tri-weekly or q3w), once every four weeks (monthly or q4w), once every five weeks (q5w), once every six weeks (q6w), once every eight weeks (q8w), once every twelve weeks (q12w), or less frequently so long as a therapeutic response is achieved, are provided. In certain embodiments involving the administration of a pharmaceutical composition comprising an anti-IL-4R antibody, once a week dosing of an amount of about 75 mg, 100 mg, 150 mg, 200 mg, or 300 mg, can be employed. In other embodiments involving the administration of a pharmaceutical composition comprising an anti-IL-4R antibody, once every two weeks dosing (every two weeks is used interchangeably with every other week, bi-weekly or q2w) of an amount of about 75 mg, 100 mg, 150 mg, 200 mg, or 300 mg, can be employed. In other embodiments involving the administration of a pharmaceutical composition comprising an anti-IL-4R antibody, once every three weeks dosing of an amount of about 75 mg, 100 mg, 150 mg, 200 mg, or 300 mg, can be employed. In other embodiments involving the administration of a pharmaceutical composition comprising an anti-IL-4R antibody, once every four weeks dosing (monthly dosing) of an amount of about 75 mg, 100 mg, 150 mg, 200 mg, or 300 mg, can be employed. In other embodiments involving the administration of a pharmaceutical composition comprising an anti-IL-4R antibody, once every five weeks dosing of an amount of about 75 mg, 100 mg, 150 mg, 200 mg, or 300 mg, can be employed. In other embodiments involving the administration of a pharmaceutical composition comprising an anti-IL-4R antibody, once every six weeks dosing of an amount of about 75 mg, 100 mg, 150 mg, 200 mg, or 300 mg, can be employed. In other embodiments involving the administration of a pharmaceutical composition comprising an anti-IL-4R antibody, once every eight weeks dosing of an amount of about 75 mg, 100 mg, 150 mg, 200 mg, or 300 mg, can be employed. In other embodiments involving the administration of a pharmaceutical composition comprising an anti-IL-4R antibody, once every twelve weeks dosing of an amount of about 75 mg, 100 mg, 150 mg, 200 mg, or 300 mg, can be employed. In one embodiment, the route of administration is subcutaneous.

The term "week" or "weeks" refers to a period of (n×7 days)±2 days, e.g. (n×7 days)±1 day, or (n×7 days), wherein "n" designates the number of weeks, e.g. 1, 2, 3, 4, 5, 6, 8, 12 or more.

The terms "initial dose," "secondary doses," and "tertiary doses," refer to the temporal sequence of administration of the IL-4R antagonist. Thus, the "initial dose" is the dose that is administered at the beginning of the treatment regimen (also referred to as the "baseline dose"); the "secondary doses" are the doses that are administered after the initial dose; and the "tertiary doses" are the doses that are administered after the secondary doses. The initial, secondary, and tertiary doses may all contain the same amount of IL-4R antagonist, but generally may differ from one another in terms of frequency of administration. In certain embodiments, however, the amount of IL-4R antagonist contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses"). In one embodiment, the maintenance dose may be lower than the loading dose. For example, one or more loading doses of 600 mg of IL-4R antagonist may be administered followed by maintenance doses of about 75 mg to about 300 mg.

In certain embodiments, the loading dose is about 400 to about 600 mg of the IL-4R antagonist. In one embodiment, the loading dose is 400 mg of the IL-4R antagonist. In another embodiment, the loading dose is 600 mg of the IL-4R antagonist.

In certain embodiments, the maintenance dose is about 200 to about 300 mg of the IL-4R antagonist. In one embodiment, the maintenance dose is 200 mg of the IL-4R antagonist. In another embodiment, the maintenance dose is 300 mg of the IL-4R antagonist.

In certain embodiments, the loading dose is two times the maintenance dose.

In some embodiments, the loading dose comprises 600 mg of the antibody or antigen-binding fragment thereof, and the one or more maintenance doses comprises 300 mg of the antibody or antigen-binding fragment thereof administered every other week (every other week is used interchangeably with every two weeks, bi-weekly or q2w).

In some embodiments, a subject has OCS-dependent asthma, and the loading dose comprises 600 mg of the antibody or antigen-binding fragment thereof, and the one or more maintenance doses comprises 300 mg of the antibody or antigen-binding fragment thereof administered every other week.

In some embodiments, a subject has co-morbid moderate-to-severe atopic dermatitis, and the loading dose comprises 600 mg of the antibody or antigen-binding fragment thereof, and the one or more maintenance doses comprises 300 mg of the antibody or antigen-binding fragment thereof administered every other week.

In some embodiments, the loading dose comprises 400 mg of the antibody or antigen-binding fragment thereof, and the one or more maintenance dose comprises 200 mg of the antibody or antigen-binding fragment thereof administered every other week.

In some embodiments, a subject has OCS-dependent asthma, and the loading dose comprises 400 mg of the antibody or antigen-binding fragment thereof, and the one or more maintenance doses comprises 200 mg of the antibody or antigen-binding fragment thereof administered every other week.

In some embodiments, a subject has co-morbid moderate-to-severe atopic dermatitis, and the loading dose comprises 400 mg of the antibody or antigen-binding fragment thereof, and the one or more maintenance doses comprises 200 mg of the antibody or antigen-binding fragment thereof administered every other week.

In some embodiments, the loading dose comprises 600 mg of the antibody or antigen-binding fragment thereof, and the one or more maintenance doses comprises 300 mg of the antibody or antigen-binding fragment thereof administered every fourth week.

In some embodiments, a subject has OCS-dependent asthma, and the loading dose comprises 600 mg of the antibody or antigen-binding fragment thereof, and the one or more maintenance doses comprises 300 mg of the antibody or antigen-binding fragment thereof administered every fourth week.

In some embodiments, a subject has co-morbid moderate-to-severe atopic dermatitis, and the loading dose comprises 600 mg of the antibody or antigen-binding fragment thereof, and the one or more maintenance doses comprises 300 mg of the antibody or antigen-binding fragment thereof administered every fourth week.

In some embodiments, the loading dose comprises 400 mg of the antibody or antigen-binding fragment thereof, and the one or more maintenance doses comprises 200 mg of the antibody or antigen-binding fragment thereof administered every fourth week.

In some embodiments, a subject has OCS-dependent asthma, and the loading dose comprises 400 mg of the antibody or antigen-binding fragment thereof, and the one or more maintenance doses comprises 200 mg of the antibody or antigen-binding fragment thereof administered every fourth week.

In some embodiments, a subject has co-morbid moderate-to-severe atopic dermatitis, and the loading dose comprises 400 mg of the antibody or antigen-binding fragment thereof, and the one or more maintenance doses comprises 200 mg of the antibody or antigen-binding fragment thereof administered every fourth week.

In one exemplary embodiment, each secondary and/or tertiary dose is administered 1 to 14 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, or more) weeks after the immediately preceding dose. The phrase "the immediately preceding dose" means, in a sequence of multiple administrations, the dose of IL-4R antagonist that is administered to a patient prior to the administration of the very next dose in the sequence with no intervening doses.

The methods may include administering to a patient any number of secondary and/or tertiary doses of an IL-4R antagonist. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Methods comprising sequential administration of an IL-4R antagonist and a second therapeutic agent, to a patient to treat asthma (e.g., allergic asthma, asthma associated with ABPA, moderate-to-severe asthma, persistent asthma or the like) or an associated condition are provided. In some embodiments, the methods comprise administering one or more doses of an IL-4R antagonist followed by one or more doses (e.g., 2, 3, 4, 5, 6, 7, 8, or more) of a second therapeutic agent. For example, one or more doses of about 75 mg to about 300 mg of the IL-4R antagonist may be administered after which one or more doses (e.g., 2, 3, 4, 5, 6, 7, 8, or more) of a second therapeutic agent (e.g., an inhaled corticosteroid or a beta2-agonist or any other therapeutic agent, as described elsewhere herein) may be administered to treat, alleviate, reduce or ameliorate one or more symptoms of asthma. In some embodiments, the IL-4R antagonist is administered at one or more doses (e.g., 2, 3, 4, 5, 6, 7, 8, or more) resulting in an improvement in one or more asthma-associated parameters followed by the administration of a second therapeutic agent to prevent recurrence of at least one symptom of asthma. Alternative embodiments pertain to concomitant administration of an IL-4R antagonist and a second therapeutic agent. For example, one or more doses (e.g., 2, 3, 4, 5, 6, 7, 8, or more) of an IL-4R antagonist are administered and a second therapeutic agent is administered at a separate dosage at a similar or different frequency relative to the IL-4R antagonist. In some embodiments, the second therapeutic agent is administered before, after or concurrently with the IL-4R antagonist.

In certain embodiments, the IL-4R antagonist is administered every other week for 12 weeks, 14 weeks, 16 weeks, 18 weeks, 20 weeks, 22 weeks, 24 weeks, 26 weeks, 28 weeks, 30 weeks, 32 weeks, 34 weeks, 36 weeks, 38 weeks, 40 weeks, 42 weeks, 44 weeks, 46 weeks, 48 weeks or more. In other embodiments, the IL-4R antagonist is administered every four weeks for 12 weeks, 16 weeks, 20 weeks, 24 weeks, 28 weeks, 32 weeks, 36 weeks, 40 weeks, 44 weeks, 48 weeks or more. In specific embodiments, the IL-4R antagonist is administered for at least 24 weeks.

Methods for treating a subject having severe uncontrolled asthma (e.g., severe steroid-dependent asthma) comprising administering to the subject a loading dose of an antibody or an antigen-binding fragment thereof that specifically binds to IL-4R are provided. In certain embodiments, the methods comprise administering to the subject a plurality of maintenance doses of the antibody or the antigen-binding fragment thereof, wherein the plurality of maintenance doses are administered during a treatment phase. The treatment phase comprises an induction phase, an OCS reduction phase, and an OCS maintenance phase.

In certain exemplary embodiments, the induction phase comprises a period during which subjects continuously receive their OCS dose(s). In certain exemplary embodiments, the reduction phase comprises a period during which subjects receive a lower OCS dose relative to the dose received during the induction phase. In certain exemplary embodiments, the maintenance phase comprises a period during which a subject receives a certain stable amount or dose(s) of OCS. Alternatively, the maintenance phase comprises a period in which OCS therapy/administration is reduced or eliminated. In certain embodiments, OCS use by the patient is completely eliminated and the patient is steroid free within less than 1 year of treatment with the IL4R antibody or fragment thereof (e.g., within 1 year, 6 months, 3 months or 1 month of initial treatment).

In another aspect, a method for treating a subject having severe steroid-dependent asthma and/or severe uncontrolled asthma comprises administering to the subject a loading dose of about 600 mg of an antibody or an antigen-binding fragment thereof that specifically binds to interleukin-4 receptor (IL-4R), and administering to the subject a plurality of maintenance doses of the antibody or the antigen-binding fragment thereof. Each maintenance dose is about 300 mg of the antibody or antigen-binding fragment thereof, wherein the plurality of maintenance doses are administered during a treatment phase comprising an induction phase, an oral corticosteroid (OCS) reduction phase, and a maintenance phase, and wherein the antibody or antigen-binding fragment thereof comprises heavy and light chain CDR sequences from the HCVR/LCVR sequence pair comprises SEQ ID NOs: 1 and 2.

Treatment Populations

The methods provided herein include administering to a subject in need thereof a therapeutic composition comprising an IL-4R antagonist. The expression "a subject in need thereof" means a human or non-human animal that exhibits one or more symptoms or indicia of asthma (e.g., allergic asthma, e.g., moderate-to-severe uncontrolled allergic asthma or asthma associated with ABPA) and/or ABPA, or who has been diagnosed with asthma (e.g., allergic asthma, asthma associated with ABPA, moderate-to-severe asthma, persistent asthma or the like) and/or ABPA. For example, "a subject in need thereof" may include, e.g., subjects who, prior to treatment, exhibit (or have exhibited) one or more asthma-associated (e.g., allergic asthma-associated) parameter, such as, e.g., impaired $FEV_1$ (e.g., less than 2.0 L), impaired FEF25-75%; impaired AM PEF (e.g., less than 400 L/min), impaired PM PEF (e.g., less than 400 L/min), an ACQ5 score of at least 2.5, at least 1 nighttime awakenings per night, and/or a SNOT-22 score of at least 20. In various embodiments, the methods may be used to treat mild, moderate-to-severe, and severe asthma (e.g., allergic asthma, asthma associated with ABPA, moderate-to-severe asthma, persistent asthma or the like) and/or ABPA in patients in need thereof. In certain embodiments, the methods may be used to treat mild, moderate-to-severe, and severe asthma e.g., allergic asthma, asthma associated with ABPA, moderate-to-severe asthma, persistent asthma or the like) and/or ABPA in patients in need thereof, wherein the patients further exhibit comorbid moderate-to-severe atopic dermatitis.

In certain embodiments, "a subject in need thereof" means a human or non-human animal that exhibits subject a total serum IgE level of at least about 1000 IU/mL, an *Aspergillus fumigatus*-specific IgE level of greater than 0.35 kU/L, or a baseline blood eosinophil count of at least about 500 cells/µl. In certain embodiments, "a subject in need thereof" means a human or non-human animal that exhibits at least two of a total serum IgE level of at least about 1000 IU/mL, an *Aspergillus fumigatus*-specific IgE level of greater than 0.35 kU/L, and a baseline blood eosinophil count of at least about 500 cells/µl. In certain embodiments, "a subject in need thereof" means a human or non-human animal that exhibits a total serum IgE level of at least about 1000 IU/mL, an *Aspergillus fumigatus*-specific IgE level of greater than 0.35 kU/L, and a baseline blood eosinophil count of at least about 500 cells/µl.

In a related embodiment, a "subject in need thereof" may be a subject who, prior to receiving an IL-4R antagonist, has been prescribed or is currently taking a combination of ICS/LABA. Examples of ICS include mometasone furoate, budesonide, and fluticasone propionate. Examples of LABA include formoterol and salmeterol. Examples of ICS/LABA therapies include fluticasone/salmeterol combination therapy and budesonide/formoterol combination therapy. For example, methods that comprise administering an IL-4R antagonist to a patient who has been taking a regular course of ICS/LABA for two or more weeks immediately preceding the administration of the IL-4R antagonist (such prior treatments are referred to herein as "background treatments") are provided. Therapeutic methods in which background treatments are continued in combination with administration of the IL-4R antagonist are provided. In yet other embodiments, the amount of the ICS component, the LABA component, or both, is gradually decreased prior to or after the start of IL-4R antagonist administration. In some embodiments, methods to treat patients with persistent asthma for at least ≥12 months are provided. In one embodiment, a patient with persistent asthma may be resistant to treatment by a therapeutic agent, such as a corticosteroid, and may be administered an IL-4R antagonist according to the present methods.

In some embodiments, a "subject in need thereof" may be a subject with elevated levels of an asthma-associated biomarker. Examples of asthma-associated and/or ABPA-associated biomarkers include, but are not limited to, IgE (e.g., total IgE and/or *A. fumigatus*-specific IgE), thymus and activation regulated chemokine (TARC), blood eosinophils, eotaxin-3, CEA, YKL-40, and periostin. In some embodiments, a "subject in need thereof" may be a subject with blood eosinophils ≥300 cells/µL, 200-299 cells/µL, or <200 cells/µL. In one embodiment, a "subject in need thereof" may be a subject with elevated level of bronchial or airway inflammation as measured by the fraction of exhaled nitric oxide (FeNO). In another embodiment, a "subject in need thereof" may be a subject with elevated eotaxin levels. In another embodiment, a "subject in need thereof" may be a subject with elevated TARC levels. In another embodiment, a "subject in need thereof" may be a subject with elevated IgE levels (e.g., total IgE and/or *A. fumigatus*-specific IgE levels).

In some embodiments, a "subject in need thereof" is selected from the group consisting of: a subject age 18 years old or older, a subject 12 years or older, a subject age 12 to 17 years old (12 to <18 years old), a subject age 6 to 11 years old (6 to <12 years old), and a subject age 2 to 5 years old (2 to <6 years old). In some embodiments, a "subject in need thereof" is selected from the group consisting of: an adult, an adolescent, and a child. In some embodiments, a "subject in need thereof" is selected from the group consisting of: an adult age 18 years of age or older, an adolescent age 12 to 17 years old (12 to <18 years old), a child age 6 to 11 years old (6 to <12 years old), and a child age 2 to 5 years old (2 to <6 years old). The subject can be less than 2 years of age, e.g., 12 to 23 months, or 6 to 11 months.

In some embodiments, a "subject in need thereof" is a subject who is a current smoker. In some embodiments, the subject is a current smoker who smokes, e.g., cigarettes, cigars, pipes, water pipes, and/or vaporizers (i.e., "vapes"). In some embodiments, the subject is a current smoker who has a smoking history of smoking greater than or equal to 10 packs of cigarettes per year. In some embodiments, the subject is a current smoker and has a smoking history of smoking fewer than 10 packs of cigarettes per year. In some embodiments, the subject is a current smoker and has a smoking history of smoking more than 1, 5, 10, 15, 20, 25, 30, 35, 40, 45, 50 or more packs of cigarettes per year. In some embodiments, the subject is a current smoker who has a smoking history of smoking for 6 months, 1 year, 2 years, 3 years, 5 years, 10 years or longer.

In some embodiments, a "subject in need thereof" is a subject who is a former smoker. In some embodiments, the subject is a former smoker who has a history of smoking cigarettes, cigars, pipes, water pipes and/or vapes. In some embodiments, the subject is a former smoker who has a smoking history of smoking greater than or equal to 10 packs of cigarettes per year. In some embodiments, the subject is a former smoker who has a smoking history of smoking fewer than 10 packs per year. In some embodiments, the subject is a former smoker who has a smoking history of smoking more than 1, 5, 10, 15, 20, 25, 30, 35, 40, 45, 50 or more packs of cigarettes per year. In some embodiments, the subject is a former smoker who has a smoking history of smoking for 6 months, 1 year, 2 years, 3 years, 5 years, 10 years or longer. In some embodiments, the subject is a former smoker who has ceased smoking for at least 1, 2, 3, 4, 5, 6, 7, 8, 9, 10, 11, or 12 months. In some embodiments, the subject is a former smoker who has ceased smoking for at least 6 months. In some embodiments, the subject is a former smoker that intends to quit permanently.

In some embodiments, a "subject in need thereof" is a subject who is a non-smoker. In some embodiments, a subject is a non-smoker that does not have a history of smoking cigarettes, cigars, pipes, water pipes and/or vapes. In some embodiments, a subject is a non-smoker that does not have a history of smoking tobacco.

In some embodiments, a "subject in need thereof" is a subject who is treated with a vaccine, e.g., a viral vaccine or a bacterial vaccine. In some embodiments, the vaccine is a live vaccine, e.g., a live (e.g., live-attenuated) viral vaccine or a live (e.g., live-attenuated) bacterial vaccine.

Suitable vaccines include, but are not limited to adenovirus, anthrax (e.g., AVA vaccine (BioThrax)), cholera (e.g., Vaxchora), diphtheria (e.g., DTaP (Daptacel, Infanrix), Td (Tenivac, generic), DT (generic), Tdap (Adacel, Boostrix), DTaP-IPV (Kinrix, Quadracel), DTaP-HepB-IPV (Pediarix), DTaP-IPV/Hib (Pentacel)), hepatitis A (e.g., HepA (Havrix, Vaqta), HepA-HepB (Twinrix)), hepatitis B (e.g., HepB (Engerix-B, Recombivax HB, Heplisav-B), DTaP-HepB-IPV (Pediarix), HepA-HepB (Twinrix)), *Haemophilus influenzae* type b (Hib) (e.g., Hib (ActHIB, PedvaxHIB, Hiberix), DTaP-IPV/Hib (Pentacel)), human papillomavirus (HPV) (e.g., HPV9 (Gardasil 9)), influenza (flu) (e.g., IIV (also called IIV3, IIV4, RIV3, RIV4 and ccIIV4) (Afluria, Fluad, Flublok, Flucelvax, FluLaval, Fluarix, Fluvirin, Fluzone, Fluzone High-Dose, Fluzone Intradermal), LAIV (FluMist)), Japanese encephalitis (e.g., JE (Ixiaro)), measles (e.g., MMR (M-M-R II), MMRV (ProQuad)), meningococcus (e.g., MenACWY (Menactra, Menveo), MenB (Bexsero, Trumenba)), mumps (e.g., MMR (M-M-R II), MMRV (ProQuad)), pertussis (e.g., DTaP (Daptacel, Infanrix), Tdap (Adacel, Boostrix), DTaP-IPV (Kinrix, Quadracel), DTaP-HepB-IPV (Pediarix), DTaP-IPV/Hib (Pentacel)), pneumococcus (e.g., PCV13 (Prevnar13), PPSV23 (Pneumovax 23)), polio (e.g., Polio (Ipol), DTaP-IPV (Kinrix, Quadracel), DTaP-HepB-IPV (Pediarix), DTaP-IPV/Hib (Pentacel)), rabies (e.g., Rabies (Imovax Rabies, RabAvert)), rotavirus (e.g., RV1 (Rotarix), RV5 (RotaTeq)), rubella (e.g., MMR (M-M-R II), MMRV (ProQuad)), shingles (e.g., ZVL (Zostavax), RZV (Shingrix)), smallpox (e.g., Vaccinia (ACAM2000)), tetanus (e.g., DTaP (Daptacel, Infanrix), Td (Tenivac, generic), DT (generic), Tdap (Adacel, Boostrix), DTaP-IPV: (Kinrix, Quadracel), DTaP-HepB-IPV (Pediarix), DTaP-IPV/Hib (Pentacel)), tuberculosis, typhoid fever (e.g., Typhoid Oral (Vivotif), Typhoid Polysaccharide (Typhim Vi)), varicella (e.g., VAR (Varivax), MMRV (ProQuad)), yellow fever (e.g., YF (YF-Vax)) and the like. Suitable vaccines are also listed at the US Centers for Disease Control vaccine list, incorporated herein in its entirety for all purposes (cdc.gov/vaccines/vpd/vaccines-list.html).

In some embodiments, the vaccine is an inactivated vaccine, a recombinant vaccine, a conjugate vaccine, a subunit vaccine, a polysaccharide vaccine, or a toxoid vaccine. In some embodiments, the vaccine is a yellow fever vaccine. In some embodiments, the subject treated with the vaccine concurrently is treated for a type 2 inflammatory disease with an IL-4R antagonist. In some embodiments, the subject treated with the vaccine concurrently is treated for asthma with an IL-4R antagonist. In some embodiments, the subject suspends treatment with an IL-4R antagonist prior to administration of the vaccine.

In certain embodiments the subject suspends treatment with the IL-4R antagonist about 1 to about 9 (e.g., about 1, about 1½, about 2, about 2½, about 3, about 3½, about 4, about 4½, about 5, about 5½, about 6, about 6½, about 7, about 7½, about 8, about 8½, about 9, or more) weeks prior to administration of the vaccine. In certain embodiments, the subject suspends treatment with the IL-4R antagonist about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60 days prior to administration of the vaccine.

In certain embodiments, the subject resumes treatment with the IL-4R antagonist subsequent to treatment with the vaccine. In certain embodiments, the subject resumes treatment with the IL-4R antagonist 1 to 14 (e.g., about 1, about 1½, about 2, about 2½, about 3, about 3½, about 4, about 4½, about 5, about 5½, about 6, about 6½, about 7, about 7½, about 8, about 8½, about 9, about 9½, about 10, about 10½, about 11, about 11½, about 12, about 12½, about 13, about 13½, about 14, about 14½, or more) weeks subsequent to administration of the vaccine. In certain embodiments, the subject resumes treatment with the IL-4R antagonist about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, or about 90 days subsequent to administration of the vaccine.

A normal IgE level in healthy subjects is typically less than about 100 IU/mL (e.g., as measured using the IMMUNOCAP® assay (Phadia, Inc. Portage, MI)). Thus, methods comprising selecting a subject who exhibits an elevated serum IgE level, which is a serum IgE level greater than about 100 IU/mL, greater than about 150 IU/mL, greater than about 500 IU/mL, greater than about 700 IU/mL, greater than about 1000 IU/mL, greater than about 1500 IU/mL, greater than about 2000 IU/mL, greater than about 2500 IU/mL, greater than about 3000 IU/mL, greater than about 3500 IU/mL, greater than about 4000 IU/mL, greater than about 4500 IU/mL, or greater than about 5000 IU/mL, and administering to the subject a pharmaceutical composition comprising a therapeutically effective amount of an IL-4R antagonist, are provided.

A normal *Aspergillus fumigatus* (Af)-specific IgE level in healthy subjects is typically less than about 0.10 kU/L (e.g., as measured using the IMMUNOCAP® assay (Phadia, Inc. Portage, MI)). Thus, methods comprising selecting a subject who exhibits an elevated serum IgE level, which is a serum IgE level greater than or equal to about 0.1 kU/L, greater than about 0.35 kU/L, greater than about 0.70 kU/L, greater than about 3.50 kU/L, greater than about 17.50 kU/L, greater than about 50.00 kU/L, or greater than about 100.00 kU/L, and administering to the subject a pharmaceutical composition comprising a therapeutically effective amount of an IL-4R antagonist, are provided.

In certain embodiments, IgE levels (e.g., total IgE levels and/or *A. fumigatus*-specific IgE levels) are improved relative to baseline, e.g., an improvement of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100% or more from baseline.

TARC levels in healthy subjects are in the range of 106 ng/L to 431 ng/L, with a mean of about 239 ng/L. (An exemplary assay system for measuring TARC level is the TARC quantitative ELISA kit offered as Cat. No. DDN00 by R&D Systems, Minneapolis, MN.) Thus, methods comprising selecting a subject who exhibits an elevated TARC level, which is a serum TARC level greater than about 431 ng/L, greater than about 500 ng/L, greater than about 1000 ng/L, greater than about 1500 ng/L, greater than about 2000 ng/L, greater than about 2500 ng/L, greater than about 3000 ng/L, greater than about 3500 ng/L, greater than about 4000 ng/L, greater than about 4500 ng/L, or greater than about 5000 ng/L, and administering to the subject a pharmaceutical composition comprising a therapeutically effective amount of an IL-4R antagonist, are provided. In certain embodiments, TARC levels are improved relative to baseline, e.g., an improvement of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100% or more from baseline.

Eotaxin-3 belongs to a group of chemokines released by airway epithelial cells, which is up-regulated by the Th2 cytokines IL-4 and IL-13 (Lilly et al 1999, J. Allergy Clin. Immunol. 104:786-790). Methods comprising administering an IL-4R antagonist to treat patients with elevated levels of eotaxin-3, such as more than about 100 pg/ml, more than about 150 pg/ml, more than about 200 pg/ml, more than about 300 pg/ml, or more than about 350 pg/ml, are provided. Serum eotaxin-3 levels may be measured, for example, by ELISA. In certain embodiments, serum eotaxin-3 levels are improved relative to baseline, e.g., an improvement of about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100% or more from baseline.

Periostin is an extracellular matrix protein involved in the Th2-mediated inflammatory processes. Periostin levels are found to be up-regulated in patients with asthma (Jia et al 2012 J Allergy Clin Immunol. 130:647-654.e10. doi: 10.1016/j.jaci.2012.06.025. Epub 2012 Aug. 1). Methods comprising administering an IL-4R antagonist to treat patients with elevated levels of periostin are provided.

Fractional exhaled NO (FeNO) is a biomarker of bronchial or airway inflammation. FeNO is produced by airway epithelial cells in response to inflammatory cytokines including IL-4 and IL-13 (Alwing et al 1993, Eur. Respir. J. 6:1368-1370). FeNO levels in healthy adults range from 2 to 30 parts per billion (ppb). An exemplary assay for measuring FeNO is by using a NIOX instrument by Aerocrine AB, Solna, Sweden. The assessment may be conducted prior to spirometry and following a fast of at least an hour. Methods comprising administering an IL-4R antagonist to patients with elevated levels of exhaled NO (FeNO), such as more than about 30 ppb, more than about 31 ppb, more than about 32 ppb, more than about 33 ppb, more than about 34 ppb, or more than about 35 ppb, are provided.

Carcinoembryogenic antigen (CEA) (also known as CEA cell adhesion molecule 5 [CEACAM5]) is a tumor marker that is found correlated to non-neoplastic diseases of the lung (Marechal et al. 1988, Anticancer Res. 8:677-680). CEA levels in serum may be measured by ELISA. Methods comprising administering an IL-4R antagonist to patients with elevated levels of CEA, such as more than about 1.0 ng/ml, more than about 1.5 ng/ml, more than about 2.0 ng/ml, more than about 2.5 ng/ml, more than about 3.0 ng/ml, more than about 4.0 ng/ml, or more than about 5.0 ng/ml, are provided.

YKL-40 (named for its N-terminal amino acids tyrosine (Y), lysine (K) and leucine (L) and its molecular mass of 40 kD) is a chitinase-like protein found to be up regulated and correlated to asthma exacerbation, IgE, and eosinophils (Tang et al 2010 Eur. Respir. J. 35:757-760). Serum YKL-40 levels are measured by, for example, ELISA. Methods comprising administering an IL-4R antagonist to patients with elevated levels of YKL-40, such as more than about 40 ng/ml, more than about 50 ng/ml, more than about 100 ng/ml, more than about 150 ng/ml, more than about 200 ng/ml, or more than about 250 ng/ml, are provided.

Periostin is a secreted matricellular protein associated with fibrosis, and its expression is upregulated by recombinant IL-4 and IL-13 in cultured bronchial epithelial cells and bronchial fibroblasts (Jia et al. (2012) J. Allergy Clin. Immunol. 130:647). In human asthmatic patients periostin expression levels correlate with reticular basement membrane thickness, an indicator of subepithelial fibrosis. Id. Methods comprising administering an IL-4R antagonist to patients with elevated levels of periostin are provided.

Induced sputum eosinophils and neutrophils are well-established direct markers of airway inflammation (Djukanovic et al. 2002, Eur. Respire. J. 37: 1S-2S). Sputum is induced with inhalation of hypertonic saline solution and processed for cell counts according to methods known in the art, for example, the guidelines of European Respiratory Society.

In some embodiments, the subjects are stratified into the following groups: a blood eosinophil count (high blood eosinophils) ≥300 cells/μL (HEos) or 300-499 cells/μL or ≥500 cells/μL, a blood eosinophil count of 200 to 299 cells/μL (moderate blood eosinophils), or a blood eosinophil count <200 cells/μL (low blood eosinophils), and are administered an anti-IL-4R antibody or antigen binding fragment thereof at a dose or dosing regimen based upon the eosinophil level.

In some embodiments, the subjects are stratified into the following groups: a blood eosinophil count of ≥300 cells/μL, of 300-499 cells/μL, or of ≥500 cells/μL (high blood eosinophils); a blood eosinophil count of ≥150 cells/μL (moderate blood eosinophils); or a blood eosinophil count of <150 cells/μL (low blood eosinophils), and are administered an anti-IL-4R antibody or antigen binding fragment thereof at a dose or dosing regimen based upon the eosinophil level.

In some embodiments, a subject has "eosinophilic phenotype" asthma defined by a blood eosinophil count of ≥150 cells/μL, a blood eosinophil count of ≥300 cells/μL, a blood eosinophil count of 300-499 cells/μL, or a blood eosinophil count of ≥500 cells/μL, and is administered an anti-IL-4R antibody or antigen binding fragment thereof.

In some embodiments, the subjects are stratified into the following groups: a total baseline serum IgE concentration of ≥30 IU/mL; a total baseline serum IgE concentration of ≥100 IU/mL; a total baseline serum IgE concentration of ≥200 IU/mL; a total baseline serum IgE concentration of ≥300 IU/mL; a total baseline serum IgE concentration of ≥400 IU/mL; a total baseline serum IgE concentration of ≥500 IU/mL; a total baseline serum IgE concentration of ≥600 IU/mL; a total baseline serum IgE concentration of ≥700 IU/mL (e.g., high serum IgE); a total baseline serum IgE concentration of ≥800 IU/mL; a total baseline serum IgE concentration of ≥900 IU/mL; or a total baseline serum IgE concentration of ≥1000 IU/mL (e.g., very high IgE), and are administered an anti-IL-4R antibody or antigen binding fragment thereof at a dose or dosing regimen based upon the IgG concentration.

In some embodiments, the subjects are stratified into the following groups: an allergen-specific IgE (e.g., an *A. fumigatus*-specific) concentration of ≥0.05 kU/L; an allergen-specific (e.g., an *A. fumigatus*-specific) IgE concentration of ≥0.10 kU/L; an allergen-specific (e.g., an *A. fumigatus*-specific) IgE concentration of ≥0.15 kU/L; an allergen-specific (e.g., an *A. fumigatus*-specific) IgE concentration of ≥0.20 kU/L; an allergen-specific (e.g., an *A. fumigatus*-specific) IgE concentration of ≥0.25 kU/L; an allergen-specific (e.g., an *A. fumigatus*-specific) IgE concentration of ≥0.30 kU/L; an allergen-specific (e.g., an *A. fumigatus*-specific) IgE concentration of ≥0.35 kU/L; an allergen-specific (e.g., an *A. fumigatus*-specific) IgE concentration of ≥0.40 kU/L; an allergen-specific (e.g., an *A. fumigatus*-specific) IgE concentration of ≥0.45 kU/L; or an allergen-specific (e.g., an *A. fumigatus*-specific) IgE concentration of ≥0.50 kU/L, and are administered an anti-IL-4R antibody or antigen binding fragment thereof at a dose or dosing regimen based upon the allergen-specific (e.g., an *A. fumigatus*-specific) IgE concentration.

In some embodiments, the subjects are stratified into the following groups: a baseline FeNO value of ≥20 ppb; a baseline FeNO value of ≥25 ppb; a baseline FeNO value of ≥50 ppb (e.g., high FeNO); a baseline FeNO value of <25 ppb (e.g., low FeNO); a baseline FeNO value of <50 ppb; or a baseline FeNO value of between about 25 ppb and about 50 ppb, and are administered an anti-IL-4R antibody or antigen binding fragment thereof at a dose or dosing regimen based upon the FeNO value.

Methods for Assessing Pharmacodynamic Asthma-Associated Parameters and/or ABPA-Associated Parameters Methods for assessing one or more pharmacodynamic asthma-associated parameters and/or one or more pharmacodynamic ABPA-associated parameters a subject in need thereof, caused by administration of a pharmaceutical composition comprising an IL-4R antagonist, are provided. A reduction in the incidence of an asthma exacerbation (as described above) or an improvement in one or more asthma-associated parameters (as described above) may correlate with an improvement in one or more pharmacodynamic asthma-associated parameters; however, such a correlation is not necessarily observed in all cases.

Examples of "pharmacodynamic asthma-associated parameters" or "pharmacodynamic ABPA-associated parameters" include, for example, the following: (a) biomarker expression levels; (b) serum protein and RNA analysis; (c) induced sputum eosinophils and neutrophil levels; (d) exhaled nitric oxide (FeNO); and (e) blood eosinophil count. An "improvement in a pharmacodynamic asthma-associated parameter" means, for example, a decrease from baseline of one or more biomarkers, such as TARC, eotaxin-3 or IgE, a decrease in sputum eosinophils or neutrophils, FeNO, periostin or blood eosinophil count. As used herein, the term "baseline," with regard to a pharmacodynamic asthma-associated parameter, means the numerical value of the pharmacodynamic asthma-associated parameter for a patient prior to or at the time of administration of a pharmaceutical composition described herein.

To assess a pharmacodynamic asthma-associated parameter or a pharmacodynamic ABPA-associated parameter, the parameter is quantified at baseline and at a time point after administration of the pharmaceutical composition. For example, a pharmacodynamic asthma-associated parameter or a pharmacodynamic ABPA-associated parameter may be measured at about day 1, about day 2, about day 3, day 4, about day 5, about day 6, about day 7, about day 8, about day 9, about day 10, about day 11, about day 12, about day 14, or at about week 3, about week 4, about week 5, about week 6, about week 7, about week 8, about week 9, about week 10, about week 11, about week 12, about week 13, about week 14, about week 15, about week 16, about week 17, about week 18, about week 19, about week 20, about week 21, about week 22, about week 23, about week 24, or longer, after the initial treatment with the pharmaceutical composition. The difference between the value of the parameter at a particular time point following initiation of treatment and the value of the parameter at baseline is used to establish whether there has been change, such as an "improvement," in the pharmacodynamic asthma-associated parameter (e.g., an increase or decrease, as the case may be, depending on the specific parameter being measured).

In certain embodiments, administration of an IL-4R antagonist to a patient causes a change, such as a decrease or increase, in expression of a particular biomarker. Asthma-associated biomarkers and/or ABPA-associated biomarkers include, but are not limited to, the following: (a) total IgE; (b) Af-specific IgE; (c) thymus and activation-regulated chemokine (TARC); (d) YKL-40; (e) carcinoembryonic antigen in serum; (f) eotaxin-3 in plasma; (g) periostin in serum; and (h) eosinophil levels in serum. For example, administration of an IL-4R antagonist to an asthma patient and/or an ABPA patient can cause one or more of a decrease in TARC or eotaxin-3 levels, or a decrease in total serum IgE levels. The decrease can be detected at about week 1, about week 2, about week 3, about week 4, about week 5, or longer following administration of the IL-4R antagonist. Biomarker expression can be assayed by methods known in the art. For example, protein levels can be measured by ELISA (Enzyme Linked Immunosorbent Assay). RNA levels can be measured, for example, by reverse transcription coupled to polymerase chain reaction (RT-PCR).

Biomarker expression, as discussed above, can be assayed by detection of protein or RNA in serum. The serum samples can also be used to monitor additional protein or RNA biomarkers related to response to treatment with an IL-4R antagonist, IL-4/IL-13 signaling, asthma, atopy or eosinophilic diseases (e.g., by measuring soluble IL-4Rα, IL-4, IL-13, periostin). In some embodiments, RNA samples are used to determine RNA levels (non-genetic analysis), e.g., RNA levels of biomarkers; and in other embodiments, RNA samples are used for transcriptome sequencing (e.g., genetic analysis).

Formulations

In some embodiments, the antibody or antigen binding fragment thereof is formulated in a composition comprising: i) about 150 mg/mL of antibody or an antigen-binding fragment thereof that specifically binds to IL-4R, ii) about 20 mM histidine, iii) about 12.5 mM acetate, iv) about 5% (w/v) sucrose, v) about 25 mM arginine hydrochloride, vi) about 0.2% (w/v) polysorbate 80, wherein the pH of the formulation is about 5.9, and wherein the viscosity of the formulation is about 8.5 cPoise.

In alternative embodiments, the antibody or antigen binding fragment thereof is formulated in a composition comprising: i) about 175 mg/mL of antibody or an antigen-binding fragment thereof that specifically binds to IL-4R, ii) about 20 mM histidine, iii) about 12.5 mM acetate, iv) about 5% (w/v) sucrose, v) about 50 mM arginine hydrochloride, and vi) about 0.2% (w/v) polysorbate 80, wherein the pH of the formulation is about 5.9, and wherein the viscosity of the formulation is about 8.5 cPoise.

In specific embodiments, the antibody or antigen-binding fragment thereof comprises an HCVR comprising the amino acid sequence of SEQ ID NO: 1 and an LCVR comprising the amino acid sequence of SEQ ID NO: 2.

Suitable stabilized formulations are also set forth in U.S. Pat. No. 8,945,559, which is incorporated herein by reference in its entirety for all purposes.

The present invention is further illustrated by the following examples which should not be construed as further limiting. The contents of the figures and all references, patents and published patent applications cited throughout this application are expressly incorporated herein by reference for all purposes.

Furthermore, in accordance with the present invention there may be employed conventional molecular biology, microbiology, and recombinant DNA techniques within the skill of the art. Such techniques are explained fully in the literature. See, e.g., Green & Sambrook, *Molecular Cloning: A Laboratory Manual*, Fourth Edition (2012) Cold Spring Harbor Laboratory Press, Cold Spring Harbor, New York; *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994).

EXAMPLES

The following examples are put forth so as to provide those of ordinary skill in the art with a complete disclosure and description of how to make and use the methods and compositions featured in the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

The exemplary IL-4R antagonist used in the following Examples is the human anti-IL-4R antibody named dupilumab (also referred to herein as "mAb1").

Example 1: Methods—Allergic Asthma

Study Design

QUEST was a phase 3, randomized, double-blind, placebo-controlled study that assessed the efficacy and safety of dupilumab in patients with uncontrolled, moderate-to-severe asthma. A total of 1902 patients aged ≥12 years were randomized in a 2:2:1:1 ratio to add-on subcutaneous dupilumab 200 mg (loading dose 400 mg) or 300 mg (loading dose 600 mg) every 2 weeks (q2w) or matched-volume placebos for 52 weeks. The study was conducted in accordance with the Declaration of Helsinki, International Conference on Harmonization Good Clinical Practice guidelines and applicable regulatory requirements. An independent data and safety monitoring committee conducted blinded monitoring of patient safety data. The local institutional review board or ethics committee at each study center oversaw trial conduct and documentation. All patients provided written informed consent before participating in the trial.

The effect of dupilumab on key asthma outcome measures in subgroups of patients with and without evidence of allergic asthma at baseline in the QUEST study was compared. Allergic asthma was defined using the most common criteria in clinical practice in the US for determining eligibility for biologic therapy with omalizumab (i.e., total serum IgE≥30 IU/mL and ≥1 perennial aeroallergen-specific IgE≥0.35 kU/L at baseline) (US Food and Drug Administration, available at the website: accessdata.fda.gov/drugsatfda_docs/label/2003/omalgen062003LB.pdf).
Because dupilumab treatment is not limited by weight or serum levels of total IgE, no upper threshold for serum total IgE was specified.

The study enrolled adults and adolescents (aged ≥12 years) with physician-diagnosed asthma for at least 12 months (based on Global Initiative for Asthma (GINA) 2014 guidelines) that were receiving treatment with a medium-to-high dose inhaled glucocorticoid and up to two additional controllers. Eligible patients fulfilled the following criteria: forced expiratory volume in 1 second ($FEV_1$) before bronchodilator use ≤80% of predicted normal value for adults and ≤90% of predicted normal value for adolescents; $FEV_1$ reversibility of ≥12% and 200 mL; a score of ≥1.5 on the 5-item Asthma Control Questionnaire (ACQ-5); and worsening of asthma in the previous year that led to hospitalization, emergency medical care, or treatment with systemic glucocorticoids for 3 days or more. Complete inclusion and exclusion criteria are published at Clinical Trials.gov (LIBERTY ASTHMA QUEST (NCT02414854)), which study is incorporated herein by reference in its entirety.

Patients

Patients were classified by whether or not they met the criteria for allergic asthma based on the following: a total serum IgE≥30 IU/mL and ≥1 positive perennial aeroallergen-specific IgE value (≥0.35 kU/L) at baseline. The perennial allergens used were *Dermatophagoides farinae*, *Dermatophagoides pteronyssinus*, *Alternaria alternata*, *Cladosporium herbarum*, cat and dog danders, German cockroach, Oriental cockroach and *Aspergillus fumigatus*. Percutaneous allergy skin testing was not performed. The baseline demographics for the study are summarized in Table 1.

A total of 1083 patients (57% of the QUEST study ITT population) met the criteria used to define allergic asthma: a total serum IgE≥30 IU/mL and ≥1 positive perennial aeroallergen-specific IgE≥0.35 kU/L at baseline. The remaining patients (n=819; 43% of ITT population) did not meet the criteria for allergic asthma. Of these 819 patients, 7% (n=55) had ≥1 positive perennial aeroallergen-specific IgE at baseline but a total serum IgE of <30 IU/mL, 14% (n=114) had ≥1 positive seasonal allergen but tested negative for all perennial allergens, 38% (n=314) had a history of allergic rhinitis but tested negative for all perennial and seasonal allergens, and 41% (n=336) did not have a history of allergic rhinitis and also tested negative for all perennial and seasonal allergens.

Patients who met the criteria for allergic asthma were generally younger (mean 44.5 years vs. 52.5 years), had asthma onset at an earlier age (mean 21.6 years vs 34.2 years), and a higher proportion had comorbid atopic conditions (96% vs 64%) compared with the subgroup that did not meet the criteria for allergic asthma (Table 1). Furthermore, the allergic asthma subgroup had fewer mean severe exacerbations in the previous year (1.94 vs 2.30) and a higher mean prebronchodilator $FEV_1$ (1.85 L vs 1.67 L). These patients, compared with patients who did not meet the criteria for allergic asthma, also had higher serum TARC concentrations (median 327 pg/mL vs 277 pg/mL) and similar levels of FeNO (median 26 ppb vs 23 ppb) and blood eosinophil counts (median 250 cells/μL vs 260 cells/μL).

Endpoints

Endpoints analyzed were annualized severe exacerbation rates, change from baseline in prebronchodilator $FEV_1$ (L), and change from baseline in ACQ-5 score over the 52-week treatment period in the subgroups of patients that met and did not meet the allergic asthma criteria. Within each subgroup, severe exacerbations during the 52-week treatment period and changes from baseline in prebronchodilator $FEV_1$ (L) at week 12 were also analyzed in populations of patients with baseline blood eosinophils ≥150 cells/μL, ≥300 cells/µL, and baseline fractional exhaled nitric oxide (FeNO) ≥25 ppb. An additional analysis was performed on the subset of allergic asthma patients with baseline serum total IgE>700 IU/mL, patients for whom omalizumab therapy is not indicated in the US.

The effect of dupilumab treatment on the following biomarkers of type 2 inflammation was also assessed in the allergic asthma vs. the non-allergic asthma subgroups: serum total IgE levels; FeNO levels; and serum thymus and activation-regulated chemokine (TARC) levels. The effect of dupilumab treatment on serum-specific IgE levels for each of the perennial aeroallergens tested during the 52-week treatment period was also examined in those patients who tested positive (≥0.35 kU/L) at baseline.

TABLE 1

Baseline demographic and disease characteristics

| | Allergic asthma (n = 1083) | | | | Did not meet the criteria for allergic asthma (n = 819) | | | |
|---|---|---|---|---|---|---|---|---|
| | 1.14 mL/200 mg q2 w | | 2 mL/300 mg q2 w | | 1.14 mL/200 mg q2 w | | 2 mL/300 mg q2 w | |
| | Placebo (n = 183) | Dupilumab (n = 360) | Placebo (n = 179) | Dupilumab (n = 361) | Placebo (n = 134) | Dupilumab (n = 271) | Placebo (n = 142) | Dupilumab (n = 272) |
| Age, mean (SD), years | 44.0 (16.8) | 45.5 (16.0) | 44.1 (14.9) | 43.9 (15.8) | 54.0 (11.8) | 51.0 (13.7) | 53.2 (12.8) | 52.7 (13.6) |
| Female, n (%) | 101 (55.2) | 196 (54.4) | 114 (63.7) | 216 (59.8) | 97 (72.4) | 191 (70.5) | 104 (73.2) | 178 (65.4) |
| BMI, mean (SD), kg/m² | 29.3 (7.35) | 28.47 (6.35) | 28.78 (6.88) | 28.91 (6.91) | 30.39 (7.09) | 29.82 (6.67) | 29.76 (7.02) | 29.27 (6.37) |
| Age at asthma onset, mean (SD), years | 20.9 (17.9) | 23.0 (19.5) | 20.9 (16.9) | 20.8 (17.8) | 35.9 (17.3) | 32.5 (17.3) | 35.7 (17.4) | 34.2 (18.8) |
| With ongoing atopic medical condition,* n (%) | 176 (96.2) | 337 (93.6) | 173 (96.6) | 354 (98.1) | 90 (67.2) | 172 (63.5) | 93 (65.5) | 170 (62.5) |
| Atopic dermatitis | 21 (11.5) | 48 (13.3) | 32 (17.9) | 42 (11.6) | 14 (10.4) | 13 (4.8) | 6 (4.2) | 20 (7.4) |
| Allergic rhinitis | 142 (77.6) | 265 (73.6) | 140 (78.2) | 284 (78.7) | 79 (59) | 156 (57.6) | 85 (59.9) | 154 (56.6) |
| Food allergy | 21 (11.5) | 35 (9.7) | 25 (14.0) | 32 (8.9) | 7 (5.2) | 13 (4.8) | 11 (7.7) | 15 (5.5) |
| Hives | 13 (7.1) | 16 (4.4) | 9 (5.0) | 22 (6.1) | 6 (4.5) | 14 (5.2) | 6 (4.2) | 8 (2.9) |
| Former smokers, n (%) | 27 (14.8) | 75 (20.8) | 38 (21.2) | 67 (18.6) | 32 (23.9) | 51 (18.8) | 29 (20.4) | 49 (18.0) |
| Severe asthma exacerbations in the past year, mean (SD), n | 1.89 (1.48) | 1.98 (2.99) | 2.22 (1.99) | 1.79 (1.33) | 2.32 (1.68) | 2.18 (2.16) | 2.43 (2.17) | 2.33 (2.35) |
| Pre-bronchodilator FEV$_1$, mean (SD), L | 1.84 (0.64) | 1.85 (0.64) | 1.84 (0.61) | 1.88 (0.58) | 1.66 (0.55) | 1.70 (0.58) | 1.64 (0.49) | 1.66 (0.61) |
| ACQ-5 score,† mean (SD) | 2.69 (0.69) | 2.73 (0.82) | 2.73 (0.76) | 2.74 (0.78) | 2.75 (0.77) | 2.80 (0.77) | 2.81 (0.79) | 2.80 (0.74) |
| Total serum IgE, median (IQR), IU/mL; n | 337.0 (147.0-629.0); 183 | 304.0 (137.0-835.5); 360 | 315.0 (142.0-763.0); 179 | 326.0 (152.0-762.0); 361 | 60.0 (24.0-147.0); 131 | 63.0 (24.0-135.0); 264 | 67.0 (24.0-154.0); 139 | 64.0 (24.0-150.0); 265 |
| FeNO, median (IQR), ppb; n | 27.0 (15.0-50.0); 180 | 25.0 (16.0-45.0); 358 | 30.0 (17.5-53.0); 176 | 24.0 (14.0-42.0); 358 | 24.0 (14.0-42.0); 131 | 22.0 (13.0-36.0); 266 | 22.5 (13.5-39.5); 140 | 24.0 (14.0-43.0); 269 |
| Serum TARC, median (IQR), pg/mL; n | 307.0 (218.0-508.0); 179 | 351.0 (224.5-478.5); 360 | 313.0 (206.0-525.0); 179 | 317.0 (198.0-456.0); 357 | 284.0 (196.0-421.0); 130 | 265.0 (187.5-402.5); 264 | 281.5 (186.0-449.0); 140 | 276.0 (178.0-386.0); 265 |
| Blood eosinophil count, median (IQR), cells/µL; n | 290.0 (150.0-490.0); 183 | 240.0 (120.0-470.0); 359 | 260.0 (160.0-440.0); 179 | 240.0 (140.0-430.0); 361 | 250.0 (130.0-470.0); 134 | 250.0 (120.00-460.0); 271 | 270.0 (120.0-470.0); 141 | 270.0 (130.0-510.0); 272 |

Statistical Analyses

Efficacy analyses were performed in the intention-to-treat (ITT) population, defined as all randomized patients, separated by subgroups (i.e., with or without total serum IgE≥30 IU/mL and ≥1 positive perennial aeroallergen-specific IgE value (≥0.35 kU/L) at baseline). Data were analyzed for each subgroup according to the four assigned treatment groups (dupilumab vs placebo) regardless of whether an intervention was received (Castro et al. (2018) New Engl. J. Med. 378:2486-96). Annualized rates of severe exacerbations over the 52-week treatment period were analyzed using a negative binomial regression model, which included as covariates the assigned intervention groups, age, geographic region, baseline eosinophil strata, baseline dose of inhaled glucocorticoid, and number of severe exacerbations in the previous year. All severe exacerbations that occurred during the 52-week treatment period were included regardless of whether the patient remained on treatment.

The change from baseline in prebronchodilator $FEV_1$ (L) and ACQ-5 scores during the 52-week treatment period were analyzed using mixed-effect models with repeated measures, which included as covariates the four assigned intervention groups, age, geographic region, baseline eosinophil strata, baseline dose of inhaled glucocorticoid, visit, visit-by-intervention interaction, corresponding baseline value, and baseline-by-visit interaction. In addition, sex and baseline height were also included as covariates for $FEV_1$ analyses. If treatment was discontinued, any measurements recorded after discontinuation were included throughout the 52-week treatment period.

Biomarker analyses were performed in the exposed population, defined as all patients exposed to study medication. For both patient subgroups, differences between dupilumab and matched placebo in the change from baseline in levels of eosinophils and FeNO, considered as key biomarkers of type 2 inflammation, were analyzed using a rank analysis of covariance model including the 4 assigned intervention groups, age, sex, geographic region, baseline eosinophil strata, baseline dose of inhaled glucocorticoid, and corresponding baseline value as covariates. For the analysis of specific IgEs, the analyses were restricted to patients who were positive (≥0.35 kU/L) for the specific IgEs at baseline.

A nominal P value of <0.05 for the comparison between each dupilumab dose and matched placebo (within each subgroup) was considered statistically significant.

Figure 6A:
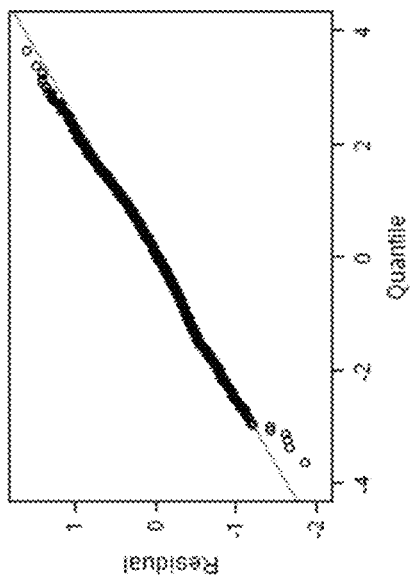
FIG. 6A-FIG. 6B show statistical analyses of IgE≥700 IU/ml patients.
Figure 6B:
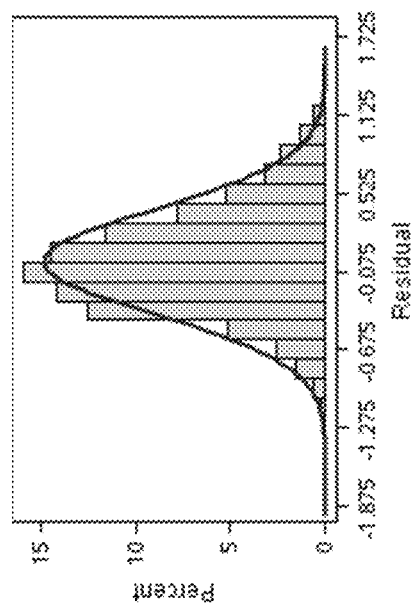

The residuals from the linear mixed model for the allergic subgroup with baseline serum IgE>700 IU/mL were examined to ensure normally distributed population. The histogram of the residuals as well as the q-q plot are shown in FIG. 6.

Example 2: Annualized Rate of Severe Asthma Exacerbations—Allergic Asthma

Figure 1D:
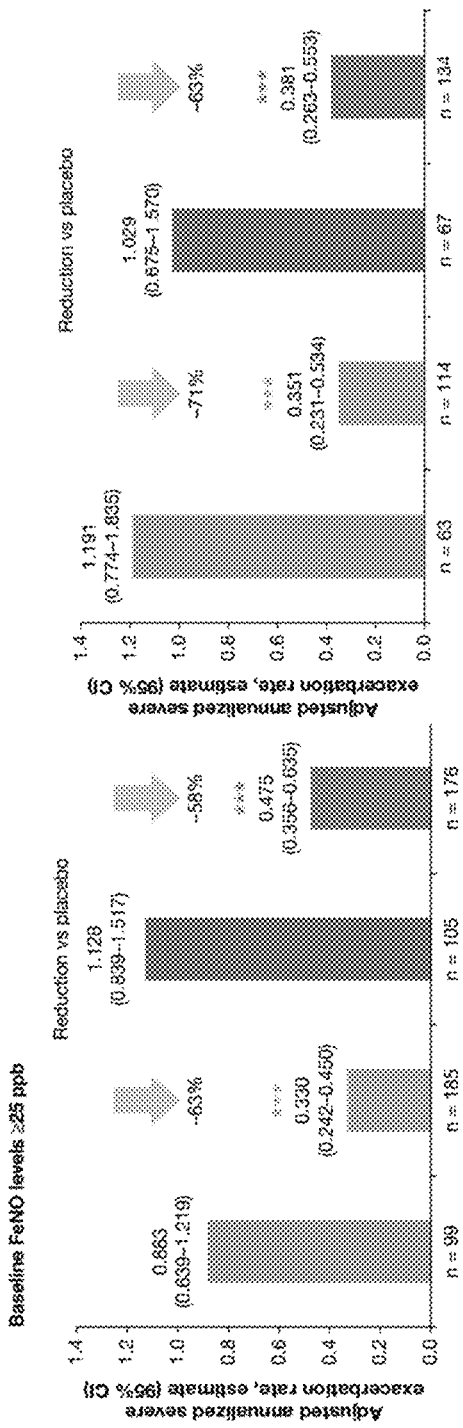

In the allergic asthma subgroup, dupilumab reduced the adjusted annualized rate of severe exacerbations compared with matched placebo by 36.9% with 200 mg q2w (95% confidence interval (CI) 13.4%-54.0%; nominal P=0.004) and 45.5% with 300 mg q2w (95% CI 26.0% to 59.9%; nominal P<0.001; FIG. 1A). In patients who did not meet the criteria for allergic asthma, the adjusted annualized rate of severe exacerbation events was also significantly reduced by 60.0% with dupilumab 200 mg q2w (95% CI 42.7% to 72.1%; nominal P<0.001), and by 44.6% with 300 mg q2w (95% CI 21.5% to 60.9%; nominal P<0.001) compared with placebo (FIG. 1A). In both the allergic asthma subgroup and the subgroup that did not meet the criteria for allergic asthma, dupilumab 200 mg and 300 mg q2w significantly (all nominal P<0.01) reduced the rate of severe exacerbations in patients with baseline blood eosinophils ≥150 cells/μL and ≥300 cells/μL, and in those with baseline FeNO≥25 ppb. The magnitude of effect was numerically greater compared with the respective overall subgroup (FIG. 1B-1D). Among patients in the allergic asthma subgroup with baseline serum total IgE>700 IU/mL, both dupilumab doses significantly (nominal P<0.001) reduced severe exacerbation rates during the 52-week treatment period compared with matched placebo, and the magnitude of effect was numerically greater versus the overall allergic asthma subgroup (FIG. 1E).

Example 3: Prebronchodilator $FEV_1$—Allergic Asthma

Figure 2A:
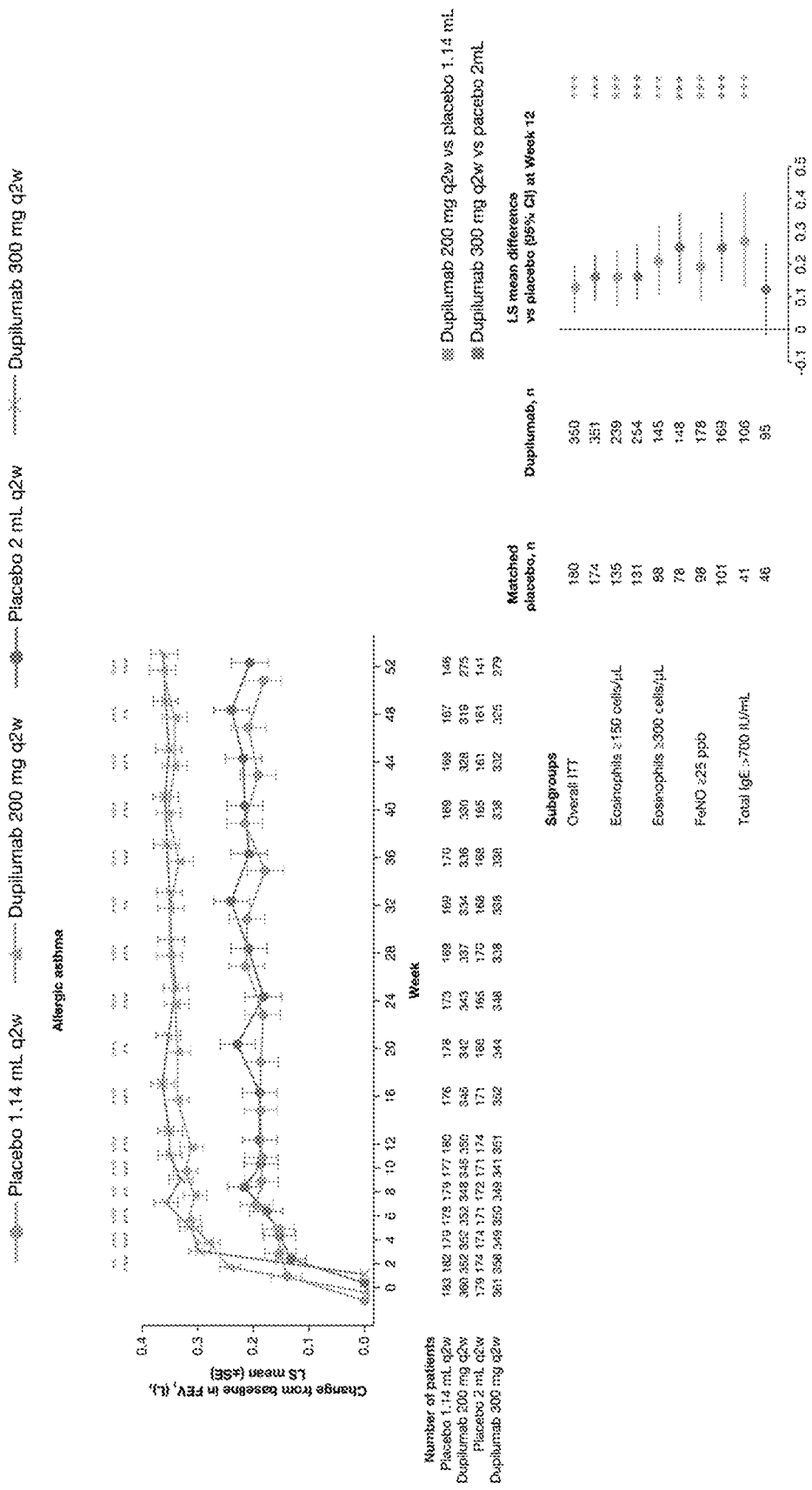

At week 12, dupilumab 200 mg and 300 mg q2w treatment significantly improved prebronchodilator $FEV_1$ vs placebo by least squares (LS) mean 0.13 L (95% CI 0.05 to 0.20; nominal P<0.001) and 0.16 L (95% CI 0.09 to 0.23; nominal P<0.001), respectively, in the allergic asthma subgroup, and by 0.14 L (95% CI 0.07 to 0.22; nominal P<0.001) and 0.09 L (95% CI 0.01 to 0.16; nominal P=0.02) vs placebo, respectively, in those patients who did not meet the criteria (FIG. 2A). As observed for severe exacerbations, the magnitude of improvement versus placebo in prebronchodilator $FEV_1$ at week 12 was equal to or greater than in patients with baseline blood eosinophils ≥150 cells/μL and ≥300 cells/μL and those with baseline FeNO≥25 ppb than in the respective overall subgroups (all nominal P<0.05; FIG. 2B). Among patients in the allergic asthma subgroup with baseline serum total IgE>700 IU/mL, dupilumab 300 mg q2w showed a similar magnitude of effect on prebronchodilator $FEV_1$ at week 12 compared with the overall subgroup (LS mean difference vs placebo 0.12 L (95% CI −0.03 to 0.26; nominal P=0.11)), whereas a greater magnitude of effect was observed in patients treated with dupilumab 200 mg q2w (LS mean difference vs placebo 0.27 L (95% CI 0.13 to 0.42); nominal P<0.001).

In both the allergic and non-allergic subgroups, improvements in prebronchodilator $FEV_1$, were observed as early as the first evaluation at week 2 and persisted through week 52 (FIG. 2A).

Example 4: Asthma Control—Allergic Asthma

Figure 3:
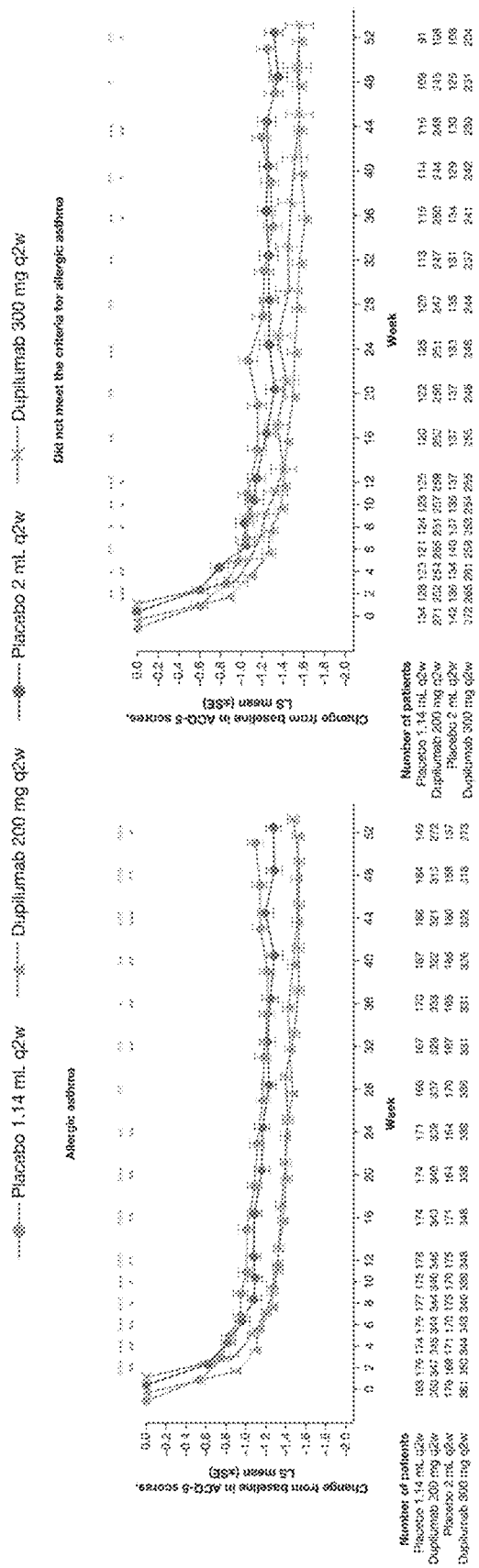
FIG. 3. depicts the effect of dupilumab on asthma control (as measured by ACQ-5) during the 52-week treatment period in the overall allergic asthma subgroup and the overall asthma subgroup that did not meet the criteria for allergic asthma. ACQ-5, 5-item asthma control questionnaire; LS, least squares; q2w, every 2 weeks; SE, standard error.

In the allergic asthma subgroup, the LS mean change from baseline in ACQ-5 score was improved by −1.39 (standard error [SE] 0.05) with a difference vs placebo of −0.28 (95% CI −0.46 to −0.11; nominal P<0.01) in dupilumab 200 mg q2w-treated patients and by −1.42 (SE 0.05) with a difference vs placebo of −0.26 (95% CI −0.44 to −0.08; nominal P<0.01) at week 24 (FIG. 3) in dupilumab 300 mg q2w-treated patients. In the subgroup that did not meet the allergic asthma criteria, the improvement in ACQ-5 score from baseline at week 24 was −1.51 (SE 0.06) with a difference vs. placebo of −0.44 (95% CI −0.65 to −0.22; nominal P<0.0001) in dupilumab 200 mg q2w-treated patients, and −1.35 (SE 0.06) with a difference vs placebo of −0.08 (95% CI −0.29 to 0.12; nominal P=0.43) observed in patients treated with dupilumab 300 mg q2w (FIG. 3).

Example 5: Serum Total IgE and Aeroallergen-Specific IgE—Allergic Asthma

Figure 4A:
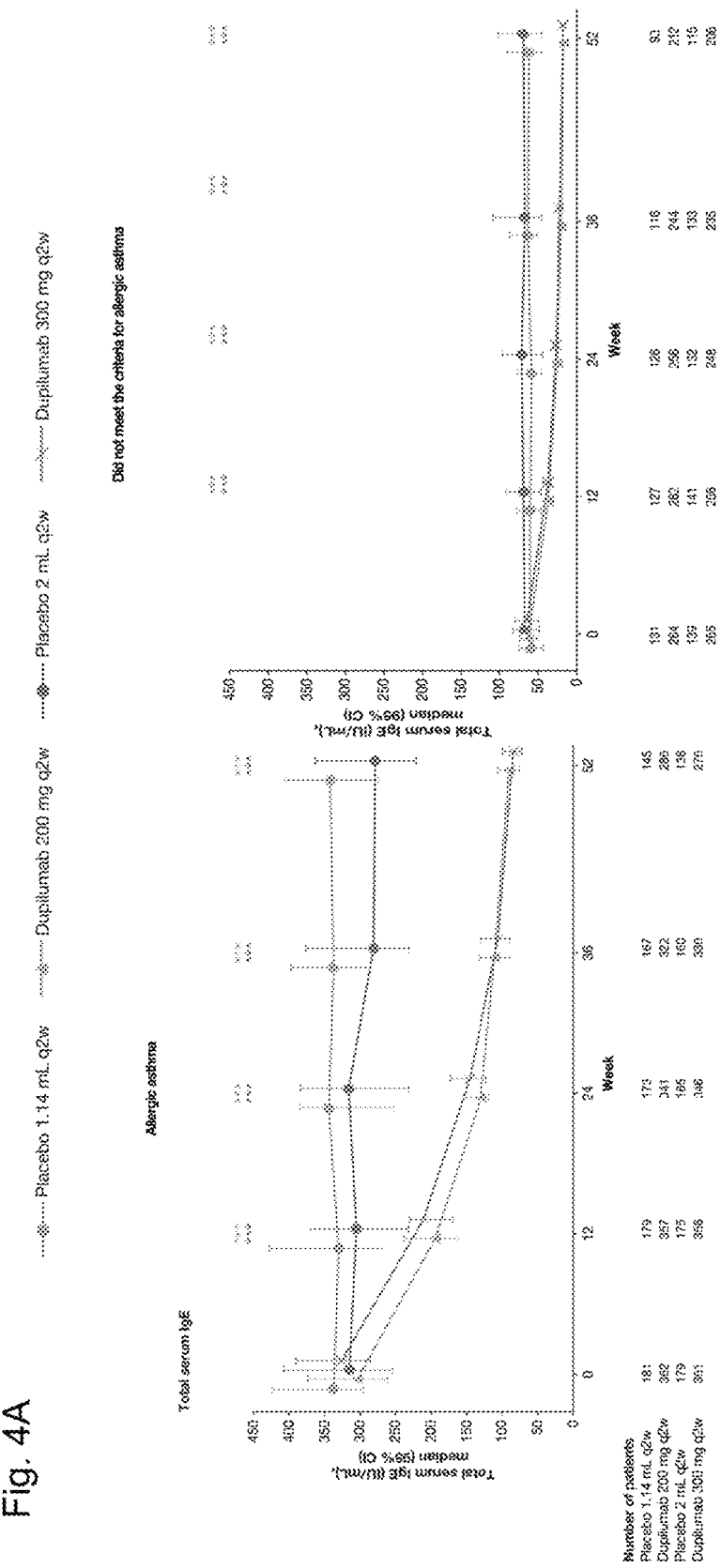
FIG. 4A-FIG. 4C depict the effect of dupilumab on various biomarkers.

In the allergic asthma subgroup and the subgroup that did not meet the criteria for allergic asthma, both dupilumab 200 mg and 300 mg q2w dose regimens significantly reduced total serum IgE compared with matched placebo at week 12 (the earliest assessed time point; nominal P<0.001; FIG. 4A). Reductions in total serum IgE occurred gradually throughout the treatment period (nominal P<0.001 vs placebo at all time points).

In patients with allergic asthma who tested positive at baseline (≥0.35 kU/L) for the respective perennial aeroallergen, significant reductions from baseline in percentage of antigen-specific serum IgE levels were observed over time for each of the 8 perennial aeroallergens that were assessed (FIG. 5A-H). These reductions were statistically significant at week 12 (the earliest assessed time point) compared with matched placebo (nominal P<0.05) and continued over the 52-week treatment period. Too few patients tested positive for oriental cockroach allergens at baseline to allow for a meaningful analysis.

Example 6: FeNO and Serum TARC—Allergic Asthma

Figure 4B:
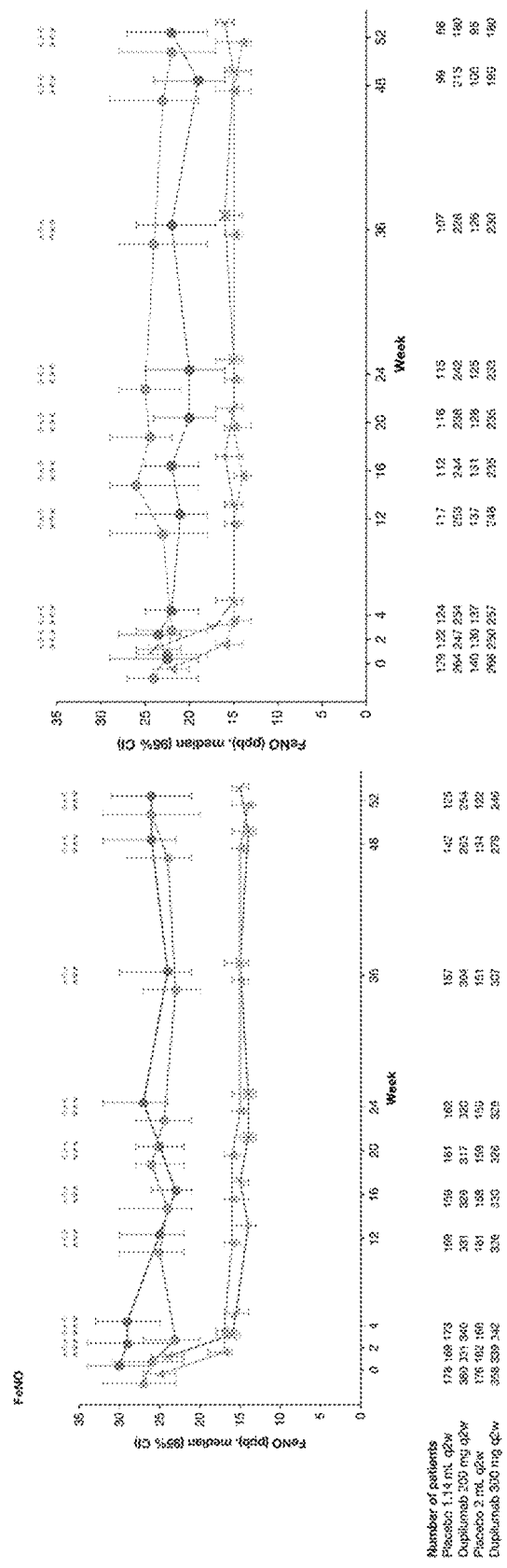

In both the allergic asthma subgroup and the subgroup that did not meet the criteria for allergic asthma, dupilumab 200 mg and 300 mg q2w dose regimens vs. placebo were associated with a marked decrease in FeNO by the first evaluation, after 2 weeks of treatment. The decrease in FeNO was sustained throughout the 52-week treatment period (nominal P<0.001 at all time points) (FIG. 4B). By week 52, median FeNO values for the dupilumab 200 mg and 300 mg q2w doses in both subgroups were similar to the published median value for healthy volunteers (16 ppb).

Figure 4C:
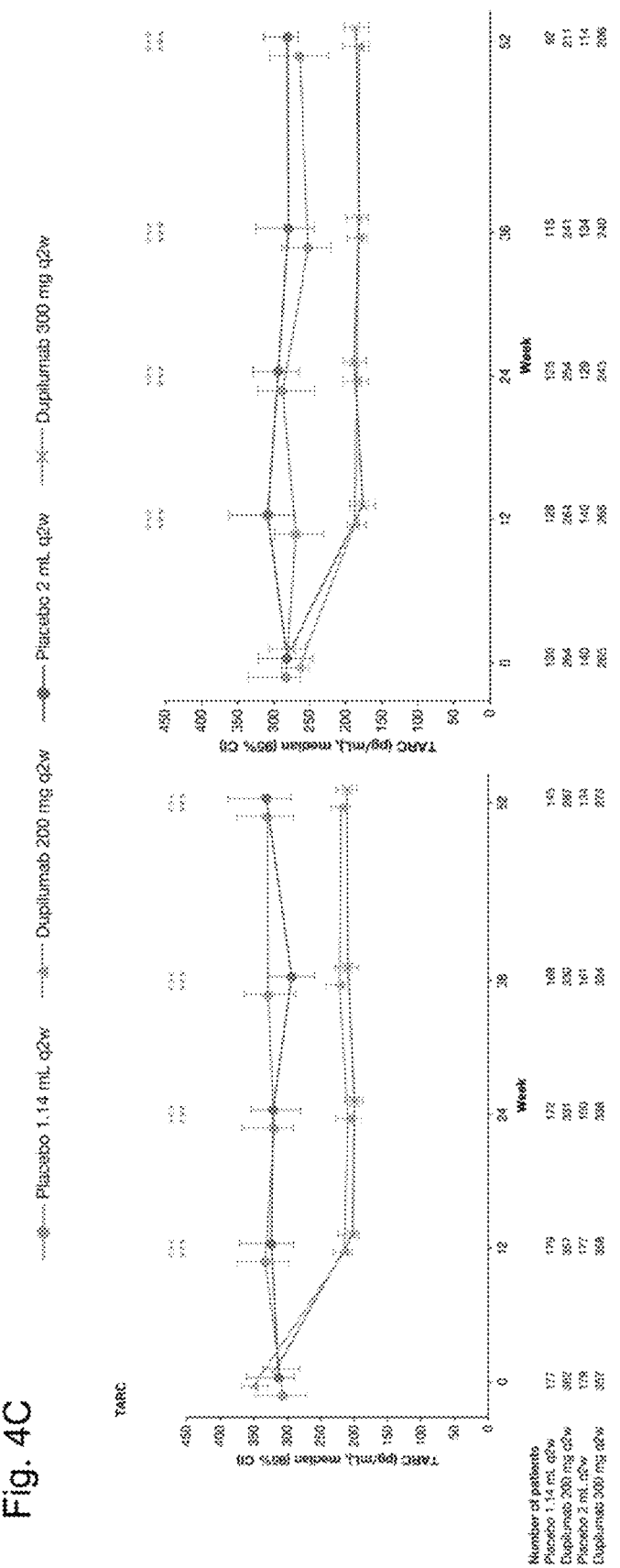

In both the allergic asthma subgroup and the subgroup that did not meet the criteria for allergic asthma, serum TARC concentrations were significantly reduced vs. matched placebo at week 12 (the earliest assessed time point) in patients treated with dupilumab 200 mg or 300 mg q2w. These reductions were sustained throughout the 52-week treatment period (nominal P<0.001 at all time points) (FIG. 4C).

Example 7: Discussion—Allergic Asthma

Dupilumab significantly reduced severe exacerbation rates and improved $FEV_1$ and asthma control (as measured by ACQ-5) in patients with allergic asthma. Improvements in $FEV_1$ and asthma control were evident by the first evaluation at week 2, and sustained throughout the 52-week treatment period. Some variability in the magnitude of exacerbation rates and asthma control was observed between the two dupilumab doses vs. their respective placebo. Without intending to be bound by scientific theory, this was likely related to the need to use two different matched-volume placebos. Reductions in severe exacerbation rates and improvements in $FEV_1$ were greater in patients with higher baseline levels of type 2 inflammatory biomarkers. The proportion of patients who met the criteria for allergic asthma (57%) in this study was significantly lower than patients who reported a history of ≥1 atopic condition in the overall QUEST population (Castro et al. (2018) New Engl. J. Med. 378:2486-96). This difference is primarily due to the exclusion of patients who had a history of allergic rhinitis but did not have evidence of hypersensitivity to aeroallergens, the exclusion of patients who had hypersensitivity only to seasonal allergens (to a lesser extent), and the exclusion of patients with perennial allergen sensitivity but whose total serum IgE was <30 IU/mL. It should be acknowledged that the timing of specific IgE measurements in this global study was not designed to coincide with peak seasonal allergen exposure in each country/region.

Dupilumab was shown to be effective in patients with allergic asthma as well as those who did not meet the criteria for allergic asthma. These findings support the critical roles of IL-4 and IL-13 in driving IgE-mediated and non-IgE-mediated type 2 inflammation in asthma. The clinical benefits observed in this study extended to those patients with allergic asthma whose serum total IgE exceeded 700 IU/mL at baseline. This is a clinically relevant subset of allergic asthma patients for whom anti-IgE therapy with omalizumab is not indicated in the US. (See USDA website: access-data.fda.gov/drugsatfda_docs/label/2003/omalgen062003LB.pdf, accessed Apr. 2, 2019). This subgroup was included in the analysis because dosing of dupilumab, unlike omalizumab, is not limited by body weight and serum total serum IgE in adolescent and adult patients with uncontrolled, moderate-to-severe asthma.

Consistent with the mechanism of action of dupilumab in suppressing IgE production, dupilumab significantly reduced serum total IgE and aeroallergen-specific IgE in patients with allergic asthma, and reduced serum total IgE in those who did not meet the criteria for allergic asthma.

Similarly, dupilumab significantly reduced levels of other type 2 inflammatory biomarkers including FeNO and serum TARC in both patient subgroups. The decline in total and specific IgE is slower relative to other biomarkers such as FeNO. The decline in IgE concentrations did not plateau during the 52-week treatment period.

In summary, this is the first demonstration of the clinical and pharmacodynamic effects of dual IL-4 and IL-13 inhibition with dupilumab in patients with allergic asthma defined by the presence of total serum IgE≥30 IU/mL and ≥1 perennial aeroallergen-specific IgE≥0.35 kU/L at baseline. Dupilumab significantly reduced the rate of severe exacerbations, improved $FEV_1$, and demonstrated clinically meaningful improvements in asthma control (ACQ-5) during the 52-week treatment period regardless of subgroup, and treatment was generally well tolerated in the overall study population. Markers of type 2 inflammation, including FeNO, total IgE, and TARC, were also significantly reduced with dupilumab treatment in both subgroups. The findings from this study support the roles of IL-4 and IL-13 in IgE- and non-IgE-mediated inflammatory pathways in asthma. IL-4/IL-13 inhibition by dupilumab therapy is beneficial for both allergic and non-allergic asthma phenotypes.

Example 8: Dupilumab Efficacy in Patients with Uncontrolled, Moderate-to-Severe Asthma and Serologic Evidence of Allergic Bronchopulmonary Aspergillosis (ABPA)

Allergic bronchopulmonary aspergillosis (ABPA) is a severe allergic pulmonary disease caused by hypersensitivity to *Aspergillus fumigatus* (Af) antigen. Not all patients with asthma develop ABPA when exposed to the fungus. However, individuals with a genetic predisposition (HLA-DR2 (HLA-DRB1*1501 and *HLA-DRB1*1503) & HLA-DR5) are susceptible to develop ABPA when exposed to Af antigen. SNPs of IL-4Rα and IL-13 also are involved in genetic susceptibility, and these individuals mount profound type 2 immune response with very high IgE, eosinophilia, elevated FeNO, etc.

The mainstay of ABPA treatment is systemic steroids. However, not all patients respond to systemic steroids, and the disease may progress to bronchiectasis and fibrosis. Accordingly, there is a high unmet need to treat subjects having ABPA.

Study

Phase 3 LIBERTY ASTHMA QUEST study (NCT02414854). Patients with serologic evidence of ABPA (baseline serum total IgE>1000 IU/mL, positive serum IgE-Af>0.35 IU/mL, blood eosinophils >500 cells/µL) receiving add-on dupilumab (200 mg or 300 mg) every 2 weeks vs. placebo were assessed.

Population

Of 1902 patients with moderate-to-severe asthma enrolled in QUEST, 30 patients with serologic evidence of ABPA (ABPA-S) were identified (1.6%). The baseline characteristics of these and the remaining intention-to-treat (ITT) population of QUEST (n=1872) are shown in Table 2. At baseline, no meaningful differences in mean age, $FEV_1$, ACQ-5, or Asthma Quality of Life Questionnaire (AQLQ) were observed in patients with and without ABPA-S, although ABPA-S patients had higher baseline levels of the type 2 biomarkers eosinophils, IgE, and FeNO compared with asthma patients without ABPA-S.

Endpoints/Visit

The annualized event rate of severe exacerbations (defined as a deterioration of asthma symptoms requiring treatment for ≥3 days with systemic corticosteroids, or hospitalization or an emergency room visit requiring systemic corticosteroids), and the change from baseline in pre-bronchodilator $FEV_1$ (L) and patient-reported 5-item Asthma Control Questionnaire (ACQ-5) score, assessed at baseline and at regular intervals throughout the 52-week treatment period (FIG. 7). The LS mean change from baseline in pre-bronchodilator FEV1 (L) was determined at weeks 24 and 52 in an ITT population (FIG. 8). Total (absolute) serum IgE was determined at week 52 in an exposed population (FIG. 9). Total (absolute) Af-specific serum IgE was determined at week 52 in an exposed population (FIG. 10). Total (absolute) FeNO levels were determined at week 52 in an expose population (FIG. 11).

Treatment Arms

Dupilumab 200 mg q2w, dupilumab 300 mg q2w, and matched placebo, pooled.

Results

Annualized severe exacerbation rates during the 52-week treatment period were analyzed using negative binomial regression models. LS mean change in $FEV_1$ from baseline to weeks 24 and 52 was determined using mixed-effect models with repeated measures. Total IgE, IgE-Af, and FeNO at week 52 were assessed using Wilcoxon rank-sum test.

Figure 12:
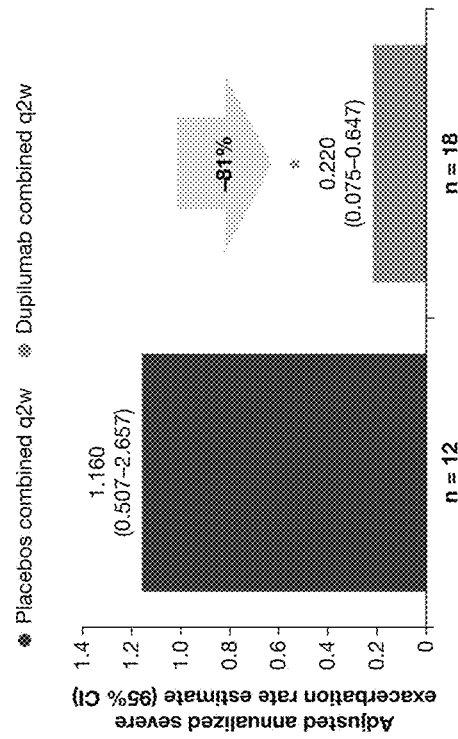
FIG. 12 graphically depicts the effect of dupilumab q2w on annualized severe exacerbation rate during the 52-week treatment period in ITT patient population with serologic evidence of ABPA.

In patients with ABPA-S, dupilumab significantly reduced the adjusted annualized rate of severe exacerbations compared with placebo by 81.1% (95% confidence interval [CI] 0.052-0.693; P=0.01) (FIG. 12).

Pre-bronchodilator FEV1

Figure 13:
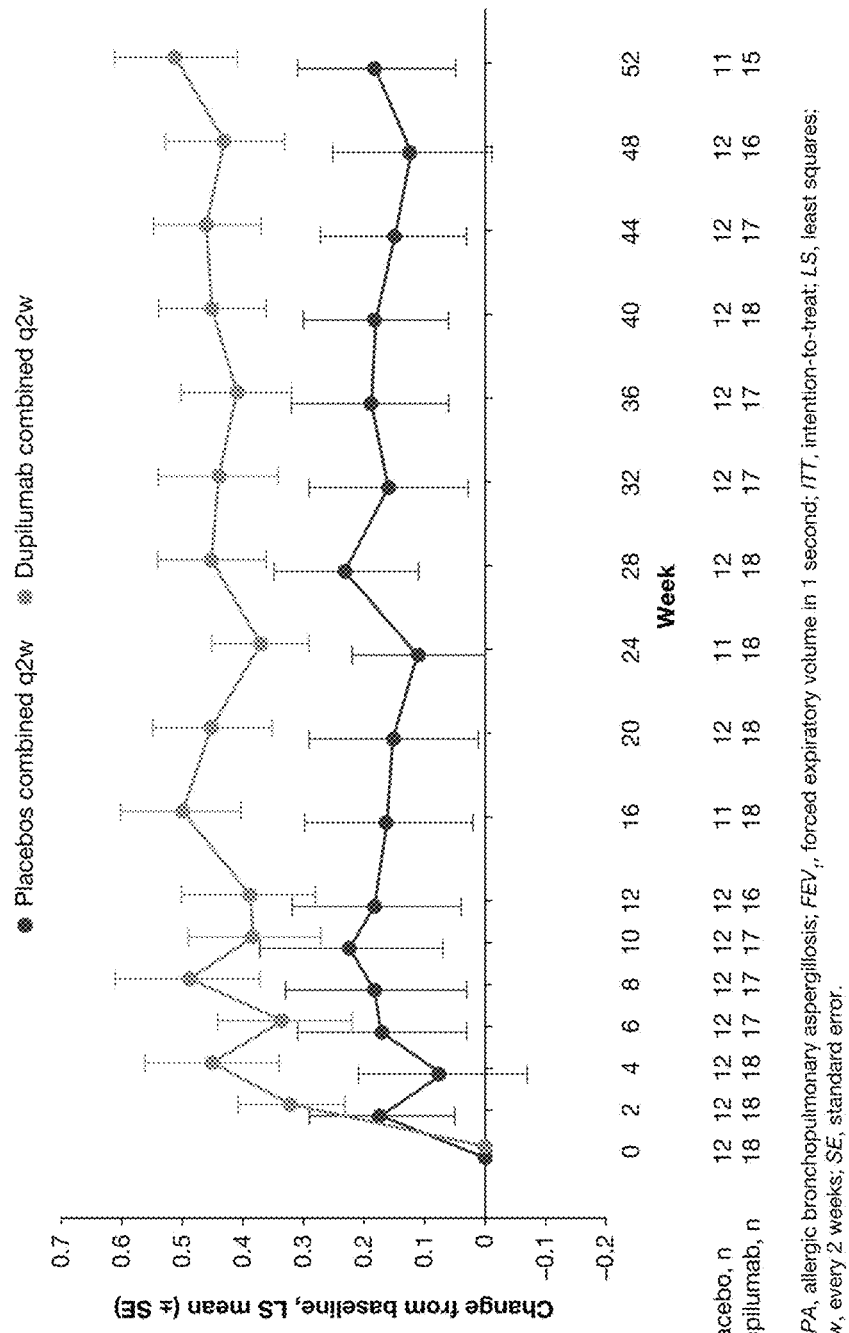
FIG. 13 graphically depicts the effect of dupilumab q2w on pre-bronchodilator $FEV_1$ (L) during the 52-week treatment period in ITT patient population with serologic evidence of ABPA.

Numerical improvements in pre-bronchodilator FEV1 were observed in dupilumab-treated versus placebo-treated patients with ABPA-S. Improvements were observed as early as week 2, the first time point at which patients were assessed, and were maintained throughout the 52-week treatment period (FIG. 13). Dupilumab versus placebo improved pre-bronchodilator $FEV_1$ in patients with ABPA-S by a least squares (LS) mean difference of 0.21 L (95% CI −0.18 to 0.60; P=0.28) at week 12, and by 0.33 L (−0.02 to 0.68; P=0.07) at week 52.

Asthma Control

Figure 14:
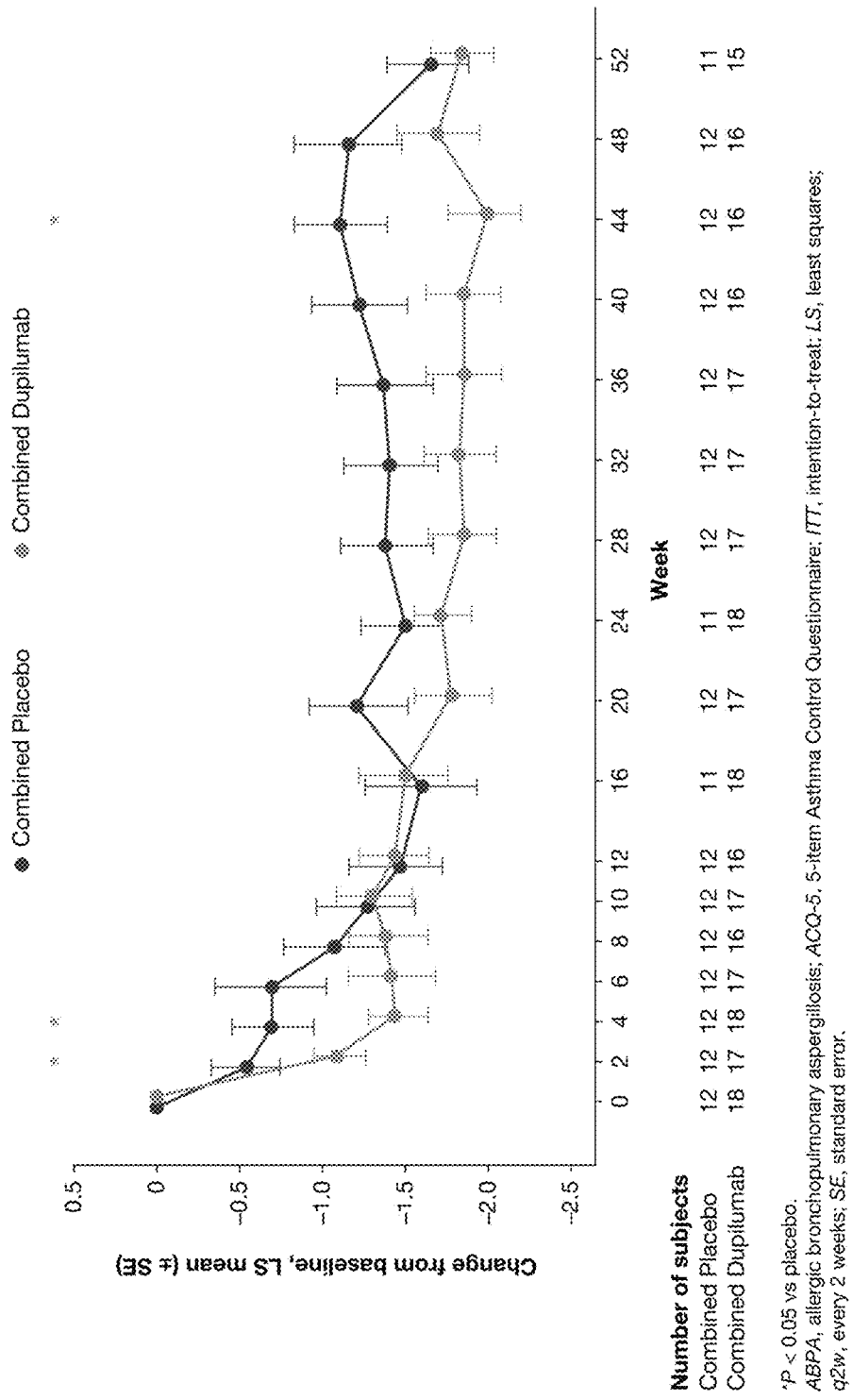
FIG. 14 graphically depicts the effect of dupilumab q2w on ACQ-5 score during the 52-week treatment period in ITT patient population with serologic evidence of ABPA.

In patients with ABPA-S, dupilumab improved ACQ-5 score as early as 2 weeks after treatment commenced, with an LS mean difference of −0.56 (95% CI −1.09 to −0.02; P<0.05) versus placebo. This continued over the 52-week treatment period, with numerical improvements in ACQ-5 score at each time point except for weeks 12 and 16. At week 52, dupilumab improved ACQ-5 score by an LS mean difference of −0.20 (−0.86 to 0.46; P=0.54) versus placebo (FIG. 14).

Serum Total IgE and A. fumigatus-Specific IgE

Figures 15A, 15B:
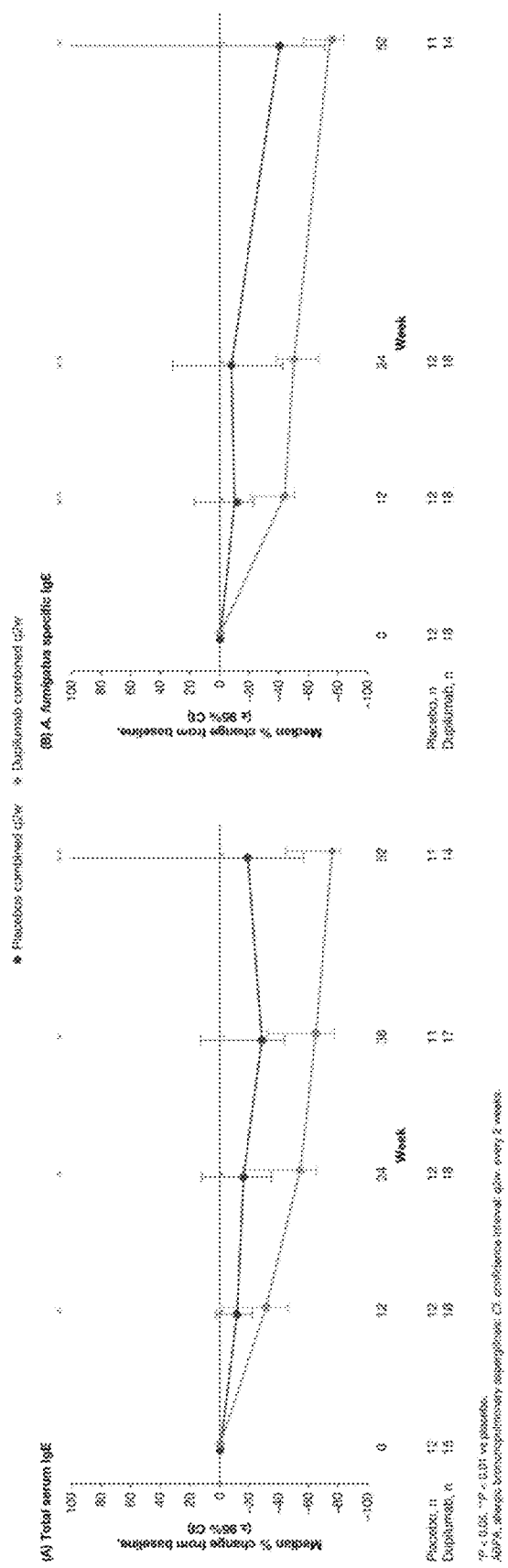
FIG. 15A-FIG. 15B graphically depict the effect of dupilumab q2w on serum total IgE (IU/mL) (FIG. 15A) and *A. fumigatus*-specific serum IgE (IU/mL) (FIG. 15B) during the 52-week treatment period in exposed patients with serologic evidence of ABPA.

Baseline serum total IgE was markedly elevated in ABPA-S patients compared with asthma patients without ABPA-S (median values: 2148-3383 IU/mL vs 159-165 IU/mL). During treatment, substantial reductions in serum total IgE were observed in dupilumab-treated ABPA-S patients compared with placebo-treated ABPA-S patients from the earliest assessed time point at Week 12 (FIG. 15A). These reductions continued to decline progressively throughout the treatment period, and by week 52 the median serum total IgE concentration was 691.5 IU/mL (95% CI 323.0-2617.0) with a median percentage change from baseline of −75.6% (−81.6 to −44.6). In placebo-treated patients, the concentration at week 52 was 1714.0 IU/mL (95% CI 727.0-3048.0) with a median percentage change from baseline of −19.6% (95% CI −56.3 to 102.6; P<0.01) (FIG. 15A). This was similar to the median percentage change from baseline in serum total IgE observed in the overall ITT population of the QUEST study (dupilumab −69.5% [95% CI −79.0 to −56.9] versus placebo −3.6% [95% CI −22.7 to 20.8]), demonstrating that the median percentage change of serum total IgE from baseline with dupilumab was similar, irrespective of baseline IgE values.

Dupilumab treatment in patients with ABPA-S also suppressed levels of A. fumigatus-specific IgE from a baseline median value of 2.4 IU/mL (95% CI 0.6-11.2) (placebo group baseline median value 3.0 IU/mL [95% CI 0.5-28.8]). These reductions were evident by week 12. After further gradual reductions, the median A. fumigatus-specific IgE concentration at week 52 was 0.8 IU/mL (95% CI 0.1-2.6), with a median percentage change from baseline of −74.8% (95% CI −83.5 to −56.2) in dupilumab-treated patients. Corresponding values in placebo-treated patients were 4.6 IU/mL (95% CI 0.6-21.5) and −40.4% (95% CI −71.2 to 208.9; P<0.05) (FIG. 15B).

Other Type 2 Biomarkers

Figure 16A:
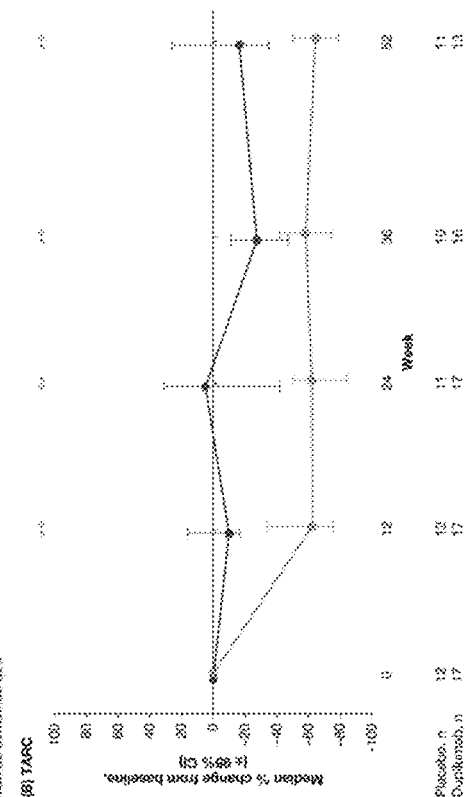
FIG. 16A-FIG. 16D graphically depict the effect of dupilumab q2w on type 2 biomarkers during the 52-week treatment period in exposed patients with serologic evidence of ABPA. FeNO (ppb) (FIG. 16A), TARC (pg/mL) (FIG. 16B), eotaxin-3 (pg/mL) (FIG. 16C), and peripheral blood eosinophils (cells/μL) (FIG. 16D).

In patients with ABPA-S, median baseline concentrations of FeNO were 49.0 ppb (95% CI 24.0-68.0) and 31.0 ppb (95% CI 19.0-63.0) in dupilumab and placebo groups, respectively. Dupilumab decreased FeNO concentration from baseline as early as week 2 of treatment, with a median concentration of 18.0 ppb (95% CI 12.0-26.0) and median percentage change of −50.8% (95% CI −62.5 to −41.9) in the dupilumab group versus 38.0 ppb (95% CI 23.0-50.0), percentage change −5.0% (95% CI −25.4 to 50.0) in the placebo group (P<0.01). Reduction in FeNO was sustained up to week 52 with a median of 18.0 ppb (95% CI 12.0-26.0) and median percentage change of −60.0% (95% CI −75.0 to −32.7) in dupilumab-treated patients versus a median 25.0 ppb (95% CI 10.0-56.0) and median percentage change of −24.3% (95% CI −52.2 to 57.1) in placebo-treated patients (P<0.05) (FIG. 16A). Dupilumab treatment reduced FeNO to levels similar to the published median value of 16 ppb for healthy volunteers.

Figure 16B:
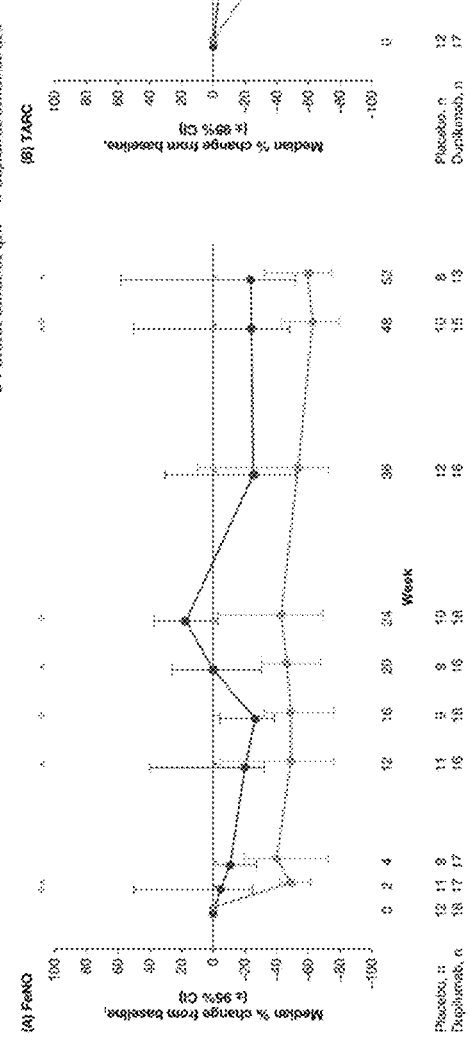

Serum concentrations of TARC were also reduced by dupilumab treatment in patients with ABPA-S. Baseline median serum TARC concentrations were 553.0 pg/mL (95% CI 442.0-1510.0) and 646.0 pg/mL (385.0-894.0) in the dupilumab and placebo groups, respectively. At week 12, dupilumab reduced serum TARC concentrations to a median of 257.0 pg/mL (193.0-438.0) with a median percentage change from baseline of −62.0% (−76.0 to −35.3) versus a median value of 674.0 pg/mL (462.0-900.0) and median percentage change of −10.1% (−17.9 to 15.1) in patients treated with placebo (P<0.01). These significant reductions were sustained throughout the 52-week treatment period, with a median value 234.0 pg/mL (182.0-336.0) and median percentage change from baseline of −66.1% (−79.6 to −51.0) at week 52 in patients treated with dupilumab versus 580.0 pg/mL (451.0-1020.0) and −17.4% (−35.7 to 25.8) with placebo (P<0.01) (FIG. 16B).

Figure 16C:
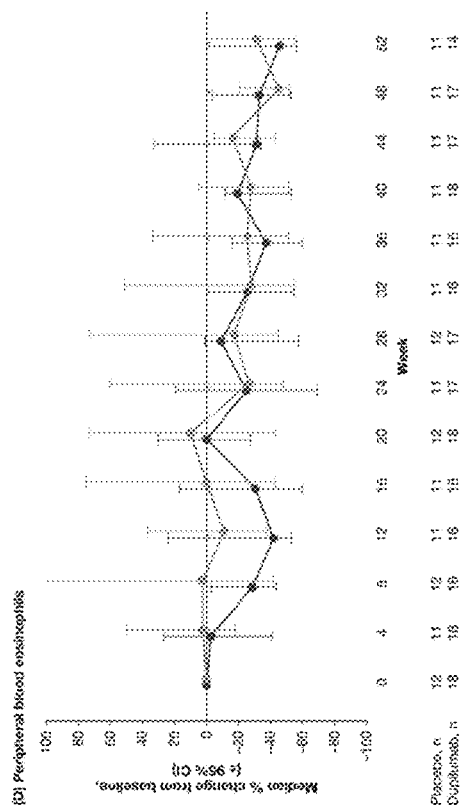

Treatment with dupilumab also reduced serum concentrations of eotaxin-3 in patients with ABPA-S. Reductions were observed from week 12, with a median value of 24.5 pg/mL (95% CI 18.0-41.7) and median percentage change from baseline of −64.9% (−83.3 to −44.7) in dupilumab-treated patients versus 53.1 pg/mL (23.0-125.0) and −5.4% (−40.6 to 34.8) in the placebo-treated group (P<0.01). These reductions were sustained up to week 52, with a median value of 23.2 pg/mL (16.1-32.1) and percentage change of −73.1% (−85.0 to −48.6) in the dupilumab group versus 35.7 pg/mL (19.3-78.7) and −29.3% (−80.2 to 27.2) in the placebo group (P<0.05) (FIG. 16C).

Figure 16D:
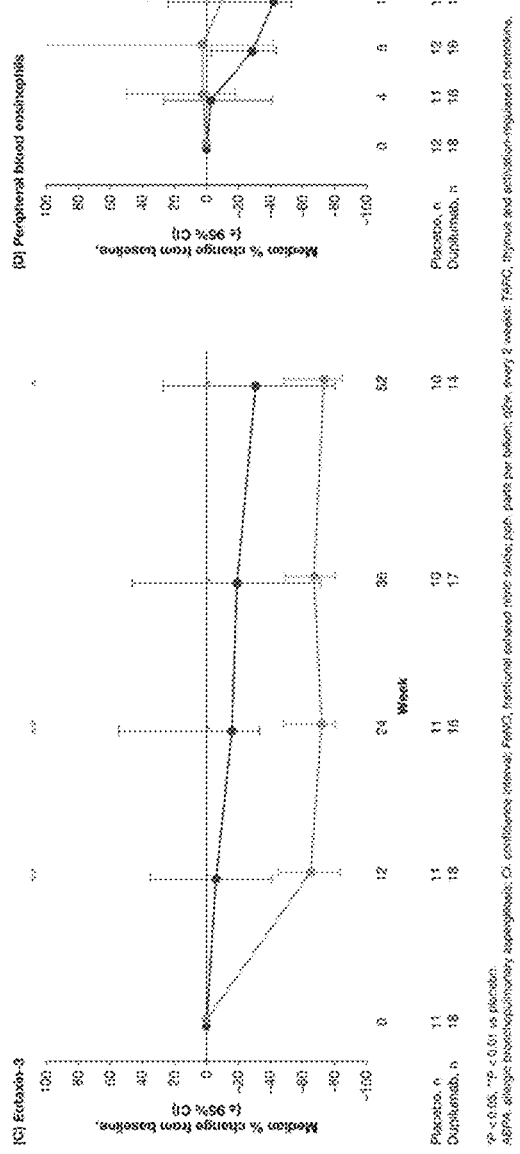

Median blood eosinophil counts at baseline were elevated (825-1075 eosinophils/µL) in ABPA-S patients. At week 52, patients treated with dupilumab had a median blood eosinophil count of 595.0 cells/µL (95% CI 360.0-1160.0) and a median percentage change from baseline of −31.3% (−55.2 to 0) versus 590.0 cells/µL (340.0-1080.0) and −45.5% (−55.5 to 0) in placebo-treated patients (P=0.69) (FIG. 16D).

Safety in Patients with ABPA-S

The incidence of treatment-emergent adverse events (TEAEs) in patients with ABPA-S was similar irrespective of treatment received (94.4% in combined dupilumab and 100% in combined placebo) (Table 3). The most frequent TEAE, occurring at a higher rate among patients who received dupilumab than in those who received placebo, was upper respiratory tract infection (27.8% of patients receiving dupilumab vs. 25.0% of patients receiving placebo). Injection-site reactions (Medical Dictionary for Regulatory Activities High Level Term) occurred in 16.7% of dupilumab-treated patients versus 0% of placebo-treated patients. Per the trial protocol, all cases of an eosinophil count >3000/mm3 during the 52-week intervention period were reported as adverse events. 1 ABPA-S patient (5.6%) treated with dupilumab 200 mg every 2 weeks (q2w) reported moderate eosinophilia. This was a laboratory finding with no associated symptoms, and the patient completed the 52-week treatment period. No patient treated with dupilumab 300 mg or placebo reported eosinophilia. Serious TEAEs were reported in 1 (5.6%) dupilumab-treated patient and 2 (16.7%) placebo-treated patients. No TEAEs leading to death were reported in this population.

DISCUSSION

In the LIBERTY ASTHMA QUEST study, dupilumab demonstrated beneficial effects in a subgroup of patients identified post hoc as meeting the diagnostic criteria for ABPA-S. Treatment with dupilumab markedly reduced severe exacerbation rates and demonstrated a trend towards improved lung function. Although the improvement in $FEV_1$ did not meet statistical significance, probably due to the small sample size, the mean change from baseline of 510 mL at week 52 in dupilumab-treated patients was clinically meaningful. $FEV_1$ improvement occurred rapidly, as early as 2 weeks after treatment commenced, and was sustained throughout the 52-week treatment period. Dupilumab treatment also improved asthma control (ACQ-5 score) in this subgroup of patients with typically difficult to control symptoms.

Consistent with the pathophysiology of ABPA, this subgroup of patients had evidence of robust type 2 inflammation, with markedly elevated baseline levels of the type 2 biomarkers, including FeNO, blood eosinophils, TARC, serum total IgE, and *A. fumigatus*-specific IgE, compared with asthma patients without serologic evidence of ABPA. Without intending to be bound by scientific theory, the increased FeNO concentration in ABPA patients likely represents concomitant airway inflammation, not driven by the allergic response, further underscoring the utility of FeNO as a marker for type 2 inflammation. Two of the defining diagnostic features of ABPA are very high serum concentrations of total IgE and *A. fumigatus*-specific IgE. Studies have shown that B cells from patients with ABPA have higher sensitivity to IL-4, and spontaneously produce large amounts of IgE, IgG, and IgA antibodies against *A. fumigatus* antigens. Indeed, serum total IgE concentrations are routinely monitored in the management of ABPA to assess disease activity, with reductions to near normal levels considered a marker of disease remission. Treatment with dupilumab markedly suppressed both total and specific IgE, consistent with the mechanism of action of dupilumab, which, by blocking IL-4 and IL-13 signaling, inhibits isotype switching of B cells and therefore the production of IgE. In addition, biomarkers of type 2 inflammation, both in blood (TARC and eotaxin-3) and in local airways (FeNO), were also rapidly suppressed in dupilumab-treated ABPA-S patients, indicating that through its dual blockade of IL-4 and IL-13, dupilumab was able to rapidly control the underlying pathogenic type 2 inflammation common to ABPA patients.

Dupilumab was generally well tolerated in ABPA patients, with similar occurrences of TEAEs in dupilumab- and placebo-treated patients. The most frequent TEAE observed in dupilumab-treated patients was upper respiratory tract infection. Unlike the transient eosinophilia that has been observed in patients with asthma, only 1 (5.6%) dupilumab-treated ABPA patient reported eosinophilia during the treatment period in this analysis, despite these patients being hypereosinophilic at baseline (median concentration 925.0 cells/µL). Furthermore, unlike in asthma studies where eosinophil counts at week 52 are unchanged, in this analysis ABPA-S patients showed an overall reduction in median blood eosinophil counts during the 52-week treatment period.

Clinically, asthma patients with ABPA have poor symptom control and more frequent exacerbations compared with those who do not have ABPA. Unlike asthma, if ABPA diagnosis is delayed or the disease is undertreated, it progresses to lung function decline and fibrotic end-stage lung disease. These data indicate the utility of dupilumab as a novel treatment for patients with ABPA, improving symptoms and lung function by controlling the underlying pathogenic type 2 inflammation.

TABLE 2

Baseline demographics and clinical characteristics of overall ITT patient population with and without serologic evidence of ABPA.

|  | With ABPA | | Without ABPA | |
| --- | --- | --- | --- | --- |
|  | Placebo combined q2 w (n = 12) | Dupilumab 200/300 mg q2 w combined (n = 18) | Placebo combined q2 w (n = 626) | Dupilumab 200/300 mg q2 w combined (n = 1246) |
| Age, mean (SD), y | 48.5 (19.4) | 40.0 (19.7) | 48.2 (15.1) | 47.9 (15.3) |
| Female, n (%) | 8 (66.7) | 7 (38.9) | 408 (65.2) | 774 (62.1) |
| BMI, mean (SD), kg/m$^2$ | 30.66 (6.61) | 24.04 (4.70) | 29.46 (7.11) | 29.13 (6.59) |
| Pre-bronchodilator FEV$_1$, mean (SD), L | 1.59 (0.49) | 2.00 (0.68) | 1.76 (0.59) | 1.78 (0.61) |
| Pre-bronchodilator FEV$_1$, mean (SD), % predicted | 58.33 (13.98) | 60.94 (15.30) | 58.39 (13.54) | 58.41 (13.49) |
| FEV$_1$ reversibility, mean (SD), % | 13.64 (8.44) | 23.43 (12.73) | 25.99 (18.27) | 26.60 (23.42) |
| Exacerbations in past year, mean (SD), n | 2.50 (1.68) | 2.28 (1.53) | 2.19 (1.85) | 2.04 (2.30) |
| High-dose ICS/LABA use, n (%) | 10 (83.3) | 9 (50.0) | 329 (52.6) | 631 (50.6) |
| ACQ-5 score, mean (SD) | 2.82 (0.83) | 2.70 (0.67) | 2.74 (0.75) | 2.76 (0.78) |
| AQLQ global score, mean (SD) | 4.36 (0.73) | 4.53 (1.05) | 4.28 (1.03) | 4.29 (1.07) |
| Blood eosinophil count, cells/μL | | | | |
| Median | 1075.00 | 825.00 | 260.00 | 250.00 |
| (IQR, Q1-Q3) | (645.00-1365.00) | (670.00-1100.00) | (140.00-450.00) | (130.00-440.00) |
| Mean (SD) | 1075.00 (438.96) | 936.11 (379.60) | 367.52 (367.49) | 341.61 (350.04) |
| ECP, ng/mL | | | | |
| Median | 37.00 | 38.50 | 17.00 | 16.00 |
| (IQR Q1-Q3), | (21.00-54.00) | (23.00-59.00) | (9.00-31.00) | (8.00-32.00) |
| Mean (SD) | 40.36 (24.27) | 56.22 (57.12) | 26.33 (29.44) | 24.79 (27.76) |
| FeNO, ppb | | | | |
| Median | 31.00 | 49.00 | 26.00 | 24.00 |
| (IQR, Q1-Q3) | (19.50-53.00) | (24.00-68.00) | (15.00-47.00) | (14.00-42.00) |
| Mean (SD) | 39.08 (27.17) | 50.33 (30.06) | 36.39 (33.81) | 33.99 (32.40) |
| Total IgE, IU/mL | | | | |
| Median | 2148.00 | 3383.00 | 165.00 | 159.00 |
| (IQR, Q1-Q3) | (1445.50-2734.00) | (1480.00-5000.00) | (59.00-423.00) | (61.00-432.50) |
| Mean (SD) | 2128.58 (878.16) | 3335.67 (1687.73) | 388.31 (672.17) | 395.65 (651.79) |
| *A. fumigatus*-specific IgE, IU/mL | | | | |
| Median | 2.96 | 2.44 | 0.05 | 0.05 |
| (IQR, Q1-Q3) | (0.52-28.80) | (0.64-11.20) | (0.05-0.05) | (0.05-0.05) |
| Mean (SD) | 11.58 (17.03) | 7.27 (10.34) | 0.50 (2.66) | 0.36 (1.66) |
| Periostin, ng/mL | | | | |
| Median | 88.10 | 108.30 | 71.00 | 69.70 |
| (IQR, Q1-Q3) | (58.10-115.35) | (84.70-151.60) | (54.10-94.30) | (54.30-92.70) |
| Mean (SD) | 86.72 (33.51) | 136.78 (78.09) | 80.16 (38.81) | 78.34 (37.06) |
| Eotaxin-3, pg/mL | | | | |
| Median | 46.50 | 66.95 | 36.70 | 38.50 |
| (IQR, Q1-Q3) | (29.40-165.00) | (51.50-153.00) | (22.80-62.20) | (25.10-59.20) |
| Mean (SD) | 95.30 (96.82) | 123.33 (136.33) | 50.72 (72.68) | 73.17 (419.78) |

TABLE 2-continued

Baseline demographics and clinical characteristics of overall ITT patient population with and without serologic evidence of ABPA.

|  | With ABPA | | Without ABPA | |
|---|---|---|---|---|
|  | Placebo combined q2 w (n = 12) | Dupilumab 200/300 mg q2 w combined (n = 18) | Placebo combined q2 w (n = 626) | Dupilumab 200/300 mg q2 w combined (n = 1246) |
| TARC, pg/mL | | | | |
| Median | 646.00 | 553.00 | 296.00 | 301.00 |
| (IQR, Q1-Q3) | (470.50-891.50) | (442.00-1510.00) | (202.00-460.50) | (197.00-443.00) |
| Mean (SD) | 670.00 (321.41) | 1387.35 (2065.80) | 382.61 (315.47) | 365.31 (284.44) |

ABPA, allergic bronchopulmonary aspergillosis;
ACQ-5, 5-item Asthma Control Questionnaire;
AQLQ, Asthma Quality of Life Questionnaire;
BMI, body mass index;
ECP, eosinophil cationic protein;
ICS, inhaled corticosteroids;
IQR, interquartile range;
ITT, intention-to-treat;
FeNO, fractional exhaled nitric oxide;
FEV1, forced expiratory volume in 1 second;
LABA, long-acting β2-agonist;
ppb, parts per billion;
q2 w, , every 2 weeks;
SD, standard deviation;
TARC, thymus and activation-regulated chemokine.

TABLE 3

Treatment-emergent adverse events in patients with serologic evidence of ABPA that emerged during the intervention period—safety population

| Event, n (%) | Matched placebo combined q2 w (n = 12) | Dupilumab 200/300 mg q2 w combined (n = 18) |
|---|---|---|
| Any TEAE | 12 (100) | 17 (94.4) |
| Any serious TEAE† | 2 (16.7) | 1 (5.6) |
| Any TEAE leading to death | 0 | 0 |
| TEAEs occurring in ≥10% of patients (MedDRA PT)‡ | | |
| Upper respiratory tract infection | 3 (25.0) | 5 (27.8) |
| Viral upper respiratory tract infection | 6 (50.0) | 3 (16.7) |
| Conjunctivitis, allergic | 0 | 2 (11.1) |
| Arthralgia | 2 (16.7) | 3 (16.7) |
| Musculoskeletal chest pain | 0 | 2 (11.1) |
| Accidental overdose | 0 | 2 (11.1) |
| Injection-site reactions§ | 0 | 3 (16.7) |

ABPA, allergic bronchopulmonary aspergillosis;
MedDRA, Medical Dictionary for Regulatory Activities;
PT, Preferred Term;
q2 w, every 2 weeks;
TEAE, treatment-emergent adverse event.
One ABPA-S patient in the dupilumab-treated group reported eosinophilia versus none in the placebo-treated group.
†Serious TEAEs included gastroenteritis and asthma in placebo-treated patients and musculoskeletal chest pain and osteoarthritis in dupilumab-treated patients.
‡Adverse events in this category were reported according to the PTs in the MedDRA, version 20.0, unless otherwise indicated.
§Injection-site reaction is a high level term in MedDRA.

Example 9: Yellow Fever Vaccine Post-Hoc Analysis: Open-Label Extension Study to Evaluate the Long-Term Safety and Tolerability of Dupilumab in Patients with Asthma Who Participated in a Previous Dupilumab Asthma Clinical Study Study Design The LTS12551 (TRAVERSE) study was a multinational, multicenter, single-arm, open-label, extension study to evaluate the long-term safety and tolerability of dupilumab 300 mg q2w in patients with asthma, who completed the treatment and follow-up periods in Study DRI12544, or who completed the treatment period in Studies EFC13579, EFC13691, or PDY14192. DRI12544 (N=776) was a phase 2b, randomized, double-blind, placebo-controlled, dose ranging, parallel group study comparing different doses and regimens of dupilumab subcutaneous (SC) for 24 weeks in adult patients with moderate to severe, uncontrolled asthma. PDY14192 (N=42) was a phase 2a, exploratory, randomized, double-blind, placebo-controlled study of the effects of dupilumab 300 mg q2w SC for 12 weeks on airway inflammation of adults with uncontrolled persistent asthma. EFC13579 (N=1902) was a phase 3, randomized, double-blind, placebo-controlled, parallel group study to evaluate the efficacy and safety of dupilumab 200 mg and 300 mg q2w SC for 52 weeks in adult and adolescent patients with uncontrolled persistent asthma. EFC13691 (N=210) was a phase 3, randomized, double-blind, placebo-controlled study to evaluate the efficacy and safety of dupilumab 300 mg q2w SC for 24 weeks in adult and adolescent patients with severe OCS dependent asthma.

While the study LTS12551 was ongoing, a yellow fever outbreak in Brazil required yellow fever vaccine (YFV) administration for all non-vaccinated individuals located in regions at risk. The sponsor implemented the regional protocol amendment 5 which permitted the administration of YFV (a live attenuated vaccine) to all patients requiring YFV in the outbreak affected area. All affected patients were required to discontinue dupilumab, and vaccination administration could occur after dupilumab discontinuation. Patients were allowed to re-start dupilumab at investigator discretion following demonstration of adequate yellow fever neutralization titers (i.e., plaque-reduction neutralization titers; PRNT). Patients who were not vaccinated were eligible to restart study treatment after the outbreak had subsided.

All patients continued to be followed until the end-of-study, regardless of whether dupilumab treatment was re-established. For those patients where yellow fever vaccination was planned, samples for drug pharmacokinetics (PK) and immunogenicity assessments, along with pre- and post-vaccination antibody titers, were to be collected both before and 4-6 weeks and might be extended up to 8 weeks after vaccination, upon patient consent. Overall, thirty-seven patients discontinued treatment with dupilumab, and were subsequently vaccinated with YFV. Although patients were allowed to resume dupilumab treatment after demonstration of neutralizing titers at the discretion of the treating physician, none of the patients resumed dupilumab due to delay of the results.

A post-hoc YFV analysis was conducted to evaluate the humoral immune response, and safety/tolerability of YFV in this subset of 37 patients who participated in the LTS12551 study and received YFV.

Study Objectives

The objective of this study was to evaluate the humoral immune response, safety and tolerability of YFV, a live attenuated vaccine, in patients with moderate to severe asthma who participated in the study LTS12551 and were treated with dupilumab.

Patients

A total of 37 patients who participated in the LTS12551 study (an open label asthma study) and received YFV were included in this analysis. Of these, 33 were rolled over from EFC13579 study, and four were rolled over from EFC13691 study. Of the patients enrolled from EFC13579, 11 were previously treated with placebo in the parent study and then received dupilumab in the LTS12551 study (placebo/dupilumab category), and 22 were previously treated with dupilumab in the parent study and continued dupilumab in the LTS12551 study (dupilumab/dupilumab category). Of the patients enrolled from EFC13691 study, three patients were previously treated with placebo in the parent study and then received dupilumab in the LTS12551 study (placebo/dupilumab category) and one was previously treated with dupilumab in the parent study and continued dupilumab in the LTS12551 study (dupilumab/dupilumab category).

Demographics and Other Baseline Characteristics

The baseline demographic and patient characteristics for the 37 patients who received YFV were generally similar among patients who previously received placebo or dupilumab within each parent study (see Table 4, below). The mean age of the population was 46.5 years with a range of 24 to 68 years, 5 (13.5%) patients were aged ≥65 years, and 12 (32.4%) patients were male. The mean (SD) BMI (body mass index) was 30.1 (5.7) kg/m$^2$.

TABLE 4

Demographics and patient characteristics as of yellow fever vaccination - Exposed population—Patients with yellow fever vaccination in LTS12551 study

| | Patients from EFC13579 study | | Patients front EFC13691 study | | |
| --- | --- | --- | --- | --- | --- |
| | Placebo/ Dupilumab (N = 11) | Dupilimab/ Dupilumab (N = 22) | Placebo/ Dupilumab (N = 3) | Dupilimab/ Dupilumab (N = 1) | All (N = 37) |
| Age (years) | | | | | |
| Number | 11 | 22 | 3 | 1 | 37 |
| Mean (SD) | 48.1 (11.3) | 44.9 (11.8) | 47.0 (17.1) | 63.0 (NC) | 46.5 (12.0) |
| Median | 51.0 | 44.5 | 42.0 | 63.0 | 46.0 |
| Min:Max | 30:65 | 24:68 | 33:66 | 63:63 | 24:68 |
| Age group (years) [n (%)] | | | | | |
| Number | 11 | 22 | 3 | 1 | 37 |
| <18 | 0 | 0 | 0 | 0 | 0 |
| 18-64 | 9 (81.8%) | 20 (90.9%) | 2 (66.7%) | 1 (100%) | 32 (86.5%) |
| 65-74 | 2 (8.2%) | 2 (9.1%) | 1 (33.3%) | 0 | 5 (13.5%) |
| 75-84 | 0 | 0 | 0 | 0 | 0 |
| Sex [n (%)] | | | | | |
| Number | 11 | 22 | 3 | 1 | 37 |
| Male | 5 (45.5%) | 5 (22.7%) | 1 (33.3%) | 1 (100.%) | 12 (32.4%) |
| Female | 6 (54.5%) | 17 (77.3%) | 2 (66.7%) | 0 | 25 (67.6%) |
| Race [n (%)] | | | | | |
| Number | 11 | 22 | 3 | 1 | 37 |
| Caucasian/White | 5 (45.5%) | 14 (63.6%) | 2 (66.7%) | 0 | 21 (56.8%) |
| Black/of African descent | 3 (27.3%) | 5 (22.7%) | 1 (33.3%) | 1 (100%) | 10 (27.0%) |
| Asian/Orieratal | 1 (9.1%) | 0 | 0 | 0 | 1 (2.7%) |
| Other | 2 (18.2%) | 3 (13.6%) | 0 | 0 | 5 (13.5%) |
| Ethnicity [n (%)] | | | | | |
| Number | 11 | 22 | 3 | 1 | 37 |
| Hispanic | 7 (63.6%) | 17 (77.3%) | 0 | 0 | 24 (64.9%) |
| Not Hispanic | 4 (36.4%) | 5 (22.7%) | 3 (100%) | 1 (100%) | 13 (35.1%) |

TABLE 4-continued

Demographics and patient characteristics as of yellow fever vaccination -
Exposed population—Patients with yellow fever vaccination in LTS12551 study

| | Patients from EFC13579 study | | Patients front EFC13691 study | | |
|---|---|---|---|---|---|
| | Placebo/ Dupilumab (N = 11) | Dupilimab/ Dupilumab (N = 22) | Placebo/ Dupilumab (N = 3) | Dupilimab/ Dupilumab (N = 1) | All (N = 37) |
| Height (cm) | | | | | |
| Number: | 11 | 22 | 3 | 1 | 37 |
| Mean (SD) | 160.09 (8.03) | 162.02 (11.44) | 161.67 (7.23) | 171.00 (NC) | 161.66 (10.02) |
| Median | 161.00 | 158.25 | 158.00 | 171.00 | 159.50 |
| Min:Max | 149.0:174.0 | 145.0:190.0 | 157.0:170.0 | 171.0:171.0 | 145.0:190.0 |
| Weight (kg) | | | | | |
| Number | 11 | 22 | 3 | 1 | 37 |
| Mean (SD) | 80.80 (14.77) | 77.32 (16.39) | 75.37 (18.38) | 88.40 (NC) | 78.50 (15.56) |
| Median | 81.00 | 75.05 | 81.50 | 88.40 | 79.50 |
| Min:Max | 56.5:110.2 | 54.5:111.0 | 54.7:89.9 | 88.4:88.4 | 54.5:111.0 |
| Weight group (kg) [n (%)] | | | | | |
| Number | 11 | 72 | 3 | 1 | 37 |
| <50 | 0 | 0 | 0 | 0 | 0 |
| ≥50-<100 | 10 (90.9%) | 20 (90.9%) | 3 (100%) | 1 (100%) | 34 (91.9%) |
| ≥100 | 1 (9.1%) | 2 (9.1%) | 0 | 0 | 3 (8.1%) |
| Body mass index (BMI)(kg/m$^2$) | | | | | |
| Number | 11 | 22 | 3 | 1 | 37 |
| Mean (SD) | 31.52 (5.27) | 29.52 (6.21) | 28.65 (5.64) | 30.23 (NC) | 30.09 (5.74) |
| Median | 31.14 | 29.31 | 31.11 | 30.23 | 30.23 |
| Min:Max | 23.5:42.0 | 21.1:9.3 | 22.2:32.6 | 30.2:30.2 | 21.1:49.3 |
| BMI group (kg/m$^2$) (%) | | | | | |
| Number | 11 | 22 | 3 | 1 | 37 |
| <25 | 1 (9.1%) | 6 (27.3%) | 1 (33.3%) | 0 | 8 (21.6%) |
| ≥25-<30 | 3 (27.3%) | 6 (27.3%) | 0 | 0 | 9 (24.3%) |
| ≥30 | 7 (63.6%) | 10 (45.5%) | 2 (66.7%) | 1 (100%) | 20 (54.1%) |
| Region [n (%)] | | | | | |
| Number | 11 | 22 | 3 | 1 | 37 |
| Latin America | 11 (100%) | 22 (100%) | 3 (100%) | 1 (100%) | 37 (100%) |
| Territory[b] [n (%)] | | | | | |
| Number | 11 | 22 | 3 | 1 | 37 |
| Rest of World | 11 (100%) | 22 (100%) | 3 (100%) | 1 (100%) | 37 (100%) |

Note:
The age, weight, height and BMI summarize the last available asssessments before yellow fever vaccination; and, the other demographics are from the baseline of parent studies. Percentages are calculated using number of patients assessed as denominator.

[a] Asia: Japan, South Korea and Taiwan; Latin America: Argentina, Brazil, Colmnbia, Chile and Mexico; East Europe: Hungary, Poland, Russia, Turkey and Ukraine; Western Countries: Australia, Canada, France, Germany, Italy, South Africa, Spain, United Kingdom and USA

[b] North America: Canada and USA; European Union: France, Germany, Hungary, Italy, Poland, Spain and United Kingdom; Rest of World: Argentina, Australia, Brazil, Colombia, Chile, Japan, Mexico, Russia, South Africa, South Korea Taiwan, Turkey and Ukraine Medical History Patients' comorbidity history is presented in Table 5. The majority of patients (91.9%) had a history of comorbid disease, with allergic rhinitis being the most frequent (86.5%).

TABLE 5

Comorbidity history of parent study—Exposed population—Patients with yellow fever vaccination in LTS12551 study

|  | Patients from EFC13579 study | | Patients from EFC13691 study | | |
|---|---|---|---|---|---|
|  | Placebo/ Dupilumab (N = 11) | Dupilimab/ Dupilumab (N = 22) | Placebo/ Dupilumab (N = 3) | Dupilimab/ Dupilumab (N = 1) | All (N = 37) |
| Any comorbidity medical history[a] [n (%)] | | | | | |
| Number | 11 | 22 | 3 | 1 | 37 |
| Yes | 9 (81.8%) | 21 (95.5%) | 3 (100%) | 1 (100%) | 34 (91.9%) |
| No | 2 (18.2%) | 1 (4.5%) | 0 | 0 | 3 (8.1%) |
| Ongoing condition | 9 (81.8%) | 21 (95.5%) | 3 (100%) | 1 (100%) | 34 (91.9%) |
| Atopic dermatitis history [n (%)] | | | | | |
| Number | 11 | 22 | 3 | 1 | 37 |
| Yes | 1 (9.1%) | 2 (9.1%) | 0 | 0 | 3 (8.1%) |
| No | 10 (90.9%) | 20 (90.9%) | 3 (100%) | 1 (100%) | 34 (91.9%) |
| Ongoing condition | 1 (9.1%) | 2 (9.1%) | 0 | 0 | 3 (8.1%) |
| Allergic conjunctivitis and allergic rhinitis history [n (%)] | | | | | |
| Number | 11 | 22 | 3 | 1 | 37 |
| Yes | 0 | 0 | 0 | 0 | 0 |
| No | 11 (100%) | 22 (100%) | 3 (100% | 1 (100%) | 37 (100%) |
| Ongoing condition[b] | 0 | 0 | 0 | 0 | 0 |
| Allergic conjunctivitis history [n (%)] | | | | | |
| Number | 11 | 22 | 3 | 1 | 37 |
| Yes | 0 | 0 | 0 | 0 | 0 |
| No | 11 (100%) | 22 (100%) | 3 (100%) | 1 (100%) | 37 (100%) |
| Ongoing condition | 0 | 0 | 0 | 0 | 0 |
| Allergic rhinitis history [n (%)] | | | | | |
| Number | 11 | 22 | 3 | 1 | 37 |
| Yes | 7 (63.6%) | 21 (95.5%) | 3 (100%) | 1 (100%) | 32 (86.5%) |
| No | 4 (36.4%) | 1 (4.5%) | 0 | 0 | 5 (13.5%) |
| Ongoing condition | 7 (63.6%) | 21 (95.5%) | 3 (100%) | 1 (100%) | 32 (86.5%) |
| Chronic rhinosinusitis [n (%)] | | | | | |
| Number | 11 | 22 | 3 | 1 | 37 |
| Yes | 2 (18.2%) | 1 (4.5%) | 0 | 0 | 3 (9.1%) |
| No | 9 (81.8%) | 21 (95.5%) | 3 (100%) | 1 (100%) | 34 (91.9%) |
| Ongoing condition | 2 (18.2%) | 1 (4.5%) | 0 | 0 | 3 (8.1%) |
| Nasal polyposis history [n (%)] | | | | | |
| Number | 11 | 22 | 3 | 1 | 37 |
| Yes | 0 | 1 (4.5%) | 1 (33.3%) | 0 | 2 (5.4%) |
| No | 11 (100%) | 21 (95.5%) | 2 (66.7%) | 1 (100%) | 35 (94.6%) |
| Ongoing condition | 0 | 1 (4.5%) | 1 (33.3%) | 0 | 2 (5.4%) |
| Eosinophilic esophagitis | | | | | |

TABLE 5-continued

Comorbidity history of parent study—Exposed population—Patients with yellow fever vaccination in LTS12551 study

| | Patients from EFC13579 study | | Patients from EFC13691 study | | |
|---|---|---|---|---|---|
| | Placebo/ Dupilumab (N = 11) | Dupilimab/ Dupilumab (N = 22) | Placebo/ Dupilumab (N = 3) | Dupilimab/ Dupilumab (N = 1) | All (N = 37) |
| history [n (%)] | | | | | |
| Number | 11 | 22 | 3 | 1 | 37 |
| Yes | 0 | 0 | 0 | 0 | 0 |
| No | 11 (100%) | 22 (100%) | 3 (100%) | 1 (100%) | 37 (100%) |
| Ongoing condition | 0 | 0 | 0 | 0 | 0 |
| Food allergy history [n (%)] | | | | | |
| Number | 11 | 22 | 3 | 1 | 37 |
| Yes | 1 (9.1%) | 0 | 0 | 0 | 1 (2.7%) |
| No | 10 (90.9%) | 22 (100%) | 3 (100%) | 1 (100%) | 36 (97.3%) |
| Ongoing condition | 1 (9.1%) | 0 | 0 | 0 | 1 (2.7%) |
| Hives history [n (%)] | | | | | |
| Number | 11 | 22 | 3 | 1 | 37 |
| Yes | 2 (18.2%) | 1 (4.5%) | 1 (33.3%) | 0 | 4 (10.8%) |
| No | 9 (81.5%) | 21 (95.5%) | 2 (66.7%) | 1 (100%) | 33 (89.2%) |
| Ongoing condition | 1 (9.1%) | 1 (4.5%) | 1 (33.3%) | 0 | 3 (8.1%) |

Note:
the comorbidity history is from the baseline of the parent studies.
[a]A patient wilt be considered with comorbidity history, or ongoing comorbidity disease if the patient had or has any of the following diseases: atopic dermatitis, allergic conjunctivitis, allergic rhinitis, chronic rhinosinusitis, nasal polyposis, food allergy and hives history.
[b]Both allergic conjunctivitis and allergic rhinitis are ongoing.

Safety Evaluation
Extent of Exposure

The extent of exposure to investigational medicinal product in the exposed population in LTS12551 before yellow fever vaccination is summarized in Table 6. The mean (SD) duration of treatment with dupilumab in study LTS12551 was of 242.2 (34.4) days and was similar across all patients who received YFV. In patients who rolled over from EFC13579 study, the mean treatment duration was similar between the placebo/dupilumab and the dupilumab/dupilumab categories (255.0 and 230.1 days, respectively). In patients who rolled over from EFC13691 study, the mean treatment duration was similar between the placebo/dupilumab and the dupilumab/dupilumab categories (274.7 and 268.0 days, respectively).

TABLE 6

Exposure to investigational product before yellow fever vaccination—Exposed population—Patients with yellow fever vaccination in LTS12551 study

| | Patients front EFC13579 study | | Patients froth EFC13691 study | | |
|---|---|---|---|---|---|
| | Placebo/ Dupilmuab (N = 11) | Dupilmuab/ Dupilmuab (N = 22) | Placebo/ Dupilmuab (N = 3) | Dupilmuab/ Dupilmuab (N = 1) | All (N = 37) |
| Cumulative exposure to study treatment (in year) | 7.7 | 13.9 | 2.3 | 0.7 | 24.5 |
| Average exposure per patient (in year) | 0.7 | 0.6 | 0.8 | 0.7 | 0.7 |
| Duration of study treatment (Day) | | | | | |
| Number | 11 | 22 | 3 | 1 | 37 |
| Mean (SD) | 255.0 (29.0) | 230.1 (28.2) | 274.7 (66.2) | 268.0 (NC) | 242.2 (34.4) |
| Median | 253.0 | 224.5 | 303.0 | 268.0 | 237.0 |
| Min:Max | 214:294 | 184:291 | 199:322 | 268:268 | 184:322 |

As shown in Table 7, the time between the last dose of dupilumab and yellow fever vaccination varied from 7 to 51 days, with a mean (SD) of 22.3 (±11.9) days.

TABLE 7

Summary of duration between the last IMP injection and yellow fever vaccination—Exposed population—Patients with yellow fever vaccination in LTS12551 study

| | Patients from EFC13579 study | | Patients from EFC13691 study | | |
|---|---|---|---|---|---|
| | Placebo/ Dupilmuab (N = 11) | Dupilmuab/ Dupilmuab (N = 22) | Placebo/ Dupilmuab (N = 3) | Dupilmuab/ Dupilmuab (N = 1) | All (N = 37) |
| Duration between the last IMP injection and yellow fever vaccination (Day) | | | | | |
| Number | 11 | 22 | 3 | 1 | 37 |
| Mean (SD) | 23.8 (11.2) | 23.3 (12.7) | 11.0 (2.0) | 18.0 (NC) | 22.3 (11.9) |
| Median | 24.0 | 23.0 | 11.0 | 18.0 | 18.0 |
| Min:Max | 11:42 | 7:51 | 9:13 | 18:18 | 7:51 |

Note:
the duration is between the dare of last IMP injection before the yellow fever vaccination and the date of yellow fever vaccination.

As shown in Table 8, the mean (SD) follow-up period for all patients after yellow fever vaccination was 186.6 (±72.3) days and ranged between 98 to 553 days.

TABLE 8

Summary of follow-up duration post yellow fever vaccination—Exposed population—Patients with yellow fever vaccination in LTS12551 study
Table 5—Summary of follow-up duration post yellow fever vaccination—Exposed population—Patients with yellow fever vaccination in L1S12551 study

| | Patients from EFC13579 study | | Patients from EFC13691 study | | |
|---|---|---|---|---|---|
| | Placebo/ Dupilmuab (N = 11) | Dupilmuab/ Dupilmuab (N = 22) | Placebo/ Dupilmuab (N = 3) | Dupilmuab/ Dupilmuab (N = 1) | All (N = 37) |
| Duration of post-vaccination follow-up (Day) | | | | | |
| Number | 11 | 22 | 3 | 1 | 37 |
| Mean (SD) | 164.4 (33.1) | 205.0 (84.3) | 146.0 (66.6) | 149.0 (NC) | 186.6 (72.3) |
| Median | 168.0 | 200.0 | 118.0 | 149.0 | 185.0 |
| Min:Max | 126:205 | 121:553 | 98:222 | 149:149 | 98:553 |

Adverse Events

A total of 37 patients received YFV. The vaccine was administered 7 to 51 days after the last dose of dupilumab. One out of 37 patients experienced a non-serious adverse event of body pain, feeling of malaise and dizziness after receiving the vaccine, reported as "vaccination complication." This occurred in a 45 year old female patient with a history of atopic dermatitis (AD), allergic conjunctivitis, and chronic rhinosinusitis. The event occurred 7 days after the yellow fever vaccination and resolved within 2 weeks. The remaining 36 patients tolerated the vaccine and did not report any adverse event which could be related to yellow fever vaccination. There were no reports of hypersensitivity reactions to vaccine. None of the patients resumed dupilumab due to delay of the results. There were no deaths, treatment-emergent SAEs (serious adverse events), or other significant AEs (adverse events) reported among the 37 patients who received yellow fever vaccination in LTS12551 study.

Safety Conclusions

YFV administered 7 to 51 days after discontinuation of dupilumab was well-tolerated in a group of 37 patients with asthma. Thirty-six out of 37 of these patients did not report any adverse reaction to YFV. One patient reported a transitory non-serious adverse event that was fully resolved, and is a common reaction to yellow fever vaccination (Monath T P, Nichols R, Archambault W T, Moore L, Marchesani R, Tian J, et al. Comparative safety and immunogenicity of two yellow fever 17D vaccines (ARILVAX and YF-VAX) in a phase III multicenter, double-blind clinical trial. Am J Trop Med Hyg. 2002; 66(5):533-541.). Therefore, patients with therapeutic or sub therapeutic levels of dupilumab in this trial tolerated YFV.

Pharmacokinetic, Immune Response, and Immunogenicity Evaluations

Humoral Immune Response to Vaccine

The humoral immune response to YFV was determined using a standard plaque reduction neutralization titer (PRNT) assay (Q Squared solutions, LLC), where the reciprocal dilution in which 50% of the virus was neutralized (PRNT50) was calculated. Post-vaccine neutralization titers were obtained for all 37 patients, and pre- and post-vaccine PRNT titers were obtained for 23 of 37 patients (Table 9).

Prior history of yellow fever vaccination and/or infection of the patients was unknown. As shown in FIGS. 17A and 17B, of the 23 patients who provided serum pre-vaccination, 13 had PRNT<1:10 (defined as 'seronegative'), while the other 10 patients had titers in the 1:10 to 1:160 range (defined as 'seropositive').

All 37 patients showed seroprotective titers post-vaccination, defined as a PRNT titer >1:10, with an average post-vaccination titer of 1:7699 (±10951 SD; median 2560, range 80 to 40960). As shown in FIGS. 17A and 17B, while two of 23 patients had pre-vaccination titers that were not boosted post-vaccination, both patients already had seroprotective titers before YFV. Thus, all 37 vaccinated patients had seroprotective yellow fever neutralization titers post vaccination, including 13 patients with pre- and post-vaccine titers who demonstrated seroconversion.

TABLE 9

PK sample collection and vaccinated patients with PRNT titers

|  | N with post-vaccine sero-protective titer (>1:10) | N with pre-vaccine sample on the same day of YF Vaccine | N with pre-vaccine sample 1-25 days before YF vaccination | N without pre-vaccine sample |
|---|---|---|---|---|
| PK population (N = 37) | 37 | 19 | 16 | 2 |
| ADA population (N = 37) | 37 | 18 | 16 | 3 |
| Pre-and post-YF vaccine PRNT titers obtained (N = 23*) | 23 | 15 | 18 | 2 |
| Post-YF vaccine PRNT titer only (N = 14) | 14 | 4 | 8 | 1 |

*13 seronegative at baseline

Pharmacokinetics and Immunogenicity Evaluations

Pre-vaccination and post-vaccination PK and ADA (anti-drug antibody) samples were collected. Functional dupilumab concentrations in serum were measured pre-vaccination and post-vaccination. Among the 37 patients, 35 and 34 patients had pre-vaccination PK samples and pre-vaccination ADA samples collected, respectively. All 37 patients had a post-vaccination PK and ADA sample collected. Nineteen patients had PK samples obtained on the day of vaccination. Sixteen patients had pre-vaccine PK obtained before the YFV administration (Table 9).

The duration between the last dupilumab dose to administration of yellow fever vaccination, duration between pre-vaccination PK sampling and administration of yellow fever vaccination, as well as duration between administration of yellow fever vaccination and post-vaccination PK sampling are summarized in Table 10.

Dupilumab Concentration Before and After Yellow Fever Vaccination

At the time of yellow fever vaccination, patients had been exposed to dupilumab 300 mg q2w in LTS12551 for at least 24 weeks, and reached steady state with mean trough concentration of 73.3 mg/L at week 24. On average, the duration between the last dupilumab dose to administration of YFV was approximately 3 weeks (median duration of 18 days, Table 7). Pre-vaccination PK samples were collected in 35/37 patients. The mean concentration of all pre-vaccination PK samples was 59.5 mg/L with the limitation that not all PK samples were collected at the same day of yellow fever vaccination administration (Table 11). Pre-vaccination PK samples were collected on the same day as YFV administration in 19 patients. The mean dupilumab concentration in serum in those patients was 72.5 mg/L, which was similar to the mean steady state trough dupilumab concentration observed in patients treated with dupilumab 300 mg q2w in clinical studies of dupilumab in asthma and AD. For 16 patients, pre-vaccination PK samples were collected 1 to 25 days before YFV administration, and for these patients, the mean concentration was 44.0 mg/L.

Post-vaccine PK samples were collected approximately 5 weeks (ranged 28-54 days) after YFV administration and approximately 8 weeks (39 to 79 days) after the last dupilumab dose (Table 10). The observed mean concentration of post-vaccination PK samples was 13.7 mg/L (N=37), in the range of expected dupilumab concentrations with an approximately 8 weeks washout period after the last steady-state dose of 300 mg q2w (Table 11).

TABLE 10

Summary of PK serum sample time before and after yellow fever vaccination—
PK population—Patients with yellow fever vaccination in LTS12551 study

|  | Patients from EFC13579 study | | Patients from EFC13691 study | | |
| --- | --- | --- | --- | --- | --- |
|  | Placebo/ Dupilmuab (N = 11) | Dupilmuab/ Dupilumab (N = 22) | Placebo/ Dupilumab (N = 3) | Dupilmuab/ Dupilumab (N = 1) | All (N = 37) |
| Last visit before yellow fever vaccination Duration between the last IMP injection and PK sampling (day) | | | | | |
| Number | 11 | 20 | 3 | 1 | 35 |
| Mean (SD) | 20.18 (8.65) | 18.50 (8.90) | 11.00 (2.00) | 18.00 (NC) | 18.37 (8.51) |
| Median | 17.00 | 16.00 | 11.00 | 18.00 | 15.00 |
| Min:Max | 11.0:35.0 | 7.0:44.0 | 9.0:13.0 | 18.0:18.0 | 7.0:44.0 |
| Duration between PK sampling and yellow fever vaccination (day) | | | | | |
| Number | 11 | 20 | 3 | 1 | 35 |
| Mean (SD) | 3.64 (4.80) | 5.45 (8.04) | 0.00 (0.00) | 0.00 (NC) | 4.26 (6.78) |
| Median | 3.00 | 0.50 | 0.00 | 0.00 | 0.00 |

TABLE 10-continued

Summary of PK serum sample time before and after yellow fever vaccination—
PK population—Patients with yellow fever vaccination in LTS12551 study

| | Patients from EFC13579 study | | Patients from EFC13691 study | | |
|---|---|---|---|---|---|
| | Placebo/ Dupilmuab (N = 11) | Dupilmuab/ Dupilmuab (N = 22) | Placebo/ Dupilmuab (N = 3) | Dupilmuab/ Dupilmuab (N = 1) | All (N = 37) |
| Min:Max | 0.0:15.0 | 0.0:25.0 | 0.0:0.0 | 0.0:0.0 | 0.0:25.0 |
| First visit after yellow fever vaccination Duration between the last IMP injection and PK sampling (day) | | | | | |
| Number | 11 | 22 | 3 | 1 | 37 |
| Mean (SD) | 58.36 (8.55) | 57.95 (9.33) | 50.00 (2.65) | 60.00 (NC) | 57.49 (8.75) |
| Median | 56.00 | 55.50 | 49.00 | 60.00 | 55.00 |
| Min:Max | 46.0:74.0 | 39.0:79.0 | 48.0:53.0 | 60.0:60.0 | 39.0:79.0 |
| Duration between PK sampling and yellow fever vaccination (day) | | | | | |
| Number | 11 | 22 | 3 | 1 | 37 |
| Mean (SD) | 34.55 (5.68) | 34.64 (7.12) | 39.00 (1.00) | 42.00 (NC) | 35.16 (6.43) |
| Median | 33.00 | 34.00 | 39.00 | 42.00 | 35.00 |
| Min:Max | 280:44.0 | 28.0:54.0 | 34.0:40.0 | 42.0:42.0 | 28.0:54.0 |
| Follow-up visit Duration between the last IMP injection and PK sampling (day) | | | | | |
| Number | 11 | 22 | 3 | 1 | 37 |
| Mean (SD) | 184.36 (28.66) | 203.36 (29.21) | 157.00 (66.30) | 167.00 (NC) | 192.97 (34.43) |
| Median | 196.00 | 208.50 | 127.00 | 167.00 | 197.00 |
| Min:Max | 139.0:219.0 | 145.0:259.0 | 111.0:233.0 | 167.0:167.0 | 111.0:259.0 |
| Duration between PK sampling and yellow fever vaccination (day) | | | | | |
| Number | 11 | 22 | 3 | 1 | 37 |
| Mean (SD) | 160.55 (29.11) | 180.05 (30.86) | 146.00 (66.57) | 149.00 (NC) | 170.65 (34.44) |
| Median | 168.00 | 184.00 | 118.00 | 149.00 | 175.00 |
| Min:Max | 126.0:204.0 | 121.0:241.0 | 98.0:222.0 | 149.0:149.0 | 98.0:241.0 |

Note:
the PK sampling time on the visit before or after yellow fever vaccination were for the unscheduled serum samples particularly collected for the yellow fever vaccination.
When concentration values are below the lower limit of quantification (LLOQ) of 78 ng/mL, one-half (39 ng/mL) of the LLOQ is used in the statistical summary.

TABLE 11

Summary of serum concentrations of dupilumab before and after yellow fever
vaccination—PK population—Patients with yellow fever vaccination in LTS12551 study

| | Patients from EFC13579 study | | Patients from EFC13691 study | | |
|---|---|---|---|---|---|
| | Placebo/ Dupilmuab (N = 11) | Dupilmuab/ Dupilmuab (N = 22) | Placebo/ Dupilmuab (N = 3) | Dupilmuab/ Dupilmuab (N = 1) | All (N = 37) |
| PK CONCEN- TRATION (ng/mL) Baseline of the parent study | | | | | |
| Number | 0 | 20 | 0 | 1 | 21 |
| Mean (SD) | | 18.35 (82.06) | | 0.00 (NC) | 17.48 (80.09) |
| SEM | | 18.350 | | NC | 17.476 |
| CV | | 447.214 | | NC | 458.258 |
| Geometric Mean | | 0.00 | | 0.00 | 0.00 |

TABLE 11-continued

Summary of serum concentrations of dupilumab before and after yellow fever vaccination—PK population—Patients with yellow fever vaccination in LTS12551 study

| | Patients from EFC13579 study | | Patients from EFC13691 study | | |
|---|---|---|---|---|---|
| | Placebo/ Dupilmuab (N = 11) | Dupilmuab/ Dupilmuab (N = 22) | Placebo/ Dupilmuab (N = 3) | Dupilmuab/ Dupilmuab (N = 1) | All (N = 37) |
| Median | | 0.00 | | 0.00 | 0.00 |
| Min:Max | | 0.0:367.0 | | 0.0:0.0 | 0.0:367.0 |
| Last visit before yellow fever vaccination | | | | | |
| Number | 11 | 20 | 3 | 1 | 35 |
| Mean (SD) | 56400.82 (40990.68) | 57981.95 (35838.83) | 85600.00 (33246.35) | 45200.00 (NC) | 59487.09 (36709.06) |
| SEM | 12359.155 | 8013.806 | 19194.791 | NC | 6204.963 |
| CV | 72.677 | 61.810 | 38.839 | NC | 61.709 |
| Geometric Mean | 23339.51 | 35832.35 | 81612.15 | 45200.00 | 33828.82 |
| Median | 59200.00 | 53850.00 | 74400.00 | 45200.00 | 57700.00 |
| Min:Max | 39.9:112000.0 | 39.0:127000.0 | 59400.0:123000.0 | 45209.0:45200.0 | 39.0:127000.0 |
| First visit after yellow fever vaccination | | | | | |
| Number | 11 | 22 | 3 | 1 | 37 |
| Mean (SD) | 14472.45 (13841.78) | 11802.68 (13963.92) | 26896.67 (29653.68) | 6810.00 (NC) | 13685.30 (15298.98) |
| SEM | 4173.453 | 2977.117 | 17120.563 | NC | 2514.988 |
| CV | 95.642 | 118.311 | 110.250 | NC | 111.785 |
| Geometric Mean | 3927.38 | 2428.14 | 17058.22 | 6810.00 | 3122.53 |
| Median | 14400.00 | 7430.00 | 14100.00 | 6810.00 | 7780.00 |
| Min:Max | 39.0:36700.0 | 39.0:50100.0 | 5790.0:60809.0 | 6810.9:6810.0 | 39.0:60800.0 |
| Follow-up visit | | | | | |
| Number | 11 | 22 | 3 | 1 | 37 |
| Mean (SD) | 39.00 (0.00) | 39.00 (0.00) | 39.00 (0.00) | 39.00 (NC) | 39.00 (0.00) |
| SEM | 0.000 | 0.000 | 0.000 | NC | 0.000 |
| CV | 0.000 | 0.000 | 0.000 | NC | 0.000 |
| Geometric Mean | 39.00 | 39.00 | 39.00 | 39.00 | 39.00 |
| Median | 39.00 | 39.00 | 39.00 | 39.00 | 39.00 |
| Min:Max | 39.0:39.0 | 39.0:39.0 | 39.0:39.0 | 39.0:39.0 | 39.0:39.0 |

SEM standard error of the mean,
CV: coefficient of variation
Note:
Serum samples are collected prior to the administration of IMP.
The PK concentrations on the visit before or after yellow fever vaccination were from the unscheduled serum samples particularly collected for the yellow fever vaccination.
When concentration values are below the lower limit of quantification (LLOQ) of 78 ng/mL, one-half (39 ng/mL) of the LLOQ is used in the statistical summary.

Pre-vaccination PK samples were collected on the same day of YFV administration in 15 out of 23 patients. The mean concentration of dupilumab in these 15 patients was 76.4 mg/L. Thirteen out of 15 patients had dupilumab concentrations higher than the mean trough concentration of 37.4 mg/L. Concentrations in serum above this level were assumed to be therapeutic and consistent with saturating levels of IL-4Rα blockade since 37.4 mg/L was the steady state mean trough concentration observed for asthma patients at 200 mg q2w in the parent Phase 3 study (EFC13579).

Figure 18:
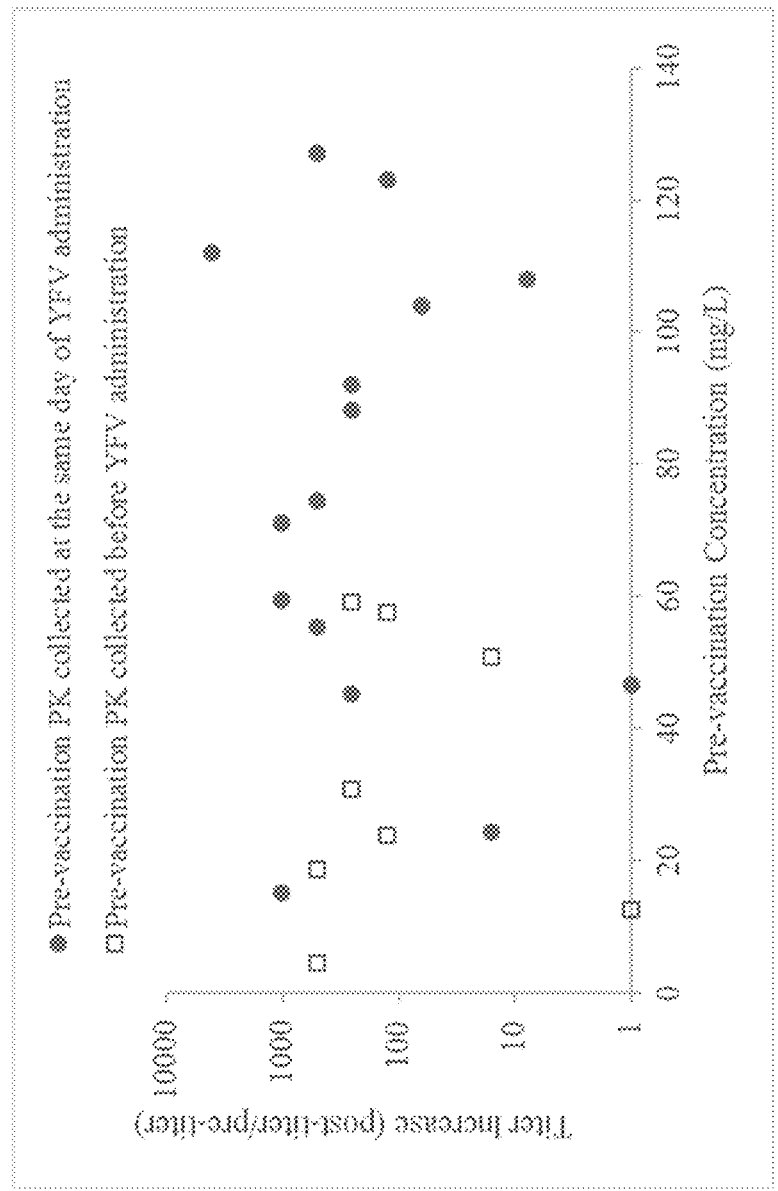
FIG. 18 graphically depicts (log) PRNT titer increase (post-vs. pre-titer) vs. pre-vaccination dupilumab concentration. Pre-vaccination PK samples were collected on the same day of YFV administration in 15 out of 23 patients. All 13 patients with serum dupilumab concentrations >37.4 mg/L had seroprotective PRNT titers after YFV. Twelve of these patients demonstrated an increase in post-vaccination titers, while one of these 13 patients did not demonstrate an increase in titer, but was already within a seroprotective threshold at baseline. The fold change in PRNT titer level for these patients is demonstrated in FIG. 18. Pre-titer <1:10, 10 was used to calculate the titer-fold increase.

All 13 patients with serum dupilumab concentrations >37.4 mg/L had seroprotective PRNT titers after YFV. Twelve of these patients demonstrated an increase in post-vaccination titers, while one of these 13 patients did not demonstrate an increase in titer, but was already within a seroprotective threshold at baseline. The fold change in PRNT titer level for these patients is demonstrated in FIG. 18. The neutralization titer of all 13 patients post-vaccination ranged from 1:80 to 1:40960 which is comparable to the post-vaccination titers in the patients who had dupilumab concentrations <37.4 mg/L (1:160 to 1:40960).

In summary, in this subset of 23 patients with pre- and post-vaccine PK and PRNT titers, there did not appear to be any relation between serum dupilumab levels and PRNT titer.

ADA Incidence and Titer Before and After Yellow Fever Vaccination

The ADA incidence before and after YFV administration and ADA titer category observed in patients is summarized in table 12. Positive ADA assay responses were observed in three patients both before and after the yellow fever vaccination. Among patients with a positive ADA assay response, one patient had low ADA titers (<1000), and two patients had high ADA titers (>10000). The number of patients in each ADA titer category did not change before and after yellow fever vaccination, suggesting no apparent impact of yellow fever vaccination on ADA responses. At the end of study, in addition to three patients who were positive before and after the yellow fever vaccination, positive ADA assay response was observed in one more patient in the follow up visit. Thus, among the total of four patients with positive ADA assay responses, two patients had low ADA titers (<1000), and two patients had high ADA titers (>10 000) in the follow up visit.

TABLE 12

Summary of ADA titer before and after yellow fever vaccination—ADA population—Patients with yellow fever vaccination in LTS12551

|  | Patients from EFC13579 study | | Patients from EFC13691 study | | |
|---|---|---|---|---|---|
|  | Placebo/ Dupilmuab (N = 11) | Dupilmuab/ Dupilmuab (N = 22) | Placebo/ Dupilmuab (N = 3) | Dupilmuab/ Dupilmuab (N = 1) | All (N = 37) |
| Baseline of the parent study | | | | | |
| Number | 11 | 21 | 3 | 1 | 36 |
| Patients with ADA negative sample | 11/11 (100%) | 20/21 (95.2%) | 3/3 (100%) | 1/1 (100%) | 35/36 (97.2%) |
| Patients with ADA positive sample | 0/11 | 1/21 (4.8%) | 0/3 | 0/1 | 1/36 (2.8%) |
| Titer | | | | | |
| Number | 0 | 1 | 0 | 0 | 1 |
| Median |  | 30.0 |  |  | 30 0 |
| Q1:Q3 |  | 30.0:30.0 |  |  | 33.0:30.0 |
| Min:Max |  | 30:30 |  |  | 30:30 |
| Low (<1000) | 0/11 | 1/21 (4.8%) | 0/3 | 0/1 | 1.36 (2.8%) |
| Moderate (1000-10000) | 0/11 | 0/21 | 0/3 | 0/1 | 0.36 |
| High (>10000) | 0/11 | 0/21 | 0/3 | 0/1 | 0/36 |
| Last visit before yellow fever vaccination | | | | | |
| Number | 11 | 19 | 3 | 1 | 34 |
| Patients with ADA negative sample | 10/11 (90.9%) | 17/19 (89.5%) | 3/3 (100%) | 1/1 (100%) | 31/34 (91.2%) |
| Patients with ADA positive sample | 1/1 (9.1%) | 2/19 (10.5%) | 0/3 | 0/1 | 3/34 (8.5%) |
| Titer | | | | | |
| Number | 1 | 2 | 0 | 0 | 3 |
| Median | 61440.0 | 245850.0 |  |  | 61440.0 |
| Q1:Q3 | 61440.0:61440.0 | 240.0:491520.0 |  |  | 249.0:491520.0 |
| Min: Max | 61440:61440 | 240:491520 |  |  | 240:491520 |
| Low (<1000) | 0/11 | 1/19 (5.3%) | 0/3 | 0/1 | 1/34 (2.9%) |
| Modertile (1000-10000) | 0/11 | 0/19 | 0/3 | 0/1 | 0/34 |
| High (>10000) | 1/11 (9.1%) | 1/19 (5.3%) | 0/3 | 0/1 | 2/34 (5.9%) |
| First visit after yellow fever vaccination | | | | | |
| Number | 11 | 22 | 3 | 1 | 37 |
| Patients with ADA negative sample | 10/11 (90.9%) | 20/22 (90.9%) | 3/3 (100%) | 1/1 (100%) | 34/37 (91.9%) |
| Patients with ADA positve sample | 1/11 (9.1%) | 2/22 (9.1%) | 0/3 | 0/1 | 3/37 (8.1%) |
| Titer | | | | | |
| Number | 1 | 7 | 0 | 0 | 3 |
| Median | 61440.0 | 123300.0 |  |  | 61440.0 |
| Q1:Q3 | 61440.0:61440.0 | 240.0:245760.0 |  |  | 240.0:245760.0 |
| Min:Max | 61440:61440 | 240:245760 |  |  | 240:245760 |
| Low (>100) | 0/11 | 1/22 (4.5%) | 0/3 | 0/1 | 1/37 (2.7%) |
| Moderate (1000-10000) | 0/11 | 0/22 | 0/3 | 0/1 |  |
| High (>10000) | 1/11 (9.1%) | 1/22 (4.5%) | 0/3 | 0/1 | 2/37 (5.4%) |
| Follow-up visit | | | | | |
| Number | 11 | 22 | 3 | 1 | 37 |
| Patients with ADA negative sample | 10/11 (90.9%) | 19/22 (86.4%) | 3/3 (100%) | 1/1 (100%) | 33/37 (89.2%) |
| Patients with ADA positive sample | 1/11 (9.1%) | 3/22 (13.6%) | 0/3 | 0/1 | 4/37 (10.8%) |
| Titer | | | | | |
| Number | 1 | 3 | 0 | 0 | 4 |
| Median | 15360.0 | 960.0 |  |  | 8160.0 |
| Q1:Q3 | 15360.0:15360.0 | 60.0:153600 |  |  | 51041:15360.0 |
| Min:Max | 15360:15360 | 60:15360 |  |  | 60:15360 |

TABLE 12-continued

Summary of ADA titer before and after yellow fever vaccination—ADA population—Patients with yellow fever vaccination in LTS12551

|  | Patients from EFC13579 study | | Patients from EFC13691 study | | |
| --- | --- | --- | --- | --- | --- |
|  | Placebo/ Dupilmuab (N = 11) | Dupilmuab/ Dupilmuab (N = 22) | Placebo/ Dupilmuab (N = 3) | Dupilmuab/ Dupilmuab (N = 1) | All (N = 37) |
| Low (<1000) | 0/11 | 2/22 (9.1%) | 0/3 | 0/1 | 2/37 (5.4%) |
| Mode:ate (1000-10000) | 0/11 | 0/22 | 0/3 | 0/1 | 0/37 |
| High (>10000) | 1/11 (9.1%) | 1/22 (4.5%) | 0/3 | 0/1 | 2/37 (5.4%) |

Note:
Percentages are calculated using the denominator as the number of patients of the ADA population with reportable ADA status at the visit and with yellow fever vaccination in LTS12551 study.
The ADA titers on the visit before or after yellow fever vaccination were from the unscheduled ADA samples particularly collected for the yellow fever vaccination.

Conclusions Based on Immune Response and Dupilumab PK

Immune response and dupilumab PK data suggest that therapeutic serum levels of dupilumab do not inhibit the protective immune responses to yellow fever vaccination, a live attenuated vaccine. Since dupilumab was not restarted after vaccination, serum levels continued to decline until the post-vaccination titer assessment.

Impact of Immune Response to Vaccine on Efficacy of Dupilumab

Figure 19:
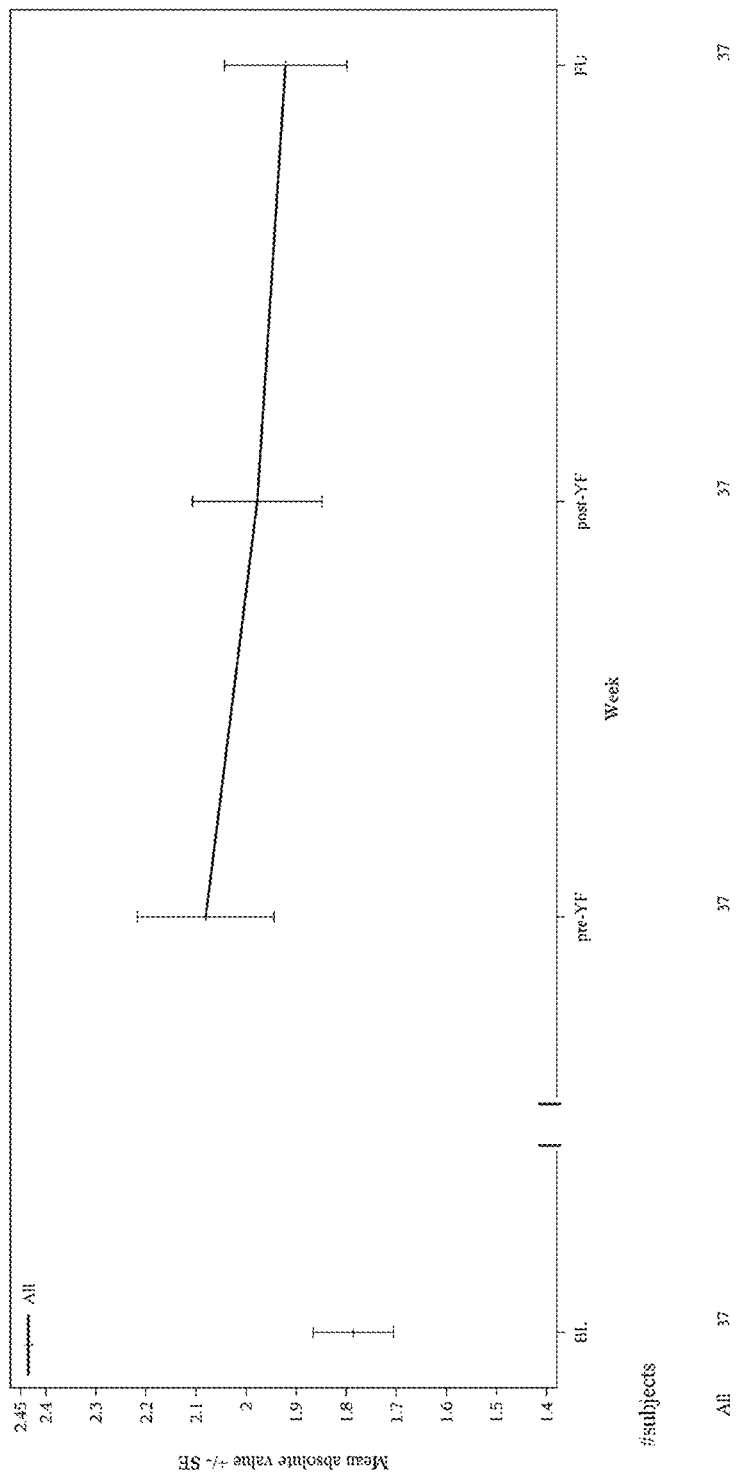
FIG. 19 graphically depicts mean absolute $FEV_1$ (L) before and after yellow fever vaccination in patients with yellow fever vaccination in the LTS12551 study.
Figure 20:
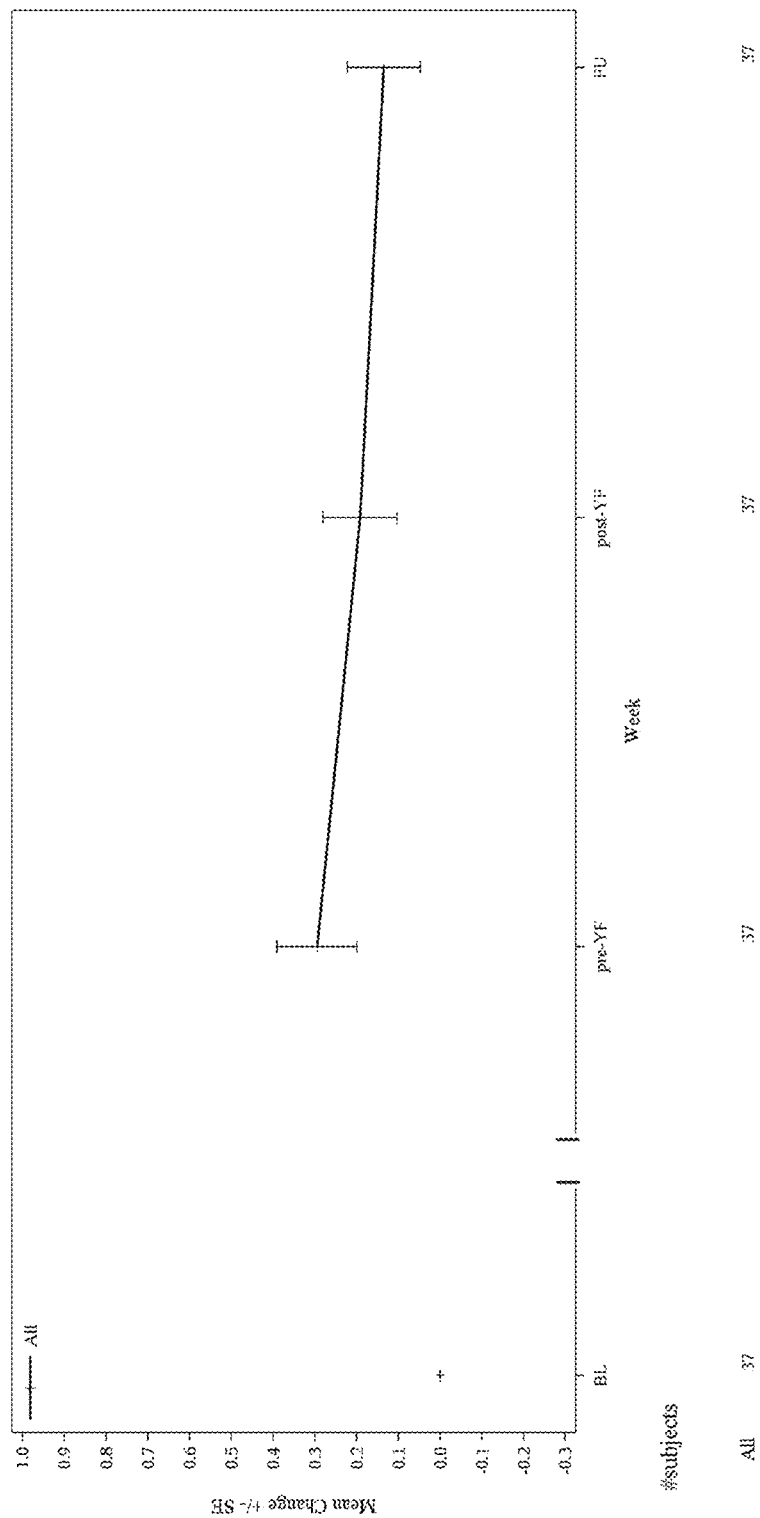
FIG. 20 graphically depicts the mean change from baseline in $FEV_1$ (L) before and after yellow fever vaccination in patients with yellow fever vaccination in the LTS12551 study.

The potential impact of yellow fever vaccination on dupilumab efficacy was evaluated by examining the change in $FEV_1$ before and after vaccine administration. All patients that discontinued treatment with dupilumab due to yellow fever vaccination had been exposed to dupilumab in LTS12551 for an average 0.7 years and achieved a stable improvement in lung function prior to discontinuation of dupilumab (Table 6). The $FEV_1$ was stable between the visit before the YFV was administered and at the first visit after YFV (FIG. 19, FIG. 20). The mean (SD) $FEV_1$ was 2.08 (0.83) L and 1.98 (0.79) L, respectively (Table 13). In general, based on observed data in EFC13579 and DRI12544, $FEV_1$ levels may be anticipated to fall around 12 weeks after discontinuation of dupilumab.

TABLE 13

Analysis of change from baseline in $FEV_1$ (L) before and after yellow fever vaccination—Exposed population—Patients with yellow fever vaccination in LTS12551 study

|  | Patients from EFC13579 study | | Patients from EFC13691 study | | |
| --- | --- | --- | --- | --- | --- |
| FEV1 (L) | Placebo/ Dupilmuab (N = 11) | Dupilmuab/ Dupilmuab (N = 22) | Placebo/ Dupilmuab (N = 3) | Dupilmuab/ Dupilmuab (N = 1) | All (N = 37) |
| Baseline of the percent study Value | | | | | |
| Number | 11 | 22 | 3 | 1 | 37 |
| Mean (SD) | 1.70 (0.28) | 1.86 (0.59) | 1.61 (0.31) | 1.61 (NC) | 1.79 (0.49) |
| Median | 1.71 | 1.80 | 1.54 | 1.61 | 1.71 |
| Q1:Q3 | 1.52:1.87 | 1.39:2.28 | 1.34:1.95 | 1:61:1.61 | 1.47:2.08 |
| Min:Max | 1.3:2.2 | 1.0:3.5 | 1.3:2.0 | 1.6:1.6 | 1.0:3.5 |
| Last visit before yellow fever vaccination Value | | | | | |
| Number | 11 | 22 | 3 | 1 | 17 |
| Mean (SD) | 1.85 (0.54) | 2.20 (0.99) | 2.11 (0.43) | 1.91 (NC) | 2.08 (0.83) |
| Median | 1.72 | 1.96 | 1.92 | 1.91 | 1.92 |
| Q1:Q3 | 1.42:2.40 | 1.62:2.53 | 1.81:2.60 | 1.91:1.91 | 1.58:2.42 |
| Min:Max | 1.2:2.9 | 1.0:4.7 | 1.8:2.6 | 1.9:1.9 | 1.0:4.7 |
| Change from baseline | | | | | |
| Number | 11 | 22 | 3 | 1 | 37 |
| Mean (SD) | 0.15 (0.45) | 0.34 (0.65) | 0.30 (0..71) | 0.30 (NC) | 0.29 (0.58) |
| Median | 0.01 | 0.17 | 0.38 | 0.30 | 0.15 |

TABLE 13-continued

Analysis of change from baseline in FEV₁ (L) before and after yellow fever vaccination—Exposed population—Patients with yellow fever vaccination in LTS12551 study

| $FEV1$ (L) | Patients from EFC13579 study | | Patients from EFC13691 study | | |
|---|---|---|---|---|---|
| | Placebo/ Dupilmuab (N = 11) | Dupilmuab/ Dupilmuab (N = 22) | Placebo/ Dupilmuab (N = 3) | Dupilmuab/ Dupilmuab (N = 1) | All (N = 37) |
| Q1:Q3 | −0.13:0.29 | −0.11:0.52 | −0.14:1.26 | 0.30:0.30 | −0.11:0.49 |
| Min:Max | −0.3:13 | −0.3:2.7 | −0.1:1.3 | 0.3:0.3 | −0.3:0.3 |
| Percent change from baseline | | | | | |
| Number | 11 | 22 | 3 | 1 | 37 |
| Mean (SD) | 8.74 (27.24) | 16.92 (32.36) | 37.18 (51.75) | 18.63 (NC) | 16.18 (31.94) |
| Median | 0.58 | 12.90 | 24.68 | 18.63 | 8.40 |
| Q1:Q3 | −7.05:16.96 | −5.00:26.78 | −7.18:94.03 | 18.63:18.63 | −6.25:24.68 |
| Min:Max | −15.5:79.6 | −23.1:136.2 | −7.2:94.0 | 18.6:18.6 | −23.1:136.2 |
| First visit after yellow fever vaccination Value | | | | | |
| Number | 11 | 22 | 3 | 1 | 37 |
| Mean(SD) | 1.79 (0.56) | 2.07 (0.94) | 1.90 (0.29) | 2.18 (NC) | 0.98 (0.79) |
| Median | 1.68 | 1.92 | 1.89 | 2.18 | 1.89 |
| Q1:Q3 | 0.34:2.41 | 1.38:2.58 | 1.62:2.20 | 2.18:2.18 | 1.53:2.26 |
| Min:Max | 0.9:2.6 | 0.9:4.5 | 1.6:2.2 | 2.2:2.2 | 0.9:4.5 |
| Change from baseline | | | | | |
| Number | 11 | 22 | 3 | 1 | 37 |
| Mean (SD) | 0.10 (0.43) | 0.21 (0.61) | 0.29 (0.50) | 0.57 (NC) | 0.19 (0.54) |
| Median | 0.20 | 0.15 | 0.08 | 0.57 | 0.15 |
| Q1:Q3 | −0.35:0.25 | −0.14:0.42 | −0.06:0.86 | 0.57:0.57 | −0.14:0.42 |
| Min:Max | −0.4:1.0 | −0.4:2.5 | −0.1:0.9 | 0.6:0.6 | −0.4:2.5 |
| Percent change from baseline | | | | | |
| Number | 11 | 22 | 3 | 1 | 37 |
| Mean (SD) | 5.08 (26.72) | 9.53 (31.24) | 22.10 (36.68) | 35.40 (NC) | 9.93 (29.66) |
| Median | 10.70 | 10.51 | 5.19 | 35.40 | 10.70 |
| Q1:Q3 | −21.64:18.32 | −8.77:19.38 | −3.08:64.18 | 35.40:35.40 | −8.77:19.38 |
| Min:Max | −27.3:59.9 | −27.3:126.6 | −3.1:64.2 | 35.4:35.4 | −27.3:126.6 |
| Follow-up visit Value | | | | | |
| Number | 11 | 22 | 3 | 1 | 37 |
| Mean (SD) | 1.73 (0.45) | 2.07 (0.88) | 1.68 (0.38) | 1.51 (NC) | 1.92 (0.74) |
| Median | 1.51 | 1.77 | 1.76 | 1.51 | 1.69 |
| Q1:Q3 | 1.31:2.21 | 1.39:2.39 | 1.27:2.01 | 1.51:1.51 | 1.39:2.14 |
| Min:Max | 1.3:2.4 | 1.1:4.4 | 1.3:2.0 | 1.5:1.5 | 1.1:4.4 |
| Change from baseline | | | | | |
| Number | 11 | 72 | 3 | 1 | 37 |
| Mean (SD) | 0.03 (0.40) | 0.21 (0.61) | 0.07 (0.52) | −0.10 (NC) | 0.14 (0.53) |
| Median | 0.00 | 0.12 | −0.19 | −0.10 | 0.03 |
| Q1:Q3 | −0.37:0.28 | −0.10:0.39 | −0.27:0.67 | −0.10:−0.10 | −0.17:0.31 |
| Min:Max | −0.5:0.8 | −0.7:2.4 | −0.3:0.7 | −0.1:−0.1 | −0.7:2.4 |
| Percent change from baseline | | | | | |
| Number | 11 | 22 | 3 | 1 | 37 |
| Mean (SD) | 2.34 (23.48) | 11.20 (30.22) | 7.57 (36.95) | −6.21 (NC) | 7.90 (27.99) |
| Median | 0.00 | 6.75 | −9.74 | −6.21 | 1.92 |
| Q1:Q3 | −19.79:15.27 | −6.03:17.48 | −17.53:50.00 | −6.21:−6.21 | −7.46:16.81 |
| Min:Max | −23.7:49.4 | −29.0:122.6 | −17.5:50.0 | −6.2:−6.2 | −29.0:122.6 |

CONCLUSIONS

In response to a regional yellow fever outbreak, 37 patients enrolled in LTS12551 discontinued dupilumab treatment and subsequently received YFV. Dupilumab did not decrease efficacy of a live-attenuated yellow fever virus vaccine. All 37 patients who were provided YFV demonstrated post-vaccine yellow fever virus antibody titers consistent with seroprotection. Pre- and post-vaccination neutralizing titers were obtained for 23 patients, with 15 of these patients having pre-vaccination serum obtained on the day of YFV administration. Of these 23 patients, 10 had pre-vaccine PRNT titers >1:10, indicating potential prior exposure to virus or previous vaccination. The remaining 13 patients had PRNT titers <1:10 (i.e., "seronegative"), suggesting no prior exposure or waning antibody response over time. Mean post-vaccination titer levels obtained between 28-42 days after vaccination were 1:7699 (±10951 SD; median 2560, range 80 to 40960), with all but 2 patients showing increased titers post-vaccination, and all 23 patients showing neutralizing titers at levels consistent with seroprotection against yellow fever.

Therapeutic levels of dupilumab did not appear to inhibit seroprotective immune responses to dupilumab. In 15 patients who had both pre- and post-vaccine yellow fever titers, PK measurements were also obtained on the same day as vaccination. At the time of vaccination, 13 out of 15 patients had concentrations of dupilumab in serum higher than the mean concentration of 37.4 mg/L, a serum level considered sufficient to saturate the IL-4Rα in asthma (based on the indicated 200 mg q2w regimen). All 13 patients demonstrated seroprotective immune responses. While 12 of the 13 patients demonstrated an increase in neutralization titers post-vaccination, one patient's serum sample had the same neutralization titer pre- and post-vaccination. These data are supportive that therapeutic dupilumab concentrations in serum at the time of vaccination did not inhibit seroprotective immune responses, and all but one of these 13 patients showed a boosting of neutralizing antibody titers to yellow fever.

YFV was well-tolerated for all exposed patients. Of the 37 patients that received YFV, one patient reported a non-serious adverse event reported as a "vaccination complication" (i.e., body pain, feeling of malaise and dizziness), which is a common reaction to YFV, and has been reported in up to 30% of patients (Monath T P, Nichols R, Archambault W T, Moore L, Marchesani R, Tian J, et al. Comparative safety and immunogenicity of two yellow fever 17D vaccines (ARILVAX and YF-VAX) in a phase III multi-center, double-blind clinical trial. Am J Trop Med Hyg. 2002; 66(5):533-541.). The patient's symptoms were reported as non-serious, and the patient was fully recovered within 2 weeks.

Yellow fever virus vaccination did not appear to impact dupilumab efficacy. All patients that were vaccinated had achieved a stable improvement in their lung function as measured by $FEV_1$. The $FEV_1$ remained stable both before and after yellow fever virus vaccination.

Taken as a whole, these data support the overall safety and tolerability of yellow fever vaccination in asthma patients who recently discontinued dupilumab. Without intending to be bound by scientific theory, the similar increase in neutralizing antibody titers post-vaccination between asthma patients who had therapeutic serum levels of dupilumab and those that had sub-therapeutic serum levels indicate suggest that, in the setting of dupilumab, immunocompetence of the humoral arm of the adaptive immune system is maintained to a live attenuated YFV.

What is claimed is:

1. A method for treating a subject having allergic asthma comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a baseline fractional exhaled nitric oxide (FeNO) level of at least about 20 ppb, a baseline allergen-specific IgE level of at least about 0.35 kU/L, a baseline total serum IgE greater than 30 IU/mL or any combination thereof, wherein the allergen comprises an animal, fungus, or plant allergen.

2. The method of claim 1, wherein:
   (a) the subject has a baseline blood eosinophil count of at least about 300 cells/μl; or
   (b) the subject has a baseline fractional exhaled nitric oxide (FeNO) level of at least about 25 ppb; or
   (c) the subject has a total serum IgE level of at least about 700 IU/mL; or
   (d) treatment results in a reduction in annualized severe asthma exacerbations; or
   (e) treatment results in an improvement in lung function as measured by forced expiratory volume (FEV$_1$) or by forced expiratory flow at 25-75% of the pulmonary volume (FEF25-75%); or
   (f) the antibody or antigen-binding fragment thereof comprises a heavy chain variable region (HCVR) sequence comprising SEQ ID NO: 1 and a light chain variable region (LCVR) sequence comprising SEQ ID NO: 2; or
   (g) the antibody is dupilumab; or
   (h) the subject has moderate-to-severe uncontrolled allergic asthma; or
   (i) any combination thereof.

3. The method of claim 1, wherein the antibody or antigen-binding fragment thereof is administered to the subject as a loading dose followed by a plurality maintenance doses, wherein:
   (a) the antibody or antigen-binding fragment thereof is administered with an autoinjector, a needle and syringe, or a pen; or
   (b) a maintenance dose of antibody or antigen-binding fragment thereof is administered once every other week (q2w); or
   (c) the loading dose is about 600 mg or about 400 mg of the antibody or the antigen-binding fragment thereof; or
   (d) each maintenance dose of antibody or antigen-binding fragment thereof is about 300 mg or about 200 mg of the antibody or the antigen-binding fragment thereof; or
   (e) the maintenance doses of the antibody or antigen-binding fragment thereof are administered for at least 24 weeks; or
   (f) a first maintenance dose of antibody or antigen-binding fragment thereof is administered two weeks after the loading dose of antibody or antigen-binding fragment thereof; or
   (g) any combination thereof.

4. A method of: improving lung function as measured by forced expiratory volume (FEV$_1$) or by forced expiratory flow at 25-75% of pulmonary volume (FEF25-75%); or reducing annualized severe asthma exacerbations; or improving Asthma Control Questionnaire (ACQ-5) score in a subject having allergic asthma, comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a baseline fractional exhaled nitric oxide (FeNO) level of at least about 20 ppb, a baseline allergen-specific IgE level of at least about 0.35 kU/L, a baseline total serum IgE greater than 30 IU/mL, or any combination thereof, wherein the allergen comprises an animal, fungus, or plant allergen.

5. The method of claim 4, wherein:
the antibody or antigen-binding fragment thereof comprises a heavy chain variable region (HCVR) sequence comprising SEQ ID NO: 1 and a light chain variable region (LCVR) sequence comprising SEQ ID NO: 2; or
the antibody is dupilumab; or
the subject has moderate-to-severe uncontrolled allergic asthma; or any combination thereof.

6. A method for treating a subject having allergic bronchopulmonary aspergillosis (ABPA) comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, wherein the subject has a baseline *Aspergillus fumigatus*-specific IgE level of greater than 0.35 kU/L, baseline serum total IgE greater than 1000 IU/mL, baseline blood eosinophils greater than 500 cells/mL, or any combination thereof.

7. The method of claim 6, wherein treatment results in an improvement in lung function as measured by forced expiratory volume ($FEV_1$) or by forced expiratory flow at 25-75% of the pulmonary volume (FEF25-75%).

8. The method of claim 6, wherein the antibody or antigen-binding fragment thereof is administered to the subject as a loading dose followed by a plurality maintenance doses, wherein the antibody or antigen-binding fragment thereof is administered using an autoinjector, a needle and syringe, or a pen.

9. A method of improving lung function as measured by: forced expiratory volume ($FEV_1$) or by forced expiratory flow at 25-75% of the pulmonary volume (FEF25-75%); or reducing annualized severe asthma exacerbations; or improving Asthma Control Questionnaire (ACQ-5) score in a subject having asthma associated with allergic bronchopulmonary aspergillosis (ABPA) comprising administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively, and wherein the subject has a baseline *Aspergillus fumigatus*-specific IgE level of greater than 0.35 kU/L, baseline serum total IgE greater than 1000 IU/mL, baseline blood eosinophils greater than 500 cells/mL, or any combination thereof.

10. The method of claim 9, wherein:
the antibody or antigen-binding fragment thereof comprises a heavy chain variable region (HCVR) sequence comprising SEQ ID NO: 1 and a light chain variable region (LCVR) sequence comprising SEQ ID NO: 2;
the antibody is dupilumab;
the subject has moderate-to-severe uncontrolled allergic asthma, or any combination thereof.

11. A method for treating a subject having allergic bronchopulmonary aspergillosis (ABPA) comprising
administering to the subject an antibody or an antigen-binding fragment thereof that specifically binds interleukin-4 receptor (IL-4R), wherein the antibody or antigen-binding fragment thereof comprises three heavy chain CDR sequences comprising SEQ ID NOs: 3, 4, and 5, respectively, and three light chain CDR sequences comprising SEQ ID NOs: 6, 7, and 8, respectively,
wherein the subject has a baseline *Aspergillus fumigatus*-specific IgE level of greater than 0.35 kU/L and a baseline blood eosinophil count of at least about 500 cells/μl.

12. The method of claim 11, wherein:
(a) the subject further has a baseline total serum IgE level of at least about 1000 IU/mL; or
(b) treatment results in an improvement in lung function as measured by forced expiratory volume ($FEV_1$) or by forced expiratory flow at 25-75% of the pulmonary volume (FEF25-75%); or
(c) treatment results in a decrease serum *Aspergillus fumigatus*-specific IgE levels; or
(d) treatment results in a decrease in one or more of TARC levels, eotaxin-3 levels and peripheral blood eosinophil levels; or
(e) FeNO (ppb) is reduced; or
(f) the antibody or antigen-binding fragment thereof comprises a heavy chain variable region (HCVR) sequence comprising SEQ ID NO: 1 and a light chain variable region (LCVR) sequence comprising SEQ ID NO: 2; or
(g) the antibody is dupilumab; or
(h) the subject has moderate-to-severe uncontrolled asthma; or
(i) the subject exhibits comorbid asthma; or
(j) the subject exhibits comorbid cystic fibrosis; or
(k) the subject exhibits comorbid asthma and comorbid cystic fibrosis; or
(l) or any combination thereof.

13. The method of claim 11, wherein the antibody or antigen-binding fragment thereof is administered to the subject as a loading dose followed by a plurality maintenance doses, wherein:
(a) the antibody or antigen-binding fragment thereof is administered with an autoinjector, a needle and syringe, or a pen; or
(b) a maintenance dose of antibody or antigen-binding fragment thereof is administered once every other week (q2w); or
(c) the loading dose is about 600 mg or about 400 mg of the antibody or the antigen-binding fragment thereof; or
(d) each maintenance dose of antibody or antigen-binding fragment thereof is about 300 mg or about 200 mg of the antibody or the antigen-binding fragment thereof; or
(e) the maintenance doses of the antibody or antigen-binding fragment thereof are administered for at least 24 weeks; or
(f) a first maintenance dose of antibody or antigen-binding fragment thereof is administered two weeks after the loading dose of antibody or antigen-binding fragment thereof; or
(g) any combination thereof.

14. The method of claim 6, wherein the subject has a baseline blood eosinophil count of at least about 300 cells/μl.

15. The method of claim 6, wherein treatment results in a decrease in one or both of total serum IgE levels and serum *Aspergillus fumigatus*-specific IgE levels.

16. The method of claim 6, wherein treatment results in a decrease in one or more of TARC levels, eotaxin-3 levels and peripheral blood eosinophil levels.

17. The method of claim 6, wherein FeNO (ppb) is reduced.

18. The method of claim 6, wherein the antibody or antigen-binding fragment thereof comprises a heavy chain variable region (HCVR) sequence comprising SEQ ID NO: 1 and a light chain variable region (LCVR) sequence comprising SEQ ID NO: 2, the antibody is dupilumab or the subject has moderate-to-severe uncontrolled asthma.

19. The method of claim 6, wherein the antibody or antigen-binding fragment thereof is administered to the subject as a loading dose followed by a plurality maintenance doses, wherein a maintenance dose of antibody or antigen-binding fragment thereof is administered once every other week (q2w).

20. The method of claim 19, wherein the loading dose is about 600 mg of the antibody or the antigen-binding fragment thereof and/or each maintenance dose of antibody or antigen-binding fragment thereof is about 300 mg of the antibody or the antigen-binding fragment thereof.

21. The method of claim 19, wherein the loading dose is about 400 mg of the antibody or the antigen-binding fragment thereof and/or each maintenance dose of the antibody or antigen-binding fragment thereof is about 200 mg of the antibody or the antigen-binding fragment thereof.

22. The method of claim 19, wherein the maintenance doses of the antibody or antigen-binding fragment thereof are administered for at least 24 weeks.

23. The method of claim 19, wherein a first maintenance dose of antibody or antigen-binding fragment thereof is administered two weeks after the loading dose of antibody or antigen-binding fragment thereof.

* * * * *

SEQUENCE LISTING

```
<160> NUMBER OF SEQ ID NOS: 10

<210> SEQ ID NO 1
<211> LENGTH: 124
<212> TYPE: PRT
<213> ORGANISM: Artificial Sequence
<220> FEATURE:
<223> OTHER INFORMATION: Description of Artificial Sequence: Synthetic
      HCVR polypeptide

<400> SEQUENCE: 1

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser
        115                 120

<210> SEQ ID NO 2
<211> LENGTH: 112
<212> TYPE: PRT
<213> ORGANISM: Artificial Sequence
<220> FEATURE:
```

```
<223> OTHER INFORMATION: Description of Artificial Sequence: Synthetic
      LCVR polypeptide

<400> SEQUENCE: 2

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
            100                 105                 110

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      HCDR1 peptide

<400> SEQUENCE: 3

Gly Phe Thr Phe Arg Asp Tyr Ala
1               5

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      HCDR2 peptide

<400> SEQUENCE: 4

Ile Ser Gly Ser Gly Gly Asn Thr
1               5

<210> SEQ ID NO 5
<211> LENGTH: 18
<212> TYPE: PRT
<213> ORGANISM: Artificial Sequence
<220> FEATURE:
<223> OTHER INFORMATION: Description of Artificial Sequence: Synthetic
      HCDR3 peptide

<400> SEQUENCE: 5

Ala Lys Asp Arg Leu Ser Ile Thr Ile Arg Pro Arg Tyr Tyr Gly Leu
1               5                   10                  15

Asp Val

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      LCDR1 peptide
```

```
<400> SEQUENCE: 6

Gln Ser Leu Leu Tyr Ser Ile Gly Tyr Asn Tyr
1               5                   10

<210> SEQ ID NO 7
<211> LENGTH: 3
<212> TYPE: PRT
<213> ORGANISM: Artificial Sequence
<220> FEATURE:
<223> OTHER INFORMATION: Description of Artificial Sequence: Synthetic
      LCDR2 peptide

<400> SEQUENCE: 7

Leu Gly Ser
1

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      LCDR3 peptide

<400> SEQUENCE: 8

Met Gln Ala Leu Gln Thr Pro Tyr Thr
1               5

<210> SEQ ID NO 9
<211> LENGTH: 451
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: HC
      aa 1-124: HCVR
      aa 125-451: HC constant

<400> SEQUENCE: 9

Glu Val Gln Leu Val Glu Ser Gly Gly Gly Leu Glu Gln Pro Gly Gly
1               5                   10                  15

Ser Leu Arg Leu Ser Cys Ala Gly Ser Gly Phe Thr Phe Arg Asp Tyr
            20                  25                  30

Ala Met Thr Trp Val Arg Gln Ala Pro Gly Lys Gly Leu Glu Trp Val
        35                  40                  45

Ser Ser Ile Ser Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Ser Ile Thr Ile Arg Pro Arg Tyr Tyr Gly Leu
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
```

```
                165                 170                 175
Thr Phe Pro Ala Val Leu Gln Ser Ser Gly Leu Tyr Ser Leu Ser Ser
            180                 185                 190

Val Val Thr Val Pro Ser Ser Ser Leu Gly Thr Lys Thr Tyr Thr Cys
            195                 200                 205

Asn Val Asp His Lys Pro Ser Asn Thr Lys Val Asp Lys Arg Val Glu
        210                 215                 220

Ser Lys Tyr Gly Pro Pro Cys Pro Pro Cys Pro Ala Pro Glu Phe Leu
225                 230                 235                 240

Gly Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

Gln Glu Asp Pro Glu Val Gln Phe Asn Trp Tyr Val Asp Gly Val Glu
            275                 280                 285

Val His Asn Ala Lys Thr Lys Pro Arg Glu Glu Gln Phe Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Gly Leu Pro Ser Ser
            325                 330                 335

Ile Glu Lys Thr Ile Ser Lys Ala Lys Gly Gln Pro Arg Glu Pro Gln
            340                 345                 350

Val Tyr Thr Leu Pro Pro Ser Gln Glu Glu Met Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Arg Leu Thr
            405                 410                 415

Val Asp Lys Ser Arg Trp Gln Glu Gly Asn Val Phe Ser Cys Ser Val
            420                 425                 430

Met His Glu Ala Leu His Asn His Tyr Thr Gln Lys Ser Leu Ser Leu
        435                 440                 445

Ser Leu Gly
    450

<210> SEQ ID NO 10
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: LC
      aa 1-112: LCVR
      aa 112-219: LC constant

<400> SEQUENCE: 10

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Ile Gly Tyr Asn Tyr Leu Asp Trp Tyr Leu Gln Lys Ser Gly Gln Ser
        35                  40                  45
```

```
Pro Gln Leu Leu Ile Tyr Leu Gly Ser Asn Arg Ala Ser Gly Val Pro
    50              55                  60

Asp Arg Phe Ser Gly Ser Gly Ser Gly Thr Asp Phe Thr Leu Lys Ile
65              70                  75                      80

Ser Arg Val Glu Ala Glu Asp Val Gly Phe Tyr Tyr Cys Met Gln Ala
                85                  90                  95

Leu Gln Thr Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
            115             120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210             215
```